United States Patent [19]
Chong et al.

[11] Patent Number: 6,013,514
[45] Date of Patent: Jan. 11, 2000

[54] HAEMOPHILUS OUTER MEMBRANE PROTEIN

[75] Inventors: Pele Chong, Richmond Hill, Canada; Wayne Thomas, Nedlands, Australia; Yan Ping Yang, Willowdale, Canada; Sheena Loosmore, Aurora, Canada; Dwo Yuan Charles Sia, Thornhill, Canada; Michel Klein, Willowdale, Canada

[73] Assignee: Connaught Laboratories Limited, Toronto, Canada

[21] Appl. No.: 08/433,522

[22] PCT Filed: Nov. 23, 1993

[86] PCT No.: PCT/CA93/00501

§ 371 Date: Sep. 12, 1995

§ 102(e) Date: Sep. 12, 1995

[87] PCT Pub. No.: WO94/12641

PCT Pub. Date: Jun. 9, 1994

[30] Foreign Application Priority Data

Nov. 23, 1992 [GB] United Kingdom .................. 9224584

[51] Int. Cl.[7] ........................ A61K 39/102; C07H 21/04; C07K 14/285; C12N 15/31
[52] U.S. Cl. ...................... 435/320.1; 424/139.1; 424/150.1; 424/164.1; 424/256.1; 424/185.1; 424/190.1; 424/192.1; 424/197.11; 435/69.3; 435/91.41; 435/252.3; 514/44; 530/350; 536/23.1; 536/23.7
[58] Field of Search ................... 435/320.1, 69.3, 435/91.41, 252.3; 424/256.1, 139.1, 150.1, 164.1, 185.1, 190.1, 192.1, 197.11; 514/44; 530/350; 536/23.1, 23.7

[56] References Cited

U.S. PATENT DOCUMENTS 4,888,170 12/1989 Curtis .

OTHER PUBLICATIONS

Loeb, M.R. et al—Outer Membrane Protein Composition in Disease Isolates of *Haemophilus influenzae:* Pathogenic and Epidemiological Implications—Inf. and Imm. Dec. 1980, pp. 709,717.

Barenkamp, S.J. et al—Subtyping Isolates of *Haemophilus influenzae* Type b by Outer–Membrane Protein Profiles—J. Of Inf. Diseases, vol. 143, No. 5, May 1981.

Gulig, P.A., et al—Antibody Response of Infants to Cell Surface–Exposed Outer Membrane Proteins of *Haemophilus influenzae* type b After Systemic Haemophilus Disease—Inf. and Immunity, Jul. 1982, pp. 82–88.

Vachon V.—Transmembrane Permeability Channels across the Outer Membrane of *Haemophilus influenzae* J. of Bacteriology, Type b—Jun. 1985, pp. 918–924.

Thomas W. et al—Molecular Cloning of DNA Coding for Outer Membrane Proteins of Haemophilus Type b—Inf. and Imm. Jun. 1986, pp. 812–817.

Thomas et al. "Expression in *Escherichia coli* of a High––Molecular–Weight . . . " Infection and Immunity 58(6), Jun. 1990, pp. 1909–1913.

Report and Recommendations of the Panel to Assess the NIH Investment in Research on Gene Therapy, Dec. 7, 1995.

Coglan. New Scientist, Nov. 25, 1995, pp. 14–15.

*Primary Examiner*—Ponnathapura Achutamurthy
*Assistant Examiner*—Phuong T. Bui
*Attorney, Agent, or Firm*—Sim & McBurney

[57] ABSTRACT

Purified and isolated nucleic acid from specific strains of *Haemophilus influenzae* is provided which encodes at least a portion of the D15 outer membrane protein of Haemophilus. The nucleic acid is used to produce peptides, polypeptides and proteins free of contaminant associated with Haemophilus for purposes of diagnosis and medical treatment. Furthermore, the nucleic acid may be used in the diagnosis of Haemophilus infection. Antisera obtained following immunization with the nucleic acid D15 outer membrane protein or peptides also may be used for the purpose of diagnosis and medical treatment.

8 Claims, 82 Drawing Sheets

FIG. 1A.

H. influenzae b Ca strain D15 sequence

```
           Hind III              -35
GATTACGCCAAGCTTAACGGTGTTTGCATTATTTAATGATTTTTTACGTCTATAATTTAT
         10        20        30        40        50        60
                                                           -10

RBS       MET LYS LYS LEU LEU ILE ALA SER LEU PHE GLY THR THR THR T
ATAGGATACAAATCGATGAAAAAACTTCTAATCGCAAGTTTATTCGGTACGACAACGA
         70        80        90       100       110       120 start truncated GST/D15
HR VAL PHE ALA ALA PRO PHE VAL ALA LYS ASP ILE ARG VAL ASP GLY VAL GLN GLY ASP L
CTGTGTTTGCCGCACCCTTTTGTGGCAAAAGATATTCGTGTGGATGGTGTTCAAGGTGACT
        130       140       150       160       170       180

EU GLU GLN GLN ILE ARG ALA SER LEU PRO VAL ARG ALA GLY GLN ARG VAL THR ASP ASN A
TAGAACAACAAATCCGAGCAAGTTTACCTGTTCGTGCCGGTCAGCGTGTGACTGACAATG
        190       200       210       220       230       240 spurious thrombin site
SP VAL ALA ASN ILE VAL ARG SER LEU PHE VAL SER GLY ARG PHE ASP ASP VAL LYS ALA H
ATGTGGCTAATATTGTCCGCTCTCTTTATTCGTAAGTGGTCGATTCGATGATGTGAAAGCGC
        250       260       270       280       290       300

IS GLN GLU GLY ASP VAL LEU VAL VAL SER VAL VAL ALA LYS SER ILE ILE SER ASP VAL L
ATCAAGAAGGCGATGTGCTTGTTGTTAGCGTTGTGGCTAAATCGATCATTTCAGATGTTA
        310       320       330       340       350       360
```

FIG. 1A. (CONTINUED)

```
YS  ILE  LYS  GLY  ASN  SER  VAL  ILE  PRO  THR  GLU  ALA  LEU  LYS  GLN  ASN  LEU  ASP  ALA  ASN  G
A A A T C A A A G G T A A C T C T G T T A T T C C C A C T G A A G C A C T T A A A C A A A A C T T A G A T G C T A A C G
              370                  380                  390                  400                  410                  420

LY  PHE  LYS  VAL  GLY  ASP  VAL  LEU  ILE  ARG  GLU  LYS  LEU  ASN  GLU  PHE  ALA  LYS  SER  VAL  L
G G T T T A A A G T T G G C G A T G T T T T A A T T C G A G A A A A T T G A A T G A A T T T G C C A A A A G T G T A A
              430                  440                  450                  460                  470                  480

YS  GLU  HIS  TYR  ALA  SER  VAL  GLY  ARG  TYR  ASN  ALA  THR  VAL  GLU  PRO  ILE  VAL  ASN  THR  L
A A G A G C A C T A T G C A A G T G T A G G T C G C T A T A A C G C A A C A G T T G A A C C T A T T G T C A A T A C G C
              490                  500                  510                  520                  530                  540

EU  PRO  ASN  ARG  ALA  GLU  ILE  LEU  ILE  ASN  GLU  ILE  ASN  GLU  ASP  LYS  ALA  LYS  LEU  A
T A C C A A A T A A T C G C G C T G A A A T T T T A A T T C A A T C A A T G A A G A T G A T A A A G C A A A A T T G G
              550                  560                  570                  580                  590                  600

LA  SER  LEU  THR  PHE  LYS  ASN  ASP  SER  VAL  SER  SER  THR  LEU  GLN  GLU  GLN  MET  G
C A T C A T T A A C T T T C A A G G G G A A C G A A T C T G T T A G T A G C A C T A C A T T A C A A G A A C A A A T G G
              610                  620                  630                  640                  650                  660

LU  LEU  GLN  PRO  ASP  SER  TRP  TRP  LYS  LEU  TRP  GLY  ASN  LYS  PHE  GLU  GLY  ALA  GLN  PHE  G
A A T T A C A A C C C T G A T T C T T G G T G G A A A T T A T G G G G A A A T A A A T T T G A A G G T G C G C A A T T C G
              670                  680                  690                  700                  710                  720
end truncated GST/D15
LU  LYS  ASP  LEU  GLN  SER  ILE  ARG  ASP  TYR  TYR  ASP  ASN  GLY  TYR  LEU  ASN  ALA  LYS  ALA  GLN  I
A G A A A G A T T T G C A G T C A A T T C G T G A T T A T T A T G A T A A T G G C T A T G C C A A A G C A C A A A
              730                  740                  750                  760                  770                  780
```

FIG.1A.(CONTINUED)

```
LE  THR LYS THR ASP VAL GLN LEU ASN ASP GLU LYS THR LYS VAL ASN VAL THR ILE ASP V
TTACTAAAACGGATGTTCAGCTAAATGATGAAAAAACAAAAGTTAATGTAACCATTGATG
        790       800       810       820       830       840

AL  ASN GLU GLY LEU GLN TYR ASP LEU ARG SER ALA ARG ILE ILE GLY ASN LEU GLY GLY M
TAAATGAAGGTTTACAGTATGACCTTCGTAGTGCACGCATTATAGGTAATCTTGGGAGGTA
        850       860       870       880       890       900

ET  SER ALA GLU LEU GLU PRO LEU LEU SER ALA LEU HIS LEU ASN ASP THR PHE ARG ARG S
TGTCTGCCGAGCTTGAACCTTTACTTTCAGCATTACATTTAAATGATACTTTCCGCCGTA
        910       920       930       940       950       960

ER  ASP ILE ALA ASP VAL GLU ASN ALA ILE LYS ALA LYS LEU GLY GLU ARG GLY TYR GLY S
GTGATATTGCAGATGTAGAAAATGCAATTAAAGCAAAACTTGGAGAACGCGGTTACGGTA
        970       980       990      1000      1010      1020

ER  ALA THR VAL ASN SER VAL PRO ASP PHE ASP ALA ASN LYS THR LEU ALA ILE THR L
GCGCAACGGTAAATTCAGTACCTGATTTTGATGCAAATAAAACATTAGCGATAACCC
       1030      1040      1050      1060      1070      1080

EU  VAL VAL ASP ALA GLY ARG ARG LEU THR VAL ARG GLN LEU ARG PHE GLU GLY ASN THR V
TTGTTGTTGATGCTGGACGACGTTTAACTGTTCGCCAACTTCGCTTTGAAGGAAATACCG
       1090      1100      1110      1120      1130      1140
```

FIG. 1A. (CONTINUED)

```
AL  SER ALA ASP SER THR LEU ARG GLN GLU MET ARG GLN GLN GLU GLY THR TRP TYR ASN S
    TTTCTGCTGATAGCACTTTACGTCAGGAAATGCGCCAACAAGAAGGAACTTGGTATAATT
            1150              1160              1170              1180              1190              1200

ER  GLN LEU VAL GLU LEU GLY LYS ILE ARG LEU ASP ARG THR GLY PHE PHE GLU THR VAL G
    CACAAATTAGTTGAGTTAGGAAAAATTCGCCTTAGATCGTACAGGTTTCTTCGAAACAGTCG
            1210              1220              1230              1240              1250              1260

LU  ASN ARG ILE ASP PRO ILE ASN GLY SER ASN ASP GLU VAL ASP GLU VAL TYR LYS VAL L
    AAAACCGAATTGATCCTATCAATGGTAGTAATGATGAAGTGGATGTCGTATATAAAGTCA
            1270              1280              1290              1300              1310              1320

YS  GLU ARG ASN THR GLY SER ILE ASN PHE GLY ILE GLY TYR GLY TYR GLU SER GLY ILE S
    AAGAAACGTAACACGGGTAGTATCAACTTTGGTATTGGTTACGGTTACGGAGAGTGGTATTA
            1330              1340              1350              1360              1370              1380

ER  TYR GLN ALA SER VAL LYS GLN ASP ASN PHE LEU GLY ALA ALA VAL SER ILE A
    GTTATCAAGCAAGTGTTAAACAAGATAATTTCTTGGGAACAGGGGCGGCCAGTAAGTATAG
            1390              1400              1410              1420              1430              1440

LA  GLY THR LYS ASN ASP TYR GLY THR SER VAL ASN LEU GLY TYR THR GLU PRO TYR PHE T
    CTGGTACGAAAAATGATTATGGTACGAGTGTCAATTTGGGTTATACCGAGCCCTATTTTA
            1450              1460              1470              1480              1490              1500

HR  LYS ASP GLY VAL SER LEU GLY VAL GLY ASN VAL PHE PHE GLU ASN TYR ASP ASN SER LYS S
    CTAAAGATGGTGTAAGTCTTGGTGTGGAAATGTTTTTTGAAAACTACGATAACTCTAAAA
            1510              1520              1530              1540              1550              1560
```

FIG.1A.(CONTINUED)

```
ER  ASP THR SER SER ASN TYR LYS ARG THR THR TYR GLY SER ASN VAL THR LEU GLY PHE P
    GTGATACATCCTCTAACTATAAGCGTACGACTTACGGAAGTAATGTTACTTTAGGTTTCC
              1570            1580            1590            1600            1610            1620

RO  VAL ASN GLU ASN ASN SER TYR TYR VAL GLY LEU GLY HIS THR TYR ASN LYS ILE SER A
    CTGTAAATGAAAATAACTCCTATTATGTAGGATTAGGTCATACCTATAAAATTAGTA
              1630            1640            1650            1660            1670            1680

SN  PHE ALA LEU GLU TYR ASN ARG ASN LEU TYR ILE GLN SER MET LYS PHE LYS GLY ASN G
    ACTTTGCTCTAGAATATAACCGTAATTTATATATTCAATCAATGAAATTTAAAGGTAATG
              1690            1700            1710            1720            1730            1740

LY  ILE LYS THR ASN ASP PHE ASP PHE SER PHE GLY TRP ASN TYR ASN SER LEU ASN ARG G
    GCATTAAAACAAAATGACTTTGATTTTTCTTTTGGTTGGAACTATAACAGCCTTAATAGAG
              1750            1760            1770            1780            1790            1800

LY  TYR PHE PRO THR LYS TYR TYR LYS LEU ALA SER LEU GLY GLY ARG VAL THR ILE PRO GLY S
    GCTATTTCCCAACTAAAGGGGTTAAAGCAAGTCTTGGTGGACGAGTTACTATTCCAGGTT
              1810            1820            1830            1840            1850            1860

ER  ASP ASN LYS TYR TYR LYS LEU SER ALA ASP VAL GLN GLY PHE TYR PRO LEU ASP ARG A
    CTGATAACAAATACTACAAACTAAGTGCAGATGTACAGGGTTTCTACCCATTAGACAGAG
              1870            1880            1890            1900            1910            1920

SP  HIS LEU TRP VAL VAL SER ALA LYS ALA SER TYR ALA ASN GLY PHE GLY ASN L
    ATCACCTCTGGGTTGTATCTCTGCAAAAGCATCTGCAGGATATGCAAAATGGTTTTGGAAACA
              1930            1940            1950            1960            1970            1980
```

FIG. 1A.(CONTINUED)

```
YS  ARG LEU PRO PHE TYR GLN THR TYR THR ALA GLY GLY ILE GLY SER LEU ARG GLY PHE A
A G C G T T T A C C G T T C T A T C A A A C T T A T A C A G C G G G T G G C A T C G G T T C A T T A C G T G G T T T T G
              1990                2000                2010                2020                2030                2040

LA  TYR GLY SER ILE GLY PRO ASN ALA ILE TYR ALA GLU TYR GLY ASN GLY SER GLY THR G
C T T A T G G T A G T A T T G G A C C T A A C G C A A T T T A T G C C G A A T A T G G T A A T G G T A G T G G T A C T G
              2050                2060                2070                2080                2090                2100

LY  THR PHE LYS LYS ILE SER SER ASP VAL ILE GLY GLY ASN ALA ILE ALA THR ALA SER A
G T A C T T T T A A G A A G A T A A G T T C T G A T G T G A T T G G T G G T A A T G C A A T C G C T A C A G C T A G C G
              2110                2120                2130                2140                2150                2160

LA  GLU LEU ILE VAL PRO THR PRO PHE VAL SER ASP LYS SER GLN ASN THR VAL ARG THR S
C A G A G T T A A T T G T G C C A A C T C C A T T T G T G A G C G A T A A G A G C C A A A A T A C G G T C C G A A C C T
              2170                2180                2190                2200                2210                2220

ER  LEU PHE VAL ASP ALA ALA SER VAL TRP ASN THR LYS TRP LYS SER ASP LYS ASN GLY L
C C T T A T T T G T T T G A T G C G G C A A G T G T T T G G A A T A C T A A A T G G A A A T C A G A T A A A A A T G G A T
              2230                2240                2250                2260                2270                2280

EU  GLU SER ASP VAL LEU LYS ARG LEU PRO ASP TYR GLY LYS SER SER ARG ILE ARG ALA S
T A G A G A G C G A T G T A T T A A A A A G A T T G C C C T G A T T A T G G C A A A T C A A G C C G T A T T C G C G C C T
              2290                2300                2310                2320                2330                2340
```

FIG.1A.(CONTINUED)

```
ER  THR GLY VAL GLY PHE GLN TRP GLN SER PRO ILE GLY PRO LEU VAL PHE SER TYR ALA L
C T A C A G G T G T C G G A T T C C A A T G G C A A T C T C C T A T T G G G C C A T T G G T A T T C T C T T A T G C C A
                2350                  2360                  2370                  2380                  2390                  2400

YS  PRO ILE LYS LYS TYR GLU ASN ASP ASP VAL GLU GLN PHE GLN PHE SER ILE GLY GLY S
A A C C A A T T A A A A A A A T A T G A A A A T G A T G A T G T C G A A C A G T T C C A A T T T A G T A T T G G A G G T T
                2410                  2420                  2430                  2440                  2450                  2460

ER  PHE *** *** ***
C T T T C T A A T A A A A T T G A A C T T T T T T C T T C A T C A G A A C T C A A A A C A A C G T T C T C T G C C T A A
                2470                  2480                  2490                  2500                  2510                  2520

```
AGCAAAAAGAAGTTGATGATAAAATTGCTGCTCGTAAAAAGTAGAAGCAAAAGTT
      2770              2780              2790              2800              2810              2820
GCGGCTTTAGAAAAGATGCACCTCGCTTACGTCAAGCTGATATTCAAAACGCCAACAG
      2830              2840              2850              2860              2870              2880
GAGATTAATAAATTAGGTGCGGCTGAAGATGCTGAATTACAAAAATTAATGCAAGAACAA
      2890              2900              2910              2920              2930              2940
GATAAAAAA
```

FIG. 1B.

DS-712-2-1 DNA, Eagan D15 sequence
IS THE SEQUENCE BEING TRANSLATED

```
                      MET LYS LYS LEU LEU ILE ALA SER LEU LEU PHE GLY THR THR THR
TAGGATACAATCGATGAAAAACTTCTAATCGCAAGTTTATTATTCGGTACGACGAC
370       380       390       400       410       420

VAL PHE ALA ALA PRO PHE VAL ALA LYS ASP ILE ARG VAL ASP GLY VAL GLN GLY ASP LEU
TGTGTTTGCCGCACCCTTTTGTGGCAAAAGATATTCGTGTGGATGGTGTTCAAGGTGACTT
430       440       450       460       470       480

GLU GLN ILE GLN ASN PRO SER LYS PHE THR CYS SER LEU PRO VAL ARG ALA GLY GLN ARG VAL THR ASP ASN ASP
AGAACAAACAAATCCGAGCAAGTTTACCTGTTCGTGCCCGGTCAGCGTGTGACTGACAATGA
490       500       510       520       530       540

VAL ALA ASN ILE VAL SER LEU PHE VAL SER GLY ARG PHE ASP ASP VAL LYS ALA HIS
TGTGGCTAATATTGTTCCGCTCTTTGTATTCGTAAGTGGTCGATTCGATGATGTGAAAGCGCA
550       560       570       580       590       600

GLN GLU GLY ASP VAL VAL LEU VAL ALA LYS SER ILE ILE SER ASP VAL LYS
TCAAGAAGGCGATGTGTCTTGTTGTTAGCGTTGTGGCTAAATCGATCATTCAGATGTTAAA
610       620       630       640       650       660

ILE LYS GLY ASN SER VAL ILE PRO THR GLU ALA LEU LYS GLN ASN LEU ASP ALA ASN GLY
AATCAAAGGTAACTCTGTTATTCCCACTGAAGCACTTAAACAAAACTTAGATGCTAACGG
670       680       690       700       710       720
```

FIG. 1B.(CONTINUED)

```
PHE LYS VAL GLY ASP VAL LEU ILE ARG GLU LYS LEU ASN GLU PHE ALA LYS SER VAL LYS
GTTTAAAGTTGGCGATGTTTTAATTCGAGAAAAATTAAATGAATTTGCCAAAAGTGTAAAA
          730                 740                 750                 760                 770                 780

GLU HIS TYR ALA SER VAL GLY ARG TYR ASN ALA THR VAL GLU PRO ILE VAL ASN THR LEU
AGAGCACTATGCAAGTGTAGGTCGCTATAACGCAACAGTTGAACCTATTGTCAATACGCT
          790                 800                 810                 820                 830                 840

PRO ASN ASN ARG ALA GLU ILE LEU ILE LYS ILE GLN GLU ASP ASP LYS ALA LYS LEU ALA
ACCAAATAATCGCGCTGAAATTTTAATTAAAATTCAAGAAGATGATAAAGCAAAATTGGC
          850                 860                 870                 880                 890                 900

SER LEU THR PHE LYS GLY ASN GLU THR VAL SER SER SER THR LEU GLN GLN GLN MET GLU
ATCATTAACTTTCAAGGGGAACGAATCTGTTAGTAGCAGTACATTACAAGAACAAATGGA
          910                 920                 930                 940                 950                 960

LEU GLN PRO ASP SER TRP TRP LYS LEU PHE GLY ASN LYS PHE GLU GLY ALA GLN PHE GLU
ATTACAACCTGATTCTTGGTGGAAATTATGGGGAAATAAATTTGAAGGTGCGCAATTCGA
          970                 980                 990                1000                1010                1020

LYS ASP LEU GLN SER ILE ARG ASP TYR TYR LEU ASN ASN GLY TYR ALA LYS ALA GLN ILE
GAAAGATTTGCAGTCAATTCGTGATTATTATTTAAATAATGGCTATGCCAAAGCACAAAT
         1030                1040                1050                1060                1070                1080

THR LYS ASP VAL GLN LEU ASN ASP GLU LYS THR LYS VAL ASN VAL THR ILE ASP VAL
TACTAAAACGGATGTTCAGCTAAATGATGAAAAAACAAAAGTTAATGTAACCATTGATGT
         1090                1100                1110                1120                1130                1140
```

FIG. 1B.(CONTINUED)

```
ASN GLU GLY LEU GLN TYR ASP LEU ARG SER ALA ARG ILE ILE GLY ASN LEU GLY GLY MET
A A A T G A A G G T T T A C A G T A T G A C C T T C G T A G T G C A C G C A T T A T A G G T A A T C T G G G A G G T A T
                    1150                    1160                    1170                    1180                    1190                    1200

SER ALA GLU LEU GLU PRO LEU LEU SER ALA LEU HIS LEU ASN ASP THR PHE ARG ARG SER
G T C T G C C G A G C T T G A A C C T T T A C T T T C A G C A T T A A A T G A T A C T T T C C G C C G T A G
                    1210                    1220                    1230                    1240                    1250                    1260

ASP ILE ALA ASP VAL GLU ASN ALA ILE LYS ALA LYS LEU GLY GLU ARG GLY TYR GLY SER
T G A T A T T G C A G A T G T A G A A A A T G C A A T T A A A G C A A A A C T T G G A G A A C G C G G T T A C G G G T A G
                    1270                    1280                    1290                    1300                    1310                    1320

ALA THR VAL ASN SER VAL PRO ASP PHE ASP ALA ASN LYS THR LEU ALA ILE THR LEU
C G C A A C G G T A A A T T C A G T A C C T G A T T T T G A T G C A A A T A A A A C A T T A G C G A T A A C C C T
                    1330                    1340                    1350                    1360                    1370                    1380

VAL VAL ASP ALA GLY ARG ARG LEU THR VAL ARG GLN LEU ARG PHE GLU GLY ASN THR VAL
T G T T G T T G A T G C T G G A C G A C G T T T A A C T G T T C G C C A A C T T C G C T T T G A A G G A A A T A C C G T
                    1390                    1400                    1410                    1420                    1430                    1440

SER ALA ASP SER THR LEU ARG GLN GLU MET ARG GLN GLU GLY THR TRP TYR ASN SER
T T C T G C T G A T A G C A C T T T A C G T C A G G A A A T G C G C C A A G A A G G A A C T T G G T A T A A T T C
                    1450                    1460                    1470                    1480                    1490                    1500
```

FIG.1B.(CONTINUED)

```
GLN LEU VAL GLU LEU GLY LYS ILE ARG LEU ASP ARG THR GLY PHE PHE GLU THR VAL GLU
ACAATTAGTTGAGTTAGGAAAAATTCGCTTAGATCGTACAGGTTTCTTCGAAACAGTCGA
         1510          1520          1530          1540          1550          1560

ASN ARG ILE ASP PRO ILE ASN GLY SER ASN ASP GLU VAL ASP VAL TYR LYS VAL LYS
AAACCGAATTGATCCTATCAATGGTAGTAATGATGAAGTGGATGTCGTATATAAAGTCAA
         1570          1580          1590          1600          1610          1620

GLU ARG ASN THR GLY ASN THR GLY SER ILE ASN PHE GLY TYR GLY TYR THR GLU SER GLY ILE SER
AGAACGTAACACGGGTAGTATCAACTTTGGTTATGGTTACGGTTACAGAGAGTGGTATTAG
         1630          1640          1650          1660          1670          1680

TYR GLN ALA SER VAL LYS GLN ASP LEU GLY ASN PHE LEU GLY THR GLY ALA ALA VAL SER ILE ALA
TTATCAAGCAAGTGTTAAACAAGATAATTTCTTGGGAACAGGCGGCCAGTAAGTATAGC
         1690          1700          1710          1720          1730          1740

GLY THR LYS ASN ASP TYR GLY THR SER VAL ASN LEU GLY TYR GLU PRO TYR PHE THR
TGGTACGAAAAATGATTATGGTACGAGTGTCAATTTGGGTTATACCGAGCCCTATTTTAC
         1750          1760          1770          1780          1790          1800

LYS ASP GLY VAL SER LEU GLY GLY ASN VAL PHE PHE GLU ASN TYR ASP ASN SER LYS SER
TAAAGATGGTGTAAGTCTTGGTGGGAAATGTTTTCTTTTGAAAACTACGATAACTCTAAAAAG
         1810          1820          1830          1840          1850          1860
```

FIG.1B.(CONTINUED)

```
ASP THR SER SER ASN TYR LYS ARG THR THR TYR GLY SER ASN VAL THR LEU GLY PHE PRO
TGATACATCCCTCTAACTATAAGCGTACGACTTACGGAAGTAATGTTACTTTAGGTTTCCC
        1870            1880            1890            1900            1910            1920

VAL ASN GLU ASN ASN SER TYR TYR VAL GLY LEU GLY HIS THR TYR ASN LYS ILE SER ASN
TGTAAATGAAAATAACTCCTATTATGTAGGATTAGGTCATACCTATAATAAAATTAGTAA
        1930            1940            1950            1960            1970            1980

PHE ALA LEU GLU TYR ASN ARG ASN LEU TYR ILE GLN SER MET LYS PHE LYS GLY ASN GLY
CTTTGCTCTAGAATATAACCGTAATTTATATTCAATCAATGAAATTTAAAGGTAATGG
        1990            2000            2010            2020            2030            2040

ILE LYS THR ASN ASP PHE ASP PHE SER PHE GLY TRP ASN TYR SER LEU ASN ARG GLY
CATTAAAACAAATGACTTTGATTTTTCTTTTGGTTGGAACTATAACAGCCCTTAATAGAGG
        2050            2060            2070            2080            2090            2100

TYR PHE PRO THR LYS GLY VAL LYS ALA SER ALA ASP VAL GLN GLY PHE TYR PRO GLY SER
CTATTTCCCAACTAAAGGGGTTAAAGCAAGTGCAGATGTACAGGGTTTCTACCCAGGTTC
        2110            2120            2130            2140            2150            2160

ASP ASN LYS TYR TYR LYS LEU SER ALA ASP VAL GLN GLY PHE TYR PRO LEU ASP ARG ASP
TGATAACAAATACTACAAACTAAGTGCAGATGTACAGGGTTTCTACCCATTAGACAGAGA
        2170            2180            2190            2200            2210            2220

HIS LEU TRP VAL VAL SER ALA LYS ALA GLY TYR ALA ASN GLY PHE GLY ASN LYS
TCACCTCTGGGTTGTATCTGCAAAAGCATCTGCAGGATATGCAAATGGTTTTGGAAACAAG
        2230            2240            2250            2260            2270            2280
```

FIG.1B.(CONTINUED)

```
ARG  LEU  PRO  PHE  TYR  GLN  THR  TYR  THR  ALA  GLY  GLY  ILE  GLY  SER  LEU  ARG  GLY  PHE  ALA
GCGTTTACCGTTCTATCAAACTTATACAGCGGGTGGCATCGGTTCATTACGTGGTTTTGC
          2290                2300                2310                2320                2330                2340

TYR  GLY  SER  ILE  GLY  PRO  ASN  ALA  ILE  TYR  ALA  GLU  TYR  GLY  ASN  GLY  SER  GLY  THR  GLY
TTATGGTAGTATTGGACCTAACGCAATTTATGCCGAATATGGTAATGGTAGTGGTACTGG
          2350                2360                2370                2380                2390                2400

THR  PHE  LYS  LYS  ILE  SER  SER  ASP  VAL  ILE  GLY  GLY  ASN  ALA  ILE  ALA  THR  ALA  SER  ALA
TACTTTTAAGAAGATAAGTTCTGATGTGATTGGTGGTAATGCAATCGCTACAGCTAGCGC
          2410                2420                2430                2440                2450                2460

GLU  LEU  ILE  VAL  PRO  THR  PRO  PHE  VAL  SER  VAL  ASP  LYS  SER  GLN  ASN  THR  VAL  ARG  THR  SER
AGAGTTAATTGTGCCAACTCCATTTGTGAGCGTTGATAAGAGCCAAAATACGGTCCGAACCTC
          2470                2480                2490                2500                2510                2520

LEU  PHE  VAL  ASP  ALA  ALA  SER  VAL  TRP  ASN  THR  LYS  SER  ASP  LYS  ASN  GLY  LEU
CTTATTTGTTGATGCGGCAAGTGTTTGGAATACTAAATGGAAATCAGATAAAAATGGATT
          2530                2540                2550                2560                2570                2580

GLU  SER  ASP  VAL  LEU  LYS  ARG  LEU  PRO  ASP  TYR  GLY  LYS  SER  SER  ARG  ILE  ARG  ALA  SER
AGAGAGCGATGTATTAAAAAGATTGCCTGATTATGGCAAATCAAGCCGTATTCGCGCCTC
          2590                2600                2610                2620                2630                2640
```

FIG. 1B.(CONTINUED)

```
THR GLY VAL GLY PHE GLN TRP GLN SER PRO ILE GLY PRO LEU VAL PHE SER TYR ALA LYS
TACAGGTGTCGGATTCCAATGGCAATCTCCTATTGGGCCATTGGTATTCTCTTATGCCAA
     2650              2660              2670              2680              2690              2700

PRO ILE LYS LYS TYR GLU ASN ASP VAL GLU GLN PHE GLN PHE SER ILE GLY GLY SER
ACCAATTAAAAAATATGAAAATGATGTCGAACAGTTCCAATTTAGTATTGGGAGGTTC
     2710              2720              2730              2740              2750              2760

PHE ***  ***
TTTCTAATAAATTGAACTTTTTTTCTTCATCAGAACTCAAAAACAACGTTCTCTGCCTAAT
     2770              2780              2790              2800              2810              2820

TTAAATTGGGCAGAGAAAAATATTAAAACCCATCATTTAATTAAGGATATTTATCAAATGAAA
     2830              2840              2850              2860              2870              2880

AACATCGCAAAAGTAACCGCACTTGCTTTAGGTATTGCACTTGCTTCAGGCTATGCTTCC
     2890              2900              2910              2920              2930              2940

GCTGAAGAAAAAATTGCTTTCATTAATGCACTTATATTTTTCAA
     2950              2960              2970              2980
```

FIG.1C.

DS-691-1-5 DNA, Minn A D15 sequence
IS THE SEQUENCE BEING TRANSLATED

```
                                                    MET LYS LYS LEU LEU ILE ALA SER LEU
T T T A C G T C T A T A A T T T A T A T A G G A T A C A A T C G A T G A A A A A C T T C T A A T C G C A A G T T T A
          310                 320                 330                 340                 350              360

LEU PHE GLY THR THR THR VAL PHE ALA ALA PRO PHE VAL ALA LYS ASP ILE ARG VAL
T T A T T C G G T A C G A C A A C G A C T G T G T T T G C C G C A C C T T T T G T G G C A A A A G A T A T T C G T G T G
          370                 380                 390                 400                 410              420

ASP GLY VAL GLN GLY ASP LEU GLN GLY GLN ILE ARG ALA SER LEU PRO VAL ARG ALA GLY
G A T G G T G T T C A A G G T G A C T T A G A A C A A A T C C G A G C A A G T T T A C C T G T T C G T G C C G G T
          430                 440                 450                 460                 470              480

GLN ARG VAL THR ASP ASN ILE VAL ALA ASN ILE VAL ARG SER LEU PHE VAL SER GLY ARG
C A G C G T G T G A C T G A C A A T G A T G T G G C T A A T A T T G T C C G C T C T T T A T T C G T A A G T G G T C G A
          490                 500                 510                 520                 530              540

PHE ASP ASP VAL LYS ALA HIS GLN GLU LYS ALA ASP VAL LEU VAL VAL SER VAL VAL ALA LYS
T T C G A T G A T G T G A A A G C G C A T C A A G A A A A G G C G A T G T G C T T G T T G T T A G C G T T G T G G C T A A A
          550                 560                 570                 580                 590              600

SER ILE ILE SER ASP VAL LYS ILE LYS GLY ASN SER VAL ILE PRO THR GLU ALA LEU LYS
T C G A T C A T T T C A G A T G T T A A A A T C A A A G G T A A C T C T G T T A T T C C C A C T G A A G C A C T T A A A
          610                 620                 630                 640                 650              660
```

FIG.1C.(CONTINUED)

```
GLN ASN LEU ASP ALA ASN GLY PHE LYS VAL GLY ASP VAL LEU ILE ARG GLU LYS LEU ASN
CAAAACTTAGATGCTAACGGGTTTAAAGTTGGCGATGTTTTAATTCGAGAAAAATTAAAT
                  670            680            690            700            710            720

GLU PHE ALA LYS SER VAL LYS GLU HIS TYR ALA SER VAL GLY ARG TYR ASN ALA THR VAL
GAATTTGCCAAAAGTGTAAAAGAGCACTATGCAAGTGTAGGTCGCTATAACGCAACAGTT
                  730            740            750            760            770            780

GLU PRO ILE VAL ASN THR LEU PRO ASN ASN ARG ALA GLU ILE LEU GLN ILE ASN GLU
GAACCTATTGTCAATACGCTACCAAATAATCGCGCTGAAATTTTAATTCAAATCAATGAA
                  790            800            810            820            830            840

ASP ASP LYS ALA LYS LEU ALA SER LEU ILE LEU GLN MET GLU LEU GLN PRO ASP SER TRP LYS LEU TRP GLY ASN GLU THR PHE LYS GLY ASN LYS SER VAL SER SER SER
GATGATAAAGCAAAATTGGCATCATTAACTTTCAAGGGGAACGAATCTGTTAGTAGCAGT
                  850            860            870            880            890            900

THR LEU GLN GLU GLN MET GLU LEU GLN PRO ASP SER TRP LYS LEU TRP GLY ASN LYS
ACATTACAAGAACAAATGGAATTACAACCTGATTCTTGGTGGAAATTATGGGAAATAAAA
                  910            920            930            940            950            960

PHE GLU GLY ALA GLN PHE GLU LYS ASP LEU GLN SER ILE ARG ASP TYR TYR LEU ASN ASN
TTTGAAGGTGCGCAATTCGAGAAAGATTTGCAGTCAATTCGTGATTATTTAAATAAT
                  970            980            990           1000           1010           1020
```

FIG.1C.(CONTINUED)

```
GLY TYR ALA LYS ALA GLN ILE THR LYS THR ASP VAL GLN LEU ASN ASP GLU LYS THR LYS
GGCTATGCCAAAGCACACAAATTACTAAAACGGATGTTCAGCTAAATGATGAAAAACAAAA
        1030              1040              1050              1060              1070              1080

VAL ASN VAL THR ILE ASP VAL ASN GLU GLY LEU GLN TYR ASP LEU ARG SER ALA ARG ILE
GTTAATGTAACCATTGACGTAAATGAAGGTTTACAGTATGACCTTCGTAGTGCACGCATT
        1090              1100              1110              1120              1130              1140

ILE GLY ASN LEU GLY GLY MET SER ALA GLU LEU GLU PRO LEU LEU SER ALA LEU HIS LEU
ATAGGTAATCTGGGAGGTATGTCTGCCGAGCTTGAACCTTTACTTTCAGCATTACATTTA
        1150              1160              1170              1180              1190              1200

ASN ASP THR PHE ARG ARG SER ASP ILE ALA ASP VAL GLU ASN ALA ILE LYS ALA LYS LEU
AATGATACTTTCCGCCGTAGTGATATTGCAGATGTAGAAAATGCAATTAAAGCAAAACTT
        1210              1220              1230              1240              1250              1260

GLY GLU ARG GLY TYR GLY SER ALA THR VAL ASN SER VAL PRO ASP PHE ASP ALA ASN
GGAGAACGCGGTTACGGTTAGCGCAACGGTAAATTCAGTACCTGATTTTGATGATGCAAAT
        1270              1280              1290              1300              1310              1320

LYS THR LEU ALA ILE THR LEU VAL VAL ASP ALA GLY ARG ARG LEU THR VAL ARG GLN LEU
AAAACATTAGCGATAACCCTTGTTGTTGATGCTGGACGTTTAACTGTTCGCCAACTT
        1330              1340              1350              1360              1370              1380
```

FIG.1C.(CONTINUED)

```
ARG PHE GLU GLY ASN THR VAL SER ALA ASP SER THR LEU ARG GLN GLU MET ARG GLN GLN
CGCTTTGAAGGAAATACCGTTTCTGCTGATAGCACTTTACGTCAGGAAATGCGCCAACAA
         1390          1400          1410          1420          1430          1440

GLU GLY THR TRP TYR ASN SER GLN LEU VAL GLU LEU GLY LYS ILE ARG LEU ASP ARG THR
GAAGGAACTTGGTATAATTCACAATTAGTTGAGTTAGGAAAAATTCGCTTAGATCGTACA
         1450          1460          1470          1480          1490          1500

GLY PHE PHE GLU THR VAL GLU ASN ARG ILE ASP PRO ILE ASN GLY SER ASN ASP GLU VAL
GGTTTCTTCGAAACAGTCGAAAACCGAATTGATCCTATCAATGGTAGTAATGATGAAGTG
         1510          1520          1530          1540          1550          1560

ASP VAL VAL TYR LYS VAL LYS GLU ARG ASN THR GLY SER ILE ASN PHE GLY ILE GLY TYR
GATGTCGTATATAAAGTCAAAGAACGTAACACGGGGTAGTATCAACTTTGGTATTGGTTAC
         1570          1580          1590          1600          1610          1620

GLY THR GLY GLU SER GLY ILE LEU SER TYR GLN ALA SER VAL LYS GLN ASP ASN PHE LEU GLY THR
GGTACAGAGTGGTATTAGTTATCAAGCAAGTGTTAAACAAGATAATTTCTTGGGAACA
         1630          1640          1650          1660          1670          1680

GLY ALA ALA VAL SER ILE ALA GLY SER LYS ASN ASP TYR GLY THR LYS SER VAL ASN LEU GLY
GGGGCGGCAGTAAGTATAGCTGGTACGAAAAATGATTATGGTACGAGTGTCAATTTGGGT
         1690          1700          1710          1720          1730          1740
```

FIG.1C.(CONTINUED)

```
TYR THR GLU PRO TYR PHE THR LYS ASP GLY VAL SER LEU GLY GLY ASN VAL PHE PHE GLU
TATACCGAGCCCTATTTTACTAAAGATGGTGTAAGTCTTGGTGGAAATGTTTTCTTTGAA
        1750              1760              1770              1780              1790        1800

ASN TYR ASP ASN SER LYS SER ASP THR ILE TYR LYS ARG THR THR TYR GLY SER
AACTACGATAACTCTAAAAGTGATACAATCCCTCTAACTATAAGCGTACGACTTACGGAAGT
        1810              1820              1830              1840              1850        1860

ASN VAL THR LEU GLY PHE PRO VAL ASN GLU ASN ASN SER TYR TYR VAL GLY LEU GLY HIS
AATGTTACTTTAGGTTTTCCCGTAAATGAAAATAACTCCTATTATGTAGGATTAGGTCAT
        1870              1880              1890              1900              1910        1920

THR TYR ASN LYS ILE SER ASN PHE ALA LEU GLU TYR ASN ARG ASN LEU TYR ILE GLN SER
ACCTATAATAAAATTAGTAACTTTGCTCTAGAATATAACCGTAATTTATATTCAATCA
        1930              1940              1950              1960              1970        1980

MET LYS PHE LYS GLY ASN GLY ILE LYS THR ASN ASP PHE ASP PHE SER PHE GLY TRP ASN
ATGAAATTTAAAGGTAATGGCATTAAAACAAATGACTTTGATTTTTCTTTTGGTTGGAAC
        1990              2000              2010              2020              2030        2040

TYR ASN SER LEU ASN ARG GLY TYR PHE PRO THR LYS GLY VAL LYS ALA SER LEU GLY GLY
TATAACAGCCTTAATAGAGGCTATTTCCCAACTAAAGGGTTAAAGCAAGTCTTGGTGGA
        2050              2060              2070              2080              2090        2100
```

FIG.1C.(CONTINUED)

```
ARG   VAL   THR   ILE   PRO   GLY   SER   ASP   ASN   LYS   TYR   TYR   LYS   LEU   SER   ALA   ASP   VAL   GLN   GLY
C G A G T T A C T A T T C C A G G T T C T G A T A A C A A A T A C T A C A A A C T A A G T G C A G A T G T A C A G G G T
                  2110                2120                2130                2140                2150                2160

PHE   TYR   PRO   LEU   ASP   ARG   ASP   HIS   LEU   TRP   VAL   VAL   SER   ALA   LYS   ALA   SER   ALA   GLY   TYR
T T C T A C C C A T T A G A C A G A G A T C A C C T C T G G G T T G T A T C T G C A A A A G C A T C T G C A G G A T A T
                  2170                2180                2190                2200                2210                2220

ALA   ASN   GLY   PHE   GLY   ASN   LYS   ARG   LEU   PRO   PHE   TYR   GLN   THR   TYR   THR   ALA   GLY   GLY   ILE
G C A A A T G G T T T T G G A A A C A A G C G T T T A C C G T T C T A T C A A A C T T A T A C A G C G G G T G G C A T C
                  2230                2240                2250                2260                2270                2280

GLY   SER   LEU   ARG   GLY   PHE   ALA   TYR   GLY   SER   ILE   GLY   PRO   ASN   ALA   ILE   TYR   ALA   GLU   TYR
G G T T C A T T A C G T G G T T T T G C T T A T G G T A G T A T T G G A C C T A A C G C A A T T T A T G C C G A A T A T
                  2290                2300                2310                2320                2330                2340

GLY   ASN   GLY   SER   GLY   THR   GLY   THR   PHE   LYS   LYS   ILE   SER   SER   ASP   VAL   ILE   GLY   GLY   ASN
G G T A A T G G T A G T G G T A C T G G T A C T T T T A A G A A G A T A A G T T C T G A T G T G A T T G G T G G T A A T
                  2350                2360                2370                2380                2390                2400

ALA   ILE   ALA   THR   ALA   SER   ALA   GLU   LEU   ILE   VAL   PRO   THR   PRO   PHE   VAL   SER   ASP   LYS   SER
G C A A T C G C T A C A G C T A G C G C A G A G T T A A T T G T G C C A A C T C C A T T T G T G A G C G A T A A G A G C
                  2410                2420                2430                2440                2450                2460
```

FIG.1C.(CONTINUED)

```
GLN ASN THR VAL ARG THR SER LEU PHE VAL ASP ALA ALA SER VAL TRP ASN THR LYS TRP
CAAAATACGGTCCGAACCCTCCTTATTTGTTGATGCGGCAAGTGTTTGGAATACTAAATGG
         2470              2480              2490              2500              2510              2520

LYS SER ASP LYS ASN GLY LEU GLU SER ASP VAL LEU LYS ARG LEU PRO ASP TYR GLY LYS
AAATCAGATAAAAATGGATTAGAGAGCGATGTATTAAAAAGATTGCCTGATTATGGCAAA
         2530              2540              2550              2560              2570              2580

SER SER ARG ILE ARG ALA SER THR GLY VAL GLY PHE GLN TRP GLN SER PRO ILE GLY PRO
TCAAGCCGTATTCGCGCCTCTACAGGTGTCGGATTCCAATGGCAATCTCCTATTGGGCCA
         2590              2600              2610              2620              2630              2640

LEU VAL PHE SER TYR ALA LYS PRO ILE LYS LYS TYR GLU ASN ASP ASP VAL GLU GLN PHE
TTGGTATTCTCTTATGCCAAACCAATTAAAAAATATGAAAATGATGTCGAACAGTTC
         2650              2660              2670              2680              2690              2700

GLN PHE SER ILE GLY GLY SER PHE *** *** ***
CAATTTAGTATTGGAGGTTCTTTTCTAATAAATTGAACTTTTTTCTTCATCAGAACTCAAA
         2710              2720              2730              2740              2750              2760
```

FIG.1C.(CONTINUED)

```
AACAACGTTCTCTGCCTAATTTAATTGGGCAGAGAAAATATTAAACCCATCATTAATTA
     2770              2780              2790              2800              2810              2820

AGGATATTTATCAAATGAAAAACATCGCAAAAGTAACCGCACTTGCTTTAGGTATTGCAC
     2830              2840              2850              2860              2870              2880

TTGCTTCAGGCTATGCTTTCCGCTGAAGAAAAAATTGCTTTCATTAATGCGGGTTATANTT
     2890              2900              2910              2920              2930              2940

TNCAAGGCNAAGG
     2950
```

FIG.1D.

SB33 D15
IS THE SEQUENCE BEING TRANSLATED

MET LYS LYS LEU LEU ILE ALA SER LEU LEU PHE GLY
C T A T A A T T T A T A T A G G A T A C A A T C G A T G A A A A A A C T T C T A A T C G C A A G T T T A T T A T T C G G
            370                 380                 390                 400                 410                 420

THR THR THR VAL PHE ALA ALA PRO PHE VAL ALA LYS ASP ILE ARG VAL ASP ILE ARG VAL ASP GLY VAL
T A C G A C A A C G A C T G T G T T T G C C G C A C C C T T T G T G G C A A A A G A T A T T C G T G T G G A T G G G T G T
            430                 440                 450                 460                 470                 480

GLN GLY ASP LEU GLU GLN GLN ILE ARG ALA SER LEU ARG ALA LEU PRO VAL ARG ALA GLY GLN ARG VAL
T C A A G G T G A C T T A G A A C A A C A A A T C C G A G C A A G T T T A C C T G T T C G T G C C G G T C A G C G T G T
            490                 500                 510                 520                 530                 540

THR ASP ASN ASP VAL ALA ASN ILE VAL ARG SER LEU PHE VAL SER GLY ARG PHE ASP ASP
G A C T G A C A A T G A T G T G G C T A A T A T T G T C C G C T C T T T T A T T C G T A A G T G G T C G A T T C G A T G A
            550                 560                 570                 580                 590                 600

VAL LYS ALA HIS GLN GLU GLY ASP VAL LEU VAL LEU VAL SER VAL VAL ALA LYS SER ILE ILE
T G T G A A A G C G C A T C A A G A A G G C G A T G T G C T T G T T G T T G T T A G C G T T G T G G C T A A A T C G A T C A T
            610                 620                 630                 640                 650                 660
```

FIG.1D.(CONTINUED)

```
SER ASP VAL LYS ILE LYS GLY ASN SER ILE ILE PRO PRO GLU ALA LEU LYS GLN ASN LEU
TTCAGATGTTAAAATCAAAGGTAACTCTATTATTCCACCTGAAGCACTAAAACAAAACTT
        670           680           690           700           710           720

ASP ALA ASN GLY PHE LYS VAL GLY ASP ILE LEU ILE ARG GLU LYS LEU ASN GLU PHE ALA
AGATGCTAACGGGTTTAAAGTTGGCGATATTTTAATTCGAGAAAAATTAAATGAATTTGC
        730           740           750           760           770           780

GLN SER VAL LYS GLU HIS TYR ALA SER VAL GLY ARG TYR ASN ALA THR VAL GLU PRO ILE
CCAAAGTGTAAAAGAGCACTATGCAAGTGTAGGTCGTTATAACGCAACCGTTGAACCTAT
        790           800           810           820           830           840

VAL ASN THR LEU PRO ASN ASN ARG ALA GLU ILE LEU ILE ASN GLU ASP ASP LYS
TGTCAATACGCTACCAAATAATCGCGCTGAAATTTTAATTCAAATGAAGATGATAAA
        850           860           870           880           890           900

ALA LYS LEU ALA SER LEU THR PHE LYS GLY ASN GLU SER VAL SER SER THR LEU GLN
AGCCAAATTGGCATCATTAACTTTCAAGGGAACGAATCTGTTAGTAGCAGTACATTACA
        910           920           930           940           950           960

GLU GLN MET GLU LEU GLN PRO ASP SER TRP TRP LYS GLY ASN LYS PHE GLU GLY GLY
AGAACAAATGGAATTACAACCTGATTCTTGGTGGAAATTATGGGGAAAATAAATTTGAAGG
        970           980           990          1000          1010          1020
```

FIG.1D.(CONTINUED)

```
ALA GLN PHE GLU LYS ASP LEU GLN ALA ILE ARG ASP TYR TYR LEU ASN ASN GLY TYR ALA
TGCGCAATTCGAGAAAGATTTGCAGGCAATTCGTGATTATTATTTAAATAATGGCTATGC
            1030              1040              1050              1060              1070              1080

LYS ALA GLN ILE THR LYS ALA ASP VAL GLN LEU ASN ASP GLU LYS THR LYS VAL ASN VAL
CAAAGCACAAATCACTAAAGCGGATGTTCAGCTAAATGATGAAAAAACAAAAGTTAATGT
            1090              1100              1110              1120              1130              1140

THR ILE ASP VAL ASN ASN GLU LYS GLY LEU GLN TYR ASP LEU ARG SER ALA ARG ILE ILE GLY ASN
AACCATTGATGTAAATAATGAAGGTTTACAGTATGACCTTCGTAGTGCACGCATTATAGGTAA
            1150              1160              1170              1180              1190              1200

LEU GLY GLY MET SER ALA GLU GLY LEU GLU PRO LEU LEU LEU HIS LEU ASN ASP THR
TCTGGGAGGTATGTCTGCCGAGGGCTTGAACCCTTTACTTTTCAGCATTACATTTAAATGATAC
            1210              1220              1230              1240              1250              1260

PHE ARG ARG SER ASP ILE ALA ASP VAL ARG LYS ASN ALA ILE LYS ALA LEU GLY GLU ARG
TTTCCGCCGTAGTGATATTGCAGATGTAGAAAAATGCAATTAAAGCAAAACTTGGGGAACG
            1270              1280              1290              1300              1310              1320

GLY TYR GLY ASN THR THR VAL ASN SER VAL PRO ASP PHE ASP ASP ALA ASN LYS THR LEU
AGGTTACGGTAACACAACAGTAAATTCTGTACCCTGATTTTGACGATGCAAATAAAACATT
            1330              1340              1350              1360              1370              1380
```

FIG. 1D.(CONTINUED)

```
ALA ILE THR PHE VAL VAL ASP ALA GLY ARG ARG LEU THR VAL HIS GLN LEU ARG PHE GLU
AGCGATAACCTTTGTTGTTGATGCTGGACGACGTTTAACTGTTCACCAACTTCGCTTTGA
            1390              1400              1410              1420              1430              1440

GLY ASN THR VAL SER ALA ASP SER THR LEU ARG GLN GLU MET ARG GLN GLN GLU GLY THR
AGGAAATACCGTTTCTGCTGATAGTACTTTACGTCAGGAAATGCGCCAACAAGAAGGAAC
            1450              1460              1470              1480              1490              1500

TRP TYR ASN SER GLN LEU VAL GLU LEU GLY LYS ILE ARG LEU ASP ARG THR GLY PHE PHE
TTGGTATAATTCACAATTAGTTGAGTTAGGAAAAATTCGCTTAGATCGTACAGGTTTCTT
            1510              1520              1530              1540              1550              1560

GLU THR VAL GLU ASN ARG ILE ASP PRO ILE ASN GLY SER ASN ASP GLU VAL ASP VAL VAL
CGAAACAGTTGAAAACCGAATTGATCCTATCAATGGTAGCAATGATGAAGTGGATGTCGT
            1570              1580              1590              1600              1610              1620

TYR LYS VAL LYS GLU ARG ASN THR GLY SER ILE ASN PHE GLY ILE GLY TYR GLY THR GLU
ATATAAAGTCAAAGAACGTAACACGGGTAGTATCAACTTTGGTATTGGTTACGGTACAGA
            1630              1640              1650              1660              1670              1680

SER GLY ILE SER TYR GLN ALA SER VAL LYS GLN ASP ASN PHE LEU GLY THR GLY ALA ALA
GAGTGGTATTAGTTATCAAGCAAGTGTCAAACAAGATAATTTCTTGGGAACAGGGGCGGC
            1690              1700              1710              1720              1730              1740
```

FIG. 1D. (CONTINUED)

```
VAL SER ILE ALA GLY THR LYS ASN ASP TYR GLY THR SER VAL ASN LEU GLY TYR THR GLU
AGTAAGTATAGCTGGTACGAAAAATGATTATGGTACGAGTGTCAATTTGGGTTATACCGA
                1750                1760                1770                1780                1790                1800

PRO TYR PHE THR LYS ASP GLY VAL SER LEU GLY GLY ASN VAL PHE PHE GLU ASN TYR ASP
GCCCTATTTTACTAAAGATGGTGTAAGTCTTGGTGGAAATGTTTTCTTTGAAAACTACGA
                1810                1820                1830                1840                1850                1860

ASN SER LYS SER ASP THR SER SER ASN TYR LYS ARG THR THR TYR GLY SER ASN VAL THR
TAACTCTAAAAGTGATACATCCTCTAACTATAAGCGTACGACTTATGGAAGTAATGTTAC
                1870                1880                1890                1900                1910                1920

LEU GLY PHE PRO VAL ASN GLU ASN ASN SER TYR TYR VAL GLY LEU GLY HIS THR TYR ASN
TTTAGGTTTCCCTGTAAATGAAAATAACTCCTATTATGTAGGATTAGGCCATACCTATAA
                1930                1940                1950                1960                1970                1980

LYS ILE SER ASN PHE ALA LEU GLU TYR ASN ARG ASN LEU TYR ILE GLN SER MET LYS PHE
TAAAATTAGTAACTTTGCTCTAGAATATAACCGTAATTATATATTCAATCAATGAAATT
                1990                2000                2010                2020                2030                2040

LYS GLY ASN GLY ILE LYS LYS THR ASN ASP PHE SER PHE GLY TRP ASN TYR ASN SER
TAAAGGTAATGGCATTAAAAACAAATGACTTTTCTTTTGGTTGGAACTATAACAG
                2050                2060                2070                2080                2090                2100
```

FIG. 1D.(CONTINUED)

```
LEU ASN ARG GLY TYR PHE PRO THR LYS GLY VAL LYS ALA SER LEU GLY ARG VAL THR
CCT TAA TAG AGG GCT ATT TCC CAA CTA AAA GGG GTT AAA AGC AAG TCT TTG GTG ACG AGT TAC
            2110                2120                2130                2140                2150                2160

ILE PRO GLY SER ASP ASN LYS TYR TYR LYS LEU SER ALA ASP VAL GLN GLY PHE TYR PRO
AAT TCC AGG GTT CTG ATA ACA AAT ACT ACA AGT TGT CAG ATG TAC AGG GTT TCT ACC C
            2170                2180                2190                2200                2210                2220

LEU ASP ARG ASP HIS LEU THR LEU TRP VAL VAL SER ALA LYS SER ALA GLY TYR ALA ASN GLY
ATT AGA CAG AGA TCA CCT CTG GGT TGT ATC TGC AAA AAG CAT CTG CAG GAT ATG CAA ATG G
            2230                2240                2250                2260                2270                2280

PHE GLY ASN LYS ARG LEU PRO PHE TYR GLN THR TYR THR ALA GLY GLY ILE GLY SER LEU
TTT TGG AAA ACA AGC GTT TAC CGT TTC TAT CAA ACT TAT ACA GCG GGT GGC ATT GGT TCA TT
            2290                2300                2310                2320                2330                2340

ARG GLY PHE ALA TYR GLY SER ILE GLY PRO ASN ALA ASN ILE TYR GLN GLY GLN ASN LYS
ACG CGG TTT GCT TAT GGT AGC ATT GGG GCC TAA CGC AAT TAT CAA GGT CAA AAT AAT AA
            2350                2360                2370                2380                2390                2400

PHE ASN LYS ILE SER ASP VAL ILE GLY GLY ASN ALA ILE ALA THR ALA SER ALA GLU
ATT TAA TAA GAT AAG TTC TGA TGT GAT TGG TGG TAA TGC AAT CGC TAC AGC TAG CGC AGA
            2410                2420                2430                2440                2450                2460
```

FIG.1D.(CONTINUED)

```
LEU  ILE  VAL  PRO  THR  PRO  PHE  VAL  SER  ASP  LYS  SER  GLN  ASN  THR  VAL  ARG  THR  SER  LEU
GTT AAT TGT GCC AAC TCC CAT TTG TGA GAG TGA TAA GAG TCA AAA TAC AGT CCG AAC CTC CCT
            2470                2480                2490                2500                2510                2520

PHE  VAL  ASP  ALA  ALA  SER  VAL  TRP  ASN  THR  LYS  TRP  LYS  SER  ASP  LYS  ASN  GLY  LEU  GLU
ATT TGT TGA TGC GGG CAA GTG TGT TTG GAA TAC TAA ATG GAA ATC AGA TAA AAA TGG ATT AGA
            2530                2540                2550                2560                2570                2580

SER  ASN  VAL  LEU  LYS  ASP  LEU  PRO  ASP  TYR  GLY  LYS  SER  SER  ARG  THR  ARG  ALA  SER  THR
GAG CAA TGT CTC TTG AAA GAC TTA CCC GAT TAT GGC AAA TCA AGC CCG TAC TCC GCC TCT AC
            2590                2600                2610                2620                2630                2640

GLY  VAL  GLY  PHE  GLN  TRP  GLN  SER  PRO  GLY  PRO  VAL  VAL  PHE  SER  TYR  ALA  LYS  PRO
AGG TGT GTC GGA TTC CAA TGG CAA TCT CCT AGT GGA CCA GTG GTA TTT TCT TAT GCT AAA CC
            2650                2660                2670                2680                2690                2700

ILE  LYS  LYS  TYR  GLU  ASN  ASP  ASP  VAL  GLU  GLN  PHE  SER  ILE  GLY  GLY  SER  PHE
AAT TAA AAA TAT GAA CTT TTT TCG TCA TCA GAA CTT CAA AAA CAA CGT TCT CTG CCT AAT TTA
            2710                2720                2730                2740                2750                2760

***    ***
***    ***
CTA ATA AAT TGA ACT TTT TCG TCA TCA GAA CTT CAA AAA CAA CGT TCT CTG CCT AAT TTA
            2770                2780                2790                2800                2810                2820
```

FIG. 1D.(CONTINUED)

```
ATTGGGCAGAGAAAATATTAAAACCATCATTTAATTAAGGATATTTATCAAATGAAAAC
      2830            2840           2850           2860           2870      2880
ATCGCCAAAGTAACCGCACTTGCTTTAGGTATTGCACTTGCTTTCAGGCTATGCTGCAGCT
      2890            2900           2910           2920           2930      2940
GAAGAAAAATTGCTTTTATTAATGCAGGTTATA
      2950            2960           2970
```

FIG. 1E.

JB-1042-9-4 DNA, PAK D15
IS THE SEQUENCE BEING TRANSLATED

```
AAAAGGCATTGAAAAACAGGACAACTTTCCCTTTTAACCTTGAAAATATTAGGGAAATT
         10        20        30        40        50        60

ACTTACTGGCGATTTGTCATTAAATAATTTAAGTGGGCCAATTTCTATTGCAAAAGGTGC
         70        80        90       100       110       120

TGGTGCATCAGCAAATATTGGATTGGTGTATTTTTAAGTTTTATGGCATTGATTAGTGT
        130       140       150       160       170       180

AAATTTAGGGATTATGAATTTATTTCCATTACCAGTATTAGATGGCGGTCATTTAGTTTT
        190       200       210       220       230       240

TTTAACAATGGAAGCTGTTAAAGGAAAAACCTGTTTCTGAGCGGGTGCAAAGCATCTGTTA
        250       260       270       280       290       300

TCGAATTGGCGCAGCACTGTTATTAAGCTTAACGGTGTTTGCATTATTAATGATTTTT
        310       320       330       340       350       360
```

FIG. 1E.(CONTINUED)

```
                                      MET LYS LYS LEU LEU ILE ALA SER LEU LEU P
ACGTCTATAATTTATATAGGATACAATCGATGAAAAAACTTCTAATCGCAAGTTTATTAT
        370       380       390       400       410       420

HE GLY THR THR THR VAL PHE ALA ALA PRO PHE VAL ALA LYS ASP ILE ARG VAL ASP G
TCGGTACGACAACGACTGTGTTTGCCGCACCTTTTGTGGCAAAAGATATTCGTGTGGATG
        430       440       450       460       470       480

LY VAL GLN GLY ASP LEU ARG ALA GLU GLN GLN ILE ASN LEU PRO VAL ARG ALA GLY GLN A
GTGTTCAAGGTGACTTAGAGAACAAACAAATCCGAGCAAGTTTACCTGTTCGTGCTGGTCAGC
        490       500       510       520       530       540

RG VAL THR ASP ASN ASP VAL ALA ASN ILE VAL ARG SER LEU PHE VAL SER GLY ARG PHE A
GTGTGACTGACAATGATGTGGCTAATATTGTCCGCTCTCTTTATTCGTAAGTGGTCGATTCG
        550       560       570       580       590       600

SP ASP VAL LYS ALA HIS GLN GLU GLY ASP VAL LEU VAL SER VAL VAL ALA LYS SER I
ATGATGTGAAAGCGCATCAAGAAGGCGATGTGCTTGTTGTTGTTGTGGCTAAATCGA
        610       620       630       640       650       660

LE ILE SER ASP VAL LYS ILE LYS GLY ASN SER VAL ILE PRO THR GLU ALA LEU LYS GLN A
TCATTTCAGATGTTAAAATCAAAGGTAACTCTGTTATTCCCACTGAAGCACTTAAACAAA
        670       680       690       700       710       720
```

FIG.1E.(CONTINUED)

```
SN  LEU ASP ALA ASN GLY PHE LYS VAL GLY ASP VAL LEU ILE ARG GLU LYS LEU ASN GLU P
    ACT TAG ATG CTA ACG GGG TTT AAA GTT GGC GAT GTG TTT TAA TTC GAG AAA ATT AAA TGA AT
        730             740             750             760             770         780

HE  ALA LYS SER VAL LYS GLU HIS TYR ALA SER VAL GLY ARG TYR ASN ALA THR VAL GLU P
    TTG CCA AAA GTG TAA AAG AGC ACT ACG CAA GTG TAG GTC GCT ATA ACG CAA CCG TTG AAA C
        790             800             810             820             830         840

RO  ILE VAL ASN THR LEU PRO ASN ASN ARG ALA GLU ILE LEU ILE GLN ILE ASN GLU ASP A
    CTA TTG TCA ATA CGC TGC CAA ATA ACG TGC TGA AAA TTT AAT TCA AAT CAA TGA AGA TG
        850             860             870             880             890         900

SP  LYS ALA LYS LEU ALA LYS SER LEU THR ILE ASN LEU THR PHE LYS GLY ASN GLU SER VAL SER SER THR L
    ATA AAG CAA ATT GGC ATC ATT AAC TTT CAA GGG GAA CGA ATC TGT TAG TCA GTA CAT
        910             920             930             940             950         960

EU  GLN GLN MET GLU LEU GLN PRO ASP SER TRP TRP LYS LEU TRP GLY ASN LYS PHE G
    TAC AAG AAC AAA TGG AAT TAC AAC CCT GAT TCT TGG TGG AAA TTA TGG GAA ATA AAT TTG
        970             980             990             1000            1010        1020

LU  GLY ALA GLN PHE GLU LYS ASP LYS LEU GLN ALA ILE ARG ASP TYR TYR LEU ASN ASN GLY T
    AAG GTG CGC AAT TCG AGA AAG ATA AAC TGC AGG CAA TTC GTG ATT ATT TAA ATA ATG GCT
        1030            1040            1050            1060            1070        1080

YR  ALA LYS ALA GLN ILE THR LYS THR ASP VAL GLN LEU ASN ASP GLU LYS LYS THR LYS VAL A
    ATG CCA AAG CAC ACA AAT CAC TAA AAC GGA TGT TCA GCT AAA TGA TGA AAA ACA AAA GTT A
        1090            1100            1110            1120            1130        1140
```

FIG.1E.(CONTINUED)

```
SN  VAL THR ILE ASP VAL ASN GLU GLY LEU GLN TYR ASP LEU ARG SER ALA ARG ILE ILE G
A T G T A A C C A T T G A T G T A A A T G A A G G T T T A C A G T A T G A C C T T C G T A G T G C A C G C A T T A T A G
               1150                1160                1170                1180                1190                1200

LY  ASN LEU GLY GLY MET SER ALA GLU LEU GLU PRO LEU LEU SER ALA LEU HIS LEU ASN A
G T A A T C T G G G A G G T A T G T C T G C C G A G C T T G A A C C T T T A C T T T C A G C A T T A C A T T T A A A T G
               1210                1220                1230                1240                1250                1260

SP  THR PHE ARG ARG SER ASP ILE ALA ASP VAL GLU ASN ALA ILE LYS ALA LYS LEU GLY G
A T A C T T T T C C G C C G T A G T G A T A T T G C A G A T G T A G A A A A T G C A A T T A A A G C A A A A T T G G G G
               1270                1280                1290                1300                1310                1320

LU  ARG GLY TYR GLY ASN THR VAL ASN SER VAL PRO ASP PHE ASP ALA ASN LYS T
A A C G A G G T T A C G G T A A C A C A G T A A A T T C T G T A C C T G A T T T T G A C G A T G C A A A A T A A A A
               1330                1340                1350                1360                1370                1380

HR  LEU ALA ILE THR PHE VAL VAL ASP ALA GLY ARG LEU THR VAL ARG GLN LEU ARG P
C A T T A G C G A T A A C C T T T G T T G T T G A T G C T G G A C G A C G T T T A A C T G T T C G C C A A C T T T C G C T
               1390                1400                1410                1420                1430                1440

HE  GLU GLY ASN THR VAL SER ALA ASP SER THR LEU ARG GLN MET ARG GLN GLN GLU G
T T G A A G G A A A T A C C G T T T C T G C T G A T A G T A C T T T A C G T C A G G A A A T G C G A C A A C A A G A A G
               1450                1460                1470                1480                1490                1500
```

FIG.1E.(CONTINUED)

```
LY  THR TRP TYR ASN SER GLN LEU VAL GLU LEU GLY LYS ILE ARG LEU ASP ARG THR GLY P
G A A C T T G G T A T A A T T C A C A A T T A G T T G A G T T A G G A A A A A T T C G C T T A G A T C G T A C A G G T T
                1510                1520                1530                1540                1550                1560

HE  PHE GLU THR VAL GLU ASN ARG ILE ASP PRO ILE ASN GLY SER ASN ASP GLU VAL ASP V
T C T T T C G A A A C A G T T G A A A A C C G A A T T G A T C C T A T C A A T G G T A G C A A T G A T G A A G T G G A T G
                1570                1580                1590                1600                1610                1620

AL  VAL TYR LYS VAL LYS GLU ARG ASN THR GLY SER ILE ASN PHE GLY ILE GLY TYR GLY T
T C G T A T A T A A A G T C A A A G A A C G T A A C A C G G G T A G T A T C A A C T T T G G T A T T G G T T A C G G T A
                1630                1640                1650                1660                1670                1680

HR  GLU SER GLY ILE SER TYR GLN THR SER ILE LYS GLN ASP ASN PHE LEU GLY THR GLY A
C A G A G A G T G G T A T C A G T T A T C A A A C A A G T A T T A A A C A A G A T A A T T T C T T G G G A A C A G G G G
                1690                1700                1710                1720                1730                1740

LA  ALA VAL SER ILE ALA GLY THR LYS ASN ASP TYR GLY THR SER VAL ASN LEU GLY TYR T
C G G C A G T A A G T A T A G C T G G T A C G A A A A A T G A T T A T G G T A C G A G T G T C A A T T T G G G T T A T A
                1750                1760                1770                1780                1790                1800

HR  GLU PRO TYR PHE THR LYS ASP GLY VAL SER LEU GLY GLY ASN ILE PHE PHE GLU ASN T
C C G A A C C C T A T T T T T A C T A A A G A T G G T G T A A G T C T T G G T G G A A A T A T T T T C T T T G A A A A C T
                1810                1820                1830                1840                1850                1860
```

FIG.1E.(CONTINUED)

```
YR  ASP ASN SER LYS SER ASP THR SER SER ASN TYR LYS ARG THR THR TYR GLY SER ASN V
    ACGATAACTCTAAAAGTGATACATCCTAACTATAAGCGTACGACTTATGGAAGTAATG
                1870            1880            1890            1900            1910            1920

AL  THR LEU GLY PHE PRO VAL ASN GLU ASN SER TYR TYR VAL GLY LEU GLY HIS THR T
    TTACTTTTAGGTTTCCCTGTAAATGAAAATTCCTATTATGTAGGATTAGGCCATACCT
                1930            1940            1950            1960            1970            1980

YR  ASN LYS ILE SER ASN PHE ALA LEU TYR ASN ARG ASN LEU ILE GLN SER MET L
    ATAATAAAATTAGTAACTTTGCTCTAGAATATAACCGTAATTTATATATTCAATCAATGA
                1990            2000            2010            2020            2030            2040

YS  PHE LYS GLY ASN GLY ILE LYS THR ASN ASP PHE SER PHE GLY TRP ASN TYR A
    AATTTAAAGGTAATGGCATTAAAACAAATGACTTTGATTTTCTTTTGGTTGGAACTATA
                2050            2060            2070            2080            2090            2100

SN  SER LEU ASN ARG GLY TYR PHE PRO THR LYS GLY VAL LYS ALA SER LEU GLY ARG V
    ACAGCCCTTAATAGAGGCTATTTCCCAACTAAAGGGGTTAAAGCAAGTCTTGGTGGACGAG
                2110            2120            2130            2140            2150            2160

AL  THR ILE PRO GLY SER ARG PHE ASP ASN LYS TYR TYR LYS LEU SER ALA ASP VAL GLN GLY PHE T
    TTACTATTCCAGGTTCTAGATAACAAATACTACAAACTAAGTGCAGATGTACAGGGTTTCT
                2170            2180            2190            2200            2210            2220

YR  PRO LEU ASP ARG ASP HIS ARG TRP VAL VAL SER ALA LYS ALA SER ALA GLY TYR ALA A
    ACCCATTAGACAGAGATCACCGCTGGGTTGTATCTGCAAAAGCATCTGCAGGATATGCAA
                2230            2240            2250            2260            2270            2280
```

FIG. 1E.(CONTINUED)

```
SN  GLY PHE GLY ASN LYS ARG LEU PRO PHE TYR GLN THR TYR THR ALA GLY GLY ILE GLY S
    ATGGTTTTGGAAACAAGCCGTTTACCGTTCTATCAAAACTTATACAGCCGGGGTGGCATTGGTT
          2290              2300              2310              2320              2330              2340

ER  LEU ARG GLY PHE ALA TYR GLY SER ILE GLY PRO ASN ALA ILE TYR ALA GLU HIS GLY A
    CATTACGCGGGTTTTGCTTATGGTAGTATTGGGCCTAATGCAATTTATGCCGAACATGGTA
          2350              2360              2370              2380              2390              2400

SN  GLY THR PHE ASN LYS ILE SER SER ASP VAL ILE GLY GLY ASN ALA ILE THR THR ALA S
    ATGGTACTTTTAATAAGATAAGTTCTGATGTGATTGGTGGTAATGCAATCACAACTGCGA
          2410              2420              2430              2440              2450              2460

ER  ALA GLU LEU ILE VAL PRO THR PRO PHE VAL SER GLN ASN THR ASN THR VAL ARG T
    GTGCAGAACTTATTGTACCAACTCCATTTGTGAGTCAAAATACAAATACAGTCCGAA
          2470              2480              2490              2500              2510              2520

HR  SER LEU PHE VAL ASP ALA ALA SER VAL TRP ASN THR LYS TRP LYS ASP LYS SER ASN G
    CCTCCCTATTTGTTGATGCGGCAAGTGTTTGGAATACTAAATGGAAATCAGATAAAAATG
          2530              2540              2550              2560              2570              2580

LY  LEU GLU SER LYS VAL LEU LYS ASP TYR GLY LYS SER SER ARG ILE ARG A
    GATTAGAGAGCAAGGTCTTGAAAGACTTACCTGATTATGGCAAATCAAGCCGTATTCGCG
          2590              2600              2610              2620              2630              2640
```

FIG.1E.(CONTINUED)

```
LA  SER THR GLY VAL GLY PHE GLY GLN TRP GLN SER PRO ILE GLY PRO LEU VAL PHE SER TYR A
    CCTCTACAGGTGTCGGATTCCAATGGCAATCTCCTATTGGACCATTGGTATTTCTTATG
              2650              2660              2670              2680              2690              2700

LA  LYS PRO ILE LYS LYS TYR GLU ASN ASP ASP VAL GLU GLN PHE GLN PHE SER ILE GLY G
    CTAAACCAATTAAAAAATATGAAAATGATGTCGAAACAGTTCCAATTTAGTATTGGGG
              2710              2720              2730              2740              2750              2760

LY  SER PHE *** ***
    GCTCTTTCTAATAAATTGAACTTTTTTCGTCATCAGAACTCAAAAACGACGTTCTCTGCC
              2770              2780              2790              2800              2810              2820

TAATTGAATTGGGCAGAGAAAATATTAAACCCATCATTTAATTAAGGATATTTATCAAAT
              2830              2840              2850              2860              2870              2880

GAAAAACATCGCAAAAGTAACCGCACTTGCTTTAGGTTTTGCACTTGCTTCAGGCTATGC
              2890              2900              2910              2920              2930              2940

TTCCGCTGAAGAAAAATTGCTTTCATTAATGCAGGTTATATTTTTCAA
              2950              2960              2970              2980
```

FIG.1F.

1. cad15     (1-2949)
3. minnad15  (1-2953)
2. eagand15  (1-2984)
4. pakd15    (1-2989)
5. sb33d15   (1-2974)

```
cad15      1                                                                ACAGGACAgCTTTCCCTTTTAACCTTGAAAATATTAGGGAAATTA
                                                                            |||||||||||||||||||||||||||||||||||||||||||||
minnad15   1                                                                ACAGGACACAgCTTTCCCTTTTAACCTTGAAAATATTAGGGAAATTA
                                                                            |||||||||||||||||||||||||||||||||||||||||||||
eagand15   1                                                                ACAGGACACAaCTTTCCCTTTTAACCTTGAAAATATTAGGGAAATTA
                                                                            |||||||||||||||||||||||||||||||||||||||||||||
pakd15     1  aaaaGGCATTGAAAAAAACAGGACAgCTTTCCCTTTTAACCTTGAAAATATTAGGGAAATTA
              |||||||||||||||||||||||||||||||||||||||||||||||||||||||||||||
sb33d15    1       GGCATTGAAAAAAACAGGACAgCTTTCCCTTTTAACCTTGAAAATATTAGGGAAATTA consensus     aaaaggcattgaaaaaacaggacagctttccctttaaccttgaaaatattagggaaatta cad15      1
```

FIG. 1F. (CONTINUED)

```
minnad15   6   CTTaCTGGCGATTTGTCATTAAATAATTTAAGTGGGCCAATTTCTATTGCAAAAGGTGCTG
               ||| ||||||||||||||||||||||||||||||||||||||||||||||||||||||||
eagand15   46  CTTcCTGGCGATTTGTCATTAAATAATTTAAGTGGGCCAATTTCTATTGCAAAAGGTGCTG
               ||| ||||||||||||||||||||||||||||||||||||||||||||||||||||||||
pakd15     62  CTTACTGGCGATTTGTCATTAAATAATTTAAGTGGGCCAATTTCTATTGCAAAAGGTGCTG
               ||||||||||||||||||||||||||||||||||||||||||||||||||||||||||||
sb33d15    58  CTTACTGGCGATTTGTCATTAAATAATTTAAGTGGGCCAATTTCTATTGCAAAAGGTGCTG consensus      cttactggcgatttgtcattaaataatttaagtgggccaatttctattgcaaaaggtgctg cad15      1 minnad15   67  GCaCATCAGCAAATATTGGATTGGTGTGTATTTTTTAAGTTTTTATGGCACTGATTAGTGTAAA
               || |||||||||||||||||||||||||||||||||||||||||||||||||||||||||
eagand15   107 GCcCATCAGCAAATATTGGATTGGTGTGTATTTTTTAAGTTTTTATGGCACTGATTAGTGTAAA
               || |||||||||||||||||||||||||||||||||||||||||||||||||||||||||
pakd15     123 GtGCATCAGCAAATATTGGATTGGTGTGTATTTTTTAAGTTTTTATGGCATTGATTAGTGTAAA
               |  |||||||||||||||||||||||||||||||||||||||||||||||||||||||||
sb33d15    119 GcGCATCAGCAAATATTGGATTGGTGTGTATTTTTTAAGTTTTTATGGCATTGATTAGTGTAAA consensus      gcgcatcagcaaatattggattggtgtgtattttttaagttttatggca-tgattagtgtaaa
```

FIG.1F.(CONTINUED)

```
cad15       1                                                                gATTAC
                                                                             ||||||
minnad15  128  TTTAGGGATTATGAATTTATTTCCATTACCAGTATTAGATGGCGGTCATTTAGTTTTTTA
               ||||||||||||||||||||||||||||||||||||||||||||||||||||||||||||
eagand15  168  TTTAGGGATTATGAATTTATTTCCATTACCAGTATTAGATGGCGGTCATTTAGTTTTTTA
               ||||||||||||||||||||||||||||||||||||||||||||||||||||||||||||
pakd15    184  TTTAGGGATTATGAATTTATTTCCATTACCAGTATTAGATGGCGGTCATTTAGTTTTTTA
               ||||||||||||||||||||||||||||||||||||||||||||||||||||||||||||
sb33d15   180  TTTAGGGATTATGAATTTATTTCCATTACCAGTATTAGATGGCGGTCATTTAGTTTTTTA consensus      tttagggattatgaatttattccATTACcagtattagatggcggtcatttagtttttta cad15       7  ACAATGGAAGCTGTTAAAGGAAAACCTGTTTCTGAGCGGGTGCAAAGCATCTGTTATCGAA
               ||||||||||||||||||||||||||||||||||||||||||||||||||||||||||||
minnad15  189  ACAATGGAAGCTGTTAAAGGAAAACCTGTTTCTGAGCGGGTGCAAAGCATCTGTTATCGAA
               ||||||||||||||||||||||||||||||||||||||||||||||||||||||||||||
eagand15  229  ACAATGGAAGCTGTTAAAGGAAAACCTGTTTCTGAGCGGGTGCAAAGCATCTGTTATCGAA
               ||||||||||||||||||||||||||||||||||||||||||||||||||||||||||||
pakd15    245  ACAATGGAAGCTGTTAAAGGAAAACCTGTTTCTGAGCGGGTGCAAAGCATCTGTTATCGAA
               ||||||||||||||||||||||||||||||||||||||||||||||||||||||||||||
sb33d15   241  ACAATGGAAGCTGTTAAAGGAAAACCTGTTTCTGAGCGGGTGCAAAGCATCTGTTATCGAA
```

FIG.1F.(CONTINUED)

```
consensus      acaatggaagctgttaaaggaaaacctgtttctgagcgggtgcaaagcatctgttatcgaa cad15      7   gccAAGCTTAACGGTGTGTTTGCATTATTTAATGATTTTTTACGTCT
               |||||||||||||||||||||||||||||||||||||||||||||||
minnad15 250   TTGGCGCAGCACTGTTATTAAGCTTAACGGTGTGTTTGCATTATTTAATGATTTTTTACGTCT
               ||||||||||||||||||||||||||||||||||||||||||||||||||||||||||||||
eagand15 290   TTGGCGCAGCACTGTTATTAAGCTTAACGGTGTGTTTGCATTATTTAATGATTTTTTACGTCT
               ||||||||||||||||||||||||||||||||||||||||||||||||||||||||||||||
pakd15   306   TTGGCGCAGCACTGTTATTAAGCTTAACGGTGTGTTTGCATTATTTAATGATTTTTTACGTCT
               ||||||||||||||||||||||||||||||||||||||||||||||||||||||||||||||
sb33d15  302   TTGGCGCAGCACTGTTATTAAGCTTAACGGTGTGTTTGCATTATTTAATGATTTTTTACGTCT
               |||||||||||||||||||||||||||||||||||||||||||||||||||||||||||||| consensus      ttggcgcagcactgttattAAGCTTAACGGTGTGTTTGCATTATTTAATGATTTTTTACGTCT cad15     52   ATAATTTATATAGGATACAATCGATGAAAAAAACTTCTAATCGCAAGTTTATTATTCGGTAC
               |||||||||||||||||||||||||||||||||||||||||||||||||||||||||||||
minnad15 311   ATAATTTATATAGGATACAATCGATGAAAAAAACTTCTAATCGCAAGTTTATTATTCGGTAC
               |||||||||||||||||||||||||||||||||||||||||||||||||||||||||||||
eagand15 351   ATAATTTATATAGGATACAATCGATGAAAAAAACTTCTAATCGCAAGTTTATTATTCGGTAC
               |||||||||||||||||||||||||||||||||||||||||||||||||||||||||||||
pakd15   367   ATAATTTATATAGGATACAATCGATGAAAAAAACTTCTAATCGCAAGTTTATTATTCGGTgC
               ||||||||||||||||||||||||||||||||||||||||||||||||||||||||||||
```

FIG.1F.(CONTINUED)

```
sb33d15    363  ATAATTTATATAGGATACAATCGATGAAAAAACTTCTAATCGCAAGTTTATTATTCGGTaC
                     ||||||||||||||||||||||||||||||||||||||||||||||||||||||||||||
consensus        ATAATTTATATAGGATACAATCGATGAAAAAACTTCTAATCGCAAGTTTATTATTCGGTaC cad15      113  GACAACGACTGTGTTTGCCCGCACCTTTTGTGGCAAAAGATATTCGTGTGGATGGTGTTCAA
                     ||||||||||||||||||||||||||||||||||||||||||||||||||||||||||||
minnad15   372  GACAACGACTGTGTTTGCCCGCACCTTTTGTGGCAAAAGATATTCGTGTGGATGGTGTTCAA
                     ||||||||||||||||||||||||||||||||||||||||||||||||||||||||||||
eagand15   412  GACAACGACTGTGTTTGCCGCACCCTTTTGTGGCAAAAGATATTCGTGTGGATGGTGTTCAA
                     ||||||||||||||||||||||||||||||||||||||||||||||||||||||||||||
pakd15     428  GACAACGACTGTGTTTGCCGCACCCTTTTGTGCcCAAAAGATATTCGTGTGGATGGTGTTCAA
                     ||||||||||||||||||||||||||||||||||||||||||||||||||||||||||||
sb33d15    424  GACAACGACTGTGTTTGCCGCACCTTTTGTGgCAAAAGATATTCGTGTGGATGGTGTTCAA
                     ||||||||||||||||||||||||||||||||||||||||||||||||||||||||||||
consensus        GACAACGACTGTGTTTGCCGCACCCTTTTGTGGCAAAAGATATTCGTGTGGATGGTGTTCAA cad15      174  GGTGACTTAGAACAACAAATCCGAGCAAGTTTACCTGTTCGTGCCGGTCAGCGTGTGACTG
                     ||||||||||||||||||||||||||||||||||||||||||||||||||||||||||||
minnad15   433  GGTGACTTAGAACAACAAATCCGAGCAAGTTTACCTGTTCGTGCCGGTCAGCGTGTGACTG
                     ||||||||||||||||||||||||||||||||||||||||||||||||||||||||||||
eagand15   473  GGTGACTTAGAACAACAAATCCGAGCAAGTTTACCTGTTCGTGCCGGTCAGCGTGTGACTG
```

FIG. 1F. (CONTINUED)

```
pakd15    489  GGTGACTTAGAACAACAAATCCGAGCAAGTTTACCTGTTCGTGCtGGTCAGCCGTGTGACTG
               ||||||||||||||||||||||||||||||||||||||||||||| ||||||||||||||||
sb33d15   485  GGTGACTTAGAACAACAAATCCGAGCAAGTTTACCTGTTCGTGCCGGTCAGCCGTGTGACTG consensus      GGTGACTTAGAACAACAAATCCGAGCAAGTTTACCTGTTCGTGCCGGTCAGCCGTGTGACTG cad15     235  ACAATGATGTGGCTAATATTGTCCGCTCTTTATTCGTAAGTGGTCGATTCGATGATGTGAA
               ||||||||||||||||||||||||||||||||||||||||||||||||||||||||||||
minnad15  494  ACAATGATGTGGCTAATATTGTCCGCTCTTTATTCGTAAGTGGTCGATTCGATGATGTGAA
               ||||||||||||||||||||||||||||||||||||||||||||||||||||||||||||
eagand15  534  ACAATGATGTGGCTAATATTGTCCGCTCTTTATTCGTAAGTGGTCGATTCGATGATGTGAA
               ||||||||||||||||||||||||||||||||||||||||||||||||||||||||||||
pakd15    550  ACAATGATGTGGCTAATATTGTCCGCTCTTTATTCGTAAGTGGTCGATTCGATGATGTGAA
               ||||||||||||||||||||||||||||||||||||||||||||||||||||||||||||
sb33d15   546  ACAATGATGTGGCTAATATTGTCCGCTCTTTATTCGTAAGTGGTCGATTCGATGATGTGAA consensus      ACAATGATGTGGCTAATATTGTCCGCTCTTTATTCGTAAGTGGTCGATTCGATGATGTGAA cad15     296  AGCGCATCAAGAAGGCGATGTGCTTGTTGTTAGCGTTGTGGCTAAATCGATCATTTCAGAT
               ||||||||||||||||||||||||||||||||||||||||||||||||||||||||||||
minnad15  555  AGCGCATCAAGAAGGCGATGTGCTTGTTGTTAGCGTTGTGGCTAAATCGATCATTTCAGAT
```

FIG.1F.(CONTINUED)

```
eagand15   595  AGCGCATCAAGAAGGCGATGTGCTTGTGTTAGCCGTTGTGGCTAAATCGATCATTTCAGAT
                ||||||||||||||||||||||||||||||||||||||||||||||||||||||||||||
pakd15     611  AGCGCATCAAGAAGGCGATGTGCTTGTGTTAGCCGTTGTGGCTAAATCGATCATTTCAGAT
                ||||||||||||||||||||||||||||||||||||||||||||||||||||||||||||
sb33d15    607  AGCGCATCAAGAAGGCGATGTGCTTGTGTTAGCCGTTGTGGCTAAATCGATCATTTCAGAT consensus       AGCGCATCAAGAAGGCGATGTGCTTGTGTTAGCCGTTGTGGCTAAATCGATCATTTCAGAT cad15      357  GTTAAAATCAAAGGTAACTCTGTTATTCCCACTGAAGCACTTAAACAAAACTTAGATGCTA
                ||||||||||||||||||||||||||||||||||||||||||||||||||||||||||||
minnad15   616  GTTAAAATCAAAGGTAACTCTGTTATTCCCACTGAAGCACTTAAACAAAACTTAGATGCTA
                ||||||||||||||||||||||||||||||||||||||||||||||||||||||||||||
eagand15   656  GTTAAAATCAAAGGTAACTCTGTTATTCCCACTGAAGCACTTAAACAAAACTTAGATGCTA
                ||||||||||||||||||||||||||||||||||||||||||||||||||||||||||||
pakd15     672  GTTAAAATCAAAGGTAACTCTGTTATTCCCACTGAAGCACTTAAACAAAACTTAGATGCTA
                ||||||||||||||||||||||||||||| ||||||||||||||  ||||||||||||||
sb33d15    668  GTTAAAATCAAAGGTAACTCTaTTATTCCacCTGAAGCACTtAAAACAAAACTTAGATGCTA consensus       GTTAAAATCAAAGGTAACTCTgTTATTCCcaCTGAAGCACTtAAACAAAACTTAGATGCTA cad15      418  ACGGGTTTAAAGTTGGCGATGTTTTAATTCGAGAAAATTAAATGAATTTGCCAAAAGTGT
                ||||||||||||||||||||||||||||||||||||||||||||||||||||||||||||
```

FIG.1F.(CONTINUED)

```
minnad15    677  ACGGGTTTAAAGTTGGCGATGTTTTAATTCGAGAAAAATTAAATGAATTTGCCAAAAGTGT
                 ||||||||||||||||||||||||||||||||||||||||||||||||||||||||||||
eagand15    717  ACGGGTTTAAAGTTGGCGATGTTTTAATTCGAGAAAAATTAAATGAATTTGCCAAAAGTGT
                 ||||||||||||||||||||||||||||||||||||||||||||||||||||||||||||
pakd15      733  ACGGGTTTAAAGTTGGCGATGTTTTAATTCGAGAAAAATTAAATGAATTTGCCAAAAGTGT
                 ||||||||||||||||||||||||||||||||||| |||||||||||||||||| |||||
sb33d15     729  ACGGGTTTAAAGTTGGCGATaTTTTAATTCGAGAAAAATTAAATGAATTTGCcAAAAGTGT consensus        ACGGGTTTAAAGTTGGCGATgTTTTAATTCGAGAAAAATTAAATGAATTTGCcAAAAGTGT cad15       479  AAAAGAGCACTATGCAAGTGTAGGTCGCTATAACGCAACAGTTGAACCTATTGTCAATACG
                 ||||||||||||||||||||||||||||||||||||||||||||||||||||||||||||
minnad15    738  AAAAGAGCACTATGCAAGTGTAGGTCGCTATAACGCAACAGTTGAACCTATTGTCAATACG
                 ||||||||||||||||||||||||||||||||||||||||||||||||||||||||||||
eagand15    778  AAAAGAGCACTATGCAAGTGTAGGTCGCTATAACGCAACAGTTGAACCTATTGTCAATACG
                 ||||||||||||||||||||||||||||||||||||||||||||||||||||||||||||
pakd15      794  AAAAGAGCACTATGCAAGTGTAGGTCGCTATAACGCAACCGTTGAACCTATTGTCAATACG
                 |||||||||||||||||||||||||||||||||||||| |||||||||||||||||||||
sb33d15     790  AAAAGAGCACTATGCAAGTGTAGGTCGCTATAACGCAACaGTTGAACCTATTGTCAATACG consensus        AAAAGAGCACTATGCAAGTGTAGGTCGCTATAACGCAACaGTTGAACCTATTGTCAATACG
```

FIG.1F.(CONTINUED)

```
cad15      540  CTACCAAATAATCGCGCTGAAATTTTAATTCAAATCAATGAAGATGATAAAGCAAAATTGG
                ||||||||||||||||||||||||||||||||||||||||||||||||||||||||||||
minnad15   799  CTACCAAATAATCGCGCTGAAATTTTAATTCAAATCAATGAAGATGATAAAGCAAAATTGG
                ||||||||||||||||||||||||||||||||||||||||||||||||||||||||||||
eagand15   839  CTACCAAATAATCGCGCTGAAATTTTAATTCAAATCAATGAAGATGATAAAGCAAAATTGG
                ||||||||||||||||||||||||||||||||||||||||||||||||||||||||||||
pakd15     855  CTgCCAAATAATCGtGCTGAAATTTTAATTCAAATCAATGAAGATGATAAAGCAAAATTGG
                || |||||||||| ||||||||||||||||||||||||||||||||||||||||||||||
sb33d15    851  CTaCCAAATAATCGcGCTGAAATTTTAATTCAAATCAATGAAGATGATAAAGCcAAATTGG
                || |||||||||| |||||||||||||||||||||||||||||||||||||| |||||||
consensus       CTaCCAAATAATCGcGCTGAAATTTTAATTCAAATCAATGAAGATGATAAAGCaAAATTGG cad15      601  CATCATTAACTTTCAAGGGGAACGAATCTGTTAGTAGCAGTACATTACAAGAACAAATGGA
                ||||||||||||||||||||||||||||||||||||||||||||||||||||||||||||
minnad15   860  CATCATTAACTTTCAAGGGGAACGAATCTGTTAGTAGCAGTACATTACAAGAACAAATGGA
                ||||||||||||||||||||||||||||||||||||||||||||||||||||||||||||
eagand15   900  CATCATTAACTTTCAAGGGGAACGAATCTGTTAGTAGCAGTACATTACAAGAACAAATGGA
                ||||||||||||||||||||||||||||||||||||||||||||||||||||||||||||
pakd15     916  CATCATTAACTTTCAAGGGGAACGAATCTGTTAGTAGCAGTACATTACAAGAACAAATGGA
                ||||||||||||||||||||||||||||||||||||||||||||||||||||||||||||
sb33d15    912  CATCATTAACTTTCAAGGGGAACGAATCTGTTAGTAGCAGTACATTACAAGAACAAATGGA
                ||||||||||||||||||||||||||||||||||||||||||||||||||||||||||||
consensus       CATCATTAACTTTCAAGGGGAACGAATCTGTTAGTAGCAGTACATTACAAGAACAAATGGA
```

FIG.1F.(CONTINUED)

```
cad15     662  ATTACAACCTGATTCTTGGTGGAAATTATGGGGAAATAAATTTGAAGGTGCGCAATTCGAG
               ||||||||||||||||||||||||||||||||||||||||||||||||||||||||||||
minnad15  921  ATTACAACCTGATTCTTGGTGGAAATTATGGGGAAATAAATTTGAAGGTGCGCAATTCGAG
               ||||||||||||||||||||||||||||||||||||||||||||||||||||||||||||
eagand15  961  ATTACAACCTGATTCTTGGTGGAAATTATGGGGAAATAAATTTGAAGGTGCGCAATTCGAG
               ||||||||||||||||||||||||||||||||||||||||||||||||||||||||||||
pakd15    977  ATTACAACCTGATTCTTGGTGGAAATTATGGGGAAATAAATTTGAAGGTGCGCAATTCGAG
               ||||||||||||||||||||||||||||||||||||||||||||||||||||||||||||
sb33d15   973  ATTACAACCTGATTCTTGGTGGAAATTATGGGGAAATAAATTTGAAGGTGCGCAATTCGAG consensus      ATTACAACCTGATTCTTGGTGGAAATTATGGGGAAATAAATTTGAAGGTGCGCAATTCGAG cad15     723  AAAGATTTGCAGTCAATTCGTGATTATTATTTAAATAATAATGGCTATGCCAAAGCACAAATTA
               |||||||||||||||||||||||||||||||||||||||||||||||||||||||||||||||
minnad15  982  AAAGATTTGCAGTCAATTCGTGATTATTATTTAAATAATAATGGCTATGCCAAAGCACAAATTA
               |||||||||||||||||||||||||||||||||||||||||||||||||||||||||||||||
eagand15  1022 AAAGATTTGCAGTCAATTCGTGATTATTATTTAAATAATAATGGCTATGCCAAAGCACAAATTA
               ||||| ||||||||||||||||||||||||||||||||||||||||||||||||||||||||
pakd15    1038 AAAGATCTGCAGGCAATTCGTGATTATTATTTAAATAATAATGGCTATGCCAAAGCACAAATCA
               ||||| |||||| |||||||||||||||||||||||||||||||||||||||||||||||||
sb33d15   1034 AAAGATtTGCAGgCAATTCGTGATTATTATTTAAATAATAATGGCTATGCCAAAGCACAAATCA consensus      AAAGATtTGCAGtCAATTCGTGATTATTATTTAAATAATAATGGCTATGCCAAAGCACAAATta
```

FIG.1F.(CONTINUED)

```
cad15      784  CTAAAACGGATGTGTTCAGCTAAATGATGAAAAAACAAAAGTTAATGTAACCATTGATGTAAA
                ||||||||||||||||||||||||||||||||||||||||||||||||||||||||||||||
minnad15  1043  CTAAAACGGATGTGTTCAGCTAAATGATGAAAAAACAAAAGTTAATGTAACCATTGATGTAAA
                ||||||||||||||||||||||||||||||||||||||||||||||||||||||||||||||
eagand15  1083  CTAAAACGGATGTGTTCAGCTAAATGATGAAAAAACAAAAGTTAATGTAACCATTGATGTAAA
                ||||||||||||||||||||||||||||||||||||||||||||||||||||||||||||||
pakd15    1099  CTAAAACGGATGTGTTCAGCTAAATGATGAAAAAACAAAAGTTAATGTAACCATTGATGTAAA
                |||||                |||||||||||||||||||||||||||||||||||||||||
sb33d15   1095  CTAAAgCGGATGTGTTCAGCTAAATGATGAAAAAACAAAAGTTAATGTAACCATTGATGTAAA consensus       CTAAAaCGGATGTGTTCAGCTAAATGATGAAAAAACAAAAGTTAATGTAACCATTGATGTAAA cad15      845  TGAAGGTTTACAGTATGACCTTCGTAGTGCACGCATTATAGGTAATCTGGGAGGTATGTCT
                ||||||||||||||||||||||||||||||||||||||||||||||||||||||||||||
minnad15  1104  TGAAGGTTTACAGTATGACCTTCGTAGTGCACGCATTATAGGTAATCTGGGAGGTATGTCT
                ||||||||||||||||||||||||||||||||||||||||||||||||||||||||||||
eagand15  1144  TGAAGGTTTACAGTATGACCTTCGTAGTGCACGCATTATAGGTAATCTGGGAGGTATGTCT
                ||||||||||||||||||||||||||||||||||||||||||||||||||||||||||||
pakd15    1160  TGAAGGTTTACAGTATGACCTTCGTAGTGCACGCATTATAGGTAATCTGGGAGGTATGTCT
                ||||||||||||||||||||||||||||||||||||||||||||||||||||||||||||
sb33d15   1156  TGAAGGTTTACAGTATGACCTTCGTAGTGCACGCATTATAGGTAATCTGGGAGGTATGTCT consensus       TGAAGGTTTACAGTATGACCTTCGTAGTGCACGCATTATAGGTAATCTGGGAGGTATGTCT
```

FIG.1F.(CONTINUED)

```
cad15      906 GCCGAGCTTGAACCTTTACTTTCAGCATTACATTTAAATGATACTTTCCGCCGTAGTGATA
                   ||||||||||||||||||||||||||||||||||||||||||||||||||||||||||||
minnad15  1165 GCCGAGCTTGAACCTTTACTTTCAGCATTACATTTAAATGATACTTTCCGCCGTAGTGATA
                   ||||||||||||||||||||||||||||||||||||||||||||||||||||||||||||
eagand15  1205 GCCGAGCTTGAACCTTTACTTTCAGCATTACATTTAAATGATACTTTCCGCCGTAGTGATA
                   ||||||||||||||||||||||||||||||||||||||||||||||||||||||||||||
pakd15    1221 GCCGAGCTTGAACCTTTACTTTCAGCATTACATTTAAATGATACTTTCCGCCGTAGTGATA
                   ||||||||||||||||||||||||||||||||||||||||||||||||||||||||||||
sb33d15   1217 GCCGAGCTTGAACCTTTACTTTCAGCATTACATTTAAATGATACTTTCCGCCGTAGTGATA consensus      GCCGAGCTTGAACCTTTACTTTCAGCATTACATTTAAATGATACTTTCCGCCGTAGTGATA cad15      967 TTGCAGATGTAGAAAATGCAATTAAAGCAAAACTTGGAGAACGCGGTTACGGTAGCGCAAC
                   ||||||||||||||||||||||||||||||||||||||||||||||||||||||||||||
minnad15  1226 TTGCAGATGTAGAAAATGCAATTAAAGCAAAACTTGGAGAACGCGGTTACGGTAGCGCAAC
                   ||||||||||||||||||||||||||||||||||||||||||||||||||||||||||||
eagand15  1266 TTGCAGATGTAGAAAATGCAATTAAAGCAAAACTTGGAGAACGCGGTTACGGTAGCGCAAC
                   ||||||||||||||||||||||||||||||||||||||||||||||||||||||||||||
pakd15    1282 TTGCAGATGTAGAAAATGCAATTAAAGCAAAACTTGGGAACGAGGTTACGGTAACACAAC
                   ||||||||||||||||||||||||||||||||||||||||||||||||||||| ||||||
sb33d15   1278 TTGCAGATGTAGAAAATGCAATTAAAGCAAAACTTGGGAACGAGGTTACGGTAACACAAC consensus      TTGCAGATGTAGAAAATGCAATTAAAGCAAAACTTGGaGAACGcGGTTACGGTAgCgCAAC
```

FIG.1F.(CONTINUED)

```
cad15    1028  GGTAAATTCAGTACCTGATTTTGATGATGCAAATAAAACATTAGCGATAACCCTTGTTGTT
               ||||||||||||||||||||||||||||||||||||||||||||||||||||||||||||
minnad15 1287  GGTAAATTCAGTACCTGATTTTGATGATGCAAATAAAACATTAGCGATAACCCTTGTTGTT
               ||||||||||||||||||||||||||||||||||||||||||||||||||||||||||||
eagand15 1327  GGTAAATTCAGTACCTGATTTTGATGATGCAAATAAAACATTAGCGATAACCCTTGTTGTT
               ||||||||||| ||||||||||||||  ||||||||||||||||||||||||||||||||
pakd15   1343  AGTAAATTCTGTACCTGATTTTGACGATGCAAATAAAACATTAGCGATAACCTTTGTTGTT
               |||||||||  |||||||||||||  ||||||||||||||||||||||||||||||||||
sb33d15  1339  AGTAAATTCTGTACCTGATTTTGACGATGCAAATAAAACATTAGCGATAACCTTTGTTGTT consensus      gGTAAATTCaGTACCTGATTTTGAtGATGCAAATAAAACATTAGCGATAACCtTTGTTGTT cad15    1089  GATGCTGGACGACGTTTAACTGTTCGCCAACTTCGCTTTGAAGGAAATACCGTTTCTGCTG
               ||||||||||||||||||||||||||||||||||||||||||||||||||||||||||||
minnad15 1348  GATGCTGGACGACGTTTAACTGTTCGCCAACTTCGCTTTGAAGGAAATACCGTTTCTGCTG
               ||||||||||||||||||||||||||||||||||||||||||||||||||||||||||||
eagand15 1388  GATGCTGGACGACGTTTAACTGTTCGCCAACTTCGCTTTGAAGGAAATACCGTTTCTGCTG
               ||||||||||||||||||||||||||||||||||||||||||||||||||||||||||||
pakd15   1404  GATGCTGGACGACGTTTAACTGTTCGCCAACTTCGCTTTGAAGGAAATACCGTTTCTGCTG
               ||||||||||||||||||||||||||||| ||||||||||||||||||||||||||||||
sb33d15  1400  GATGCTGGACGACGTTTAACTGTTCaCCAACTTCGCTTTGAAGGAAATACCGTTTCTGCTG consensus      GATGCTGGACGACGTTTAACTGTTCgCCAACTTCGCTTTGAAGGAAATACCGTTTCTGCTG
```

FIG.1F.(CONTINUED)

```
cad15      1150  ATAGCACTTTACGTCAGGAAATGCGCCAACAAGAAGGAACTTGGTATAATTCACAATTAGT
                 ||||||||||||||||||||||||||||||||||||||||||||||||||||||||||||
minnad15   1409  ATAGCACTTTACGTCAGGAAATGCGCCAACAAGAAGGAACTTGGTATAATTCACAATTAGT
                 ||||||||||||||||||||||||||||||||||||||||||||||||||||||||||||
eagand15   1449  ATAGCACTTTACGTCAGGAAATGCGCCAACAAGAAGGAACTTGGTATAATTCACAATTAGT
                 ||||  ||||||||||||||||||||  ||||||||||||||||||||||||||||||||
pakd15     1465  ATAGTACTTTACGTCAGGAAATGCGaCAACAAGAAGGAACTTGGTATAATTCACAATTAGT
                 |||| |||||||||||||||||||| ||||||||||||||||||||||||||||||||||
sb33d15    1461  ATAGTACTTTACGTCAGGAAATGCGCCAACAAGAAGGAACTTGGTATAATTCACAATTAGT consensus        ATAGcACTTTACGTCAGGAAATGCGCCAACAAGAAGGAACTTGGTATAATTCACAATTAGT cad15      1211  TGAGTTAGGAAAAATTCGCTTAGATCGTACAGGTTTCTTCGAAACAGTCGAAAACCGAATT
                 ||||||||||||||||||||||||||||||||||||||||||||||||||||||||||||
minnad15   1470  TGAGTTAGGAAAAATTCGCTTAGATCGTACAGGTTTCTTCGAAACAGTCGAAAACCGAATT
                 ||||||||||||||||||||||||||||||||||||||||||||||||||||||||||||
eagand15   1510  TGAGTTAGGAAAAATTCGCTTAGATCGTACAGGTTTCTTCGAAACAGTCGAAAACCGAATT
                 ||||||||||||||||||||||||||||||||||||||||||||||||||||||||||||
pakd15     1526  TGAGTTAGGAAAAATTCGCTTAGATCGTACAGGTTTCTTCGAAACAGTTGAAAACCGAATT
                 |||||||||||||||||||||||||||||||||||||||||||||||| |||||||||||
sb33d15    1522  TGAGTTAGGAAAAATTCGCTTAGATCGTACAGGTTTCTTCGAAACAGTTGAAAACCGAATT consensus        TGAGTTAGGAAAAATTCGCTTAGATCGTACAGGTTTCTTCGAAACAGTcGAAAACCGAATT
```

FIG.1F.(CONTINUED)

```
cad15      1272  GATCCTATCAATGGTAGTAATGATGAAGTGGATGTCGTATATAAAGTCAAAGAACGTAACA
                 ||||||||||||||||||||||||||||||||||||||||||||||||||||||||||||
minnad15   1531  GATCCTATCAATGGTAGTAATGATGAAGTGGATGTCGTATATAAAGTCAAAGAACGTAACA
                 ||||||||||||||||||||||||||||||||||||||||||||||||||||||||||||
eagand15   1571  GATCCTATCAATGGTAGTAATGATGAAGTGGATGTCGTATATAAAGTCAAAGAACGTAACA
                 ||||||||||||||||||||||||||||||||||||||||||||||||||||||||||||
pakd15     1587  GATCCTATCAATGGTAGCAATGATGAAGTGGATGTCGTATATAAAGTCAAAGAACGTAACA
                 ||||||||||||||||||||||||||||||||||||||||||||||||||||||||||||
sb33d15    1583  GATCCTATCAATGGTAGCAATGATGAAGTGGATGTCGTATATAAAGTCAAAGAACGTAACA consensus        GATCCTATCAATGGTAGtAATGATGAAGTGGATGTCGTATATAAAGTCAAAGAACGTAACA cad15      1333  CGGGTAGTATCAACTTTGGTATTGGTTACGGTACAGAGAGTGGTATTAGTTATCAAGCAAG
                 ||||||||||||||||||||||||||||||||||||||||||||||||||||||||||||
minnad15   1592  CGGGTAGTATCAACTTTGGTATTGGTTACGGTACAGAGAGTGGTATTAGTTATCAAGCAAG
                 ||||||||||||||||||||||||||||||||||||||||||||||||||||||||||||
eagand15   1632  CGGGTAGTATCAACTTTGGTATTGGTTACGGTACAGAGAGTGGTATTAGTTATCAAGCAAG
                 ||||||||||||||||||||||||||||||||||||||||||||||||||||||||||||
pakd15     1648  CGGGTAGTATCAACTTTGGTATTGGTTACGGTACAGAGAGTGGTATCAGTTATCAAaCAAG
                 ||||||||||||||||||||||||||||||||||||||||||||||||||||||||||||
sb33d15    1644  CGGGTAGTATCAACTTTGGTATTGGTTACGGTACAGAGAGTGGTATtAGTTATCAAgCAAG consensus        CGGGTAGTATCAACTTTGGTATTGGTTACGGTACAGAGAGTGGTATtAGTTATCAAgCAAG
```

FIG.1F.(CONTINUED)

```
cad15      1394  TGTTAAACAAGATAATTTCTTGGGAACAGGGGCGGCCAGTAAGTATAGCTGGTACGAAAAAT
                 ||||||||||||||||||||||||||||||||||||||||||||||||||||||||||||||
minnad15   1653  TGTTAAACAAGATAATTTCTTGGGAACAGGGGCGGCCAGTAAGTATAGCTGGTACGAAAAAT
                 ||||||||||||||||||||||||||||||||||||||||||||||||||||||||||||||
eagand15   1693  TGTTAAACAAGATAATTTCTTGGGAACAGGGGCGGCCAGTAAGTATAGCTGGTACGAAAAAT
                 || |||||||||||||||||||||||||||||||||||||||||||||||||||||||||||
pakd15     1709  TaTTAAACAAGATAATTTCTTGGGAACAGGGGCGGCCAGTAAGTATAGCTGGTACGAAAAAT
                 || |||||||||||||||||||||||||||||||||||||||||||||||||||||||||||
sb33d15    1705  TgTcAAACAAGATAATTTCTTGGGAACAGGGGCGGCCAGTAAGTATAGCTGGTACGAAAAAT consensus        TgTtAAACAAGATAATTTCTTGGGAACAGGGGCGGCCAGTAAGTATAGCTGGTACGAAAAT cad15      1455  GATTATGGTACGAGTGTCAATTTGGGTTATACCGAGCCCTATTTTACTAAAGATGGTGTAA
                 ||||||||||||||||||||||||||||||||||||||||||||||||||||||||||||||
minnad15   1714  GATTATGGTACGAGTGTCAATTTGGGTTATACCGAGCCCTATTTTACTAAAGATGGTGTAA
                 ||||||||||||||||||||||||||||||||||||||||||||||||||||||||||||||
eagand15   1754  GATTATGGTACGAGTGTCAATTTGGGTTATACCGAGCCCTATTTTACTAAAGATGGTGTAA
                 |||||||||||||||||||||||||||||||||||||||| |||||||||||||||||||||
pakd15     1770  GATTATGGTACGAGTGTCAATTTGGGTTATACCGAaCCCTATTTTACTAAAGATGGTGTAA
                 ||||||||||||||||||||||||||||||||||||||| ||||||||||||||||||||||
sb33d15    1766  GATTATGGTACGAGTGTCAATTTGGGTTATACCGAgCCCTATTTTACTAAAGATGGTGTAA consensus        GATTATGGTACGAGTGTCAATTTGGGTTATACCGAgCCCTATTTTACTAAAGATGGTGTAA
```

FIG. 1F.(CONTINUED)

```
cad15     1516  GTCTTGGTGGAAATGTTTTCTTTGAAAACTACGATAACTCTAAAAGTGATACATCCTCTAA
                ||||||||||||||||||||||||||||||||||||||||||||||||||||||||||||
minnad15  1775  GTCTTGGTGGAAATGTTTTCTTTGAAAACTACGATAACTCTAAAAGTGATACATCCTCTAA
                ||||||||||||||||||||||||||||||||||||||||||||||||||||||||||||
eagand15  1815  GTCTTGGTGGAAATGTTTTCTTTGAAAACTACGATAACTCTAAAAGTGATACATCCTCTAA
                ||||||||||||||||| |||||||||||||||||||||||||||||||||||||||||| 
pakd15    1831  GTCTTGGTGGAAATaTTTTCTTTGAAAACTACGATAACTCTAAAAGTGATACATCCTCTAA
                ||||||||||||||||||||||||||||||||||||||||||||||||||||||||||||
sb33d15   1827  GTCTTGGTGGAAATgTTTTCTTTGAAAACTACGATAACTCTAAAAGTGATACATCCTCTAA consensus       GTCTTGGTGGAAATGTTTTCTTTGAAAACTACGATAACTCTAAAAGTGATACATCCTCTAA cad15     1577  CTATAAGCGTACGACTTACGGAAGTAATGTTACTTTTAGGTTTCCCTGTAAATGAAAATAAC
                ||||||||||||||||||||||||||||||||||||||||||||||||||||||||||||
minnad15  1836  CTATAAGCGTACGACTTACGGAAGTAATGTTACTTTTAGGTTTCCCTGTAAATGAAAATAAC
                ||||||||||||||||||||||||||||||||||||||||||||||||||||||||||||
eagand15  1876  CTATAAGCGTACGACTTACGGAAGTAATGTTACTTTTAGGTTTCCCTGTAAATGAAAATAAC
                ||||||||||||||||||||||||||||||||||||||||||||||||||||||||||||
pakd15    1892  CTATAAGCGTACGACTTATGGAAGTAATGTTACTTTTAGGTTTCCCTGTAAATGAAAATAAC
                ||||||||||||||||||||||||||||||||||||||||||||||||||||||||||||
sb33d15   1888  CTATAAGCGTACGACTTATGGAAGTAATGTTACTTTTAGGTTTCCCTGTAAATGAAAATAAC consensus       CTATAAGCGTACGACTTACGGAAGTAATGTTACTTTAGGTTTCCCTGTAAATGAAAATAAC
```

FIG. 1F. (CONTINUED)

```
cad15     1638  TCCTATTATGTAGGATTAGGTCATACCTTATAATAAAATTAGTAACTTTGCTCTAGAATATA
                ||||||||||||||||||||||||||||||||||||||||||||||||||||||||||||||
minnad15  1897  TCCTATTATGTAGGATTAGGTCATACCTTATAATAAAATTAGTAACTTTGCTCTAGAATATA
                ||||||||||||||||||||||||||||||||||||||||||||||||||||||||||||||
eagand15  1937  TCCTATTATGTAGGATTAGGTCATACCTTATAATAAAATTAGTAACTTTGCTCTAGAATATA
                ||||||||||||||||||||||||||||||||||||||||||||||||||||||||||||||
pakd15    1953  TCCTATTATGTAGGATTAGGCCATACCTTATAATAAAATTAGTAACTTTGCTCTAGAATATA
                ||||||||||||||||||||||||||||||||||||||||||||||||||||||||||||||
sb33d15   1949  TCCTATTATGTAGGATTAGGCCATACCTTATAATAAAATTAGTAACTTTGCTCTAGAATATA consensus       TCCTATTATGTAGGATTAGGtCATACCTTATAATAAAATTAGTAACTTTGCTCTAGAATATA cad15     1699  ACCGTAATTTATATATTCAATCAATGAAATTTAAAGGTAATGGCATTAAAACAAATGACTT
                ||||||||||||||||||||||||||||||||||||||||||||||||||||||||||||
minnad15  1958  ACCGTAATTTATATATTCAATCAATGAAATTTAAAGGTAATGGCATTAAAACAAATGACTT
                ||||||||||||||||||||||||||||||||||||||||||||||||||||||||||||
eagand15  1998  ACCGTAATTTATATATTCAATCAATGAAATTTAAAGGTAATGGCATTAAAACAAATGACTT
                ||||||||||||||||||||||||||||||||||||||||||||||||||||||||||||
pakd15    2014  ACCGTAATTTATATATTCAATCAATGAAATTTAAAGGTAATGGCATTAAAACAAATGACTT
                ||||||||||||||||||||||||||||||||||||||||||||||||||||||||||||
sb33d15   2010  ACCGTAATTTATATATTCAATCAATGAAATTTAAAGGTAATGGCATTAAAACAAATGACTT consensus       ACCGTAATTTATATATTCAATCAATGAAATTTAAAGGTAATGGCATTAAAACAAATGACTT
```

FIG.1F.(CONTINUED)

```
cad15    1760  TGATTTTTCTTTTGGTTGGAACTATAACAGCCTTAATAGAGGCTATTTCCCAACTAAAGGG
               ||||||||||||||||||||||||||||||||||||||||||||||||||||||||||||
minnad15 2019  TGATTTTTCTTTTGGTTGGAACTATAACAGCCTTAATAGAGGCTATTTCCCAACTAAAGGG
               ||||||||||||||||||||||||||||||||||||||||||||||||||||||||||||
eagand15 2059  TGATTTTTCTTTTGGTTGGAACTATAACAGCCTTAATAGAGGCTATTTCCCAACTAAAGGG
               ||||||||||||||||||||||||||||||||||||||||||||||||||||||||||||
pakd15   2075  TGATTTTTCTTTTGGTTGGAACTATAACAGCCTTAATAGAGGCTATTTCCCAACTAAAGGG
               ||||||||||||||||||||||||||||||||||||||||||||||||||||||||||||
sb33d15  2071  TGATTTTTCTTTTGGTTGGAACTATAACAGCCTTAATAGAGGCTATTTCCCAACTAAAGGG consensus      TGATTTTTCTTTTGGTTGGAACTATAACAGCCTTAATAGAGGCTATTTCCCAACTAAAGGG cad15    1821  GTTAAAGCAAGTCTTGGTGGACGAGTTACTATTCCAGGTTCTGATAACAAATACTACAAAC
               ||||||||||||||||||||||||||||||||||||||||||||||||||||||||||||
minnad15 2080  GTTAAAGCAAGTCTTGGTGGACGAGTTACTATTCCAGGTTCTGATAACAAATACTACAAAC
               ||||||||||||||||||||||||||||||||||||||||||||||||||||||||||||
eagand15 2120  GTTAAAGCAAGTCTTGGTGGACGAGTTACTATTCCAGGTTCTGATAACAAATACTACAAAC
               ||||||||||||||||||||||||||||||||||||||||||||||||||||||||||||
pakd15   2136  GTTAAAGCAAGTCTTGGTGGACGAGTTACTATTCCAGGTTCTGATAACAAATACTACAAAC
               ||||||||||||||||||||||||||||||||||||||||||||||||||||||||||||
sb33d15  2132  GTTAAAGCAAGTCTTGGTGGACGAGTTACtATtATTCCAGGTTCTGATAACAAATACTACAAAC consensus      GTTAAAGCAAGTCTTGGTGGACGAGTTACTATTCCAGGTTCTGATAACAAATACTACAAAC
```

FIG.1F.(CONTINUED)

```
cad15      1882  TAAGTGCAGATGTACAGGGTTTCTACCCATTAGACAGAGATCACCTCTGGGTTGTATCTGC
                 ||||||||||||||||||||||||||||||||||||||||||||||||||||||||||||
minnad15   2141  TAAGTGCAGATGTACAGGGTTTCTACCCATTAGACAGAGATCACCTCTGGGTTGTATCTGC
                 ||||||||||||||||||||||||||||||||||||||||||||||||||||||||||||
eagand15   2181  TAAGTGCAGATGTACAGGGTTTCTACCCATTAGACAGAGATCACCTCTGGGTTGTATCTGC
                 ||||||||||||||||||||||||||||||||||||||||||||||||||||||||||||
pakd15     2197  TAAGTGCAGATGTACAGGGTTTCTACCCATTAGACAGAGATCACCgCTGGGTTGTATCTGC
                 ||||||||||||||||||||||||||||||||||||||||||||| ||||||||||||||
sb33d15    2193  TAAGTGCAGATGTACAGGGTTTCTACCCATTAGACAGAGATCACCtcTGGGTTGTATCTGC consensus        TAAGTGCAGATGTACAGGGTTTCTACCCATTAGACAGAGATCACCTCTGGGTTGTATCTGC cad15      1943  AAAAGCATCTGCAGGATATGCAAATGGTTTTGGAAACAAGCGTTTACCGTTCTATCAAACT
                 ||||||||||||||||||||||||||||||||||||||||||||||||||||||||||||
minnad15   2202  AAAAGCATCTGCAGGATATGCAAATGGTTTTGGAAACAAGCGTTTACCGTTCTATCAAACT
                 ||||||||||||||||||||||||||||||||||||||||||||||||||||||||||||
eagand15   2242  AAAAGCATCTGCAGGATATGCAAATGGTTTTGGAAACAAGCGTTTACCGTTCTATCAAACT
                 ||||||||||||||||||||||||||||||||||||||||||||||||||||||||||||
pakd15     2258  AAAAGCATCTGCAGGATATGCAAATGGTTTTGGAAACAAGCGTTTACCGTTCTATCAAACT
                 ||||||||||||||||||||||||||||||||||||||||||||||||||||||||||||
sb33d15    2254  AAAAGCATCTGCAGGATATGCAAATGGTTTTGGAAACAAGCGTTTACCGTTCTATCAAACT
```

FIG.1F.(CONTINUED)

```
consensus       AAAAGCATCTGCAGGATATGCAAATGGTTTTGAAACAAGCGTTTACCGTTCTATCAAACT cad15    2004   TATACAGCGGGTGGCATCGGTTCATTACGTGGTTTTGCTTATGGTAGTATTGGACCTAACG
                |||||||||||||||||||||||||||||||||||||||||||||||||||||||||||| 
minnad15 2263   TATACAGCGGGTGGCATCGGTTCATTACGTGGTTTTGCTTATGGTAGTATTGGACCTAACG
                ||||||||||||||||||||||||||||||||||||||||||||||||||||||||||||
eagand15 2303   TATACAGCGGGTGGCATCGGTTCATTACGTGGTTTTGCTTATGGTAGTATTGGACCTAACG
                ||||||||||||||||||||||||||||||||||||||||||||||||||||||||||||
pakd15   2319   TATACAGCGGGTGGCATTGGTTCATTACGCGGTTTTGCTTATGGTAGTATTGGGCCTAAtG
                |||||||||||||||| |||||||||||| |||||||||||||||||||||| |||||| 
sb33d15  2315   TATACAGCGGGTGGCATTGGTTCATTACGCGGTTTTGCTTATGGTAGCATTGGGCCTAACG
                |||||||||||||||| |||||||||||| ||||||||||||||||| ||||||||||| consensus       TATACAGCGGGTGGCATCGGTTCATTACGtGGTTTTGCTTATGGTAGtATTGGaCCTAACG cad15    2065   CAATTTATGCCGAATATGGTAATGGTACTGGTACTTTTAAGAAGATAAGTTCTGA
                ||||||||||||||||||||||||||||||||||||||||||||||||||||||
minnad15 2324   CAATTTATGCCGAATATGGTAATGGTACTGGTACTTTTAAGAAGATAAGTTCTGA
                ||||||||||||||||||||||||||||||||||||||||||||||||||||||
eagand15 2364   CAATTTATGCCGAATATGGTAATGGTACTGGTACTTTTAAGAAGATAAGTTCTGA
                ||||||||||||||||||||||||||||||||||||||||||||||||||||||
pakd15   2380   CAATTTATGCCGAACATGGTAATGGTA
                ||||||||||||| |||||||||||| 
                                            CTTTTAATAAGATAAGTTCTGA
                                            ||||| |||||||||||||||
```

FIG.1F.(CONTINUED)

```
sb33d15  2376  CAATTTATcaaGgtCAaaaTAAT                                    aaaTTAATAAGATAAGTTCTGA consensus        CAATTTATGccGaatATggTAATggtagtggtactggtactTTTAAgAAGATAAGTTCTGA cad15  2126  TGTGATTGGTGGTAATGCAATCGCTACAGCTAGCGCAGAGTTAATTGTGCCAACTCCATTT
minnad15  2385  TGTGATTGGTGGTAATGCAATCGCTACAGCTAGCGCAGAGTTAATTGTGCCAACTCCATTT
 eagand15 2425  TGTGATTGGTGGTAATGCAATCGCTACAGCTAGCGCAGAGTTAATTGTGCCAACTCCATTT
  pakd15  2429  TGTGATTGGTGGTAATGCAATCaCaACaACTGCGAGTGCAGAAcTtATTGTaCCAACTCCATTT
 sb33d15  2422  TGTGATTGGTGGTAATGCAATCgCtACaGCTAGcGCAGAGtTaATTGTgCCAACTCCATTT consensus        TGTGATTGGTGGTAATGCAATCGCTACAGCTAGCGCAGAGtTAATTGTgCCAACTCCATTT cad15  2187  GTGAGCGATAAGAGCCAAAATACGGTCCGAACCTCCTTATTTGTTGATGCGGCAAGTGTTT
minnad15  2446  GTGAGCGATAAGAGCCAAAATACGGTCCGAACCTCCTTATTTGTTGATGCGGCAAGTGTTT
 eagand15 2486  GTGAGCGATAAGAGCCAAAATACGGTCCGAACCTCCTTATTTGTTGATGCGGCAAGTGTTT
```

FIG.1F.(CONTINUED)

```
pakd15    2490  GTGAGTGATAAaAGCCAAAATACAGTCCGAACCTCCCTATTTGTTGATGCGGCAAGTGTTT
                ||||||||||||  ||||  |||||||||||||||||||||||||||||||||||||||
sb33d15   2483  GTGAGTGATAAgAGtCAAAATACAGTCCGAACCTCCCTATTTGTTGATGCGGCAAGTGTTT
consensus       GTGAGCGATAAgAGCCAAAATACgGTCCGAACCTCCtTATTTGTTGATGCGGCAAGTGTTT cad15     2248  GGAATACTAAATGGAAATCAGATAAAAATGGATTAGAGAGCGATGTATTAAAAAGATTGCC
                ||||||||||||||||||||||||||||||||||||||||||||||||||||||||||||
minnad15  2507  GGAATACTAAATGGAAATCAGATAAAAATGGATTAGAGAGCGATGTATTAAAAAGATTGCC
                ||||||||||||||||||||||||||||||||||||||||||||||||||||||||||||
eagand15  2547  GGAATACTAAATGGAAATCAGATAAAAATGGATTAGAGAGCGATGTATTAAAAAGATTGCC
                ||||||||||||||||||||||||||||||||||||||||||||||||||||||| ||||
pakd15    2551  GGAATACTAAATGGAAATCAGATAAAAATGGATTAGAGAGCAAgGTCTTGAAAGACTTACC
                ||||||||||||||||||||||||||||||||||||||||||| |||||||||||| |||
sb33d15   2544  GGAATACTAAATGGAAATCAGATAAAAATGGATTAGAGAGCAAtGTCTTGAAAGACTTACC
consensus       GGAATACTAAATGGAAATCAGATAAAAATGGATTAGAGAGCgATGTaTTaAAAAgaTTgCC cad15     2309  TGATTATGGCAAATCAAGCCGTATTCGCGCCTCTACAGGTGTCGGATTCCAATGGCAATCT
                ||||||||||||||||||||||||||||||||||||||||||||||||||||||||||||
minnad15  2568  TGATTATGGCAAATCAAGCCGTATTCGCGCCTCTACAGGTGTCGGATTCCAATGGCAATCT
```

FIG.1F.(CONTINUED)

```
eagand15  2608  TGATTATGGCAAATCAAGCCGTATTCGCGCCTCTACAGTGTCGGATTCCAATGGCAATCT
                ||||||||||||||||||||||||||||||||||||||||||||||||||||||||||||
pakd15    2612  TGATTATGGCAAATCAAGCCGTATTCGCGCCTCTACAGTGTCGGATTCCAATGGCAATCT
                ||||||||||||||||||||||||||||||| ||||||||||||||||||||||||||||
sb33d15   2605  cGATTATGGCAAATCAAGCCGTAcTCGCGCCTCTACAGTGTCGGATTCCAATGGCAATCT consensus       tGATTATGGCAAATCAAGCCGTAtTCGCGCCTCTACAGTGTCGGATTCCAATGGCAATCT cad15     2370  CCTATTGGGCCATTGGTATTCTCTTATGCCAAACCAATTAAAAAATATGAAAATGATGATG
                ||||||||||||||||||||||||||||||||||||||||||||||||||||||||||||
minnad15  2629  CCTATTGGGCCATTGGTATTCTCTTATGCCAAACCAATTAAAAAATATGAAAATGATGATG
                ||||||||||||||||||||||||||||||||||||||||||||||||||||||||||||
eagand15  2669  CCTATTGGGCCATTGGTATTCTCTTATGCCAAACCAATTAAAAAATATGAAAATGATGATG
                |||||||||| ||||||||||||||||||||||||||||||||||||||||||||||||||
pakd15    2673  CCTATTGGaCCATTGGTATTTTCTTATGCTAAACCAATTAAAAAATATGAAAATGATGATG
                |||| |||||||| ||||| ||||||||||||||||||||||||||||||||||||||||
sb33d15   2666  CCTAgTGGaCCAgTGGTATTTTCTTATGCTAAACCAATTAAAAAATATGAAAATGATGATG consensus       CCTAtTGGgCCAtTGGTATTcTCTTATGCCAAACCAATTAAAAAATATGAAAATGATGATG cad15     2431  TCGAACAGTTCCAATTTAGTATTGGAGGTTCTTTTCTAATAAATTGAACTTTTTTCTTCATC
                ||||||||||||||||||||||||||||||||||||||||||||||||||||||||||||
```

FIG.1F.(CONTINUED)

```
minnad15  2690  TCGAACAGTTCCAATTTAGTATTGGAGGTTCTTTTCTAATAAATTGAACTTTTTCTTCATC
                ||||||||||||||||||||||||||||||||||||||||||||||||||||||||||||
eagand15  2730  TCGAACAGTTCCAATTTAGTATTGGAGGTTCTTTTCTAATAAATTGAACTTTTTTCTTCATC
                |||||||||||||||||||||||||||||||   |||    ||||||||||||||||||
pakd15    2734  TCGAACAGTTCCAATTTAGTATTGGGGGCTCTTTTCTAATAAATTGAACTTTTTCGTCATC
                ||||||||||||||||||||||||||||||||||||||||||||||||||||||||||
sb33d15   2727  TCGAACAGTTCCAATTTAGTATTGGGGGtTCTTTTCTAATAAATTGAACTTTTTCGTCATC consensus       TCGAACAGTTCCAATTTAGTATTGGaGGtTCTTTTCTAATAAATTGAACTTTTTCtTCATC cad15     2492  AGAACTCAAAAACAACGTTCTCTGCCTAATTTAATTGGGCAGAGAAAATATTAAACCCATC
                ||||||||||||||||||||||||||||||||||||||||||||||||||||||||||||
minnad15  2751  AGAACTCAAAAACAACGTTCTCTGCCTAATTTAATTGGGCAGAGAAAATATTAAACCCATC
                ||||||||||||||||||||||||||||||||||||||||||||||||||||||||||||
eagand15  2791  AGAACTCAAAAACAACGTTCTCTGCCTAATTTAATTGGGCAGAGAAAATATTAAACCCATC
                ||||||||||||||||||||||||||||||||   ||||||||||||||||||||||||
pakd15    2795  AGAACTCAAAAACgACGTTCTCTGCCTAATTgAATTGGGCAGAGAAAATATTAAACCCATC
                ||||||||||||||||||||||||||||||||| |||||||||||||||||| ||||||
sb33d15   2788  AGAACTCAAAAACaACGTTCTCTGCCTAATTtAATTGGGCAGAGAAAATATTAAAaCCATC consensus       AGAACTCAAAAACaACGTTCTCTGCCTAATTtAATTGGGCAGAGAAAATATTAAAcCCATC
```

FIG.1F.(CONTINUED)

```
cad15     2553  ATTTAATTAAGGATATATTTATCAAATGAAAAACATCGCAAAGTAACCGCACTTGCTTTAGG
                ||||||||||||||||||||||||||||||||||||||||||||||||||||||||||||
minnad15  2812  ATTTAATTAAGGATATATTTATCAAATGAAAAACATCGCAAAGTAACCGCACTTGCTTTAGG
                ||||||||||||||||||||||||||||||||||||||||||||||||||||||||||||
eagand15  2852  ATTTAATTAAGGATATATTTATCAAATGAAAAACATCGCAAAGTAACCGCACTTGCTTTAGG
                ||||||||||||||||||||||||||||||||||||||||||||||||||||||||||||
pakd15    2856  ATTTAATTAAGGATATATTTATCAAATGAAAAACATCGCAAAGTAACCGCACTTGCTTTAGG
                ||||||||||||||||||||||||||||||||||||||||||||||||||||||||||||
sb33d15   2849  ATTTAATTAAGGATATATTTATCAAATGAAAAACATCGCCAAAGTAACCGCACTTGCTTTAGG consensus       ATTTAATTAAGGATATATTTATCAAATGAAAAACATCGCaAAGTAACCGCACTTGCTTTAGG cad15     2614  TATTGCACTTGCTTCAGGCTATGCTTCCGCTGAAGAAAAATTGCTTTCATTAATGCaGGT
                |||||||||||||||||||||||||||||||||||||||||||||||||||||||||
minnad15  2873  TATTGCACTTGCTTCAGGCTATGCTTCCGCTGAAGAAAAATTGCTTTCATTAATGCgGGT
                |||||||||||||||||||||||||||||||||||||||||||||||||||||||||
eagand15  2913  TATTGCACTTGCTTCAGGCTATGCTTCCGCTGAAGAAAAATTGCTTTCATTAATGC  AcT
                |||||||||||||||||||||||||||||||||||||||||||||||||||||||
pakd15    2917  TtTTGCACTTGCTTCAGGCTATGCTTCCGCTGAAGAAAAATTGCTTTCATTAATGC  AGG
                ||||||| ||||||||||||||||||||||||||||| ||||||||||||||||
sb33d15   2910  TaTTGCACTTGCTTCAGGCTATGCTgCaGCTATGCTGAAGCTGAAGAAAAATTGCTTTtATTAATGC  AGG consensus       TaTTGCACTTGCTTcCGCTATGCTTcCGCTGAAGAAAAATTGCTTTcATTAATGC-agt
```

FIG.1F.(CONTINUED)

```
cad15    2675  atatttTTTcaAcatCacccagatcgccaagcggtagcagataaacttgatgctgaatttaa
                     |||  |||||| ||||
minnad15 2934  TATAnTTTnCAAggCnaagg
                     ||| ||| ||||
eagand15 2973  TATAtTTTTCAA
                    |||| |||||
pakd15   2977  TTATATTTTtcAa
                    |||||
sb33d15  2970  TTATA consensus       ttat-ttttcaaa-c-----gatcgccaagcggtagcagataaacttgatgctgaatttaa cad15    2736  acctgtagctgagaaattagcagcaagcaagcaaaaagaagttgatgataaaattgctgctgct
minnad15 2954
eagand15 2985
pakd15   2990
sb33d15  2975 consensus       acctgtagctgagaaattagcagcaagcaagcaaaaagaagttgatgataaaattgctgctgct
```

FIG. 1F. (CONTINUED)

```
cad15    2797  cgtaaaaaagtagaagcaaaagttgcggctttagaaaagatgcacctcgcttacgtcaag
minnad15 2954
eagand15 2985
pakd15   2990
sb33d15  2975
consensus      cgtaaaaaagtagaagcaaaagttgcggctttagaaaagatgcacctcgcttacgtcaag cad15    2858  ctgatattcaaaaacgccaacaggagattaataaattaggtgcggctgaagatgctgaatt
minnad15 2954
eagand15 2985
pakd15   2990
sb33d15  2975
consensus      ctgatattcaaaaacgccaacaggagattaataaattaggtgcggctgaagatgctgaatt
```

FIG.1F.(CONTINUED)

```
cad15    2919  acaaaaattaatgcaagaacaagataaaaa
minnad15 2954
eagand15 2985
pakd15   2990
sb33d15  2975
consensus      acaaaaattaatgcaagaacaagataaaaa
```

D15 CLONES
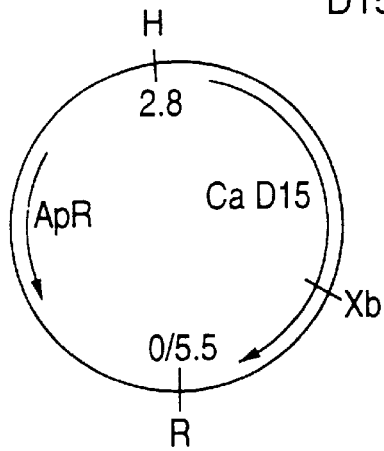
pUC19/D15
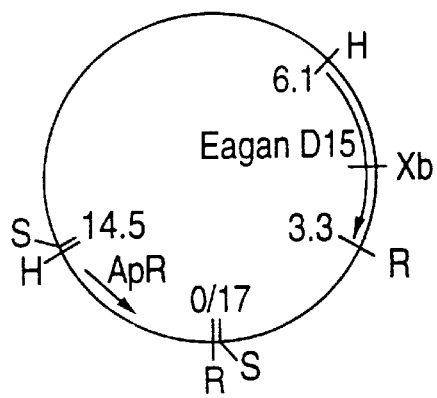
DS-712-2-1
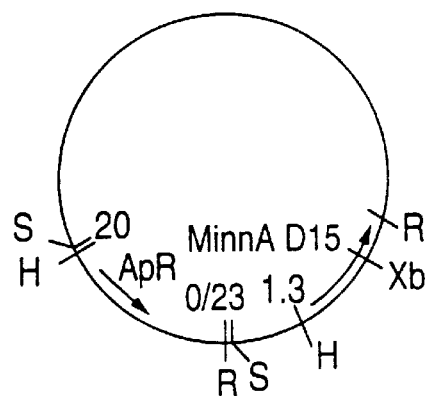
DS-691-1-5
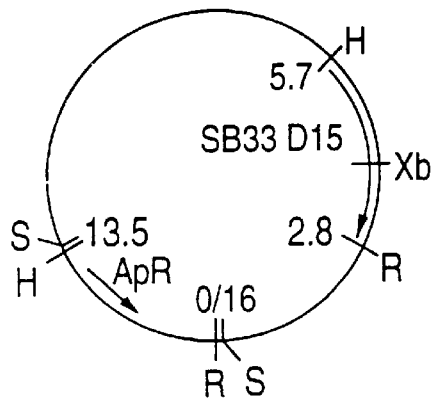
JB-1042-5-1
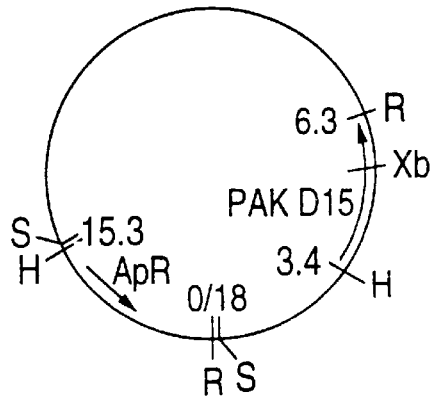
JB-1042-9-4
FIG.2.

D15 SEQUENCE COMPARISON

```
MKKLLIASLLFGITTTVFAAPFVAKDIRVDGVQGDLEQQIRASLFVRAGQRVTIDVANIVRSLFVSGRFIDVKAHQEGDVLVVSVVAKSIISDMKIKGN   Ca
..................................................................................................  Eagan
..................................................................................................  MinnA
..................................................................................................  SB33
..................................................................................................  PAK SVIPTEALKQNLDANGFKVGDVLIREKLNEFAKSVKEHYASVGRYNATVEPIVNTLPNNRAEILIQINEDKAKLASLIFKGNESVSSSTLQEQMELQPD   Ca
..................................................................................................  Eagan
........I.........................................................................................  MinnA
..................................................................................................  SB33
..................................................................................................  PAK SWWKLMGNKFECGAQFEKDLQSIRDYILNNGYAKAQITKIDVQLNDEKTKVNVTIDVNEGLQYDLRSARLIGNLGGMSAELEPLLSALHINDITFRRSDIAD   Ca
..................................................................................................  Eagan
.............A......................................................................................  MinnA
.............A......................................................................................  SB33
..................................................................................................  PAK VENAIKAKLGERGYGSATVNSVPDFDDANKILAITLVVDAGRRLIVRQLRFEGNIVSADSTLRQEMRQQEGIWNSQLVELGKIRLDRIGFFEIVENRID   Ca
..................................................................................................  Eagan
...NT...............................F.........H....................................................  MinnA
....................................................................................................  SB33
...NT...............................F..............................................................  PAK
```

FIG. 3A.

```
PIDGSNDEVDVVYKVKERNIGSINFGIGYGIESGISYQASVKQDNFLGIGAAVSIAGIKNDYGISVNLGYTEPYFTKDGVSLQGNVFFENYDNSKSDTSS    Ca
....................................................................................................    Eagan
....................................................................................................    MinnA
...................................T.I..............................................................    SB33
.................................................................I..................................    PAK NYKRITYGSNVILGFPVNENNSYYVGLGHITYNKISNFALEYNRNLYIQSMKFKGNGIKTNDFSFGMNYNSLNRGYFPTKGVKASLGGFVTIPGSDINKY    Ca
....................................................................................................    Eagan
....................................................................................................    MinnA
....................................................................................................    SB33
....................................................................................................    PAK YKLSADVQGFYPLDRDHIMVVSAKASAGYANGFGNKRLPFYQTYTAGGIGSLRGFAYGSIGPNAIYAEYGNGSGIGTFKKISSDVIGGNAIATASAELIV    Ca
....................................................................................................    Eagan
....................................................................................................    MinnA
...................................................................--Q.QNNK----.N....................    SB33
....................................................................H.----.N..........T..............    PAK PTPFVSDKSQNTVRISLFVDAASVWNTKWKSDKNGLESDVLKRLPDYGKSSRIRASIGVFQMQSPIGPLVFSYAKPIKKYENDMEQFQFSIGGSF**    Ca
................................................................................................**    Eagan
................................................................................................**    MinnA
.........................N..D..................................................................**    SB33
.........................K..D..................................................................**    PAK
```

FIG.3B.

PURIFICATION OF D15 FROM A NON-TYPEABLE
HAEMOPHILUS INFLUENZAE STRAIN 30
A
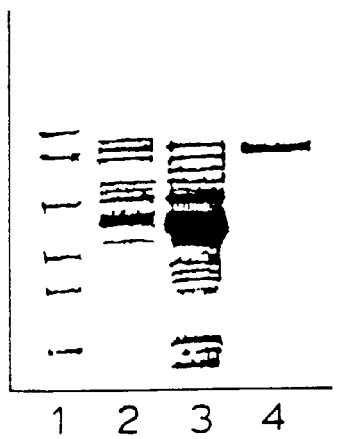
B
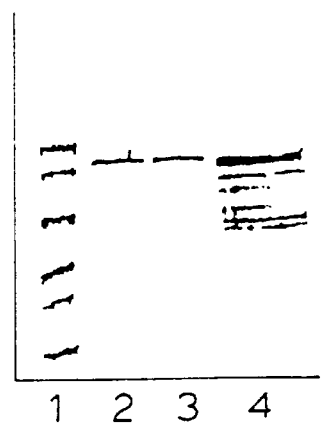
PROTEIN STAIN
WESTERN BLOT
1. Low MW markers
2. Strain 30
3. Native D15 crude extract
4. D15 after anti-D15 affinity chromatography
FIG. 5.

PURIFICATION OF FULL LENGTH RECOMBINANT D15

1. Protein M.W. Markers

2. Lysate of E. coli expressed rD15

3. Soluble protein in Tris-HC1 buffer extract

4. Soluble proteins in Tris/Triton X-100/ EDTA extraction buffer 5. rD15 inclusion bodies

PURIFICATION OF TRUNCATED D15 FROM D15-GST FUSION PROTEIN

1. Prestain low MW markers

2. GST standard

3. GST-(D15 fragment) fusion protein

4. Fusion protein cleaved by thrombin 5. rD15 fragment

6. GST

7. Low MW markers

HAEMOPHILUS OUTER MEMBRANE PROTEIN

FIELD OF INVENTION

The present invention is related to the field of molecular genetics and is particularly concerned with the cloning of an outer membrane protein D15 of Haemophilus.

BACKGROUND OF THE INVENTION

*Haemophilus influenzae* type b (Hib) is a major cause of bacterial meningitis in children under the age of five years. Protective antibodies to the disease are induced by the capsular polysaccharide of the organism and a vaccine was developed that utilises the purified polyribosyl ribitol phosphate (PRP) as the antigen. This vaccine provides 90% protection in adults and in children over 24 months of age, but was ineffective in children under 24 months Zangwill et al 1993 (The references are identified in a list of reference at the end of this disclosure). Like other polysaccharide antigens, PRP does not induce the proliferation of T-helper cells, and re-immunisation fails to elicit either a booster response or an increase in memory cells. Conjugation of the PRP polysaccharide with protein carriers confers T-cell dependent characteristics to the vaccine and substantially enhances the immunologic response to the PRP antigen. Currently, there are four PRP-carrier conjugate vaccines available. These are vaccines based upon *H. influenzae* type b capsular polysaccharide conjugated to diphtheria toxoid, tetanus toxoid, or *Neisseria meningaitidis* outer membrane protein (reviewed in Zangwill et al 1993).

However, the current Haemophilus conjugate vaccines only protect against meningitis caused by *Haemophilus influenzae* type b. They do not protect against other invasive typeable strains (types a and c) and, more importantly, against non-typeable (NTHi) strains which are a common cause of postpartum and neonatal sepsis, pneumonia and otitis media. In the United States alone, treatment of otitis media costs between 1 and 2 billion dollars per year for antibiotics and surgical procedures, such as tonsillectomies, adenoidectomies and insertion of tympanostomy tubes. To achieve universal protection against *H. influenzae* related diseases in the 2 to 6 month age group and certain high risk groups, the provision of conserved, cross-reactive non-capsular *H. influenzae* immunogens is desirable. Methods for inducing immunity against disease are constantly improving and there is presently a move to use subunits and better defined materials as antigens. This is being undertaken to minimise or eliminate potential side-effects caused by certain native immunogens, while preserving their immunogenicity to confer protection against the disease. Therefore, it would be very attractive to develop a universal vaccine against Haemophilus using cross-reactive outer membrane proteins, fragment, analogs, and/or peptides corresponding thereto as protective antigens. Such antigens may be incorporated into the conventional *H. influenzae* type b conjugate vaccines as additional immunogens or used as autologous carriers for *H. influenzae* capsular polysaccharides. A high molecular weight outer membrane protein D15 found in non-typeable and type b stains of *H. influenzae* has been identified as a cross-reactive antigen (Thomas et al., 1990). D15 appears to be cell surface-exposed in its natural state and exhibits a molecular mass of about 80 kDa as judged by SDS-PAGE analysis. It would be desirable to provide the sequence of the DNA molecule that encodes this D15 outer membrane protein and peptides corresponding to portions thereof for diagnosis, immunization and the generation of diagnostic and immunological reagents. The diseases caused by Haemophilus are serious and improved methods for preventing, detecting and treating diseases such as otitis media, epiglottitis, pneumonia, and tracheobronchitis, are required.

SUMMARY OF THE INVENTION

The present invention is directed towards the provision of purified and isolated nucleic acid molecules comprising at least a portion coding for a D15 outer membrane protein of a species of Haemophilus. The nucleic acid molecules comprising at least a portion coding for D15 outer membrane protein are useful for the specific detection of strains of Haemophilus, and for diagnosis of infection by Haemophilus. The purified and isolated nucleic acid molecules, such as DNA comprising at least a portion coding for D15 outer membrane protein, are also useful for expression of the D15 gene by recombinant DNA means for providing, in an economical manner, purified and isolated D15 outer membrane protein.

The D15 outer membrane protein or fragments thereof or analogs thereof are useful immunogenic compositions for the preparation of vaccines against diseases caused by Haemophilus, the diagnosis of infection by Haemophilus and as tools for the generation of immunological reagents. Mono- or polyclonal antisera (antibodies) raised against the D15 outer membrane protein produced in accordance with aspects of the present invention are useful for the diagnosis of infection by Haemophilus, specific detection of Haemophilus (in, for example, in vitro and in vivo assays) and for the treatment of diseases caused by infection by Haemophilus.

Peptides corresponding to portions of the D15 outer membrane protein or analogs thereof are useful immunogenic compositions for the preparation of vaccines against disease caused by Haemophilus, the diagnosis of infection by Haemophilus and as tools for the generation of immunological reagents. Mono- or polyclonal antisera raised against these peptides, produced in accordance with aspects of the present invention, are useful for the diagnosis of infection by Haemophilus, specific detection of Haemophilus (in, for example, in vitro and in vivo assays) and for use in passive immunization as a treatment of disease caused by infection by Haemophilus.

In accordance with one aspect of the present invention, therefore, there is provided a purified and isolated nucleic acid molecule, the molecule comprising at least a portion coding for a D15 outer membrane protein. The nucleic acid molecule has a DNA sequence selected from:

(a) the DNA sequence set out in any one of FIGS. 1A to 1E (as described below) or its complementary strand; and (b) DNA sequences which hybridize under stringent conditions to the DNA sequences defined in (a). The DNA sequences defined in (b) preferably has at least 90% sequence identity with the sequences defined in (a). The DNA sequence defined in (b) particularly may comprise the consensus sequence set forth in FIG. 1F (as described below).

In another aspect of the present invention, there is provided a purified and isolated D15 outer membrane protein or a portion thereof. The D15 outer membrane protein may be a Haemophilus D15 outer membrane protein and more particularly an *H. influenzae* D15 outer membrane protein and the *H. influenzae* strain may be an *H. influenzae* type b strain, such as *H. influenzae* type b strains Ca or Eagan or MinnA or a non-typeable *H. influenzae* strain, such as PAK 12085 or SB33.

In an additional embodiment, the present invention also includes a recombinant plasmid adapted for transformation of a host, the recombinant plasmid comprising a plasmid vector into which has been inserted a DNA segment comprising the purified and isolated DNA molecule provided herein. Such recombinant plasmid comprises a plasmid vector into which a DNA segment which comprises at least an 18 bp fragment selected from the DNA molecules as recited above is inserted. The recombinant plasmid may be plasmid DS-712-2-1 having ATCC accession number 75604, deposited Nov. 4, 1993 and plasmid JB-1042-5-1 having ATCC accession number 75006, deposited Nov. 4, 1993.

The plasmids may be adapted for expression of the encoded D15 outer membrane protein in a host cell, which may be a heterologous or homologous host, by incorporation into a recombinant vector, provided in accordance with a further aspect of the invention. The recombinant vector may comprise at least a DNA segment comprising at least an 18 bp fragment selected from the DNA molecules as recited above and expression means operatively coupled to the DNA segment for expression of the gene product encoded thereby in the host cell. The plasmid for expression of the encoded D15 outer membrane protein may be plasmid DS-880-1-2 having ATCC accession number 75605, deposited Nov. 4, 1993 being adapted for expression at the D15 outer membrane protein in *E. coli*. The selected DNA segment may encode a polypeptide of at least 6 residues and, in particular, may be selected from those segments encoding a polypeptide of Table 2 (below). The DNA segment may further comprise a nucleic acid sequence encoding a leader sequence for export of the gene product from the host. The host for expression may be selected from, for example, *Escherichia coli*, Bacillus, Haemophilus, fungi, yeast or the baculovirus expression system may be used.

Additional aspects of the invention include the protein encoded by the DNA molecule comprising at least a portion coding for the D15 outer membrane protein, fragment or a functional analog of such protein, the use of the protein or analog in vaccination and diagnosis, and the generation of immunological reagents. The invention also includes antisera (antibodies) raised against the D15 outer membrane protein encoded by the DNA molecule comprising at least a portion coding for a D15 outer membrane protein and purified peptides corresponding to portions of the D15 outer membrane protein and there are in passive immunization and treatment of diseases caused by Haemophilus.

According to another aspect of the invention, a purified and isolated peptide containing an amino acid sequence corresponding to the amino acid sequence of at least a portion of the D15 outer membrane protein or variant or mutant which retains immunogenicity. The peptide may be produced by recombinant methods or peptide synthesis whereby the purified peptide is free from contaminants associated with bacteria normally containing the D15 outer membrane protein. Such synthetic peptides preferably have an amino acid sequence selected from those presented in Table 2.

In accordance with an additional aspect of the invention, an immunogenic composition is provided which comprises the D15 outer membrane protein, fragments thereof, functional analogs thereof, or peptides as recited above and a physiologically-acceptable carrier therefor. Such immunogenic composition is particularly formulated as a vaccine for in vivo administration to protect against diseases caused by Haemophilus. For such purpose, the immunogenic composition may be formulated as a microparticle preparation, capsule preparation or liposome preparation. In addition, such immunogenic composition may be provided in combination with a targeting molecule for delivery to specific cells of the immune system or to mucosal surfaces.

In accordance with a further aspect of the invention, there is provided a method for inducing protection against disease caused by Haemophilus, comprising the step of administering to a subject, including a mammal, such as a human, an effective amount of the immunogenic composition or the nucleic acid molecule as recited above to provide protective immunity against Haemophilus infection.

The present invention further includes a chimeric molecule comprising a D15 protein or peptide corresponding thereto as provided herein linked to another polypeptide or protein or a polysaccharide. The linked polypeptide or protein may comprise a surface protein or peptide corresponding thereto from a pathogenic bacteria, which may be the P1, P2 or P6 outer membrane protein of *H. influenzae*. The linked polysaccharide preferably comprise a PRP molecule from *H. influenzae*.

BRIEF DESCRIPTION OF THE FIGURES

The present invention will be further understood from the following description with reference to the drawings, in which:

FIG. 1A shows the nucleotide sequence of the D15 gene from *H. influenzae* type b Ca strain (SEQ ID NO: 1) and its deduced amino acid sequence (SEQ ID NO: 2);

FIG. 1B shows the nucleotide sequence of the D15 gene from *H. influenzae* type b Eagan strain (SEQ ID NO. 3) and its deduced amino acid sequence (SEQ ID NO: 4);

FIG. 1C shows the nucleotide sequence of the D15 gene from H. influenzae type b MinnA strain (SEQ ID NO. 5) and its deduced amino acid sequence (SEQ ID NO: 6);

FIG. 1D shows the nucleotide sequence of the D15 gene from *H. influenzae* non-typeable SB33 (SEQ ID NO. 7) and its deduced amino acid sequence (SEQ ID NO: 8);

FIG. 1E shows the nucleotide sequence of the D15 gene from *H. influenzae* non-typeable PAK 12085 (SEQ ID NO. 9) and its deduced amino acid sequence (SEQ ID NO: 10);

FIG. 1F shows an alignment of the nucleotide sequences of the D15 genes (SEQ ID NOS: 1, 3, 5, 7 and 9) obtained from different *H. influenzae* isolates (typeable, Ca, Eagan and MinnA; nontypeable SB33 and PAK 12085);

FIG. 2 shows restriction maps of clones pUC19/D15 (Ca), DS-712-2-1 (Eagan), DS-691-1-5 (MinnA), JB-1042-5-1 (SB33), and JB-1042-9-4 (PAK 12085). H=HindIII; R=EcoRI; S=Sau3A I; and Xb=XbaI;

FIG. 3 shows an alignment of the amino acid sequences of D15 outer membrane proteins (SEQ ID NOS: 2, 4, 6, 8 and 10) obtained from different *H. influenzae* isolates (typeable, Ca, Eagan and MinrA; nontypeable, SB33 and PAK 12085). Amino acids are represented by the conventional one-letter code. The Ca D15 sequence is used as reference and the dots indicate amino acid residues which are identical to those of the Ca D15 outer membrane protein;

FIG. 5 shows an SDS-PAGE analysis of native D15 affinity-purified from *H. influenzae* strain 30;

GENERAL DESCRIPTION OF THE INVENTION

Figure 4:
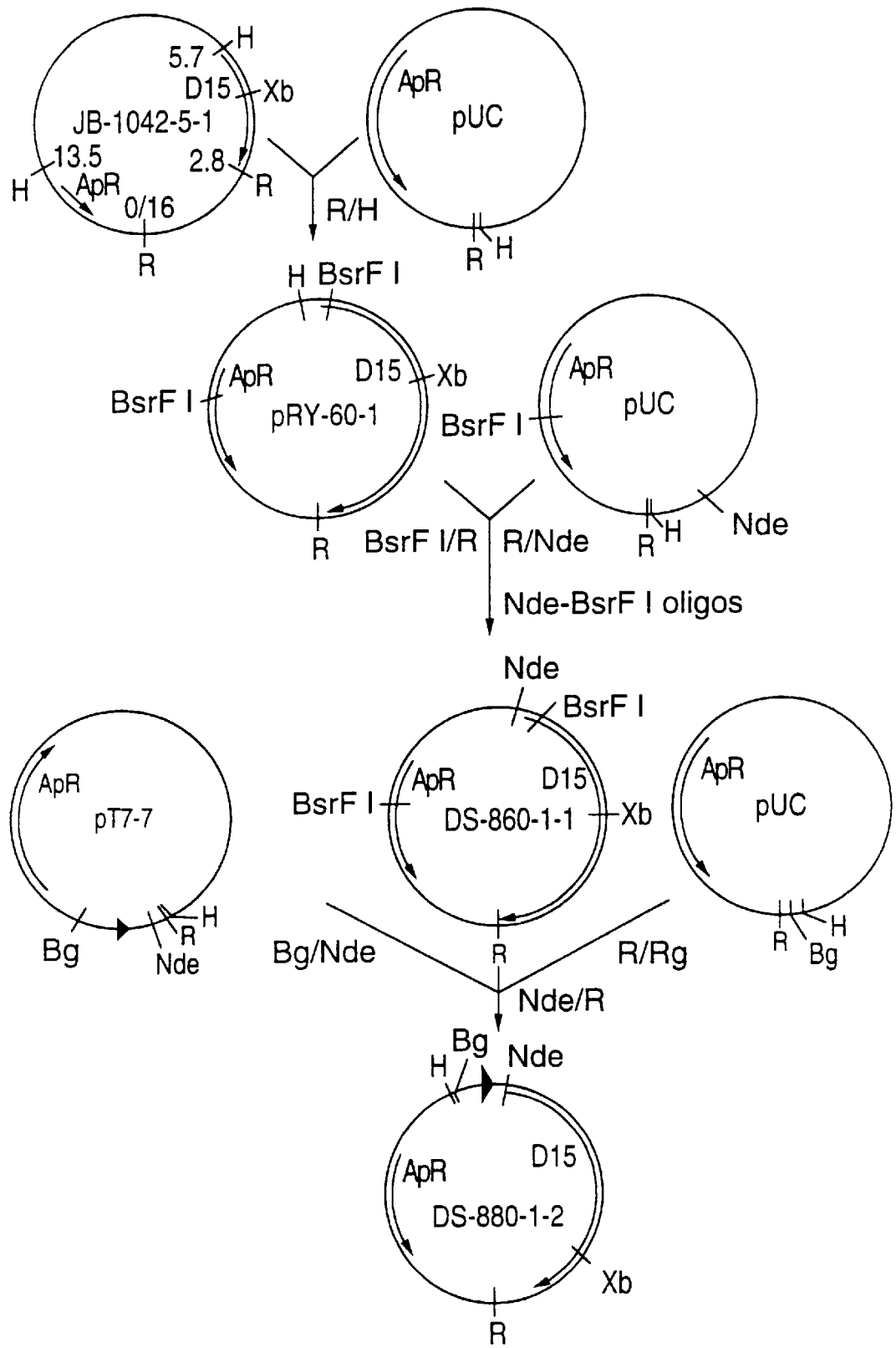
FIG. 4 shows the construction of a plasmid (DS-880-1-2) expressing full-length SB33 D15 (rD15) from the strong inducible T7 promoter.

Any Haemophilus strains that have D15 genes may be conveniently used to provide the purified and isolated nucleic acid molecules (which may be in the form of DNA molecules), comprising at least a portion coding for a D15 outer membrane protein as typified by embodiments of the present invention. Such strains are generally available from clinical sources and from bacterial culture collections, such as the American Type Culture Collection. *H. influenzae* strains may include types a, b and c strains, non-typeable strains and other bacteria that produce a D15 protein, fragment or analog thereof. Appropriate strains of Haemophilus include:

*H. influenzae* type b strain Ca;

*H. influenzae* type b strain MinnA;

*H. influenzae* type b strain Egan;

*H. influenzae* non-typeable b strain SB33; or

*H. influenzae* non-typeable b strain PAK 12085.

In this application, the term D15 outer membrane protein is used to define a family of D15 proteins which includes those having naturally occurring variations in their amino acid sequences as found in various strains of, for example, Haemophilus. The purified and isolated DNA molecules comprising at least a portion coding for D15 outer membrane protein of the present invention also include those having naturally occuring variations in their nucleic acid sequences as found in various strains of, for example Haemophilus and those DNA molecules encoding functional analogs of D15 outer membrane protein. In this application, a first protein is a functional analog of a second protein if the first protein is immunologically related with and/or has the same function as the second protein. The functional analog may be, for example, a fragment of the protein or a substitution, addition or deletion mutant thereof.

Figure 1A:
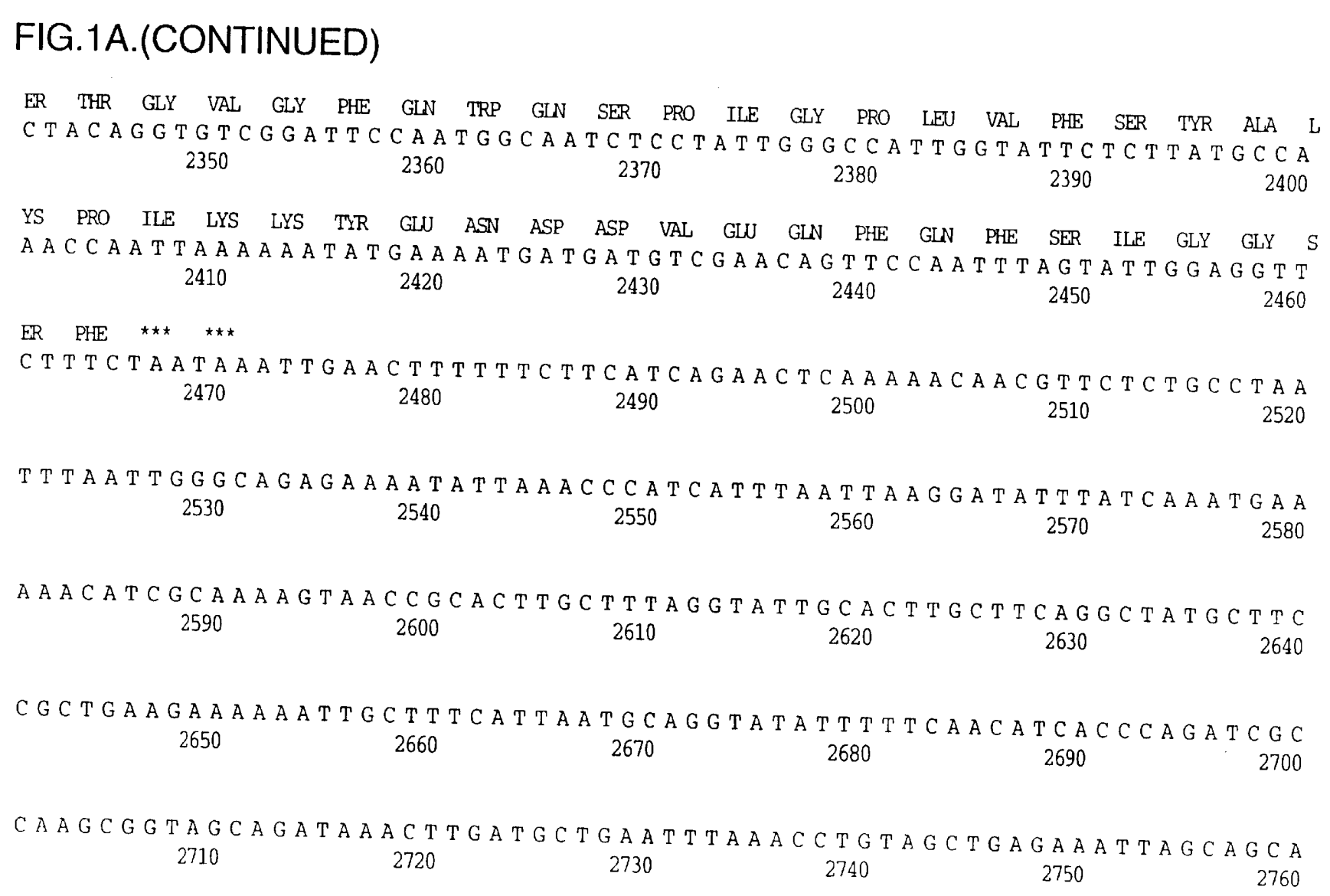
Figure 1B:
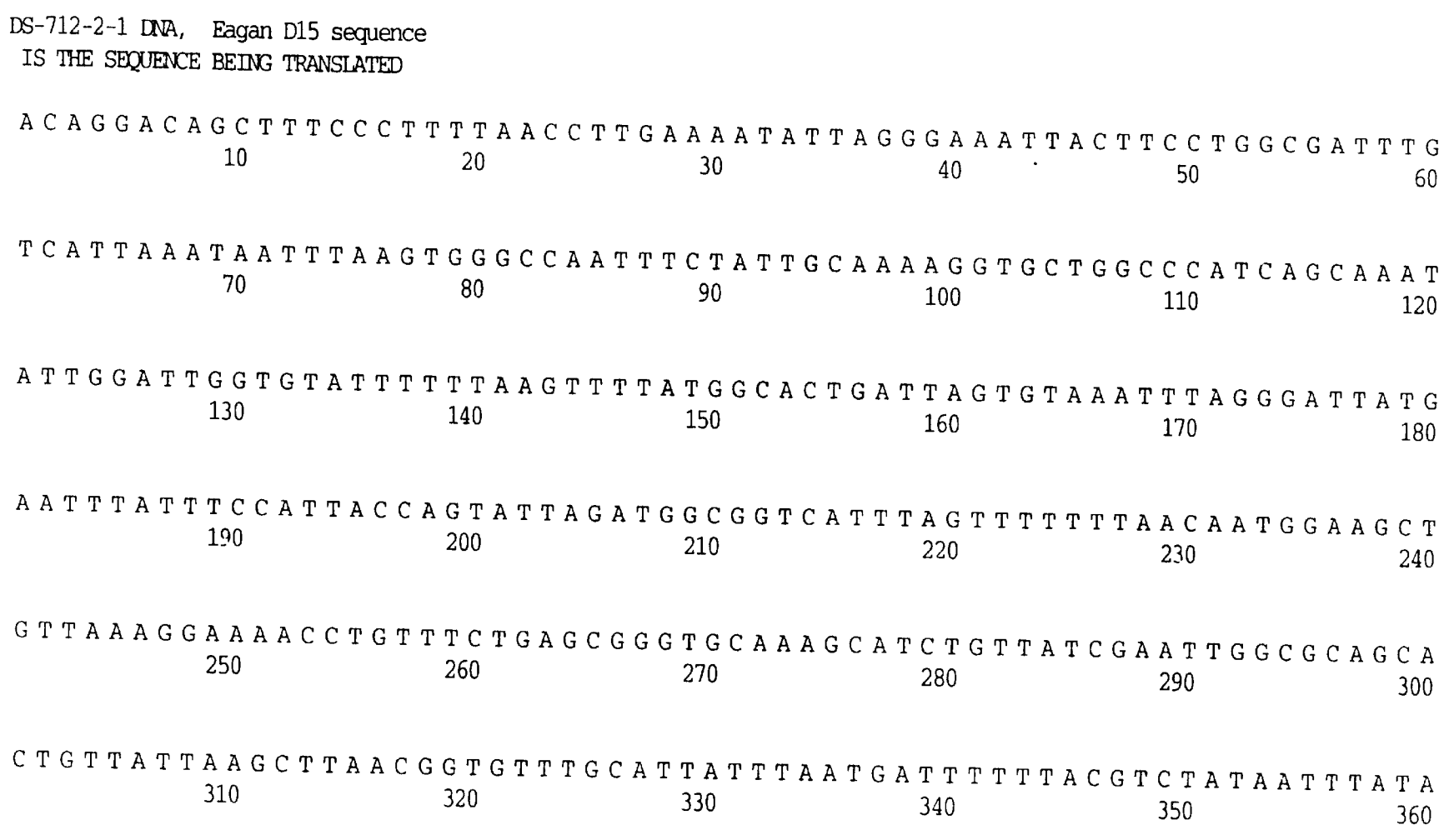
Figure 1C:
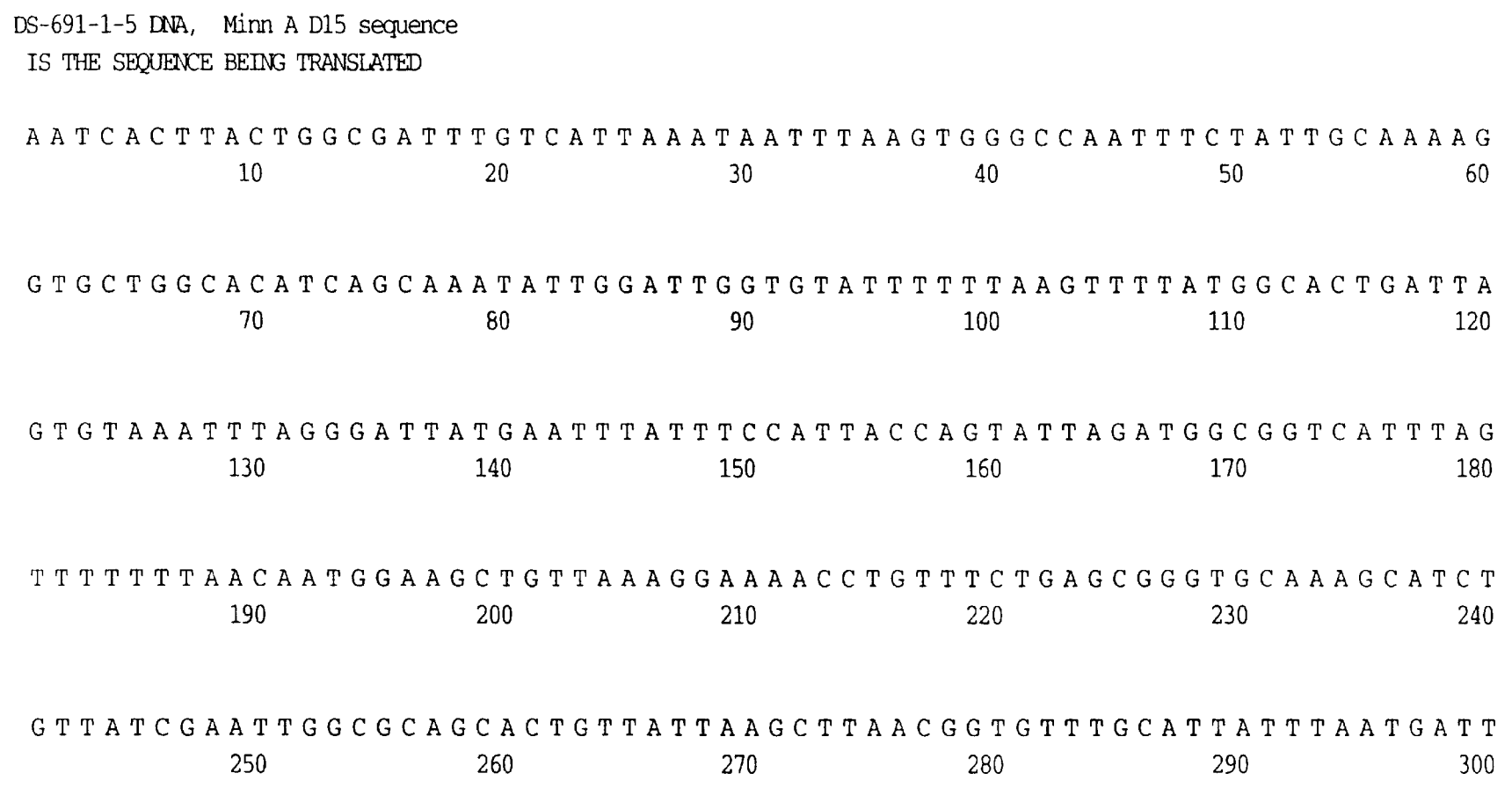

In aspects of the present invention, the D15 gene was isolated from *H. influenzae* type b strain Ca as shown in FIG. 1A; *H. influenzae* type B Eagan, FIG. 1B; *H. influenzae* type b MinnA, FIG. 1C; non-typeable *H. influenzae* SB33, FIG. 1D; non-typeable *H. influenzae* PAK 12085, FIG. 1E. A comparison of the nucleic acid sequences of the D15 genes and of the deduced amino acid sequences of the D15 outer membrane proteins from these strains of *H. influenzae* showed the genes and proteins to be highly conserved (FIGS. 1F and 3). The consensus sequence (SEQ ID NO: 55) for the D15 gene is shown in FIG. 1F.

The purified and isolated DNA molecules comprising at least a portion coding for a D15 outer membrane protein of a species of Haemophilus, typified by the embodiments described herein, are advantageous as:

nucleic acid probes for the specific identification of Haemorhilus strains in vitro or in vivo;

the products encoded by the DNA molecules are useful as diagnostic reagents, antigens for the production of Haemophilus-specific antisera, for vaccination against the diseases caused by species of Haemophilus and detecting infection by Haemophilus; and peptides corresponding to portions of the D15 outer membrane protein as typified by the embodiments described herein are advantageous as diagnostic reagents, antigens for the production of Haemophilus-specific antisera, for vaccination against the diseases caused by species of Haemophilus and for detecting infection by Haemophilus.

Reference will now be made in detail to the presently preferred embodiments of the invention, which together with the following Examples, serve to explain the principle of the invention. For clarity of disclosure, and not by way of limitation, the detailed description of the invention is divided into the following sections:

(i) The DNA sequences coding for the outer membrane protein D15 from *H. influenzae* type b Ca strain.

A clone producing the outer membrane protein designated D15 of *H. influenzae* type b (Hib) was isolated by screening a genomic library with *H. influenzae* type b OMP-specific polyclonal antibodies as previously described by Berns and Thomas 1965; Thomas and Rossi 1986. The DNA fragment encoding the D15 protein was isolated, subcloned into pUC19 to produce pUC19/D15 (FIG. 2) and used to transform *E. coli* HB101 as described in Example 1. Plasmid DNA was prepared from two individual colonies of *E. coli* HB101 containing the pUC19/D15 plasmid. Sequencing was performed on an ABI DNA sequencer model 370A using dye-terminator chemistry and oligonucleotide primers which had been synthesized on an ABI DNA synthesizer model 380B, and purified by chromatography. Nucleotide sequence analysis of the D15 gene revealed that it contains a putative promoter and an open reading frame encoding 789 amino acids (FIG. 1A).

The first 19 amino acid residues of the translated open reading frame form a typical leader sequence as found in other *H. influenzae* type b outer membrane proteins, such as P1 and P2. The N-terminal sequence of immuno-affinity purified native D15 antigen was determined by automated Edman degradation using the ABI 477A protein sequencer and was found to be Ala-Pro-Phe, which is identical to the N-terminal amino acid sequence Ala-Pro-Phe-Val-Ala-Lys- (SEQ ID NO: 11) predicted from an analysis of the sequence of the D15 gene presented in FIG. 1A.

(ii) The sequence of D15 genes from other *H. influenzae* strains.

D15 genes were isolated from other *H. influenzae* strains by screening the chromosomal libraries of *H. influenzae* type b strains Eagan, Minn A and the non-typeable *H. influenzae* (NTHi) strains SB33 and PAK 12085, as described in Examples 2, 3 and 4. Hybridization-positive clones were plated and submitted to a second round of screening. The restriction maps of the clones obtained are shown in FIG. 2. The nucleotide sequences of the D15 genes were determined for all these clones (FIGS. 1B to 1E) and their derived amino acid sequences compared (FIG. 3). The D15 amino acid sequences of the three *H. influenzae* type b strains were identical and only a few amino acid differences were observed in the amino acid sequence of the D15 protein from the non-typeable strains (FIG. 3).

(iii) Expression of D15 and its fragments in *E. coli*.

Since D15 is expressed in small quantities by strains of *H. influenzae*, it is advantageous to either express this antigen as a recombinant protein in a heterologous system, such as *E. coli*, or to modify the *H. influenzae* organism to enhance native D15 expression. The Hind III/Eco RI fragment of *H. influenzae* type b Ca strain DNA encoding the full length D15 protein was expressed in pUC19 but not pUC18, suggesting that the lac promoter is helping to express the D15 gene in *E. coli*, even though the native D15 gene promoter is present. The T7 expression system is a tightly controlled, inducible system which has great utility in expression of heterologous proteins in *E. coli*. The T7 expression system is described in U.S. Pat. No. 4,952,496. Clones were, therefore, constructed which utilize the T7 system to express a mature D15 protein that contains an additional methionine residue at the amino terminus. The D15 signal sequence was removed during this construction process. A full length recombinant D15 (termed rD15) was expressed in inclusion bodies which allow the D15 protein to be readily purified. The D15 genes from *H. influenzae* type b strain Ca and *H. influenzae* non-typeable SB33 strain have been expressed at high levels in *E. coli* using the T7 system to permit production of large quantities of rD15 protein. The construction of clone DS-880-1-2 which expresses the SB33 D15 gene is described herein (see FIG. 4 and Example 5). The rD15 protein was immunologically similar to its native counterpart isolated from *H. influenzae* typeable and non-typeable strains (see below). Thus, rD15 may be used as a cross-reactive antigen in a diagnostic kit to detect many, if not all, strains of *H. influenzae* and other bacteria that produce a D15 outer membrane protein or analog thereof. Alternatively, rD15 can be used as an antigen to specifically detect the presence of *H. influenzae* in a sample.

A truncated D15 fragment was expressed in *E. coli* as a fusion protein with glutathione S-transferase (GST), as described in Example 6. The construction was designed to express the N-terminal fragment of the D15 protein. The fusion protein was expressed at high levels from a pGEX-2T construction and the N-terminal fragment was cleaved from the GST carrier protein by treatment with thrombin. This procedure generated a molecule termed the N-terminal rD15 fragment which encompasses amino acids 63–223 of the D15 protein. This N-terminal rD15 fragment was highly immunogenic and elicited protective antibodies against challenge with live *H. influenzae*.

(iv) Purification of native D15 from *H. influenzae* cell paste.

The present invention also provides a method to prepare purified native D15 protein from *H. influenzae*. The protein is extracted and affinity-purified from the cell pastes of either *H. influenzae* typeable or non-typeable isolates by a procedure involving the dissolution of the protein in an aqueous detergent solution (see Example 13). The native D15 protein from a non-typeable *H. influenzae* strain 30 was solubilized with a 50 mM Tris-HCl/0.5% Triton X-100/10 mM EDTA buffer, pH 8.0 and further purified on a D15-specific monoclonal antibody affinity column (FIG. 5A). An 80 kDa protein was eluted from the column with 50 mM diethylamine, pH 12.0 and shown to react with a D15-specific monoclonal antibody on immunoblot analysis (FIG. 5B). The native D15 is also highly immunogenic in experimental animals. Rabbit anti-D15 antisera reacted with all *H. influenzae* isolates as determined by immunoblot analyses.

(v) Purification of a full-length recombinant D15 protein expressed in *E. coli*.

Figure 6:
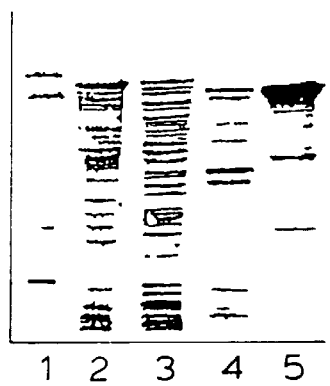
FIG. 6 shows an SDS-PAGE analysis of sequential fractions obtained during the purification of the full-length rD15 expressed in *E. coli* containing plasmid DS-880-1-2.

A full-length recombinant D15 (rD15) protein was expressed in inclusion bodies in *E. coli*. As shown in FIG. 6, purification of rD15 inclusion bodies was achieved by a sequential extraction of the *E. coli* cell lysate with 50 mM Tris-HCl, pH 8.0, then 50 mM Tris containing 0.5% Triton X-100 and 10 mM EDTA, pH 8.0. After centrifugation, more than 95% of the proteins in the resulting pellet was an 80 kDa protein by SDS-PAGE analysis, that reacted with a D15-specific monoclonal antibody on an immunoblot. The N-terminal sequence of the rD15 was found to be Met-Ala-Pro-Phe-Val-Lys-Asp-(SEQ ID NO: 54) which is identical to the predicted amino acid sequence.

The rD15 inclusion bodies were solubilized with a mixture of PBS, 0.5% Triton X-100, 10 mM EDTA and 8 M urea (see Example 8). After dialysis against PBS to remove urea, more than 80% of the D15 protein remained soluble. This soluble rD15 antigen was used for the immunogenicity studies described below. From shake-flask experiments, it was estimated that about 10 mg of soluble rD15 protein was obtained from 1 L of *E. coli* bacterial culture. It is clear that growing the recombinant *E. coli* strains under optimised fermentation conditions significantly increase the level of rD15 production.

(vi) Immunogenicity of the full-length recombinant D15 protien (rD15).

Figure 7:
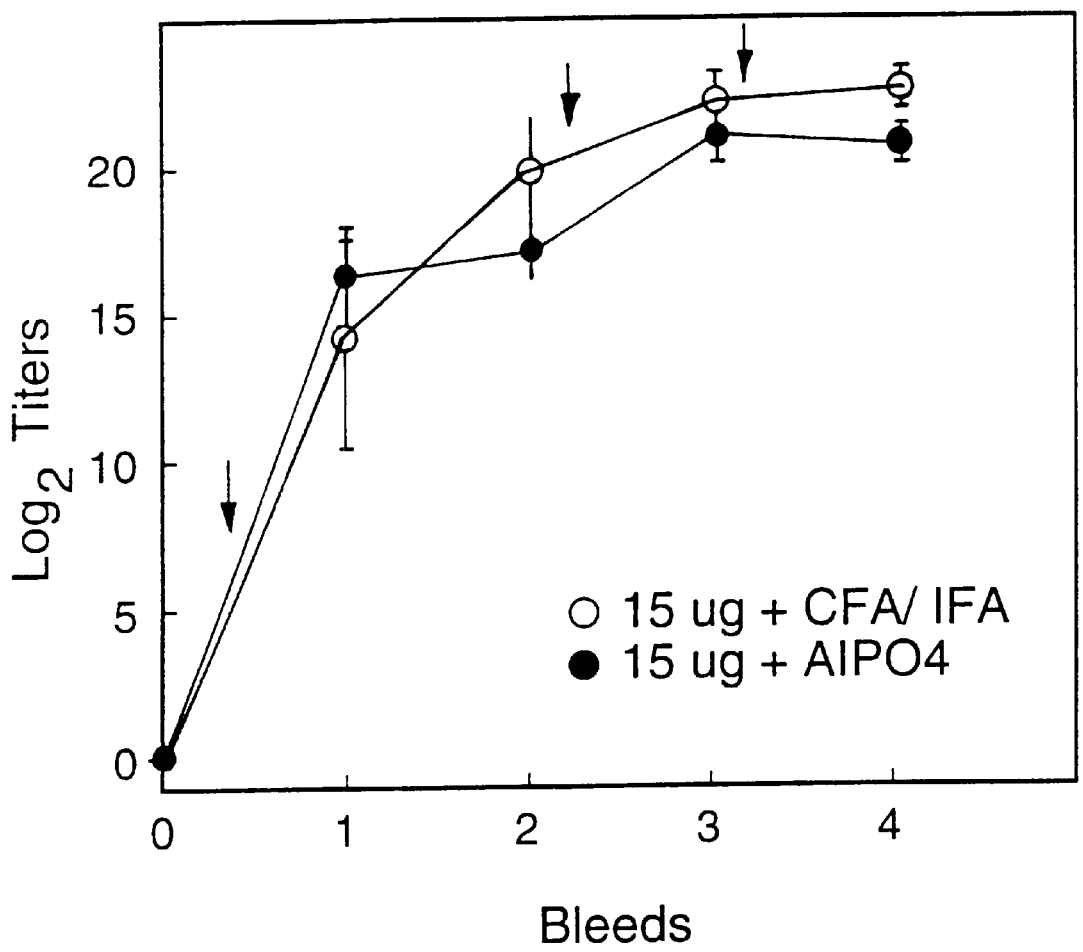
FIG. 7 shows guinea pig IgG antibody responses to full length rD15. The arrows indicate the immunization schedule. Bleeds were taken at 0, 2, 4, 6 and 8 weeks. The bars represent the standard deviation.
Figure 8:
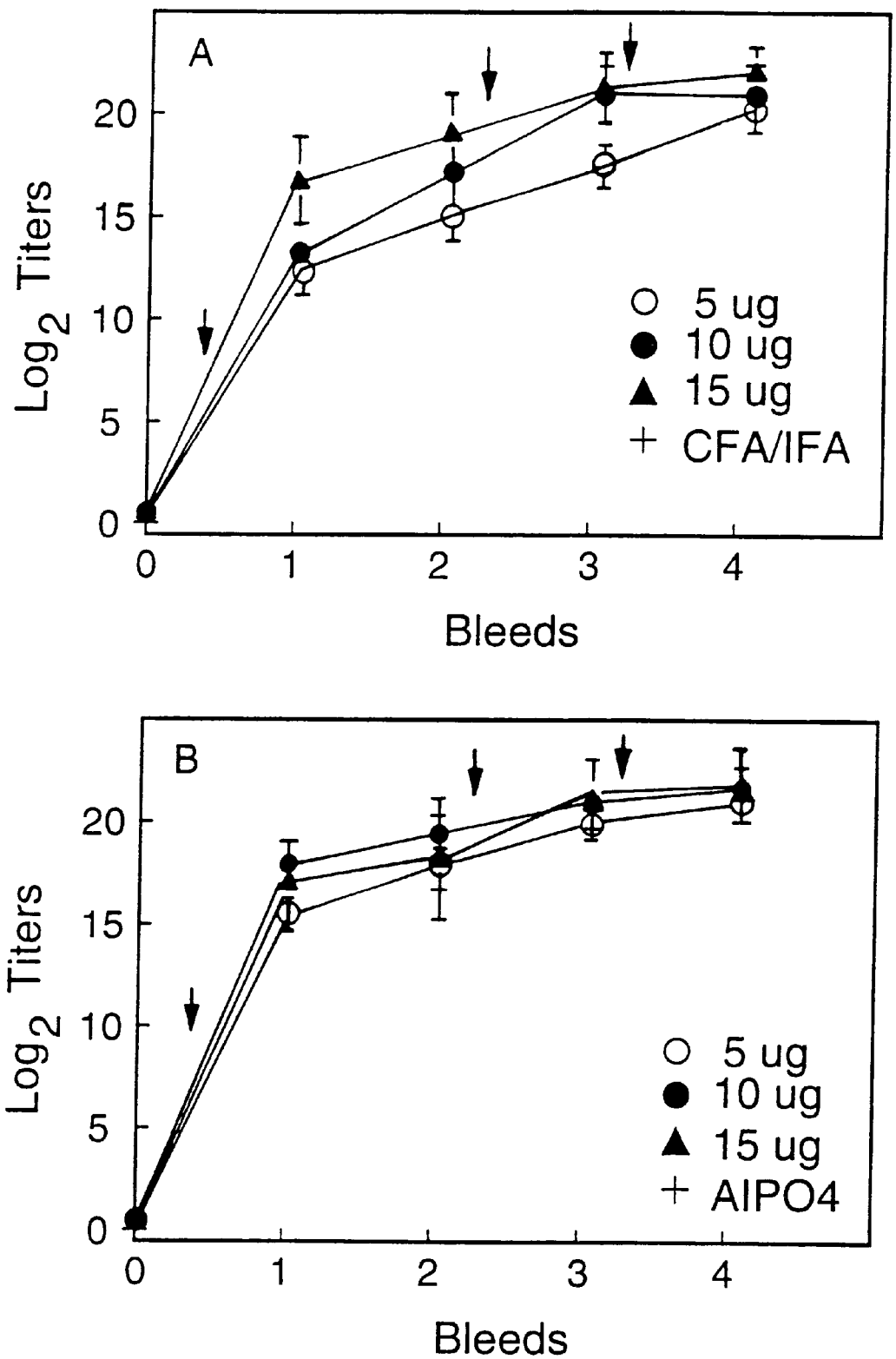
FIGS. 8A and 8B show mouse IgG antibody responses to full length rD15. The arrows indicate the immunization schedule. Bleeds were taken at 0, 1, 4, 5 and 7 weeks. The bars represent the standard deviation.

The immunogenicity of the full-length rD15 protein was studied in guinea pigs and mice. Using the immunization protocols described in FIG. 7, a 15 μg dose of rD15 induced high IgG titers in guinea pigs when administered in the presence of either Freund's adjuvant or AlPO$_4$. In the mouse dose-response study, the protein appeared to be immunogenic at a dose as low as 5 μg in either Freund's adjuvant (FIG. 8A) or AlPO$_4$ (FIG. 8B).

The protective ability of rD15 against *H. influenzae* type b infection was examined in the infant rat model of bacteremia essentially as described by Loeb (1987). Thus, infant rats passively immunized with guinea pig anti-rD15 antisera were significantly less bacteremic than controls injected with pre-bleed sera, which is consistent with the previous report by Thomas et al. (1990).

(vii) Purification and characterization of the N-terminal rD15 fragment.

Figure 9:
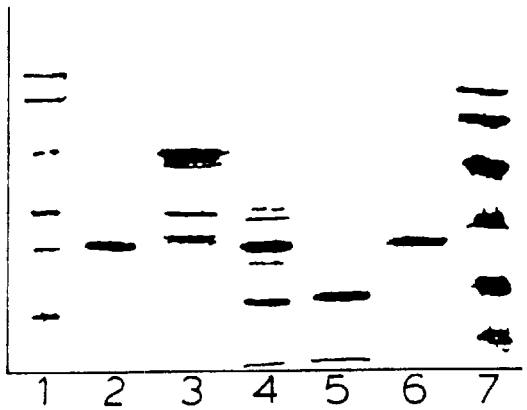
FIG. 9 shows an SDS-PAGE analysis of the N-terminal rD15 fragment purified from GST-(D15 fragment) fusion protein. Lanes: 1, prestained low molecular weight markers (14 kDa, 21 kDa, 31 kDa, 45 kDa, 68 kDa, 97 kDa); 2, GST standard; 3, GST-(D15 fragment) fusion protein; 4, fusion protein cleaved by thrombin; 5, N-terminal rD15 fragment; 6, GST; 7, low molecular weight markers.

The truncated rD15 fragment corresponding to the N-terminus of the D15 protein (residues 22 to 223) as described in Example 6, was expressed in *E. coli* as a soluble protein fused to GST. The fusion protein (46 kDa) was readily extracted using phosphate buffered saline (PBS). Purification of the GST-D15 fragment fusion protein was achieved by a single-step affinity purification process on a glutathione-Sepharose 4B column (FIG. 9, Lane 3). Cleavage of the 46 kDa fusion protein with thrombin yielded two fragments (FIG. 9, Lane 4), a 26 kDa protein which corresponded to a purified GST standard (FIG. 9, Lane 2), and a 20 kDa polypeptide which had the size expected for the N-terminal rD15 fragment (amino acid residues 63 to 223), respectively. Separation of these two proteins was achieved by a second round of glutathione-Sepharose 4B affinity chromatography. From shake-flask experiments, it was estimated that about 1 mg of purified N-terminal rD15 fragment was recovered from 1 L of *E. coli* bacterial culture. It is clear that growing the recombinant *E. coli* strains under optimised fermentation conditions will significantly increase the level of N-terminal rD15 fragment production.

The identity of the 20 kDa polypeptide and the 26 kDa protein was confirmed by both immunoblotting and protein sequencing. The N-terminal sequence of the 20 kDa polypeptide was found to be NH$_2$-Ser-Leu-Phe-Val-Ser-Gly-Arg-Phe-Asp-Asp-Val-Lys-Ala-His-Gln-Glu-Gly-Asp-Val-Leu-Val-Val-Ser- (SEQ ID NO: 12), which corresponds to residues 63 to 85 of the primary sequence of D15. This result indicates that there is a spurious thrombin cleavage site within the D15 sequence and that the first 42 amino acids of the rD15 fragment are cleaved off during thrombin digestion. Thus, the final N-terminal rD15 fragment was 161 amino acids in length corresponding to residues 63 to 223 of the primary sequence of D15. The N-terminal sequence obtained for the 26 kDa protein (NH$_2$-Met-Ser-Pro-Ile-Leu-Gly-Tyr-Trp-Lys-—SEQ ID NO: 13) confirmed that it was GST.

(viii) Immunogenicity of the N-terminal rD15 fragment.

Figure 10:
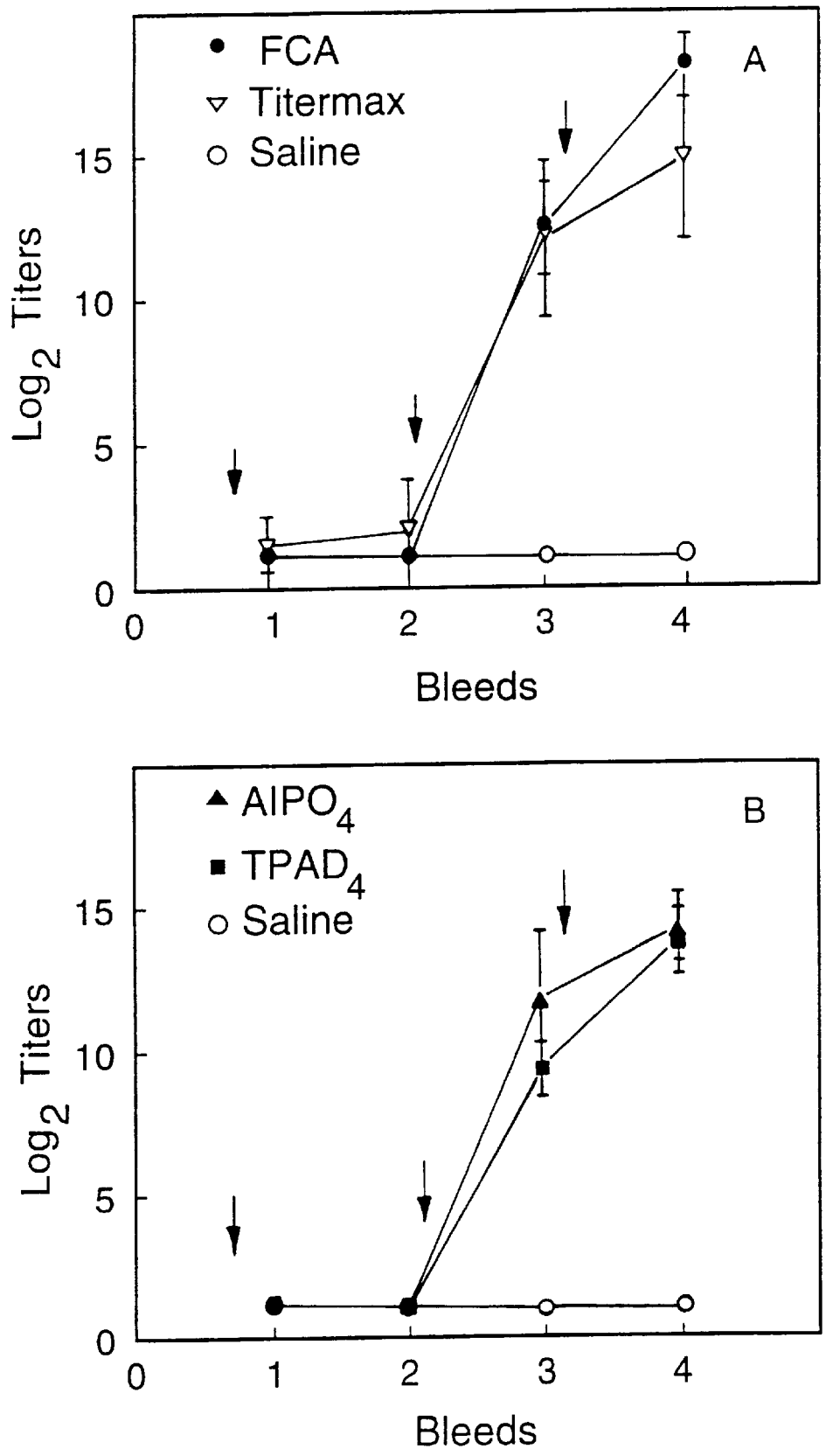
FIGS. 10A and 10B show guinea pig IgG antibody response to N-terminal rD15 fragment. The arrows indicate the immunization schedule. Bleeds were taken at 2, 4, 6 and 8 weeks. The bars represent the standard deviation.

The immunogenicity of the N-terminal rD15 fragment was tested in guinea pigs using various adjuvants. Using the immunization protocols described in FIG. 10, a 10 μg dose of N-terminal rD15 fragment induced a good booster response in guinea pigs with almost all the adjuvants tested. The highest anti-D15 IgG titer was observed in the group of guinea pigs immunized with N-terminal rD15 fragment in Freund's adjuvant. The second best adjuvant was Titermax (CytRx Inc.). The other two adjuvants, TPAD4 (tripalmityl-Cys-Ser-Glu$_4$) and AlPO$_4$ were equally potent.

(ix) Protective ability of the N-terminal rD15 fragment against *H. influenzae* type b challenge.

An in vivo challenge model for a assessing the protective abilities of antigen against diseases caused by Haemophilus is the infant rat model of bacteremia as described by Loeb 1987. The protective ability of the N-terminal rD15 fragment against *H. influenzae* type b challenge was examined in this rat model. As illustrated in Table 1, infant rats passively immunized with rabbit anti-N-terminal rD15 fragment antisera showed significantly lower bacteremia compared to those injected with pre-bleed sera.

Since passively transferred antisera against the N-terminal rD15 fragment were found to be protective in the infant rat model of bacteremia, it was of interest to identify the protective epitope(s) of this N-terminal rD15 fragment. The first nine overlapping peptides of the D15 protein as listed in Table 2 were chemically synthesized based upon the amino acid sequence derived from the sequence of the D15 gene from *H. influenzae* type b Ca (FIG. 1). These synthetic peptides were assessed for their reactivities with either rabbit or guinea pig antisera raised against purified N-terminal rD15 fragment by ELISAs. As shown in Table 3, both guinea pig and rabbit antisera reacted with a cluster of D15 peptides, including peptides D15-P4 to D15-P8 encompassing residues 93 to 209 of the D15 primary sequence.

Further studies were performed to determine whether the protection against *H. influenzae* type b observed using rabbit anti-D15 antisera in infant rats could be neutralized by D15 peptides. In the first experiment, a rabbit anti-N-terminal rD15 fragment antiserum was injected into a group of seven infant rats in the presence or absence of a mixture of the nine D15 peptides (D15-P2 to D15-P10). Animals in the positive control group were injected with the rabbit anti-N-terminal rD15 fragment antiserum mixed with purified D15 fragment and the negative control group was injected with a mixture of the nine peptides only. As illustrated in Table 4, infant rats passively immunized with a rabbit anti-N-terminal rD15 fragment antiserum (group #1) showed a significantly lower bacteremia level (3%, p=1.2×10$^{-7}$) compared to those in the negative control group (group #4, 100%), which was consistent with the previously obtained results. The protection mediated by the rabbit anti-N-terminal rD15 fragment antiserum was largely neutralized by the addition of purified N-terminal rD15 fragment (group #3, 64%), as indicated by the lack of significant difference in the bacteremia level between group #3 and group #4 (p=0.09). Although the addition of the mixture of nine D15 peptides only slightly neutralized the protection conferred by the antiserum (group #2, 13%) as compared to group #1 (3%), the difference in bacteria counts between these two groups was statistically significant (p=0.0037).

To more clearly define the protective epitope(s) of the N-terminal rD15 fragment, the above experiment was repeated with a mixture of five peptides (peptides D15-P4 to D15-P8) which were chosen for their strong reactivities with the rabbit anti-N-terminal rD15 fragment antiserum. The results obtained from this second experiment showed that the protection observed using rabbit anti-N-terminal rD15 fragment (Table 5, group #1) was completely blocked by the addition of this mixture of five peptides (Table 5, group #2, 106%, p=0.53×10$^{-8}$). These results strongly indicate that a cocktail of D15 synthetic peptides may be used as immunogens to induce protective antibodies against *H. influenzae*.

(x) Epitope prediction and peptide synthesis.

Figure 11:
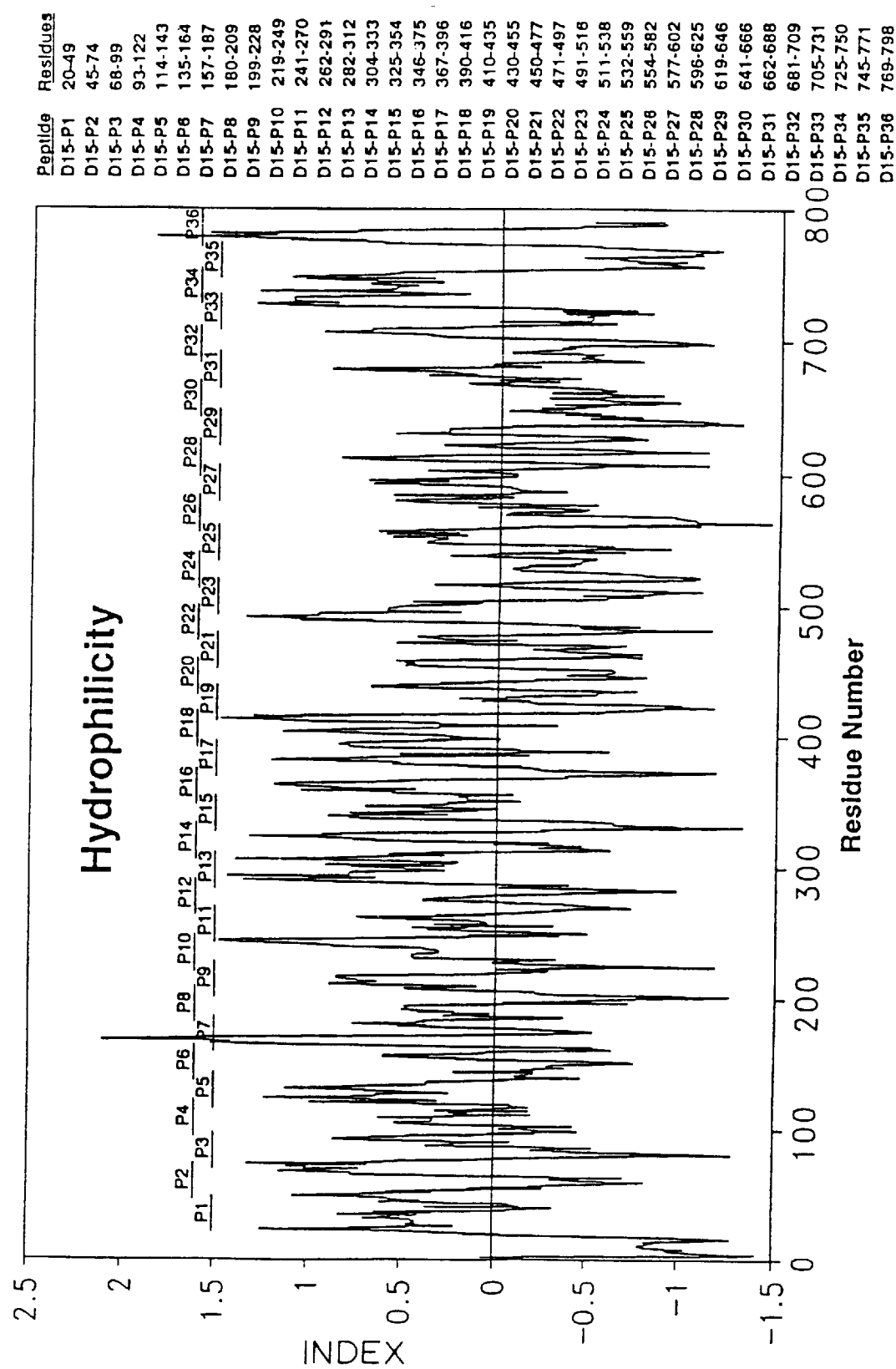
FIG. 11 shows the hydrophilicity plot of D15 established by using a window average across 7 residues according to Hope, 1986.

To map the immunodominant T-cell or B-cell epitopes of D15, overlapping synthetic peptides covering the entire D15 protein sequence (Table 2—SEQ ID NO: 14 to 49) were synthesized using the t-Boc solid-phase peptide synthesis as described in Example 15. The peptides were chosen based on their high index of hydrophillic β-turns estimated by secondary structure prediction analysis (FIG. 11). Such peptides are likely to be surface-exposed and antigenic. Peptides more than 25 residues in length were selected to better mimic native epitopes.

(xi) Identification and characterization of immunodominant epitopes of D15 using synthetic peptides.

To map the linear B-cell epitopes of D15, overlapping synthetic peptides representing the entire sequence of D15 were individually coated onto ELISA plates and probed with several anti-rD15 antisera as described in Example 19. The results are summarized in Table 6. Mouse antisera raised against rD15 reacted with all D15 peptides, but the major epitopes were located within peptides D15-P8 (residues 180–209—SEQ ID NO: 21), D15-P10 (residues 219–249—SEQ ID NO: 23), D15-P11 (residues 241–270—SEQ ID NO: 24), and D15-P26 (residues 554–582—SEQ ID NO: 39), respectively. Rabbit anti-D15 antisera recognized only peptides D15-P4 (residues 93–122—SEQ ID NO: 17), D15-P14 (residues 304–333—SEQ ID NO: 27) and D15-P36 (residues 769–798—SEQ ID NO: 49). Guinea pig antisera raised against rD15 reacted with peptides D15-P2 (residues 45–72—SEQ ID NO: 15), D15-P4 (residues 93–122—SEQ ID NO: 17), D15-P6 (residues 135–164—SEQ ID NO: 19), D15-P8 (residues 180–209—SEQ ID NO: 21), D15-P14 (residues 304–333—SEQ ID NO: 27), D15-P27 (residues 577–602—SEQ ID NO: 40). The immunodominant linear B-cell epitopes of D15 were thus found to be located within peptides D15-P4 (residues 93–122—SEQ ID NO: 17) and D15-P14 (residues 304–333—SEQ ID NO: 27), since these are the only two peptides recognized by rD15-specific antisera from all three animal species. These results indicate that the peptides containing the linear B-cell epitope sequences described above can be used as target antigens in, for example, diagnostic kits to detect the presence of anti-D15 and anti-*H. influenzae* antibodies in samples.

(xii) Identification and characterization of immunodominant T-cell epitopes of D15 using synthetic peptides.

The importance of cytokine networks in the immune and inflammatory responses in immunity and inflammation and their alteration in pathology is becoming more evident as new members of the cytokine family are identified and characterized. Mills et al. (1993) have recently reported that there is a rapid clearance of *B. pertussis* from the lungs of mice on challenge six weeks after respiratory infection or following two immunizations with the whole-cell pertussis vaccine. Spleen cells from these immunized mice were found to secrete high levels of IL-2 and IFN-γ and low levels of IL-5 in the presence of pertussis antigen (pertussis toxoid, filamentous haemagglutinin (FHA) and pertactin). This result suggests that Th1 cell (T-cells producing high levels of IL-2 and IFN-γ) proliferation is very important for recovering from respiratory infection. The generation of Th1 and Th2 cell subsets is regulated by the balance between different groups of cytokines, predominantly IL-12 and IL-4 (Trinchieri, 1993). IL-12 and IL-4 are responsible for Th1 and Th2 cells differentiation, respectively. One of the roles of Th2 cells in the immune system is to provide helper activity for eliciting high levels of antigen-specific antibodies following immunization. Antigens containing Th1 epitope(s) stimulate antigen-specific T-cells to produce high levels of IL-2 and IFN-γ, whereas Th2 epitope(s) induce high levels of IL-4 expression. Th0 epitope(s) stimulate the synthesis of IFN-γ and IL-4.

Little is known about the cellular immune response to outer membrane proteins of *H. influenzae* and its role in the protection against *H. influenzae* infection and diseases. To this end, the inventors performed studies of the cellular response elicited in mice following rD15 immunization. D15-specific T-cell epitopes were determined using D15 peptides and T-cell lines obtained from five BALB/c mice immunized with rD15 (see Example 23). The lymphocyte proliferative responses of the D15-specific T-cell lines to overlapping D15 peptides were determined in conventional cytokine assays as described in Example 24. The results summarized in Table 7, revealed that stimulation only with certain synthetic peptides elicited proliferative responses and the release of specific cytokines. Synthetic peptides corresponding to residues 114–143 (D15-P5—SEQ ID NO: 18) , 282–312 (D15-P13—SEQ ID NO: 26) and 577–602 (D15-P27 - SEQ ID NO: 40), and 219–249 (D15-P10—SEQ ID NO: 23), 262–291 (D15-P12—SEQ ID NO: 25), 390–416 (D15-P18—SEQ ID NO: 31), 410–435 (D15-P19—SEQ ID NO: 32) 554–582 (D15-P26—SEQ ID NO: 39), 596–625 (D15-P28—SEQ ID NO: 41), 725–750 (D15-P34—SEQ ID NO: 47) and 745–771 (D15-P35—SEQ ID NO: 48) were shown to be highly stimulatory for rD15-specific BALB/c Th0 cells and Th1 cells, respectively. Therefore, these immunodominant T-cell epitopes can be used as autologous carriers for PRP, and/or OMP B-cell epitopes to enhance their immunogenicity. The Th1 cell epitopes identified above may be useful in the *H. influenzae* vaccine formulations to induce *H. influenzae*-specific cellular immune responses.

(xiii) Immunogenicity of D15 peptides.

To determine whether synthetic D15 peptides were immunogenic free peptides were assessed individually for their immunogenicity. Rabbit and guinea pig anti-peptide antisera were tested for their reactivities with the immunizing peptides as well as with native D15 and rD15 by ELISA and immunoblotting. As shown in Table 8, all guinea pig anti-D15 peptide antisera except those raised against D15-P26 (SEQ ID NO: 39), D15-P29 (SEQ ID NO: 42), D15-P30 (SEQ ID NO: 43) and D15-P31 (SEQ ID NO: 44) were shown to be immunogenic by ELISAs. The induction of high titers of peptide-specific IgG antibodies by free peptides clearly indicates that most peptides contain both a functional T-helper determinant and a B-cell epitope(s). In addition, these anti-peptide antisera recognised D15 in the immunoblot assay. Since most peptides contain potent functional T-helper determinant(s) and induce strong IgG antibody responses in mammals, they are candidate immunogens for inclusion in an *H. influenzae* vaccine preparation. D15 peptide-specific antisera cross-reacted with D15 from non-typeable strains of *H. influenzae* as judged by immunoblotting. This finding indicates that immunogenic D15 peptides contain epitopes which are highly conserved among typeable and non-typeable strains of *H. influenzae*. In addition, polyclonal antibodies against these epitopes are useful to detect *H. influenzae* in biological samples.

Therefore, these conserved epitopes of D15 can be used either individually or in combination to prepare cross-reactive synthetic immunogens against typeable and non-typeable strains of *H. influenzae* and other bacteria that produce D15 protein, a fragment or an analog thereof. Peptides described above can be further polymerized, or modified with lipids as lipopeptides, or linked to polysaccharides including PRP as synthetic glycopeptide or lipoglycopeptide conjugates to produce alternate vaccines. These vaccines can be used to immunize against diseases caused by *H. influenzae* when administered to mammals, for example, by the intramuscular or parenteral route, or when delivered using microparticles, capsules, liposomes and targeting molecules, such as toxins or fragments thereof, and antibodies, to cells of the immune system or mucosal surfaces.

(xiv) Utility of D15 as carrier protein for the production of glycoconjugates.

To determine whether D15 may serve both as a protective antigen and a carrier, D15-PRP conjugation experiments were performed as described in Example 14. The D15-PRP conjugates were found to be highly immunogenic in rabbits and able to elicit both anti-D15 and anti-PRP IgG antibody responses as judged by D15-specific ELISA and PRP-BSA immunoassay (Table 9). These results clearly demonstrate the practical utility of D15 as a carrier protein for glycoconjugation technology.

In preferred embodiments of the present invention, the carrier function of D15 can be generally utilized to prepare chimeric molecules and conjugate vaccines against pathogenic bacteria, including encapsulated bacteria. Thus, the glycoconjugates of the present inventions may be applied to vaccinations to confer protection against infection with any bacteria having polysaccharide antigens, including, for example, *Haemophilus influenzae, Streptococcus pneumoniae, Escherichia coli, Neisseria meningitidis, Salmonella typhi, Streptococcus mutans, Cryptococcus neoformans, Klebsiella, Staphylococcus aureus* and *Pseudomonas aeruginosa*.

In another embodiment, the carrier function of D15 may be used, for example, to induce immunity toward abnormal polysaccharides of tumor cells, or to produce anti-tumor antibodies that can be conjugated to chemotherapeutic or bioactive agents.

Accordingly, the present invention provides the primary sequence and the preparation of an antigen (D15) of *H. influenzae* that can be used in the prevention and diagnosis of diseases caused by Haemophilus. In particular, the inventors discovered that recombinant D15 or its fragments, can elicit protective antibody responses against live *H. influenzae* type b bacteria challenge. Thus, the present inventions have utility in vaccines. The invention also discloses the nucleotide sequences of the D15 genes isolated from both *H. influenzae* type b strains and non-typeable isolates. The DNA segments encoding D15 are disclosed and show minor polymorphism in both their nucleotide and derived amino acid sequences (FIGS. 1F and 3). These DNA segments may be used to provide an immunogen essentially free from other *H. influenzae* antigens (such as PRP and lipooligosaccharides (LOS)) through the application of recombinant DNA technology. The present disclosure further provides novel techniques which can be employed for preparing essentially pure D15 or fragments thereof, as well as functional analogs. The recombinant D15 protein, fragment or analog thereof, may be produced in a suitable expression system, such as *E. coli*, Haemophilus Bordetella, Bacillus, Fungi, Yeast, Baculovirus, Poxvirus, vaccinia or mammalian expression systems.

In one embodiment, the present invention concerns the process of preparing vaccine compositions which include purified recombinant D15 protein (rD15) or rD15 fragments that are immunologically cross-reactive with native D15. In particular, the gene coding the entire D15 protein and a DNA segment encoding an N-terminal rD15 fragment fused to the glutathione-S-transferase gene have been constructed and expressed in *E. coli*. The expressed rD15 protein and its fragments were found to cross-react immunologically with the native D15 antigen isolated from both typeable and non-typeable *H. influenzae* isolates and thus represent cross-reactive immunogens for inclusion in a vaccine against diseases caused by *H. influenzae*. Furthermore, Haemophilus convalescent serum recognized D15 purified from *H. influenzae* as described herein, rD15 and N-terminal rD15 fragment.

In another embodiment, the present invention provides a gene coding for the outer membrane protein D15 from *H. influenzae* having the specific nucleotide sequences described herein or ones substantially homologous thereto (i.e. those which hybridize under stringent conditions to such sequences), for genetically engineering hybrids or chimeric proteins containing a D15 fragment fused to another polypeptide or protein or a polysaccharide, such as *H. influenzae* outer membrane proteins, for example, P1, P2, or P6 or PRP. As a result, the hybrids, chimeric proteins or glycoconjugates may have higher protectivity against *H. influenzae* than D15, or P1, or P2, or P6, or PRP alone.

Thus, D15 outer membrane protein can function both as a protective antigen and as a carrier in a conjugate vaccine to provide autologous T-cell priming, wherein the hapten part of the conjugate is the capsular polysaccharide moiety (PRP) of *H. influenzae*. This D15-carbohydrate conjugate can elicit antibodies against both PRP and D15, and thus should enhance the level of protection against *H. influenzae*-related diseases, especially in infants.

In another embodiment, the present invention comprises an essentially pure form of at least one protein or peptide containing an amino acid sequence corresponding to at least one antigenic determinant of D15, which peptide is capable of eliciting polyclonal antibodies against *H. influenzae* in mammals. These D15-specific antibodies are useful in test kits for detecting the presence of *H. influenzae* in biological samples. The peptides can have, for example, the amino acid sequences corresponding to residues 20–49, 45–74, 68–99, 93–122, 114–143, 135–164, 157–187, 180–209, 199–228, 219–249, 241–270, 262–291, 282–312, 304–333, 325–354, 346–375, 367–396, 390–416, 410–435, 430–455, 450–477, 471–497, 491–516, 511–538, 532–559, 554–582, 577–602, 596–625, 619–646, 641–666, 662–688, 681–709, 705–731, 725–750, 745–771, 769–798 (SEQ ID NOS: 14 to 49) of the D15 protein of the *H. influenzae* type b Ca strain, respectively, as set forth in Table 2 below, or any portion, variant or mutant thereof which retains immunogenicity.

In yet another embodiment, the present invention provides pure native D15 protein, extracted and chromatographically purified from cultures of *H. influenzae* typeable or non-typeable isolates. The novel procedures involves extraction of the D15 protein from cell paste by techniques known for other outer membrane proteins, with an aqueous detergent solution, followed by purification by centrifugation and chromatography. The purified native D15 antigen can be used to immunize mammals against diseases caused by *H. influenzae*, for example, by the intramuscular or the parenteral routes, or by delivering it using microparticles, capsules, liposomes and targeting molecules, such as toxins or fragments thereof, and antibodies.

Another aspect of the present invention is that the D15 outer membrane protein, fragments or analogs thereof or peptides corresponding to portions of D15 may be components of a multivalent vaccine against otitis media. This multivalent vaccine comprises at least one immunogenic determinant of D15 as described herein, along with at least one protective antigen isolated from *Streptococcus pneumoniae, Branhamella* (Moroxella) *catarrhalis, Staphylococcus aureus*, or respiratory syncytial virus, in the presence or absence of adjuvant.

The D15 peptides (Table 2) or any portion, variant or mutant thereof, can easily be synthesized either manually or with a commercially available peptide synthesizer, such as the Applied Biosystems Model 430A synthesizer.

It is clearly apparent to one skilled in the art, that the various embodiments of the present invention have many applications in the fields of vaccination, diagnosis, and treatment of diseases caused by Haemophilus infections, and the generation of immunological reagents. A further non-limiting discussion of such uses is further presented below.

1. Vaccine preparation and use

Immunogenic compositions, suitable for use as vaccines, may be prepared from immunogenic D15 outer membrane protein, fragments or analogs thereof and/or peptides corresponding to portions of D15 as disclosed herein. The vaccine elicits an immune response which produces antibodies, including anti-D15 outer membrane protein antibodies and antibodies against D15 that are opsonizing or bactericidal. Should the vaccinated subject be challenged by Haemophilus, the antibodies bind to the D15 outer membrane protein and thereby inactivate the bacterium. opsonizing and bactericidal antibodies represent examples of antibodies useful in protection against disease.

Vaccines containing peptides are generally well known in the art, as exemplified by U.S. Pat. Nos. 4,601,903; 4,599,231; 4,599,230; and 4,596,792; all of which references are incorporated herein by reference. As to any further reference to patents and references in this description, they are as well hereby incorporated by reference without any further notice to that effect. Vaccines may be prepared as injectables, as liquid solutions or emulsions. The D15 outer membrane protein, fragments or analogs thereof or peptides corresponding to portions of D15 may be mixed with physiologically-acceptable excipients which are compatible with the D15 outer membrane protein, fragments, analogs or peptides. Excipients may include, water, saline, dextrose, glycerol, ethanol, and combinations thereof. The vaccine may further contain minor amounts of auxiliary substances such as wetting or emulsifying agents, pH buffering agents, or adjuvants to enhance the effectiveness of the vaccines. Methods of achieving adjuvant effect for the vaccine includes use of agents, such as aluminum hydroxide or phosphate (alum), commonly used as 0.05 to 0.1 percent solution in phosphate buffered saline. Vaccines may be administered parenterally, by injection subcutaneously or intramuscularly. Alternatively, other modes of administration including suppositories and oral formulations may be desirable. For suppositories, binders and carriers may include, for example, polyalkalene glycols or triglycerides. Oral formulations may include normally employed incipients such as, for example, pharmaceutical grades of saccharine, cellulose, magnesium carbonate and the like. These compositions take the form of solutions, suspensions, tablets, pills, capsules, sustained release formulations or powders and contain 10–95% of the D15 outer membrane protein, fragment analogs and/or peptides.

The vaccines are administered in a manner compatible with the dosage formulation, and in an amount which is therapeutically effective, protective and immunogenic. The quantity to be administered depends on the subject to be treated, including, for example, the capacity of the individual's immune system to synthesize antibodies, and if needed, to produce a cell-mediated immune response. Precise amounts of active ingredient required to be administered depend on the judgment of the practitioner. However, suitable dosage ranges are readily determinable by one skilled in the art and may be of the order of micrograms of the D15 outer membrane protein, analog, fragment and/or peptides. Suitable regimes for initial administration and booster doses are also variable, but may include an initial administration followed by subsequent administrations. The dosage of the vaccine may also depend on the route of administration and varies according to the size of the host.

The nucleic acid molecules encoding the D15 outer membrane protein of the present invention may also be used directly for immunization by administration of the DNA directly, for example, by injection for genetic immunization or by constructing a live vector, such as Salmonella, BCG, adenovirus, poxvirus or vaccinia. A discussion of some live vectors that have been used to carry heterologous antigens to the immune system are discussed in, for example, O'Hagan (1992). Processes for the direct injection of DNA into test subjects for genetic immunization are described in, for example, Ulman et al. (1993).

The use of peptides in vivo may first require their chemical modification since the peptides themselves may not have a sufficiently long serum and/or tissue half-life. Such chemically modified peptides are referred to herein as peptide analogs. The term peptide analog extends to any functional chemical equivalent of a peptide characterized by its increased stability and/or efficacy in vivo or in vitro in respect of the practice of the invention. The term peptide analog is also used herein to extend to any amino acid derivative of the peptides as described herein. Peptide analogs contemplated herein are produced by procedures that include, but are not limited to, modifications to side chains, incorporation of unnatural amino acids and/or their derivatives during peptide synthesis and the use of cross-linkers and other methods which impose conformational constraint on the peptides or their analogs.

Examples of side chain modifications contemplated by the present invention include modification of amino groups, such as by reductive alkylation by reaction with an aldehyde followed by reduction with $NaBH_4$; amidation with methylacetimidate; acetylation with acetic anhydride; carbamylation of amino groups with cyanate; trinitrobenzylation of amino groups with 2, 4, 6, trinitrobenzene sulfonic acid (TNBS); alkylation of amino groups with succinic anhydride and tetrahydrophthalic anhydride; and pyridoxylation of lysine with pyridoxa-5'-phosphate followed by reduction with $NaBH_4$.

The guanidino group of arginine residues may be modified by the formation of heterocyclic condensation products with reagents such as 2, 3-butanedione, phenylglyoxal and glyoxal.

The carboxyl group may be modified by carbodiimide activation via o-acylisourea formation followed by subsequent derivatisation, for example, to a corresponding amide.

Sulfhydryl groups may be modified by methods, such as carboxymethylation with iodoacetic acid or iodoacetamide; performic acid oxidation to cysteic acid; formation of mixed disulphides with other thiol compounds; reaction with maleimide; maleic anhydride or other substituted maleimide; formation of mercurial derivatives using 4-chloromercuribenzoate, 4-chloromercuriphenylsulfonic acid, phenylmercury chloride, 2-chloromercuric-4-nitrophenol and other mercurials; carbamylation with cyanate at alkaline pH.

Tryptophan residues may be modified by, for example, oxidation with N-bromosuccinimide or alkylation of the indole ring with 2-hydroxy-5-nitrobenzyl bromide or sulphonyl halides. Tryosine residues may be altered by nitration with tetranitromethane to form a 3-nitrotyrosine derivative.

Modification of the imidazole ring of a histidine residue may be accomplished by alkylation with iodoacetic acid derivatives or N-carbethoxylation with diethylpyrocarbonate.

Examples of incorporating unnatural amino acids and derivatives during peptide synthesis include, but are not limited to, use of norleucine, 4-amino butyric acid, 4-amino-3-hydroxy-5-phenylpentanoic acid, 6-aminohexanoic acid, t-butylglycine, norvaline, phenylglycine, ornithine, sarcosine, 4-amino-3-hydroxy-6-methylheptanoic acid, 2-thienyl alanine and/or D-isomers of amino acids.

2. Immunoassays

The D15 outer membrane protein, analog, fragment and/or peptides of the present invention are useful as antigens in immunoassays, including enzyme-linked immunosorbent assays (ELISA), RIAs and other non-enzyme linked antibody binding assays or procedures known to the art for the detection of anti-bacterial, Haemophilus, D15 and/or peptide antibodies. In ELISA assays, the D15 outer membrane protein, fragment or analogs thereof and/or peptides corresponding to portions of D15 outer membrane protein are immobilized onto a selected surface, for example, a surface exhibiting a protein affinity, such as the wells of a polystyrene microtiter plate. After washing to remove incompletely adsorbed D15 outer membrane protein, analog, fragment and/or peptides, a nonspecific protein, such as bovine serum albumin (BSA) or casein, that is known to be antigenically neutral with regard to the test sample may be bound to the selected surface. This allows for blocking of nonspecific adsorption sites on the immobilizing surface and thus decreases the background caused by nonspecific bindings of antisera onto the surface. Normally, the peptides employed herein are in the range of 12 residues and up and preferably 14 to 30 residues.

The immobilizing surface is then contacted with a sample such as clinical or biological materials to be tested in a manner conducive to immune complex (antigen/antibody) formation. This may include diluting the sample with diluents, such as BSA, bovine gamma globulin (BGG) and/or phosphate buffered saline (PBS)/Tween. The sample is then allowed to incubate for from 2 to 4 hours, at temperatures, such as of the order of 25° to 37° C. Following incubation, the sample-contacted surface is washed to remove non-immunocomplexed material. The washing procedure may include washing with a solution such as PBS/ Tween, or a borate buffer.

Following formation of specific immunocomplexes between the test sample and the bound D15 outer membrane protein, analog, fragment and/or peptides, and subsequent washing, the occurrence, and even amount, of immunocomplex formation may be determined by subjecting the immunocomplex to a second antibody having specificity for the first antibody. If the test sample is of human origin, the second antibody is an antibody having specificity for human immunoglobulins and, in general, IgG. To provide detecting means, the second antibody may have an associated activity, such as an enzymatic activity that will generate, for example, a color development upon incubating with an appropriate chromogenic substrate. Quantification may then achieved by measuring the degree of color generation using, for example, a visible spectra spectrophotometer.

3. Use of sequences as hybridization probes

The nucleotide sequences of the present invention, comprising the sequence of the D15 outer membrane protein, now allow for the identification and cloning of the D15 outer membrane protein genes from any species of Haemophilus and other bacteria that have genes encoding D15 outer membrane proteins.

The nucleotide sequences comprising the sequence encoding the D15 outer membrane protein of the present invention are useful for their ability to selectively form duplex molecules with complementary stretches of other D15 genes. Depending on the application, a variety of hybridization conditions may be employed to achieve varying degrees of selectivity of the probe toward the other D15 genes. For a high degree of selectivity, stringent conditions are used to form the duplexes, such as low salt and/or high temperature conditions, such as provided by 0.02 M to 0.15 M NaCl at temperatures of between about 50° C. to 70° C. For some applications, less stringent hybridization conditions are required such as 0.15 M to 0.9 M salt, at temperatures ranging from between about 20° C. to 55° C. Hybridization conditions can also be rendered more stringent by the addition of increasing amounts of formamide, to destabilize the hybrid duplex. Thus, particular hybridization conditions can be readily manipulated, and will generally be a method of choice depending on the desired results.

In a clinical diagnostic embodiment, the nucleic acid sequences of the D15 outer membrane protein genes of the present invention may be used in combination with an appropriate means, such as a label, for determining hybridization. A wide variety of appropriate indicator means are known in the art, including radioactive, enzymatic or other ligands, such as avidin/biotin, which are capable of providing a detectable signal. In some diagnostic embodiments, an enzyme tag, such as urease, alkaline phosphatase or peroxidase, instead of a radioactive tag may be used. In the case of enzyme tags, calorimetric indicator substrates are known which can be employed to provide means visible to the human eye or spectrophotometrically, to identify specific hybridization with samples containing D15 gene sequences.

The nucleic acid sequences of D15 genes of the present invention are useful as hybridization probes in solution hybridizations and in embodiments employing solid-phase procedures. In embodiments involving solid phase procedures, the test DNA (or RNA) from samples, such as clinical samples, including exudates, body fluids (e. g., serum, amniotic fluid, middle ear effusion, sputum, bronchoalveolar lavage fluid) or even tissues, is adsorbed or otherwise affixed to a selected matrix or surface. The fixed, single-stranded nucleic acid is then subjected to specific hybridization with selected probes comprising the nucleic acid sequences of the D15 genes or fragments thereof of the present invention under desired conditions. The selected conditions will depend on the particular circumstances based on the particular criteria required depending on, for example, on the G+C contents, type of target nucleic acid, source of nucleic acid, size of hybridization probe etc. Following washing of the hybridization surface so as to remove non-specifically bound probe molecules, specific hybridization is detected, or even quantified, by means of the label. The selected probe should be at least 18 bp and may be in the range of 30 bp to 90 bp long.

4. Expression of the D15 outer membrane protein genes

Plasmid vectors containing replicon and control sequences which are derived from species compatible with the host cell may be used for the expression of the D15 outer membrane protein genes in expression systems. The vector ordinarily carries a replication site, as well as marking sequences which are capable of providing phenotypic selection in transformed cells. For example, E. coli may be transformed using pBR322 which contains genes for ampicillin and tetracycline resistance and thus provides easy means for identifying transformed cells. The pBR322 plasmid, or other microbial plasmid or phage must also contain, or be modified to contain, promoters which can be used by the microbial organism for expression of its own proteins.

In addition, phage vectors containing replicon and control sequences that are compatible with the host microorganism can be used as a transforming vector in connection with these hosts. For example, the phage in lambda GEM™-11 may be utilized in making recombinant phage vectors which can be used to transform host cells, such as E. coli LE392.

Promoters commonly used in recombinant DNA construction include the β-lactamase (penicillinase) and lactose promoter systems and other microbial promoters, such as the T7 promoter system. Details concerning the nucleotide sequences of promoters are known, enabling a skilled worker to ligate them functionally with plasmid vectors. The particular promoter used generally is a matter of choice depending upon the desired results. Hosts that are appropriate for expression of the transferrin receptor genes, fragment analogs or variants thereof include E. coli, Bacillus, Haemophilus, Bordetella, fungi, yeast, or the baculovirus and poxvirus expression systems may be used.

In accordance with an aspect of this invention, it is preferred to make the D15 outer membrane protein, fragment or analog thereof by recombinant methods, particularly since the naturally occurring D15 protein as purified from culture of a species of Haemophilus may include undesired contaminants, including trace amounts of toxic materials. This problem can be avoided by using recombinantly produced D15 outer membrane protein in heterologous systems which can be isolated from the host in a manner to minimize toxins in the purified material. Particularly desirable hosts for expression in this regard include Gram positive bacteria which do not have lipopolysaccharide (LPS) and are, therefore, endotoxin free. Such hosts include species of Bacillus and may be particularly useful for the production of non-pyrogenic D15 outer membrane protein, fragments or analogs thereof.

BIOLOGICAL DEPOSITS

Certain plasmids that contain at least a portion coding for a D15 outer membrane protein from strains of Haemophilus influenzae that are described and referred to herein have been deposited with the American Type Culture Collection (ATCC) located at Rockville, Md. USA pursuant to the Budapest Treaty and prior to the filing of this application. Samples of the deposited plasmids will become available to the public upon grant of a patent based upon this United States patent application. The invention described and claimed herein is not to be limited in scope by plasmids deposited, since the deposited embodiment is intended only as an illustration of the invention. Any equivalent or similar plasmids that encode similar or equivalent antigens as described in this application are within the scope of the invention.

DEPOSITE SUMMARY

| Clone | H. influenzae | ATCC Designation | Date Deposited |
| --- | --- | --- | --- |
| DS-712-2-1 | Eagan | 75604 | November 4, 1993 |
| JB-1042-5-1 | SB33 | 75606 | November 4, 1993 |
| DS-880-1-2 | Eagan | 75605 | November 4, 1993 |

The above disclosure generally describes the present invention. A more complete understanding can be obtained by reference to the following specific Examples. These Examples are described solely for purposes of illustration and are not intended to limit the scope of the invention. Although specific terms have been employed herein, such terms are intended in a descriptive sense and not for purposes of limitations. Immunological and recombinant DNA methods may not be explicitly described in this disclosure but are well within the scope of those skilled in the art.

EXAMPLES

Methods of molecular genetics, protein biochemistry, and immunology used but not explicitly described in this disclosure and these EXAMPLES are amply reported in the scientific literature and are well within the ability of those skilled in the art.

Example 1

This Example illustrates the cloning and sequencing of the D15 genes.

Genomic DNA was purified from the *Haemophilus influenzae* type b strain Ca by lysis of the bacteria with pronase and sodium dodecylsulphate followed by phenol extraction and isopropanol precipitation, according to Berns and Thomas, 1965. The DNA was then partially digested with EcoRI and the DNA fraction containing 6–10 kb fragments was isolated following electrophoresis in low-melting point agarose. These fragments were ligated into a lambda gt11 Ampl vector (Thomas and Rossi, 1986) and cloned as a lysogen into *E. coli* strain BTA282. Recombinant clones were selected for their ampicillin resistance conferred by the vector. To identify clones producing *H. influenzae* type b antigen, the clones were replica-plated on nitrocellulose filters and duplicate colonies induced for expression by temperature switch to 42° C. for 2 hours. Colonies were lysed by wetting the filters with 1% sodium dodecylsulphate (SDS). The filters were then placed into a chloroform-saturated atmosphere for 15 min. The filters were then assayed by colony radioimmuno-assay using a hyperimmune rabbit anti-*H. influenzae* type b antiserum absorbed with *E. coli* lysate for antigen expression. Clones shown by autoradiography to be producing *H. influenzae* type b antigens were further purified and their replicates retested for reactivity with the hyperimmune anti-*H. influenzae* type b antiserum. The antiserum absorbed with $10^{10}$ intact *H. influenzae* type b bacteria (strain Ca) was used as negative control.

A number of clones were identified which reacted with the unabsorbed, but not with the absorbed antiserum and were further analysed. One of the clones, D15, was purified, grown and found to produce a *H. influenzae* type b antigen which migrated in sodium dodecyl sulphate polyacrylamide gels with a $M_r$ of about 80 kDa. Lysates from the D15 clone were coupled to Sepharose™ 4B gel and used to affinity-purify anti-D15 antibodies. This procedure is described by Thomas et al, 1990, except that the apparent $M_r$ was initially reported to be about 103 kDa. The affinity-purified antibodies to D15 were then shown to react with an $M_r$ 80 kDa protein in an outer membrane protein preparation of *H. influenzae* type b (sarcosyl insoluble fraction—Carlone et al, 1986). Radioimmuno dot blots and Western blots analyses of membrane preparations from both type b and nontypeable *Haemophilus influenzae* strains showed that affinity-purified anti-D15 antibodies reacted with all isolates. These antibodies were found to be capable of passively protecting infant rats from bacteraemia following intraperitoneal injection of live *H. influenzae* type b bacteria. The specificity of the protection was confirmed by absorbing out the protective activity of anti-D15 antibodies with a lysate of *E. coli* expressing D15 coupled to Sepharose. The protection studies have been described in detail by Thomas et al, 1990.

DNA from the lambda gt11 Ampl D15 phage was isolated and a 5.7 kb fragment was released by EcoRI digestion. This fragment was subcloned into pUC19 and the resulting plasmid transformed into *E. coli* HB101. Recombinant bacteria were found to produce the expected $M_r$ 80 kDa *H. influenzae* type b antigen when examined by Western blotting. The insert DNA was then characterised by restriction endonuclease mapping. A 2.8 kb HindIII-EcoRI fragment was subcloned into pUC19 to generate plasmid pUC19/D15, which was transformed into *E. coli* HB101. The recombinant bacteria expressed a $M_r$ 80 kD protein recognized by D15-specific antibodies on Western blot analysis of *E. coli* lysates.

Plasmid DNA was prepared from two individual colonies of recombinant *E. coli* HB101 containing the pUC19/D15 plasmid using standard techniques. oligonucleotide sequencing primers of 17–25 bases in length were synthesized on the ABI model 380B DNA Synthesizer and purified by chromatography using OPC cartridges obtained from Applied Biosystems Inc., and used in accordance with the manufactures recommendations. Samples were sequenced using the ABI model 370A DNA Sequencer and dye terminator chemistry according to manufacturers' protocols. This sequence analysis indicated that the D15 gene contains an open reading frame encoding for 789 amino acids, including a putative signal sequence (FIG. 1). The derived amino acid sequence was found to contain the sequence of an internal peptide obtained by thrombin digestion of native D15 that had been chemically determined. The amino acid composition of D15 derived from the D15 gene sequence was comparable (within experimental error) to that of the native protein as determined by amino acid analysis.

Example 2

This Example illustrates the preparation of chromosomal DNA from *Haemophilus influenzae* strains Eagan, MinnA, SB33, and PAK 12085.

*H. influenzae* strains were grown on Mueller-Hinton agar or in brain heart infusion broth as described by Harkness et al., 1992.

Eagan chromosomal DNA

Bacteria from 50 mL of culture were pelleted by centrifugation at 5,000 rpm, 20 minutes, 4° C. The pellet was resuspended in 25 mL TE (10 mM Tris, 1 mM EDTA, pH 8.0) and 2×5 mL aliquots used for chromosomal DNA preparation. To each aliquot were added 0.6 mL of 10% sarkosyl and 0.15 mL of 20 mg/mL proteinase K and the samples incubated at 37° C. for 1 hour. The lysate was extracted once with Tris-saturated phenol (pH 8.0) and three times with chloroform:isoamyl alcohol (24:1). The aqueous phase was pooled for a final volume of 7 mL. Then, 0.7 mL of 3M sodium acetate (pH 5.2) and 4.3 mL of isopropanol were added to precipitate the DNA which was spooled, rinsed with 70% ethanol, dried, and resuspended in 1 mL of water.

MinnA, SB33, and PAK 12085 chromosomal DNA

Bacteria from 50 mL of culture were pelleted by centrifugation at 5,000 rpm for 15–20 minutes, at 4° C., in a Sorvall RC-3B centrifuge. The cell pellet was resuspended in 10 mL of TE (10 mM Tris-HCl, 1 mM EDTA, pH 7.5), pronase was added to 500 µg/mL, and SDS to 1%. The sample was incubated at 37° C. for about 4 hours until a clear lysate was obtained. The lysate was extracted once with Tris-saturated phenol, once with Tris-saturated phenol/chloroform (1:1), and once with chloroform. The final aqueous phase was dialysed for 24 hours against 2×500 mL of 1M NaCl at 4° C., changing the buffer once, and for 24 hours against 2×500 mL of TE at 4° C., changing the buffer once. The final dialysate was aliquotted for subsequent use.

Example 3

This Example illustrates the preparation of *Haemophilus influenzae* chromosomal libraries.

*H. influenzae* Eagan and PAK 12085 chromosomal DNAs were digested with Sau3A I (0.5 unit/10 µg DNA) at 37° C. for 15 minutes and size-fractionated by agarose gel electrophoresis. Gel slices corresponding to DNA fragments of 15–23 kb were excised and DNA was electroeluted overnight in dialysis tubing containing 3 mL of TAE (40 mM Tris-acetate, 1 mM EDTA, pH 8.0) at 14 V. The DNA was precipitated twice and resuspended in water before overnight ligation with EMBL3 BamH I arms (Promega). The ligation mixture was packaged using the Lambda in vitro packaging kit (Amersham) according to the manufacturer's instructions and plated onto *E. coli* NM539 cells. The library was titrated, then amplified and stored at 4° C. under 0.3% chloroform.

MinnA chromosomal DNA (10 µg) was digested with Sau3A I (40 units) for 2, 4, and 6 minutes then size-fractionated on a 10–30% sucrose gradient in TNE (20 mM Tris-HCl, 5mM NaCl, 1 mM EDTA, pH 8.0). Fractions containing DNA fragments >5 kb were pooled and precipitated. In a second experiment, chromosomal DNA (2.6 µg) was digested with Sau3A I (4 units) for 1, 2, and 3 minutes and size- fractionated by preparative agarose gel electrophoresis. Gel slices containing DNA fragments of 10–20 kb were excised and DNA extracted by a standard freeze/thaw technique. The size-fractionated DNA from the two experiments was pooled for ligation with BamH I arms of EMBL3 (Promega). The ligation mix was packaged using the Gigapack II packaging kit (Amersham) and plated on *E. coli* LE392 cells. The library was titrated, then amplified and stored at 4° C. under 0.3% chloroform.

SB33 chromosomal DNA (20 µg) was digested with Sau3A I (40 units) for 2, 4, or 6 minutes and size-fractionated on a 10–30% sucrose gradient in TNE (20 mM Tris-HCl, 5 mM NaCl, 1 mM EDTA, pH 8.0). Fractions containing fragments >5 kb were pooled. In a second experiment, SB33 chromosomal DNA (2 µg) was digested with Sau3A I (4 units) for 2, 4, or 6 minutes and size-fractionated on a preparative agarose gel. Gel slices containing DNA fragments of 10–20 kb were excised and DNA extracted by a standard freeze/thaw technique. The size-fractionated DNA from both experiments was pooled for ligation with BamH I arms of EMBL3 (Promega). The ligation mix was packaged using the Gigapack II packaging kit and plated on LE392 cells. The library was titrated, then amplified and stored at 4° C. under 0.3% chloroform.

Example 4

This Example illustrates the screening of the DNA libraries.

The Eagan, MinnA, SB33, and PAK 12085 DNA libraries were plated onto LE392 cells on NZCYM plates using 0.7% top agarose in NZCYM as overlay. Plaque lifts onto nitrocellulose filters were performed following standard procedures, and filters were processed and hybridized with a digoxigenin-labelled D15 probe prepared according to the manufacturer's specifications (Boehringer Mannheim). The probe was the EcoR I/Hind III fragment from pUC19/D15 containing the entire Ca D15 gene (FIG. 2). Putative plaques were plated and submitted to a second round of screening using the same procedures. Phage DNA was prepared from 500 mL of culture using standard techniques, the insert DNA was excised by Sal I digestion, and cloned into pUC to generate clones DS-712-2-1 (Eagan), DS-691-1-5 (MinnA), JB-1042-5-1 (SB33), and JB-1042-9-4 (PAK 12085), which are shown in FIG. 2.

The nucleotide sequences of the D15 genes from *H. influenzae* type b strains Eagan and MinnA the non-typeable *H. influenzae* strains SB33 and PAK 12085 were determined and compared with that for strain Ca, as seen in FIGS. 1b, 1C, 1D, 1E and 1F. The desired amino acid sequence are shown in FIGS. 1B, 1C, 1D and 1E and are compared with the amino acid sequence of the D15 protein of *H. influenzae* type b Ca (FIG. 3).

Example 5

This Example illustrates the expression of rD15 protein in *E. coli*.

A 2.8 kb fragment HindIII-EcoRI was subcloned into pUC19 and this pUC19/D15 plasmid was transformed into *E. coli* HB101. Upon induction, the positive clones expressed an 80 kDa protein which was recognized by D15-specific antisera on Western blot analysis. A HindIII-Pst I fragment was also subcloned into pUC19 and shown to express a 67 kDa protein. According to the restriction map, this 67 kDa protein corresponded to a C-terminal truncated D15 protein. On Western blot analysis, this truncated D15 was still recognized by the D15-specific antisera.

Plasmids to express the D15 gene of the non-typeable strain SB33 in *E. coli* were constructed. Plasmid JB-1042-5-1 containing the SB33 D15 gene and its flanking regions, was digested with EcoR I and Hind III and the 3 kb D15 insert subcloned into pUC to give plasmid pRY-60-1 (FIG. 4). Appropriate oligonucleotides were synthesized to restore the native D15 sequence between the ATG codon of the expression plasmid pT7–7 and the BsrF I site within the D15 gene. These oligonucleotides had the following sequence:

```
                  Nde
5'-  TATGGCACCTTTTGTGGCAAAAGATATTCGTGTGGATGGTGTTCAAGGTG

ACCGTGGAAAACACCGTTTTCTATAAGCACACCTACCACAAGTTCCACTGAATCT

ACTTAGAATCAACAAACCGAGCAAGTTTACCTGTTCGTG - SEQ ID NO: 50

TGGTTGTTTAGGCTCGTTCAAATGGACAAGCACGGCC-5'- SEQ ID NO: 51
                                 BsrF I
```

Plasmid pRY-60-1 was digested with EcoR I and BsrF I and the DNA fragment containing most of the D15 gene was purified. pUC was digested with EcoR I and Nde I and the vector fragment purified. A multi-component ligation between the pUC and D15 fragments and the oligonucleotides generated plasmid DS-860-1-1 which contains a D15 sequence without a promoter. pT7-7 was digested with Nde I and EcoR I and the vector fragment purified. DS-860-1-1 was digested with Nde I and EcoR I and the D15 insert was purified and ligated with the T7-7 vector generating plasmid DS-880-1-2 (FIG. 4).

The plasmid constructions were performed using E. coli JM109 as host. For expression, plasmid DS-880-1-2 was transformed into E. coli BL21/DE3, BL21/DE3/pLysS, or JM109/DE3 cells. Transformation of the cells was performed using either calcium chloride-treated competent cells or by electroporation using a BioRad electroporator. Transformed cells were grown in YT, M9, or NZCYM media and induced with IPTG or other inducing agents.

Example 6

This Example illustrates the construction and expression of the GST-D15 fragment hybrid gene in E. coli.

A forward sense primer (primer 1) 5'-GGGGAATTCCAAAAGATGTTCGT (SEQ ID NO: 52) and a reverse antisense primer CACGAATTCCCTGCAAATC-5' (primer 7—SEQ ID NO: 53) were used to amplify a 2.8 Kb fragment HindIII-EcoRI of the D15 gene by the polymerase chain reaction that encodes the N-terminal amino acid residues 22 to 223 of the primary sequence of D15 protein (FIG. 1A). The nucleotide sequence of the 609 bp amplified fragment was confirmed by DNA sequencing. The amplified gene segment was ligated into the pGEX-2T vector downstream from the GST gene and transformed into E. coli TG-1. Colonies expressing the H. influenzae type b antigen were screened with a rabbit anti-H. influenzae type b antiserum by colony radioimmunoassay and isolated. The glutathione-S-transferase-D15 fragment fusion protein produced by transformed E. coli was isolated by affinity purification on glutathione agarose.

Example 7

This Example describes alternative expression systems for rD15.

The D15 gene or fragments thereof are also expressed in E. coli under the control of other regulated promoters. The D15 gene or fragments thereof are expressed in the absence of the leader peptide, or in other cloning systems where toxicity of D15 expression to the host is not problematic. The gene or fragments thereof are synthesized de novo or by employing the polymerase chain reaction using suitable primers. These genes are cloned into suitable cloning vectors or bacteriophage vectors in E. coli or other suitable hosts directly when toxicity can be avoided. Expression systems are Gram-positive bacteria (such as Bacillus species), pox virus, adenovirus, baculovirus, yeast, fungi, BCG or mammalian expression systems.

Example 8

This Example illustrates the protocol for extraction and purification of rD15 from E. coli expression system.

The cell pellet from a 250 mL culture, prepared as described in Example 5, was resuspended in 40 mL of 50 mM Tris, pH 8.0, and disrupted by sonication (3×10 min, 70% duty circle). The extract was centrifuged at 20,000×g and the resulting pellet saved. The initial pellet was re-extracted with 40 mL of 50 mM Tris, 0.5% Triton X-100, 10 mM EDTA, pH 8.0. The suspension was then sonicated for 10 minutes at 70% duty circle. The extract was centrifuged at 300×g for 5 minutes. The resulting supernatant was centrifuged again at 20,000×g for 30 min and the resulting pellet was saved. The pellet was resuspended in 50 mM Tris, 0.5% Triton X-100, 10 mM EDTA, pH 8.0. The suspension was then mixed with PBS/8 M urea to a final urea concentration of 6 M. The solution was then dialyzed against PBS to remove urea. After dialysis, the solution was centrifuged at 300×g for 10 min., the supernatant was saved and stored at 4° C.

Example 9

This Example demonstrates the purification of GST-(D15 fragment) fusion protein using glutathione-Sepharose 4B affinity chromatography.

Five mg of GST-(D15 fragment) fusion protein crude extract, prepared as described in Example 6, were dissolved in 5 mL of phosphate buffer saline (PBS) containing 1% Triton X-100. The solution was then loaded onto a Glutathione-Sepharose 4B column (2 mL) equilibrated with PBS containing 1% Triton X-100. The run-through of the column was discarded. The column was washed with 20 mL of PBS and the GST-(D15 fragment) fusion protein was eluted with 50 mM Tris-HCl buffer, pH 8.0, containing 5 mM glutathione. Elution was monitored by absorbance at 280 nm. Protein-containing fractions (2 mL/fraction) were collected and pooled. The purity of the protein was assessed by SDS-PAGE (FIG. 9, lane 3). The final volume of the purified fusion protein was 6 mL.

Example 10

This Example illustrates the protocol used for thrombin digestion of proteins to release the truncated D15 molecule.

The GST-(D15 fragment) fusion protein sample from Example 9 (0.1 to 0.5 mg protein/mL) was dialyzed against 1 L of 50 mM Tris-HCl buffer (pH 8.5) 3 times with at least 2 hour intervals at 4° C. to remove protease inhibitors. After dialysis, the solution was treated with human thrombin (Sigma) at a ratio of 1 mL of solution to 25 units of thrombin. The cleavage reaction was carried out at 37° C. for 2 hr and analysed by SDS-PAGE (FIG. 9, lane 4). The reaction was stopped by placing the solution in ice.

Example 11

This Example illustrates the procedure used for N-terminal rD15 fragment purification from GST using Glutathione-Sepharose 4B affinity chromatography.

A thrombin-digested GST-(D15 fragment) sample, prepared as described in Example 10, was loaded onto a Glutathione-Sepharose 4B column (2 mL) equilibrated with PBS containing 1% Triton X-100. The run-through of the column containing the N-terminal rD15 fragment was saved. After washing the column with 20 mL of PBS, the affinity column was regenerated by removing GST using 50 mM Tris-HCl buffer, pH 8.0, containing 5 mM glutathione. The purity of rD15 fragment was analysed by SDS-PAGE (FIG. 9, lane 5). This N-terminal rD15 fragment contains amino acids 63–223 of the D15 protein as a result of cleavage at the spacious thrombin site shown in FIG. 1A.

Example 12

This Example illustrates the protocol used for the purification of D15-specific polyclonal antibodies by affinity chromatography using GST-(D15 fragment) fusion protein.

The recombinant GST-(D15 fragment) fusion protein, prepared as described in Example 9, was conjugated to cyanogen bromide-activated Sepharose. The affinity column was then used to purify antibodies from a rabbit hyperimmune anti-*H. influenzae* type b antiserum. The affinity purified-antibodies were shown by immunoblotting to react with a 80 kDa component present in the lysates of *E. coli* transformed with pUC9/D15 and in the lysates of several typeable and nontypeable *H. influenzae* isolates. These results confirmed that the DNA segment encoding the D15 fragment of the fusion protein was part of the open reading frame of the D15 gene.

Similarly, antisera raised against the recombinant fusion protein (Example 9) or the purified N-terminal rD15 fragment (Example 11) reacted with the D15 protein produced by *H. influenzae* strains (Example 13).

Example 13

This Example describes the protocol used for the purification of native D15 from *H. influenzae*.

Cell paste of the non-typeable *H. influenzae* SB33 strain, prepared from a culture grown in brain heart infusion medium supplemented with NAD (2 μg/mL) and HEMIN (2 μg/mL) at 37° C., as described in Panezutti, et al, 1993, was resuspended in 50 mM Tris-HCl, pH 8.0, containing 0.5% Triton X-100 and 10 mM EDTA (20 mL per 1 g of cell paste). The mixture was stirred at room temperature for 2 hr, then centrifuged at 20,000×g for 30 minutes. The D15 was located in the supernatant and further purified.

Purification of native D15 was achieved by affinity chromatography using a D15-specific monoclonal antibody (see Example 24). The D15 extract (25 mL) was mixed with the affinity matrix (1 mL) at room temperature for 2 hr. The mixture was packed into a column and the run-through fraction was discarded. The column was washed sequentially with the following buffers: 50 mM Tris-HCl, pH 8.0, containing 0.5% Triton X-100 and 10 mM EDTA; 1 M HEPES buffer, pH 6.8; 50 mM Tris-HCl, pH 8.0, containing 0.5% Triton X-100 and 10 mM EDTA; and 10 mM phosphate buffer, pH 8.0. D15 was then eluted from the column with 3 mL of 50 mM diethylamine, pH 12.0 and the protein solution was neutralized by 1 M HEPES, pH 6.8 (1/10 volume). The affinity-purified native D15 was analysed by SDS-PAGE and stored at −20° C.

Example 14

This Example describes the procedure used for the preparation of D15-PRP conjugates.

*Haemophilus influenzae* type b oligosaccharides (PRP) prepared by controlled acid hydrolysis were conjugated either with the purified native (Example 13) or recombinant D15 (Example 8) as well as with its fragments (Example 11) using periodate oxidation as described in U.S. Pat. No. 4,356,170 and further details of which are presented in Example 17. The mean molecular size of the PRP molecules used for conjugation was determined as being approximately 20,000 Daltons. The conjugation was carried out without a linker molecule but may also be carried out with a linker molecule. A PRP/D15 molar ratio of approximately 7 was used to provide an excess of PRP hapten.

The PRP/rD15 conjugate was tested according to the protocol of Example 18 for immunogenicity in rabbits and elicited both primary and secondary anti-PRP IgG and anti-D15 antibody responses (Table 9). Rabbit anti-rD15-PRP antisera also strongly reacted with both native D15 and rD15 as judged by immunoblot analysis. These data indicate that rD15 can be used as a carrier protein in a conjugate vaccine. In addition, a rD15-PRP conjugate vaccine should ensure a more consistent protection against *H. influenzae* type b disease, particularly in infants, as a result of the additional homotypic protection provided by antibodies directed against the D15 protein.

Example 15

This Example describes the preparation of D15 peptides.

D15 peptides (Table 2) were synthesized using an ABI 430A peptide synthesizer and optimized t-Boc chemistry as described by the manufacturer, then cleaved from the resin by hydrofluoric acid (HF). The peptides were purified by reversed-phase high performance liquid chromatography (RP-HPLC) on a Vydac C4 semi-preparative column (1×30 cm) using a 15 to 55% acetonitrile gradient in 0.1% trifluoryl acetic acid (TFA) developed over 40 minutes at a flow rate of 2 mL/min. All synthetic peptides (Table 2) used in biochemical and immunological studies were >95% pure as judged by analytical HPLC. Amino acid composition analyses of these peptides performed on a Waters Pico-Tag system were in good agreement with their theoretical compositions.

Example 16

This Example describes the protocol used for D15 peptide-specific antisera production.

Guinea pigs and rabbits were immunized with individual peptides (50 to 200 μg) emulsified with Freund's complete adjuvant and injected intramuscularly. After two booster doses with the same amount of peptide in incomplete Freund's adjuvant at +14 and +28 days, the anti-peptide antisera were collected on day +42 and tested by ELISAs and immunoblotting. Both rabbit and guinea pig antisera were shown to be monospecific for their respective immunizing peptides by the peptide-specific ELISAs (Table 6). In addition, both guinea pig and rabbit antisera raised against D15 peptides reacted with both *H. influenzae* type b and non-typeable D15 on immunoblot analyses. Since most D15 peptides induced strong anti-peptide antibody responses in at least one animal species, they are appropriate immunogens to be included in immunogenic compositions including vaccine preparations.

Example 17

This Example describes the procedure used for the preparation of PRP-BSA conjugates.

0.5 mL of periodate-oxidized PRP (25 mg in 1 mL of 0.1 M sodium phosphate buffer, pH 6.0), prepared from native PRP treated with aqueous periodic acid (Carlone et al, 1986), was added to bovine serum albumin (BSA) (1.32 mg; 0.02 µmol) in 0.5 mL of 0.2 M sodium phosphate buffer, pH 8.0, followed by the addition of sodium cyanoborohydride (14 µg ; 0.22 µmol ; 10 eqv. to BSA). After incubation at 37° C. for 5 days, the reaction mixture was dialysed against 4 L of 0.1 M phosphate buffer, pH 7.5. The resulting solution was applied onto an analytical Superose 12 column (15×300 mm, Pharmacia) equilibrated with 0.2 M sodium phosphate buffer, pH 7.2, and eluted with the same buffer. Fractions were monitored for absorbance at 230 nm. The first major protein peak was pooled and concentrated in a Centriprep 30 to 2.2 mL. The amount of protein was determined using the Bio Rad protein assay, and was found to be 300 µg/mL. The presence of PRP in the protein conjugate fraction was confirmed by the Orcinol test.

Example 18

This Example describes the protocol used for the production of anti-PRP antisera in animals using rD15-PRP conjugates.

Rabbits were immunized intramuscularly with rD15-PRP conjugates (Example 14) (5 to 50 µg PRP equivalent) mixed with 3 mg $AlPO_4$ per mL, followed by two booster doses (half amount of the same immunogen) at 2 week intervals. Antisera were collected every 2 weeks after the first injection, heat-inactivated at 56° C. for 30 minutes and stored at −20° C.

Example 19

This Example illustrates the reactivity between D15 peptides and anti-peptide and D15-specific antisera using D15-specific and peptide-specific ELISAs.

Microtiter wells (Nunc-Immunoplate, Nunc, Denmark) were coated with 200 ng of purified rD15 or 500 ng of individual peptides in 50 µL of coating buffer (15 mM $Na_2CO_3$, 35 mM $NaHCO_3$, pH 9.6) for 16 hours at room temperature. The plates were then blocked with 0.1% (w/v) BSA in phosphate buffer saline (PBS) for 30 minutes at room temperature. Serially diluted antisera were added to the wells and incubated for 1 hour at room temperature. After removal of the antisera, the plates were washed five times with PBS containing 0.1% (w/v) Tween-20 and 0.1% (w/v) BSA. F(ab')$_2$ fragments from goat anti-rabbit, guinea pig, mouse, or human IgG antibodies conjugated to horseradish peroxidase (Jackson ImmunoResearch Labs Inc., Pa.) were diluted (1/8,000) with washing buffer, and added onto the microtiter plates. After 1 hr incubation at room temperature, the plates were washed five times with the washing buffer. The plates were then developed using the substrate tetramethylbenzidine (TMB) in $H_2O_2$ (ADI, Toronto). The reaction was stopped with 1N $H_2SO_4$ and the optical density was measured at 450 nm using a Titretek Multiskan II (Flow Labs., Virginia). Two irrelevant peptides as negative controls in the peptide-specific ELISAs. Assays were performed in triplicate, and the reactive titer of each antiserum was defined as the dilution consistently showing 2-fold increase absorbance value over those obtained from the negative controls. The results obtained are summarized in Tables 3, 6 and 8 and in the DETAILED DESCRIPTION OF THE INVENTION above.

Example 20

This Example illustrates the measurement of the anti-PRP IgG titers in rabbit anti-PRP-D15 conjugate antisera using a PRP-specific ELISA.

Microtiter wells (Nunc-Immunoplate, Nunc, Denmark) were coated with 200 ng of purified PRP-BSA (see Example 17) in 200 µL of coating buffer (15 mM $Na_2CO_3$, 35 mM $NaHCO_3$, pH 9.6) for 16 hours at room temperature. The plates were then blocked with 0.1% (w/v) BSA in phosphate buffer saline (PBS) for 30 minutes at room temperature. Serially diluted rabbit antisera raised against PRP-D15 conjugates were added to the wells and incubated for 1 hour at room temperature. After removal of the antisera, the plates were washed five times with PBS containing 0.1% (w/v) Tween-20 and 0.1% (w/v) BSA. F(ab')$_2$ fragment from goat anti-rabbit IgG antibodies conjugated to horseradish peroxidase (Jackson ImmunoResearch Labs Inc., Pa.) were diluted (1/8,000) with washing buffer, and added onto the microtiter plates. After 1 hour incubation at room temperature, the plates were washed five times with the washing buffer. The plates were then developed using the substrate tetramethylbenzidine (TMB) in $H_2O_2$ (ADI, Toronto). The reaction was stopped with 1N $H_2SO_4$ and the optical density measured at 450 nm using a Titretek Multiskan II (Flow Labs., Virginia). A standard anti-PRP antiserum of known titer was included as positive control. Assays were performed in triplicate, and the reactive titer of each antiserum was defined as the reciprocal of the dilution consistently showing a 2-fold increase in O.D. value over that obtained with the preimmune serum (Table 9).

Example 21

This Example describes the protocol used for the production of D15-specific antisera using purified D15, rD15 or N-terminal rD15 fragment.

New Zealand White rabbits (Maple Lane) and guinea pigs (Charles River) were immunized intramuscularly (IM) with a 10 µg dose of either affinity-purified native D15 (Example 13), recombinant D15 (Example 8) or N-terminal rD15 fragment (Example 11) emulsified in Freund's complete adjuvant (Difco). Animals were boosted on day 28 with another 10 µg dose of affinity-purified D15 or rD15 or rD15 fragment emulsified in Freund's incomplete adjuvant and bled on day 42 via the marginal ear vein. D15-specific polyclonal antibodies were purified from this material as described in Example 12.

Example 22

This Example illustrates the protective activity of D15-specific antisera against *H. influenzae* type b challenge using the infant rat model of bacteremia.

Five-day old infant rats were inoculated subcutaneously (SC) on the dorsum with 0.15 mL of two different rabbit anti-N-terminal rD15 fragments. Pre-immune sera were used as negative controls. One day after immunization, the infant rats were injected intraperitoneally (IP) with 200 colony-forming units (cfu) of *Haemophilus influenzae* type b Minn A strain (0.1 ml) freshly grown in brain heart infusion (BHI) medium supplemented with cofactors and diluted in PBS containing 0.5 mM $MgCl_2$ and 0.15 mM $CaCl_2$. One day later, blood samples were collected via cardiac puncture under methoxyflurane anaesthesia and plated on chocolate agar plates. The number of bacteria per mL of blood was quantified after 24 hr. The statistical significance of differences observed in the levels of bacteremia relative to controls was analyzed by the Student's t-test. The results are summarized in Table 1.

Example 23

This Example describes the protocol used for the generation of D15-specific T-cell lines.

BALB/c ($H-2^d$) mice purchased from Charles River Animal Farm (Montreal, Canada) were individually primed subcutaneously with 20 μg of rD15 adsorbed to 1.5 mg of aluminium phosphate (alum). The animals were boosted twice with the same dose of immunogen at 3 week intervals. Ten days after the final boost, spleens of immunized mice were removed. Splenocytes were cultured at $5.75 \times 10^5$ cells per well in a final volume of 200 μL of RPMI 1640 medium (Flow Lab.) supplemented with 10% heat-inactivated fetal calf serum (Gibco), 2 mM L-glutamine (Flow Lab.), 100 U/mL) penicillin (Flow Lab.) and $5 \times 10^{-5}$ M 2-mercaptoethanol (Sigma) in the presence of varying concentrations (1, 10 and 100 μg per mL) of individual D15 peptides (Table 2) in 96-well plates (Nunc, Denmark). Cultures were kept in a humidified incubator in the presence of 5% $CO_2$/air. Triplicate cultures were performed for each concentration of each peptide. Five days later, 150 μL of 10% rat concanavalin A culture supernatant diluted in culture medium was added to the microtiter plate wells as a source of Interleukin-2 (IL-2) to expand peptide-specific T-cells. Six days later, 150 μL of supernatant were removed from each microculture, and 150 μL of fresh IL-2 containing culture supernatant added to further expand and maintain the viability of the peptide-specific T-cells. After a further 6 day-incubation, the cells were washed three times, each time with 200 μL of culture medium.

Each set of cultures was then stimulated with the corresponding concentrations (1, 10 and 100 μg per mL) of the peptide in the presence of $2 \times 10^5$ irradiated (1,500 rad) BALB/c spleen cells in a final volume of 200 μL of culture medium. Sixty μL of supernatant were then removed from each microculture. The supernatants from each triplicate cultures set were pooled. All supernatants were assayed for IL-2, Interleukin-4 and Interferon-gamma (IFN-γ). Detections of IL-2 and IL-4 were performed using murine IL-2 and IL-4 ELISA kits purchased from Endogen Inc. (MA, USA) respectively. Assay of IFN-γ was performed using a mouse IFN-γ ELISA kit supplied by Genzyme Corporation (MA, USA). Test culture supernatants were assayed at 1 in 5 dilution according to the manufacturers' instructions. The results obtained are set forth in Table 7.

Example 25

This Example describes the general procedure used for the production of murine D15-specific monoclonal antibodies.

BALB/c mice were immunized intraperitoneally with 20 to 50 μg of the N-terminal rD15 fragment (Example 11) emulsified in Freund's complete adjuvant. Two weeks later, the mice were given another injection of the same amount of immunogen in incomplete Freund's adjuvant (IFA). Three days before the fusion, the mice were boosted again with the same amount of immunogen in IFA. Hybridomas were produced by fusion of splenic lymphocytes from immunized mice with non-secreting Sp2/0 myeloma cells as previously described by Hamel et al. (1987). D15-specific hybridomas were cloned by sequential limiting dilutions and screened for anti-D15 monoclonal antibody production. Eight D15-specific hybridoma cell lines were identified, expanded and frozen in liquid nitrogen. One of the hybridoma cell lines, 6C8-F6-C6, has been partially characterized. The monoclonal antibody (MAb 6C8-F6-C6) reacts with peptide D15-P8. This MAb 6C8-F6-C6 was used to prepare the D15-specific MAb affinity column and purify native D15 from *H. influenzae* cell paste (Example 13).

TABLE 1

PROTECTIVE EFFECT OF PASSIVELY TRANSFERRED ANTI-N-TERMINAL RD15 FRAGMENT ANTIBODIES IN THE INFANT RAT MODEL OF BACTEREMIA[1]

| Rabbit antisera | cfu/0.1 mL blood | | p value |
|---|---|---|---|
| | Pre-immune | Post-immunization | |
| Rb#434 | 510 (6/6)[2] | 6 (1/6) | <0.001 |
| Rb#435 | 910 (4/4) | 6 (1/4) | <0.001 |

[1] Five-day old infant rats were passively inununized with 0.15 mL of rabbit anti-N-terminal rD15 fragment s.c. One day later, the infant rats were challenged with 200 cfu of H.influenzae type b strain MinnA (0.1 mL, IP). The blood samples were taken from each rat 24 hours after the challenge and analysed for bacteria counts.
[2] The parentheses indicate the number of rats found to be bacteremic out of the total number of rats challenged.

TABLE 2

SEQUENCE OF OVERLAPPING SYNTHETIC PEPTIDES ENCOMPASSING THE ENTIRE D15 ANTIGEN SEQUENCE

| PEPTIDES | RESIDUES | SEQUENCES | SEQ ID NO: |
|---|---|---|---|
| D15-P1 | 20-49 | APFVAKDIRVDGVQGDLEQQIRASLPVRAG | 14 |
| D15-P2 | 45-74 | PVRAGQRVTDNDVAMIVRSLFVSGRFDDVK | 15 |
| D15-P3 | 68-99 | GRFDDVKAHQEGDVLVVSVVAKSIISDVKIKG | 16 |

TABLE 2-continued

SEQUENCE OF OVERLAPPING SYNTHETIC PEPTIDES ENCOMPASSING
THE ENTIRE D15 ANTIGEN SEQUENCE

| PEPTIDES | RESIDUES | SEQUENCES | SEQ ID NO: |
|---|---|---|---|
| D15-P4 | 93-122 | SDVKIKGNSVIPTEALKQNLDANGFKVGDV | 17 |
| D15-P5 | 114-143 | ANGFKVGDVLIREKLNEFAKSVKEHYASVG | 18 |
| D15-P6 | 135-164 | VKEHYASVGRYNATVEPIVNTLPNNRAEIL | 19 |
| D15-P7 | 157-187 | PNNRAEILIQINEDDKAKLASLTFKGNESVS | 20 |
| D15-P8 | 180-209 | FKGNESVSSSTLQEQMELQPDSWWKKLWGNK | 21 |
| D15-P9 | 199-228 | PDSWWKLWGNKFEGAQFEKDLQSIRDYYLN | 22 |
| D15-P10 | 219-249 | LQSIRDYYLNNGYAKAQITKTDVQLNDEKTK | 23 |
| D15-P11 | 241-270 | VQLNDEKTKVNVTIDVNEGLQYDLRSARII | 24 |
| D15-P12 | 262-291 | YDLRSARIIGNLGGMSAELEPLLSALHLND | 25 |
| D15-P13 | 282-312 | PLLSALHLNDTFRRSDIADVENAIKAKLGER | 26 |
| D15-P14 | 304-333 | AIKAKLGERGYGSATVNSVPDFDDANKTLA | 27 |
| D15-P15 | 325-354 | FDDANKTLAITLVVDAGRRLTVRQLRFEGN | 28 |
| D15-P16 | 346-375 | VRQLRFEGNTVSADSTLRQEMRQQEGTWYN | 29 |
| D15-P17 | 367-396 | RQQEGTWYNSQLVELGKIRLDRTGFFETVE | 30 |
| D15-P18 | 390-416 | GFFETVENRIDPINGSNDEVDVVYKVK | 31 |
| D15-P19 | 410-435 | DVVYKVKERNTGSINFGIGYGTESGI | 32 |
| D15-P20 | 430-455 | GTESGISYQASVKQDNFLGTGAAVSI | 33 |
| D15-P21 | 450-477 | GAAVSIAGTKNDYGTSVNLGYTEPYFTK | 34 |
| D15-P22 | 471-497 | TEPYFTKDGVSLGGNVFFENYDNSKSD | 35 |
| D15-P23 | 491-516 | YDNSKSDTSSNYKRTTYGSNVTLGFP | 36 |
| D15-P24 | 511-538 | VTLGFPVNENNSYYVGLGHTYNKISNF | 37 |
| D15-P25 | 532-559 | YNKISNFALEYNRNLYIQSMKFKGNGIK | 38 |
| D15-P26 | 554-582 | KGNGIKTNDFDFSFGWNYNSLNRGYFPTK | 39 |
| D15-P27 | 577-602 | GYFPTKGVKASLGGRVTIPGSDNKYYK | 40 |
| D15-P28 | 596-625 | SDNKYYKLSADVQGFYPLDRDHLWVVSAK | 41 |
| D15-P29 | 619-646 | LWVVSAKASAGYANGFGNKRLPFYQTYT | 42 |
| D15-P30 | 641-666 | FYQTYTAGGIGSLRGFAYGSIGPNAI | 43 |
| D15-P31 | 662-688 | GPNAIYAEYGNGSGTGTFKKISSDVIG | 44 |
| D15-P32 | 681-709 | KISSDVIGGNAIATASAELIVPTPFVSDK | 45 |
| D15-P33 | 705-731 | FVSDKSQNTVRTSLFVDAASVWNTKWK | 46 |
| D15-P34 | 725-750 | VWNTKWKSDKNGLESDVLKRLPDYGK | 47 |
| D15-P35 | 745-771 | LPDYGKSSRIRASTGVGFQWQSPIGPL | 48 |
| D15-P36 | 769-798 | GPLVFSYAKPIKKYENDDVEQFQFSIGGSF | 49 |

TABLE 3

REACTIVITY OF RABBIT AND GUINEA PIG ANTI-N-TERMINAL rD15 FRAGMENT ANTISERA WITH D15 SYNTHETIC PEPTIDES

| | Reactive Titers | | | | |
|---|---|---|---|---|---|
| | Rabbit antisera | | Guinea pig antisera | | |
| Peptides | 3434 | 435 | 858 | 859 | 860 |
| D15-P1 | 400 | 1,600 | 6,400 | 6,400 | 6,400 |
| D15-P2 | 1,600 | <100 | 100 | 100 | <100 |
| D15-P3 | 400 | <100 | 100 | <100 | <100 |
| D15-P4 | 25,600 | 6,400 | <100 | <100 | <100 |
| D15-P5 | 6,400 | 400 | 1,600 | 25,600 | 400 |
| D15-P6 | 1,600 | 6,400 | 400 | 6,400 | 6,400 |
| D15-P7 | 6,400 | 1,600 | 25,600 | 25,600 | 25,600 |
| D15-P8 | 6,400 | 6,400 | 25,600 | 409,600 | 409,600 |
| D15-P9 | <100 | <100 | 400 | 1,600 | 1,600 |
| D15-P10 | <100 | <100 | 400 | 6,400 | <100 |

TABLE 4

INHIBITION OF ANTI-N-TERMINAL rD15 FRAGMENT ANTIBODY-INDUCED PROTECTION BY D15 PEPTIDES IN THE INFANT RAT MODEL OF BACTEREMIA

| Group # | Antibody | cfu/10 μL blood | cfu in each group/cfu in group #4 (control) (%) |
|---|---|---|---|
| 1 | Anti-D15 Ab + PBS | 60 ± 120 (3/7) | 3 |
| 2 | Anti-D15 Ab + peptides | 300 ± 240 (6/7) | 13 |
| 3 | Anti-D15 Ab + rD15 | 1,520 ± 1,280 (7/7) | 64 |
| 4 | PBS + peptides | 2,360 ± 1,200 (6/7) | 100 |

One half mL of rabbit anti-N-terminal rD15 fragment antiserum (Anti-rD15 fragment Ab) was mixed with either nine D15 peptides (100 μg of peptides D15-P2 to D15-P10, See TABLE 2) or with 600 μg of N-terminal rD15 fragment at room temperature for 1 hr. Antiserum and peptides mixed with PBS were used as controls. Seven-day old infant rats were injected s.c. with 0.2 mL of the various preparations. After 24 h, the infant rats were challenged I.P. with 200 cfu of *H. influenzae* type b strain MinnA. The blood samples were taken at 24 h after the challenge. The numbers in parentheses indicate the number of animals that were bacteremic out of the total number of animals challenged. The level of bacteremia is expressed as the mean of values obtained from seven infant rats tested individually ± one standard deviation (SD).

TABLE 5

INHIBITION OF THE IMMUNOPROTECTION ABILITY OF THE RABBIT ANTI-N-TERMINAL rD15 FRAGMENT ANTISERUM ABSORBED WITh D15 PEPTIDES (D15-P4 TO D15-P8) IN THE INFANT RAT MODEL OF BACTEREMIA

| Group # | Antibody | cfu/10 μL blood | cfu in each group/cfu in group #3 (%) |
|---|---|---|---|
| 1 | rD15 Ab + PBS | 220 ± 360 (3/6) | 8 |
| 2 | rD15 Ab + peptides | 2,960 ± 560 (6/6) | 106 |
| 3 | PBS + peptides | 2,800 ± 360 (6/6) | 100 |

One half mL of rabbit anti-rD15 fragment antiserum (rD15 Ab) was mixed with five D15 peptides (peptides P4 to P8, 250 μg of each peptide) at room temperature for 1 hr. Antiserum and peptides diluted in PBS were used as controls. Seven-day old infant rats were injected s.c. with 0.2 mL of the indicated material. After 24 h, the infant rats were challenged I.P. with 200 cfu of *H. influenzae* type b strain MinnA. The blood samples were collected 24 h after challenge. The numbers in parentheses indicate the number of animals that were bacteremia out of the total number of animals challenged. The level of bacteremia is expressed as the mean of values obtained from six infant rats tested individually ± one SD.

TABLE 6

REACTIVITY OF RABBIT, GUINEA PIG AND MOUSE ANTI-rD15 ANTISERA WITH D15 PEPTIDES

| | Reactive Titer[1] | | |
|---|---|---|---|
| Peptide | Rabbit[2] | Guinea Pig[3] | Mouse[4] |
| D15-P1 | − | − | + |
| D15-P2 | − | +++ | + |
| D15-P3 | − | − | + |
| D15-P4 | + | + | + |
| D15-P5 | − | − | + |
| D15-P6 | − | + | + |
| D15-P7 | − | − | + |
| D15-P8 | − | ++++ | ++++ |
| D15-P9 | − | − | + |
| D15-P10 | − | − | +++ |
| D15-P11 | − | − | +++ |
| D15-P12 | − | − | + |
| D15-P13 | − | − | + |
| D15-P14 | +++ | + | + |
| D15-P15 | − | − | + |
| D15-P16 | − | − | + |
| D15-P17 | − | − | + |
| D15-P18 | − | − | + |
| D15-P19 | − | − | + |
| D15-P20 | − | − | + |
| D15-P21 | − | − | + |
| D15-P22 | − | − | + |
| D15-P23 | − | − | + |
| D15-P24 | − | − | + |
| D15-P25 | − | − | + |
| D15-P26 | − | − | +++ |
| D15-P27 | − | + | + |
| D15-P28 | − | − | + |
| D15-P29 | − | − | + |
| D15-P30 | − | − | + |
| D15-P31 | − | − | + |
| D15-P32 | − | − | + |
| D15-P33 | − | − | + |
| D15-P34 | − | − | + |
| D15-P35 | − | − | + |
| D15-P36 | ++++ | − | + |

[1] The reactive titer is based on peptide-specific ELISAs. +, ++, +++, ++++ represent reactive titers of animal antisera tested at 1/300, 1/1000, 1/2000, and 1/5000 dilutions, respectively; − means nonreactive.
[2] Titer represents the average value of two rabbit antisera raised against rD15.
[3] Titer represents the average value of two guinea pig antisera raised against rD15.
[4] Titer represents the average value of five mouse antisera raised against r15.

TABLE 7

T-CELL STIMULATORY ACTIVITY OF D15 PEPTIDES

| | CYTOKINE RELEASE (pg/mL)[1] | | |
|---|---|---|---|
| Peptide | IL-2[2] | γ-IFN[3] | IL-4[4] |
| D15-P1 | − | − | − |
| D15-P2 | 122 | − | − |
| D15-P3 | 25 | − | − |
| D15-P4 | − | − | − |
| *D15-P5* | *742* | *38,000* | *13* |
| D15-P6 | − | − | − |

TABLE 7-continued

T-CELL STIMULATORY ACTIVITY OF D15 PEPTIDES

| Peptide | IL-2[2] | CYTOKINE RELEASE (pg/mL)[1] γ-IFN[3] | IL-4[4] |
|---|---|---|---|
| D15-P7 | – | – | – |
| D15-P8 | – | – | – |
| D15-P9 | – | – | – |
| D15-P10 | 108 | 1,900 | – |
| D15-P11 | – | – | – |
| D15-P12 | 1,052 | 6,100 | – |
| *D15-P13* | *105* | *6,200* | *56* |
| D15-P14 | – | – | – |
| D15-P15 | – | – | – |
| D15-P16 | 48 | – | – |
| D15-P17 | – | – | – |
| D15-P18 | 32 | 4,800 | – |
| D15-P19 | 882 | 24,500 | – |
| D15-P20 | – | – | – |
| D15-P21 | – | – | – |
| D15-P22 | – | – | – |
| D15-P23 | 78 | – | – |
| D15-P24 | 103 | – | – |
| D15-P25 | – | – | – |
| D15-P26 | 572 | 6,700 | – |
| *D15-P27* | *274* | *7,505* | *68* |
| D15-P28 | 142 | 742 | – |
| D15-P29 | – | – | – |
| D15-P30 | – | – | – |
| D15-P31 | – | – | – |
| D15-P32 | – | – | – |
| D15-P33 | – | – | – |
| D15-P34 | 82 | 603 | – |
| D15-P35 | 107 | 751 | – |
| D15-P36 | – | – | – |

[1] Results are expressed as mean values of triplicate cultures. All standard deviations were less than 15%. Immunodominant Th1-cell epitopes are highlighted with bold and Th0-cell epitopes are in italics.

TABLE 8

RABBIT AND GUINEA PIG ANTIBODY RESPONSES TO D15 PEPTIDES

| | Peptide-specific ELISAs | |
|---|---|---|
| | Reactive Titer[1] | |
| Immunogen | Rabbit[2] | Guinea Pig[3] |
| D15-P1 | 102,400 | 819,200 |
| D15-P2 | 204,800 | 1,637,400 |
| D15-P3 | 51,200 | 1,637,400 |
| D15-P4 | 204,800 | 819,200 |
| D15-P5 | 51,200 | 1,637,400 |
| D15-P6 | 51,200 | 409,600 |
| D15-P7 | 204,800 | 819,200 |
| D15-P8 | 51,200 | 409,600 |
| D15-P9 | 102,400 | 409,600 |
| D15-P10 | 102,400 | 819,200 |
| D15-P11 | 51,200 | 819,200 |
| D15-P12 | 102,400 | 204,800 |
| D15-P13 | NT[4] | 204,800 |
| D15-P14 | NT | 409,600 |
| D15-P15 | NT | 204,800 |
| D15-P16 | NT | 819,200 |
| D15-P17 | NT | 204,800 |
| D15-P18 | NT | 312,500 |
| D15-P19 | NT | 312,500 |
| D15-P20 | NT | 62,500 |
| D15-P21 | NT | 62,500 |
| D15-P22 | NT | 12,500 |
| D15-P23 | NT | 1,562,500 |
| D15-P24 | NT | 312,500 |
| D15-P25 | NT | 62,500 |
| D15-P26 | NT | 500 |
| D15-P27 | NT | 1,500 |
| D15-P28 | NT | 1,250 |
| D15-P29 | NT | <500 |
| D15-P30 | NT | <500 |
| D15-P31 | NT | <500 |
| D15-P32 | NT | 12,500 |
| D15-P33 | NT | 12,500 |
| D15-P34 | NT | 62,500 |
| D15-P35 | NT | 1,250 |
| D15-P36 | NT | 12,500 |

[1] The reactive titer is based on peptide-specific ELISAs. A titer below 500 indicates that the peptide is not immunogenic.
[2] Titers represent the average value of obtained for two rabbit antisera raised against the D15 peptide.
[3] Titers represent the average value obtained for two guinea pig antisera raised against the D15 peptide.
[4] NT: not tested.

TABLE 9

RABBIT IgG ANTIBODY RESPONSE TO D15-PRP CONJUGATE

| | Reactive Titer Against[2] | | | |
|---|---|---|---|---|
| | PRP | | rD15 | |
| Rabbit[1] # | 2 doses | 3 doses | 2 doses | 3 doses |
| 489-1 | 1,600 | 3,200 | 1,600 | 6,400 |
| 490-1 | 1,600 | 1,600 | 6,400 | 25,600 |

[1] Rabbits were immunized intramuscularly with rD15-PRP conjugates (5 to 50 μg PRP equivalent) mixed with 3 mg ALPO$_4$ per mL, followed by two booster doses (half amount of the same immunogen) at 2 week intervals.
[2] Reactive titres is based on PRP specific and D-15 specific ELISAs.

SUMMARY OF THE DISCLOSURE

In summary of this disclosure, the present invention provides purified and isolated nucleic acid molecules containing genes encoding the D15 outer membrane protein, the sequences of these genes and the derived amino acid sequences thereof. The invention also provides peptides corresponding to portions of the D35 outer membrane protein. In addition, the invention provides antibodies raised against D15 outer membrane protein, fragments and peptides. The genes, DNA sequences, antibodies and peptides are useful for diagnosis, immunization and the generation of diagnostic and immunological reagents. Vaccines based on expressed recombinant D35, portions thereof or peptides derived from the provided sequences can be prepared for prevention of *H. influenzae* disease. Modification are possible within the scope of the invention.

REFERENCES

O'Hagan (1992).
Ulman et al., 1993.
Berns C. A. and Thomas C. A. (1965) J. Mol. Biol. 11:476–490.
Thomas W. R. and Rossi A. A. (1986) Infect. Immun. 52:812–817.
Thomas W. R. et al. (1990) Infect. and Immun. 58:1090–1913.

Carlone G. M. et al. (1986) J. Clin. Microbiol. 24:330–331.
Smith, D. B. and Johnson K. S. (1988) Gene 67:31–40.
Harkness, R. et al. (1992) J. Bacteriol. 174:2425–2430.
Hamel et al. (1987) J. Med. Microbiol. 23:163–170.
Mills et al. (1993) Infect. Immun. 61:399–410.

Trinchieri, (1993) Immunol. Today 14:335–338.
Hope, T. P. (1986) J. Immunol. Methods 88:1–18.
Zangwill et al., 1993. MMWR 42:1–15.
Loeb et al. 1987. Infect. Immun. 55:2612–2618.
Panezutti, 1993. Infect. Immun. 61: 1867–1872.

We claim:

1. A purified and isolated nucleic acid molecule having a DNA sequence selected from the group consisting of:
   (a) a DNA sequence having SEQ ID NOS: 1, 3, 5, 7 or 9; and
   (b) a DNA sequence encoding an amino acid sequence having SEQ ID NOS: 2, 4, 6, 8 or 10.

2. The molecule of claim 1 wherein said DNA sequence is the consensus DNA sequence having SEQ ID NO:55.

3. A recombinant plasmid for transformation in a host, comprising a plasmid vector into which has been inserted a nucleic acid molecule as claimed in claim 1 or 2.

4. A recombinant vector for transformation of a host cell, comprising expression means operatively coupled to a nucleic acid molecule as claimed in claim 1 or 2 for expression of a gene product consisting of a D15 outer membrane protein of Haemophilus having a molecular weight as determined by SDS-PAGE of about 80 kDa.

5. The recombinant vector of claim 4, wherein said vector is plasmid DS-880-1-2 having ATCC accession number 75605 deposited Nov. 4, 1993 and encoding the D15 gene product of H. influenzae SB33.

6. The recombinant vector of claim 4 wherein said nucleic acid consists of a DNA sequence encoding a D15 outer membrane protein of Haemophilus of molecular weight as determined by SDS-PAGE of about 80 kDa.

7. The recombinant vector of claim 6, wherein the DNA segment further comprises a nucleic acid sequence encoding a leader sequence for export or said gene product from said host.

8. The recombinant vector of claim 5 wherein said nucleic acid consists of a DNA sequence encoding a D15 outer membrane protein of Haemophilus of molecular weight as determined by SDS-PAGE of about 80 kDa.

* * * * *

```
                           SEQUENCE LISTING (1) GENERAL INFORMATION:

(iii) NUMBER OF SEQUENCES: 55

(2) INFORMATION FOR SEQ ID NO: 1:

(i) SEQUENCE CHARACTERISTICS:
        (A) LENGTH: 2949 base pairs
        (B) TYPE: nucleic acid
        (C) STRANDEDNESS: single
        (D) TOPOLOGY: linear (ii) MOLECULE TYPE: DNA (genomic)

(ix) FEATURE:
        (A) NAME/KEY: CDS
        (B) LOCATION: 75..2465

(xi) SEQUENCE DESCRIPTION: SEQ ID NO: 1:

GATTACGCCA AGCTTAACGG TGTTTGCATT ATTTAATGAT TTTTTACGTC TATAATTTAT        60

ATAGGATACA ATCG ATG AAA AAA CTT CTA ATC GCA AGT TTA TTA TTC GGT        110
                Met Lys Lys Leu Leu Ile Ala Ser Leu Leu Phe Gly
                  1               5                  10

ACG ACA ACG ACT GTG TTT GCC GCA CCT TTT GTG GCA AAA GAT ATT CGT        158
Thr Thr Thr Thr Val Phe Ala Ala Pro Phe Val Ala Lys Asp Ile Arg
         15                  20                  25

GTG GAT GGT GTT CAA GGT GAC TTA GAA CAA CAA ATC CGA GCA AGT TTA        206
Val Asp Gly Val Gln Gly Asp Leu Glu Gln Gln Ile Arg Ala Ser Leu
     30                  35                  40

CCT GTT CGT GCC GGT CAG CGT GTG ACT GAC AAT GAT GTG GCT AAT ATT        254
Pro Val Arg Ala Gly Gln Arg Val Thr Asp Asn Asp Val Ala Asn Ile
 45                  50                  55                  60

GTC CGC TCT TTA TTC GTA AGT GGT CGA TTC GAT GAT GTG AAA GCG CAT        302
Val Arg Ser Leu Phe Val Ser Gly Arg Phe Asp Asp Val Lys Ala His
                 65                  70                  75

CAA GAA GGC GAT GTG CTT GTT GTT AGC GTT GTG GCT AAA TCG ATC ATT        350
Gln Glu Gly Asp Val Leu Val Val Ser Val Val Ala Lys Ser Ile Ile
             80                  85                  90

TCA GAT GTT AAA ATC AAA GGT AAC TCT GTT ATT CCC ACT GAA GCA CTT        398
Ser Asp Val Lys Ile Lys Gly Asn Ser Val Ile Pro Thr Glu Ala Leu
         95                 100                 105

AAA CAA AAC TTA GAT GCT AAC GGG TTT AAA GTT GGC GAT GTT TTA ATT        446
Lys Gln Asn Leu Asp Ala Asn Gly Phe Lys Val Gly Asp Val Leu Ile
    110                 115                 120

CGA GAA AAA TTA AAT GAA TTT GCC AAA AGT GTA AAA GAG CAC TAT GCA        494
Arg Glu Lys Leu Asn Glu Phe Ala Lys Ser Val Lys Glu His Tyr Ala
125                 130                 135                 140

AGT GTA GGT CGC TAT AAC GCA ACA GTT GAA CCT ATT GTC AAT ACG CTA        542
Ser Val Gly Arg Tyr Asn Ala Thr Val Glu Pro Ile Val Asn Thr Leu
                145                 150                 155

CCA AAT AAT CGC GCT GAA ATT TTA ATT CAA ATC AAT GAA GAT GAT AAA        590
Pro Asn Asn Arg Ala Glu Ile Leu Ile Gln Ile Asn Glu Asp Asp Lys
            160                 165                 170

GCA AAA TTG GCA TCA TTA ACT TTC AAG GGG AAC GAA TCT GTT AGT AGC        638
Ala Lys Leu Ala Ser Leu Thr Phe Lys Gly Asn Glu Ser Val Ser Ser
        175                 180                 185
```

```
AGT ACA TTA CAA GAA CAA ATG GAA TTA CAA CCT GAT TCT TGG TGG AAA    686
Ser Thr Leu Gln Glu Gln Met Glu Leu Gln Pro Asp Ser Trp Trp Lys
    190                 195                 200

TTA TGG GGA AAT AAA TTT GAA GGT GCG CAA TTC GAG AAA GAT TTG CAG    734
Leu Trp Gly Asn Lys Phe Glu Gly Ala Gln Phe Glu Lys Asp Leu Gln
205                 210                 215                 220

TCA ATT CGT GAT TAT TAT TTA AAT AAT GGC TAT GCC AAA GCA CAA ATT    782
Ser Ile Arg Asp Tyr Tyr Leu Asn Asn Gly Tyr Ala Lys Ala Gln Ile
                225                 230                 235

ACT AAA ACG GAT GTT CAG CTA AAT GAT GAA AAA ACA AAA GTT AAT GTA    830
Thr Lys Thr Asp Val Gln Leu Asn Asp Glu Lys Thr Lys Val Asn Val
            240                 245                 250

ACC ATT GAT GTA AAT GAA GGT TTA CAG TAT GAC CTT CGT AGT GCA CGC    878
Thr Ile Asp Val Asn Glu Gly Leu Gln Tyr Asp Leu Arg Ser Ala Arg
        255                 260                 265

ATT ATA GGT AAT CTG GGA GGT ATG TCT GCC GAG CTT GAA CCT TTA CTT    926
Ile Ile Gly Asn Leu Gly Gly Met Ser Ala Glu Leu Glu Pro Leu Leu
    270                 275                 280

TCA GCA TTA CAT TTA AAT GAT ACT TTC CGC CGT AGT GAT ATT GCA GAT    974
Ser Ala Leu His Leu Asn Asp Thr Phe Arg Arg Ser Asp Ile Ala Asp
285                 290                 295                 300

GTA GAA AAT GCA ATT AAA GCA AAA CTT GGA GAA CGC GGT TAC GGT AGC    1022
Val Glu Asn Ala Ile Lys Ala Lys Leu Gly Glu Arg Gly Tyr Gly Ser
                305                 310                 315

GCA ACG GTA AAT TCA GTA CCT GAT TTT GAT GAT GCA AAT AAA ACA TTA    1070
Ala Thr Val Asn Ser Val Pro Asp Phe Asp Asp Ala Asn Lys Thr Leu
            320                 325                 330

GCG ATA ACC CTT GTT GTT GAT GCT GGA CGA CGT TTA ACT GTT CGC CAA    1118
Ala Ile Thr Leu Val Val Asp Ala Gly Arg Arg Leu Thr Val Arg Gln
        335                 340                 345

CTT CGC TTT GAA GGA AAT ACC GTT TCT GCT GAT AGC ACT TTA CGT CAG    1166
Leu Arg Phe Glu Gly Asn Thr Val Ser Ala Asp Ser Thr Leu Arg Gln
    350                 355                 360

GAA ATG CGC CAA CAA GAA GGA ACT TGG TAT AAT TCA CAA TTA GTT GAG    1214
Glu Met Arg Gln Gln Glu Gly Thr Trp Tyr Asn Ser Gln Leu Val Glu
365                 370                 375                 380

TTA GGA AAA ATT CGC TTA GAT CGT ACA GGT TTC TTC GAA ACA GTC GAA    1262
Leu Gly Lys Ile Arg Leu Asp Arg Thr Gly Phe Phe Glu Thr Val Glu
                385                 390                 395

AAC CGA ATT GAT CCT ATC AAT GGT AGT AAT GAT GAA GTG GAT GTC GTA    1310
Asn Arg Ile Asp Pro Ile Asn Gly Ser Asn Asp Glu Val Asp Val Val
            400                 405                 410

TAT AAA GTC AAA GAA CGT AAC ACG GGT AGT ATC AAC TTT GGT ATT GGT    1358
Tyr Lys Val Lys Glu Arg Asn Thr Gly Ser Ile Asn Phe Gly Ile Gly
        415                 420                 425

TAC GGT ACA GAG AGT GGT ATT AGT TAT CAA GCA AGT GTT AAA CAA GAT    1406
Tyr Gly Thr Glu Ser Gly Ile Ser Tyr Gln Ala Ser Val Lys Gln Asp
    430                 435                 440

AAT TTC TTG GGA ACA GGG GCG GCA GTA AGT ATA GCT GGT ACG AAA AAT    1454
Asn Phe Leu Gly Thr Gly Ala Ala Val Ser Ile Ala Gly Thr Lys Asn
445                 450                 455                 460

GAT TAT GGT ACG AGT GTC AAT TTG GGT TAT ACC GAG CCC TAT TTT ACT    1502
Asp Tyr Gly Thr Ser Val Asn Leu Gly Tyr Thr Glu Pro Tyr Phe Thr
                465                 470                 475

AAA GAT GGT GTA AGT CTT GGT GGA AAT GTT TTC TTT GAA AAC TAC GAT    1550
Lys Asp Gly Val Ser Leu Gly Gly Asn Val Phe Phe Glu Asn Tyr Asp
            480                 485                 490

AAC TCT AAA AGT GAT ACA TCC TCT AAC TAT AAG CGT ACG ACT TAC GGA    1598
Asn Ser Lys Ser Asp Thr Ser Ser Asn Tyr Lys Arg Thr Thr Tyr Gly
        495                 500                 505
```

```
AGT AAT GTT ACT TTA GGT TTC CCT GTA AAT GAA AAT AAC TCC TAT TAT     1646
Ser Asn Val Thr Leu Gly Phe Pro Val Asn Glu Asn Asn Ser Tyr Tyr
    510             515                 520

GTA GGA TTA GGT CAT ACC TAT AAT AAA ATT AGT AAC TTT GCT CTA GAA     1694
Val Gly Leu Gly His Thr Tyr Asn Lys Ile Ser Asn Phe Ala Leu Glu
525             530                 535                     540

TAT AAC CGT AAT TTA TAT ATT CAA TCA ATG AAA TTT AAA GGT AAT GGC     1742
Tyr Asn Arg Asn Leu Tyr Ile Gln Ser Met Lys Phe Lys Gly Asn Gly
                545                 550                 555

ATT AAA ACA AAT GAC TTT GAT TTT TCT TTT GGT TGG AAC TAT AAC AGC     1790
Ile Lys Thr Asn Asp Phe Asp Phe Ser Phe Gly Trp Asn Tyr Asn Ser
            560                 565                 570

CTT AAT AGA GGC TAT TTC CCA ACT AAA GGG GTT AAA GCA AGT CTT GGT     1838
Leu Asn Arg Gly Tyr Phe Pro Thr Lys Gly Val Lys Ala Ser Leu Gly
        575                 580                 585

GGA CGA GTT ACT ATT CCA GGT TCT GAT AAC AAA TAC TAC AAA CTA AGT     1886
Gly Arg Val Thr Ile Pro Gly Ser Asp Asn Lys Tyr Tyr Lys Leu Ser
    590                 595                 600

GCA GAT GTA CAG GGT TTC TAC CCA TTA GAC AGA GAT CAC CTC TGG GTT     1934
Ala Asp Val Gln Gly Phe Tyr Pro Leu Asp Arg Asp His Leu Trp Val
605                 610                 615                 620

GTA TCT GCA AAA GCA TCT GCA GGA TAT GCA AAT GGT TTT GGA AAC AAG     1982
Val Ser Ala Lys Ala Ser Ala Gly Tyr Ala Asn Gly Phe Gly Asn Lys
                625                 630                 635

CGT TTA CCG TTC TAT CAA ACT TAT ACA GCG GGT GGC ATC GGT TCA TTA     2030
Arg Leu Pro Phe Tyr Gln Thr Tyr Thr Ala Gly Gly Ile Gly Ser Leu
            640                 645                 650

CGT GGT TTT GCT TAT GGT AGT ATT GGA CCT AAC GCA ATT TAT GCC GAA     2078
Arg Gly Phe Ala Tyr Gly Ser Ile Gly Pro Asn Ala Ile Tyr Ala Glu
        655                 660                 665

TAT GGT AAT GGT AGT GGT ACT GGT ACT TTT AAG AAG ATA AGT TCT GAT     2126
Tyr Gly Asn Gly Ser Gly Thr Gly Thr Phe Lys Lys Ile Ser Ser Asp
    670                 675                 680

GTG ATT GGT GGT AAT GCA ATC GCT ACA GCT AGC GCA GAG TTA ATT GTG     2174
Val Ile Gly Gly Asn Ala Ile Ala Thr Ala Ser Ala Glu Leu Ile Val
685                 690                 695                 700

CCA ACT CCA TTT GTG AGC GAT AAG AGC CAA AAT ACG GTC CGA ACC TCC     2222
Pro Thr Pro Phe Val Ser Asp Lys Ser Gln Asn Thr Val Arg Thr Ser
                705                 710                 715

TTA TTT GTT GAT GCG GCA AGT GTT TGG AAT ACT AAA TGG AAA TCA GAT     2270
Leu Phe Val Asp Ala Ala Ser Val Trp Asn Thr Lys Trp Lys Ser Asp
            720                 725                 730

AAA AAT GGA TTA GAG AGC GAT GTA TTA AAA AGA TTG CCT GAT TAT GGC     2318
Lys Asn Gly Leu Glu Ser Asp Val Leu Lys Arg Leu Pro Asp Tyr Gly
        735                 740                 745

AAA TCA AGC CGT ATT CGC GCC TCT ACA GGT GTC GGA TTC CAA TGG CAA     2366
Lys Ser Ser Arg Ile Arg Ala Ser Thr Gly Val Gly Phe Gln Trp Gln
    750                 755                 760

TCT CCT ATT GGG CCA TTG GTA TTC TCT TAT GCC AAA CCA ATT AAA AAA     2414
Ser Pro Ile Gly Pro Leu Val Phe Ser Tyr Ala Lys Pro Ile Lys Lys
765                 770                 775                 780

TAT GAA AAT GAT GAT GTC GAA CAG TTC CAA TTT AGT ATT GGA GGT TCT     2462
Tyr Glu Asn Asp Asp Val Glu Gln Phe Gln Phe Ser Ile Gly Gly Ser
                785                 790                 795

TTC TAATAAATTG AACTTTTTTC TTCATCAGAA CTCAAAAACA ACGTTCTCTG          2515
Phe

CCTAATTTAA TTGGGCAGAG AAAATATTAA ACCCATCATT TAATTAAGGA TATTTATCAA    2575

ATGAAAAACA TCGCAAAAGT AACCGCACTT GCTTTAGGTA TTGCACTTGC TTCAGGCTAT    2635
```

-continued

```
GCTTCCGCTG AAGAAAAAAT TGCTTTCATT AATGCAGGTA TATTTTTCAA CATCACCCAG       2695

ATCGCCAAGC GGTAGCAGAT AAACTTGATG CTGAATTTAA ACCTGTAGCT GAGAAATTAG       2755

CAGCAAGCAA AAAGAAGTT GATGATAAAA TTGCTGCTGC TCGTAAAAAA GTAGAAGCAA        2815

AAGTTGCGGC TTTAGAAAAA GATGCACCTC GCTTACGTCA AGCTGATATT CAAAAACGCC      2875

AACAGGAGAT TAATAAATTA GGTGCGGCTG AAGATGCTGA ATTACAAAAA TTAATGCAAG      2935

AACAAGATAA AAAA                                                        2949
```

(2) INFORMATION FOR SEQ ID NO: 2:

(i) SEQUENCE CHARACTERISTICS:
        (A) LENGTH: 797 amino acids
        (B) TYPE: amino acid
        (D) TOPOLOGY: linear (ii) MOLECULE TYPE: protein (xi) SEQUENCE DESCRIPTION: SEQ ID NO: 2:

```
Met Lys Lys Leu Leu Ile Ala Ser Leu Leu Phe Gly Thr Thr Thr Thr
  1               5                  10                  15

Val Phe Ala Ala Pro Phe Val Ala Lys Asp Ile Arg Val Asp Gly Val
                 20                  25                  30

Gln Gly Asp Leu Glu Gln Gln Ile Arg Ala Ser Leu Pro Val Arg Ala
             35                  40                  45

Gly Gln Arg Val Thr Asp Asn Asp Val Ala Asn Ile Val Arg Ser Leu
         50                  55                  60

Phe Val Ser Gly Arg Phe Asp Asp Val Lys Ala His Gln Glu Gly Asp
 65                  70                  75                  80

Val Leu Val Val Ser Val Ala Lys Ser Ile Ser Asp Val Lys
                 85                  90                  95

Ile Lys Gly Asn Ser Val Ile Pro Thr Glu Ala Leu Lys Gln Asn Leu
                100                 105                 110

Asp Ala Asn Gly Phe Lys Val Gly Asp Val Leu Ile Arg Glu Lys Leu
            115                 120                 125

Asn Glu Phe Ala Lys Ser Val Lys Glu His Tyr Ala Ser Val Gly Arg
130                 135                 140

Tyr Asn Ala Thr Val Glu Pro Ile Val Asn Thr Leu Pro Asn Asn Arg
145                 150                 155                 160

Ala Glu Ile Leu Ile Gln Ile Asn Glu Asp Asp Lys Ala Lys Leu Ala
                165                 170                 175

Ser Leu Thr Phe Lys Gly Asn Glu Ser Val Ser Ser Thr Leu Gln
            180                 185                 190

Glu Gln Met Glu Leu Gln Pro Asp Ser Trp Trp Lys Leu Trp Gly Asn
        195                 200                 205

Lys Phe Glu Gly Ala Gln Phe Gly Lys Asp Leu Gln Ser Ile Arg Asp
210                 215                 220

Tyr Tyr Leu Asn Asn Gly Tyr Ala Lys Ala Gln Ile Thr Lys Thr Asp
225                 230                 235                 240

Val Gln Leu Asn Asp Glu Lys Thr Lys Val Asn Val Thr Ile Asp Val
                245                 250                 255

Asn Glu Gly Leu Gln Tyr Asp Leu Arg Ser Ala Arg Ile Ile Gly Asn
            260                 265                 270

Leu Gly Gly Met Ser Ala Glu Leu Glu Pro Leu Leu Ser Ala Leu His
        275                 280                 285

Leu Asn Asp Thr Phe Arg Arg Ser Asp Ile Ala Asp Val Glu Asn Ala
290                 295                 300
```

-continued

```
Ile Lys Ala Lys Leu Gly Glu Arg Gly Tyr Gly Ser Ala Thr Val Asn
305                 310                 315                 320

Ser Val Pro Asp Phe Asp Ala Asn Lys Thr Leu Ala Ile Thr Leu
            325                 330                 335

Val Val Asp Ala Gly Arg Arg Leu Thr Val Arg Gln Leu Arg Phe Glu
                340                 345                 350

Gly Asn Thr Val Ser Ala Asp Ser Thr Leu Arg Gln Glu Met Arg Gln
            355                 360                 365

Gln Glu Gly Thr Trp Tyr Asn Ser Gln Leu Val Glu Leu Gly Lys Ile
370                 375                 380

Arg Leu Asp Arg Thr Gly Phe Phe Glu Thr Val Glu Asn Arg Ile Asp
385                 390                 395                 400

Pro Ile Asn Gly Ser Asn Asp Glu Val Asp Val Val Tyr Lys Val Lys
                405                 410                 415

Glu Arg Asn Thr Gly Ser Ile Asn Phe Gly Ile Gly Tyr Gly Thr Glu
                420                 425                 430

Ser Gly Ile Ser Tyr Gln Ala Ser Val Lys Gln Asp Asn Phe Leu Gly
            435                 440                 445

Thr Gly Ala Ala Val Ser Ile Ala Gly Thr Lys Asn Asp Tyr Gly Thr
            450                 455                 460

Ser Val Asn Leu Gly Tyr Thr Glu Pro Tyr Phe Thr Lys Asp Gly Val
465                 470                 475                 480

Ser Leu Gly Gly Asn Val Phe Phe Glu Asn Tyr Asp Asn Ser Lys Ser
                485                 490                 495

Asp Thr Ser Ser Asn Tyr Lys Arg Thr Thr Tyr Gly Ser Asn Val Thr
            500                 505                 510

Leu Gly Phe Pro Val Asn Glu Asn Asn Ser Tyr Tyr Val Gly Leu Gly
            515                 520                 525

His Thr Tyr Asn Lys Ile Ser Asn Phe Ala Leu Glu Tyr Asn Arg Asn
            530                 535                 540

Leu Tyr Ile Gln Ser Met Lys Phe Lys Gly Asn Gly Ile Lys Thr Asn
545                 550                 555                 560

Asp Phe Asp Phe Ser Phe Gly Trp Asn Tyr Asn Ser Leu Asn Arg Gly
                565                 570                 575

Tyr Phe Pro Thr Lys Gly Val Lys Ala Ser Leu Gly Gly Arg Val Thr
            580                 585                 590

Ile Pro Gly Ser Asp Asn Lys Tyr Tyr Lys Leu Ser Ala Asp Val Gln
            595                 600                 605

Gly Phe Tyr Pro Leu Asp Arg Asp His Leu Trp Val Val Ser Ala Lys
            610                 615                 620

Ala Ser Ala Gly Tyr Ala Asn Gly Phe Gly Asn Lys Arg Leu Pro Phe
625                 630                 635                 640

Tyr Gln Thr Tyr Thr Ala Gly Gly Ile Gly Ser Leu Arg Gly Phe Ala
                645                 650                 655

Tyr Gly Ser Ile Gly Pro Asn Ala Ile Tyr Ala Glu Tyr Gly Asn Gly
                660                 665                 670

Ser Gly Thr Gly Thr Phe Lys Lys Ile Ser Ser Asp Val Ile Gly Gly
            675                 680                 685

Asn Ala Ile Ala Thr Ala Ser Ala Glu Leu Ile Val Pro Thr Pro Phe
            690                 695                 700

Val Ser Asp Lys Ser Gln Asn Thr Val Arg Thr Ser Leu Phe Val Asp
705                 710                 715                 720

Ala Ala Ser Val Trp Asn Thr Lys Trp Lys Ser Asp Lys Asn Gly Leu
```

-continued

```
                725                 730                 735
Glu Ser Asp Val Leu Lys Arg Leu Pro Asp Tyr Gly Lys Ser Ser Arg
            740                 745                 750

Ile Arg Ala Ser Thr Gly Val Gly Phe Gln Trp Gln Ser Pro Ile Gly
        755                 760                 765

Pro Leu Val Phe Ser Tyr Ala Lys Pro Ile Lys Lys Tyr Glu Asn Asp
    770                 775                 780

Asp Val Glu Gln Phe Gln Phe Ser Ile Gly Gly Ser Phe
785                 790                 795

(2) INFORMATION FOR SEQ ID NO: 3:

(i) SEQUENCE CHARACTERISTICS:
        (A) LENGTH: 2984 base pairs
        (B) TYPE: nucleic acid
        (C) STRANDEDNESS: single
        (D) TOPOLOGY: linear (ii) MOLECULE TYPE: DNA (genomic)

(ix) FEATURE:
        (A) NAME/KEY: CDS
        (B) LOCATION: 374..2764

(xi) SEQUENCE DESCRIPTION: SEQ ID NO: 3:

ACAGGACAGC TTTCCCTTTT AACCTTGAAA ATATTAGGGA AATTACTTCC TGGCGATTTG     60

TCATTAAATA ATTTAAGTGG GCCAATTTCT ATTGCAAAAG GTGCTGGCCC ATCAGCAAAT    120

ATTGGATTGG TGTATTTTTT AAGTTTTATG GCACTGATTA GTGTAAATTT AGGGATTATG    180

AATTTATTTC CATTACCAGT ATTAGATGGC GGTCATTTAG TTTTTTTAAC AATGGAAGCT    240

GTTAAAGGAA AACCTGTTTC TGAGCGGGTG CAAAGCATCT GTTATCGAAT TGGCGCAGCA    300

CTGTTATTAA GCTTAACGGT GTTTGCATTA TTTAATGATT TTTTACGTCT ATAATTTATA    360

TAGGATACAA TCG ATG AAA AAA CTT CTA ATC GCA AGT TTA TTA TTC GGT       409
            Met Lys Lys Leu Leu Ile Ala Ser Leu Leu Phe Gly
             1               5                  10

ACG ACA ACG ACT GTG TTT GCC GCA CCT TTT GTG GCA AAA GAT ATT CGT      457
Thr Thr Thr Thr Val Phe Ala Ala Pro Phe Val Ala Lys Asp Ile Arg
            15                  20                  25

GTG GAT GGT GTT CAA GGT GAC TTA GAA CAA CAA ATC CGA GCA AGT TTA      505
Val Asp Gly Val Gln Gly Asp Leu Glu Gln Gln Ile Arg Ala Ser Leu
        30                  35                  40

CCT GTT CGT GCC GGT CAG CGT GTG ACT GAC AAT GAT GTG GCT AAT ATT      553
Pro Val Arg Ala Gly Gln Arg Val Thr Asp Asn Asp Val Ala Asn Ile
 45                 50                  55                  60

GTC CGC TCT TTA TTC GTA AGT GGT CGA TTC GAT GAT GTG AAA GCG CAT      601
Val Arg Ser Leu Phe Val Ser Gly Arg Phe Asp Asp Val Lys Ala His
                65                  70                  75

CAA GAA GGC GAT GTG CTT GTT GTT AGC GTT GTG GCT AAA TCG ATC ATT      649
Gln Glu Gly Asp Val Leu Val Val Ser Val Val Ala Lys Ser Ile Ile
            80                  85                  90

TCA GAT GTT AAA ATC AAA GGT AAC TCT GTT ATT CCC ACT GAA GCA CTT      697
Ser Asp Val Lys Ile Lys Gly Asn Ser Val Ile Pro Thr Glu Ala Leu
        95                  100                 105

AAA CAA AAC TTA GAT GCT AAC GGG TTT AAA GTT GGC GAT GTT TTA ATT      745
Lys Gln Asn Leu Asp Ala Asn Gly Phe Lys Val Gly Asp Val Leu Ile
 110                115                 120

CGA GAA AAA TTA AAT GAA TTT GCC AAA AGT GTA AAA GAG CAC TAT GCA      793
Arg Glu Lys Leu Asn Glu Phe Ala Lys Ser Val Lys Glu His Tyr Ala
125                 130                 135                 140

AGT GTA GGT CGC TAT AAC GCA ACA GTT GAA CCT ATT GTC AAT ACG CTA      841
```

```
Ser Val Gly Arg Tyr Asn Ala Thr Val Glu Pro Ile Val Asn Thr Leu
            145                 150                 155

CCA AAT AAT CGC GCT GAA ATT TTA ATT CAA ATC AAT GAA GAT GAT AAA        889
Pro Asn Asn Arg Ala Glu Ile Leu Ile Gln Ile Asn Glu Asp Asp Lys
        160                 165                 170

GCA AAA TTG GCA TCA TTA ACT TTC AAG GGG AAC GAA TCT GTT AGT AGC        937
Ala Lys Leu Ala Ser Leu Thr Phe Lys Gly Asn Glu Ser Val Ser Ser
    175                 180                 185

AGT ACA TTA CAA GAA CAA ATG GAA TTA CAA CCT GAT TCT TGG TGG AAA        985
Ser Thr Leu Gln Glu Gln Met Glu Leu Gln Pro Asp Ser Trp Trp Lys
        190                 195                 200

TTA TGG GGA AAT AAA TTT GAA GGT GCG CAA TTC GAG AAA GAT TTG CAG       1033
Leu Trp Gly Asn Lys Phe Glu Gly Ala Gln Phe Glu Lys Asp Leu Gln
205                 210                 215                 220

TCA ATT CGT GAT TAT TAT TTA AAT AAT GGC TAT GCC AAA GCA CAA ATT       1081
Ser Ile Arg Asp Tyr Tyr Leu Asn Asn Gly Tyr Ala Lys Ala Gln Ile
                225                 230                 235

ACT AAA ACG GAT GTT CAG CTA AAT GAT GAA AAA ACA AAA GTT AAT GTA       1129
Thr Lys Thr Asp Val Gln Leu Asn Asp Glu Lys Thr Lys Val Asn Val
            240                 245                 250

ACC ATT GAT GTA AAT GAA GGT TTA CAG TAT GAC CTT CGT AGT GCA CGC       1177
Thr Ile Asp Val Asn Glu Gly Leu Gln Tyr Asp Leu Arg Ser Ala Arg
        255                 260                 265

ATT ATA GGT AAT CTG GGA GGT ATG TCT GCC GAG CTT GAA CCT TTA CTT       1225
Ile Ile Gly Asn Leu Gly Gly Met Ser Ala Glu Leu Glu Pro Leu Leu
    270                 275                 280

TCA GCA TTA CAT TTA AAT GAT ACT TTC CGC CGT AGT GAT ATT GCA GAT       1273
Ser Ala Leu His Leu Asn Asp Thr Phe Arg Arg Ser Asp Ile Ala Asp
285                 290                 295                 300

GTA GAA AAT GCA ATT AAA GCA AAA CTT GGA GAA CGC GGT TAC GGT AGC       1321
Val Glu Asn Ala Ile Lys Ala Lys Leu Gly Glu Arg Gly Tyr Gly Ser
                305                 310                 315

GCA ACG GTA AAT TCA GTA CCT GAT TTT GAT GAT GCA AAT AAA ACA TTA       1369
Ala Thr Val Asn Ser Val Pro Asp Phe Asp Asp Ala Asn Lys Thr Leu
            320                 325                 330

GCG ATA ACC CTT GTT GTT GAT GCT GGA CGA CGT TTA ACT GTT CGC CAA       1417
Ala Ile Thr Leu Val Val Asp Ala Gly Arg Arg Leu Thr Val Arg Gln
        335                 340                 345

CTT CGC TTT GAA GGA AAT ACC GTT TCT GCT GAT AGC ACT TTA CGT CAG       1465
Leu Arg Phe Glu Gly Asn Thr Val Ser Ala Asp Ser Thr Leu Arg Gln
    350                 355                 360

GAA ATG CGC CAA CAA GAA GGA ACT TGG TAT AAT TCA CAA TTA GTT GAG       1513
Glu Met Arg Gln Gln Glu Gly Thr Trp Tyr Asn Ser Gln Leu Val Glu
365                 370                 375                 380

TTA GGA AAA ATT CGC TTA GAT CGT ACA GGT TTC TTC GAA ACA GTC GAA       1561
Leu Gly Lys Ile Arg Leu Asp Arg Thr Gly Phe Phe Glu Thr Val Glu
                385                 390                 395

AAC CGA ATT GAT CCT ATC AAT GGT AGT AAT GAT GAA GTG GAT GTC GTA       1609
Asn Arg Ile Asp Pro Ile Asn Gly Ser Asn Asp Glu Val Asp Val Val
            400                 405                 410

TAT AAA GTC AAA GAA CGT AAC ACG GGT AGT ATC AAC TTT GGT ATT GGT       1657
Tyr Lys Val Lys Glu Arg Asn Thr Gly Ser Ile Asn Phe Gly Ile Gly
        415                 420                 425

TAC GGT ACA GAG AGT GGT ATT AGT TAT CAA GCA AGT GTT AAA CAA GAT       1705
Tyr Gly Thr Glu Ser Gly Ile Ser Tyr Gln Ala Ser Val Lys Gln Asp
    430                 435                 440

AAT TTC TTG GGA ACA GGG GCG GCA GTA AGT ATA GCT GGT ACG AAA AAT       1753
Asn Phe Leu Gly Thr Gly Ala Ala Val Ser Ile Ala Gly Thr Lys Asn
445                 450                 455                 460

GAT TAT GGT ACG AGT GTC AAT TTG GGT TAT ACC GAG CCC TAT TTT ACT       1801
```

-continued

```
            Asp Tyr Gly Thr Ser Val Asn Leu Gly Tyr Thr Glu Pro Tyr Phe Thr
                            465                 470                 475

AAA GAT GGT GTA AGT CTT GGT GGA AAT GTT TTC TTT GAA AAC TAC GAT          1849
Lys Asp Gly Val Ser Leu Gly Gly Asn Val Phe Phe Glu Asn Tyr Asp
                480                 485                 490

AAC TCT AAA AGT GAT ACA TCC TCT AAC TAT AAG CGT ACG ACT TAC GGA          1897
Asn Ser Lys Ser Asp Thr Ser Ser Asn Tyr Lys Arg Thr Thr Tyr Gly
            495                 500                 505

AGT AAT GTT ACT TTA GGT TTC CCT GTA AAT GAA AAT AAC TCC TAT TAT          1945
Ser Asn Val Thr Leu Gly Phe Pro Val Asn Glu Asn Asn Ser Tyr Tyr
        510                 515                 520

GTA GGA TTA GGT CAT ACC TAT AAT AAA ATT AGT AAC TTT GCT CTA GAA          1993
Val Gly Leu Gly His Thr Tyr Asn Lys Ile Ser Asn Phe Ala Leu Glu
525                 530                 535                 540

TAT AAC CGT AAT TTA TAT ATT CAA TCA ATG AAA TTT AAA GGT AAT GGC          2041
Tyr Asn Arg Asn Leu Tyr Ile Gln Ser Met Lys Phe Lys Gly Asn Gly
                545                 550                 555

ATT AAA ACA AAT GAC TTT GAT TTT TCT TTT GGT TGG AAC TAT AAC AGC          2089
Ile Lys Thr Asn Asp Phe Asp Phe Ser Phe Gly Trp Asn Tyr Asn Ser
            560                 565                 570

CTT AAT AGA GGC TAT TTC CCA ACT AAA GGG GTT AAA GCA AGT CTT GGT          2137
Leu Asn Arg Gly Tyr Phe Pro Thr Lys Gly Val Lys Ala Ser Leu Gly
        575                 580                 585

GGA CGA GTT ACT ATT CCA GGT TCT GAT AAC AAA TAC TAC AAA CTA AGT          2185
Gly Arg Val Thr Ile Pro Gly Ser Asp Asn Lys Tyr Tyr Lys Leu Ser
590                 595                 600

GCA GAT GTA CAG GGT TTC TAC CCA TTA GAC AGA GAT CAC CTC TGG GTT          2233
Ala Asp Val Gln Gly Phe Tyr Pro Leu Asp Arg Asp His Leu Trp Val
605                 610                 615                 620

GTA TCT GCA AAA GCA TCT GCA GGA TAT GCA AAT GGT TTT GGA AAC AAG          2281
Val Ser Ala Lys Ala Ser Ala Gly Tyr Ala Asn Gly Phe Gly Asn Lys
                625                 630                 635

CGT TTA CCG TTC TAT CAA ACT TAT ACA GCG GGT GGC ATC GGT TCA TTA          2329
Arg Leu Pro Phe Tyr Gln Thr Tyr Thr Ala Gly Gly Ile Gly Ser Leu
            640                 645                 650

CGT GGT TTT GCT TAT GGT AGT ATT GGA CCT AAC GCA ATT TAT GCC GAA          2377
Arg Gly Phe Ala Tyr Gly Ser Ile Gly Pro Asn Ala Ile Tyr Ala Glu
        655                 660                 665

TAT GGT AAT GGT AGT GGT ACT GGT ACT TTT AAG AAG ATA AGT TCT GAT          2425
Tyr Gly Asn Gly Ser Gly Thr Gly Thr Phe Lys Lys Ile Ser Ser Asp
670                 675                 680

GTG ATT GGT GGT AAT GCA ATC GCT ACA GCT AGC GCA GAG TTA ATT GTG          2473
Val Ile Gly Gly Asn Ala Ile Ala Thr Ala Ser Ala Glu Leu Ile Val
685                 690                 695                 700

CCA ACT CCA TTT GTG AGC GAT AAG AGC CAA AAT ACG GTC CGA ACC TCC          2521
Pro Thr Pro Phe Val Ser Asp Lys Ser Gln Asn Thr Val Arg Thr Ser
                705                 710                 715

TTA TTT GTT GAT GCG GCA AGT GTT TGG AAT ACT AAA TGG AAA TCA GAT          2569
Leu Phe Val Asp Ala Ala Ser Val Trp Asn Thr Lys Trp Lys Ser Asp
            720                 725                 730

AAA AAT GGA TTA GAG AGC GAT GTA TTA AAA AGA TTG CCT GAT TAT GGC          2617
Lys Asn Gly Leu Glu Ser Asp Val Leu Lys Arg Leu Pro Asp Tyr Gly
        735                 740                 745

AAA TCA AGC CGT ATT CGC GCC TCT ACA GGT GTC GGA TTC CAA TGG CAA          2665
Lys Ser Ser Arg Ile Arg Ala Ser Thr Gly Val Gly Phe Gln Trp Gln
750                 755                 760

TCT CCT ATT GGG CCA TTG GTA TTC TCT TAT GCC AAA CCA ATT AAA AAA          2713
Ser Pro Ile Gly Pro Leu Val Phe Ser Tyr Ala Lys Pro Ile Lys Lys
765                 770                 775                 780

TAT GAA AAT GAT GAT GTC GAA CAG TTC CAA TTT AGT ATT GGA GGT TCT          2761
```

-continued

```
Tyr Glu Asn Asp Asp Val Glu Gln Phe Gln Phe Ser Ile Gly Gly Ser
            785                 790                 795

TTC TAATAAATTG AACTTTTTTC TTCATCAGAA CTCAAAAACA ACGTTCTCTG      2814
Phe

CCTAATTTAA TTGGGCAGAG AAAATATTAA ACCCATCATT TAATTAAGGA TATTTATCAA 2874

ATGAAAAACA TCGCAAAAGT AACCGCACTT GCTTTAGGTA TTGCACTTGC TTCAGGCTAT 2934

GCTTCCGCTG AAGAAAAAAT TGCTTTCATT AATGCACTTA TATTTTTCAA          2984

(2) INFORMATION FOR SEQ ID NO: 4:

(i) SEQUENCE CHARACTERISTICS:
        (A) LENGTH: 797 amino acids
        (B) TYPE: amino acid
        (D) TOPOLOGY: linear (ii) MOLECULE TYPE: protein (xi) SEQUENCE DESCRIPTION: SEQ ID NO: 4:

Met Lys Lys Leu Leu Ile Ala Ser Leu Leu Phe Gly Thr Thr Thr Thr
 1               5                  10                  15

Val Phe Ala Ala Pro Phe Val Ala Lys Asp Ile Arg Val Asp Gly Val
                20                  25                  30

Gln Gly Asp Leu Glu Gln Gln Ile Arg Ala Ser Leu Pro Val Arg Ala
            35                  40                  45

Gly Gln Arg Val Thr Asp Asn Asp Val Ala Asn Ile Val Arg Ser Leu
        50                  55                  60

Phe Val Ser Gly Arg Phe Asp Asp Val Lys Ala His Gln Glu Gly Asp
65                  70                  75                  80

Val Leu Val Val Ser Val Ala Lys Ser Ile Ser Asp Val Lys
                85                  90                  95

Ile Lys Gly Asn Ser Val Ile Pro Thr Glu Ala Leu Lys Gln Asn Leu
                100                 105                 110

Asp Ala Asn Gly Phe Lys Val Gly Asp Val Leu Ile Arg Glu Lys Leu
            115                 120                 125

Asn Glu Phe Ala Lys Ser Val Lys Glu His Tyr Ala Ser Val Gly Arg
        130                 135                 140

Tyr Asn Ala Thr Val Glu Pro Ile Val Asn Thr Leu Pro Asn Asn Arg
145                 150                 155                 160

Ala Glu Ile Leu Ile Gln Ile Asn Glu Asp Asp Lys Ala Lys Leu Ala
                165                 170                 175

Ser Leu Thr Phe Lys Gly Asn Glu Ser Val Ser Ser Thr Leu Gln
            180                 185                 190

Glu Gln Met Glu Leu Gln Pro Asp Ser Trp Trp Lys Leu Trp Gly Asn
        195                 200                 205

Lys Phe Glu Gly Ala Gln Phe Glu Lys Asp Leu Gln Ser Ile Arg Asp
210                 215                 220

Tyr Tyr Leu Asn Asn Gly Tyr Ala Lys Ala Gln Ile Thr Lys Thr Asp
225                 230                 235                 240

Val Gln Leu Asn Asp Glu Lys Thr Lys Val Asn Val Thr Ile Asp Val
                245                 250                 255

Asn Glu Gly Leu Gln Tyr Asp Leu Arg Ser Ala Arg Ile Ile Gly Asn
            260                 265                 270

Leu Gly Gly Met Ser Ala Glu Leu Glu Pro Leu Leu Ser Ala Leu His
        275                 280                 285

Leu Asn Asp Thr Phe Arg Arg Ser Asp Ile Ala Asp Val Glu Asn Ala
    290                 295                 300
```

-continued

```
Ile Lys Ala Lys Leu Gly Glu Arg Gly Tyr Gly Ser Ala Thr Val Asn
305                 310                 315                 320

Ser Val Pro Asp Phe Asp Ala Asn Lys Thr Leu Ala Ile Thr Leu
            325                 330                 335

Val Val Asp Ala Gly Arg Arg Leu Thr Val Arg Gln Leu Arg Phe Glu
            340                 345                 350

Gly Asn Thr Val Ser Ala Asp Ser Thr Leu Arg Gln Glu Met Arg Gln
            355                 360                 365

Gln Glu Gly Thr Trp Tyr Asn Ser Gln Leu Val Glu Leu Gly Lys Ile
370                 375                 380

Arg Leu Asp Arg Thr Gly Phe Phe Glu Thr Val Glu Asn Arg Ile Asp
385                 390                 395                 400

Pro Ile Asn Gly Ser Asn Asp Glu Val Asp Val Val Tyr Lys Val Lys
                405                 410                 415

Glu Arg Asn Thr Gly Ser Ile Asn Phe Gly Ile Gly Tyr Gly Thr Glu
            420                 425                 430

Ser Gly Ile Ser Tyr Gln Ala Ser Val Lys Gln Asp Asn Phe Leu Gly
            435                 440                 445

Thr Gly Ala Ala Val Ser Ile Ala Gly Thr Lys Asn Asp Tyr Gly Thr
450                 455                 460

Ser Val Asn Leu Gly Tyr Thr Glu Pro Tyr Phe Thr Lys Asp Gly Val
465                 470                 475                 480

Ser Leu Gly Gly Asn Val Phe Phe Glu Asn Tyr Asp Asn Ser Lys Ser
            485                 490                 495

Asp Thr Ser Ser Asn Tyr Lys Arg Thr Thr Tyr Gly Ser Asn Val Thr
            500                 505                 510

Leu Gly Phe Pro Val Asn Glu Asn Asn Ser Tyr Tyr Val Gly Leu Gly
            515                 520                 525

His Thr Tyr Asn Lys Ile Ser Asn Phe Ala Leu Glu Tyr Asn Arg Asn
            530                 535                 540

Leu Tyr Ile Gln Ser Met Lys Phe Lys Gly Asn Gly Ile Lys Thr Asn
545                 550                 555                 560

Asp Phe Asp Phe Ser Phe Gly Trp Asn Tyr Asn Ser Leu Asn Arg Gly
            565                 570                 575

Tyr Phe Pro Thr Lys Gly Val Lys Ala Ser Leu Gly Gly Arg Val Thr
            580                 585                 590

Ile Pro Gly Ser Asp Asn Lys Tyr Tyr Lys Leu Ser Ala Asp Val Gln
            595                 600                 605

Gly Phe Tyr Pro Leu Asp Arg Asp His Leu Trp Val Val Ser Ala Lys
610                 615                 620

Ala Ser Ala Gly Tyr Ala Asn Gly Phe Gly Asn Lys Arg Leu Pro Phe
625                 630                 635                 640

Tyr Gln Thr Tyr Thr Ala Gly Gly Ile Gly Ser Leu Arg Gly Phe Ala
            645                 650                 655

Tyr Gly Ser Ile Gly Pro Asn Ala Ile Tyr Ala Glu Tyr Gly Asn Gly
            660                 665                 670

Ser Gly Thr Gly Thr Phe Lys Lys Ile Ser Ser Asp Val Ile Gly Gly
            675                 680                 685

Asn Ala Ile Ala Thr Ala Ser Ala Glu Leu Ile Val Pro Thr Pro Phe
            690                 695                 700

Val Ser Asp Lys Ser Gln Asn Thr Val Arg Thr Ser Leu Phe Val Asp
705                 710                 715                 720

Ala Ala Ser Val Trp Asn Thr Lys Trp Lys Ser Asp Lys Asn Gly Leu
```

```
                  725                 730                 735
Glu Ser Asp Val Leu Lys Arg Leu Pro Asp Tyr Gly Lys Ser Ser Arg
            740                 745                 750

Ile Arg Ala Ser Thr Gly Val Gly Phe Gln Trp Gln Ser Pro Ile Gly
            755                 760                 765

Pro Leu Val Phe Ser Tyr Ala Lys Pro Ile Lys Lys Tyr Glu Asn Asp
            770                 775                 780

Asp Val Glu Gln Phe Gln Phe Ser Ile Gly Gly Ser Phe
785                 790                 795

(2) INFORMATION FOR SEQ ID NO: 5:

(i) SEQUENCE CHARACTERISTICS:
        (A) LENGTH: 2950 base pairs
        (B) TYPE: nucleic acid
        (C) STRANDEDNESS: single
        (D) TOPOLOGY: linear (ii) MOLECULE TYPE: DNA (genomic)

(ix) FEATURE:
         (A) NAME/KEY: CDS
         (B) LOCATION: 334..2724

(xi) SEQUENCE DESCRIPTION: SEQ ID NO: 5:
```

| | |
|---|---|
| AATCACTTAC TGGCGATTTG TCATTAAATA ATTTAAGTGG GCCAATTTCT ATTGCAAAAG | 60 |
| GTGCTGGCAC ATCAGCAAAT ATTGGATTGG TGTATTTTTT AAGTTTTATG GCACTGATTA | 120 |
| GTGTAAATTT AGGGATTATG AATTTATTTC CATTACCAGT ATTAGATGGC GGTCATTTAG | 180 |
| TTTTTTTAAC AATGGAAGCT GTTAAAGGAA AACCTGTTTC TGAGCGGGTG CAAAGCATCT | 240 |
| GTTATCGAAT TGGCGCAGCA CTGTTATTAA GCTTAACGGT GTTTGCATTA TTTAATGATT | 300 |

```
TTTTACGTCT ATAATTTATA TAGGATACAA TCG ATG AAA AAA CTT CTA ATC GCA       354
                                    Met Lys Lys Leu Leu Ile Ala
                                    1               5

AGT TTA TTA TTC GGT ACG ACA ACG ACT GTG TTT GCC GCA CCT TTT GTG       402
Ser Leu Leu Phe Gly Thr Thr Thr Thr Val Phe Ala Ala Pro Phe Val
        10                  15                  20

GCA AAA GAT ATT CGT GTG GAT GGT GTT CAA GGT GAC TTA GAA CAA CAA       450
Ala Lys Asp Ile Arg Val Asp Gly Val Gln Gly Asp Leu Glu Gln Gln
    25                  30                  35

ATC CGA GCA AGT TTA CCT GTT CGT GCC GGT CAG CGT GTG ACT GAC AAT       498
Ile Arg Ala Ser Leu Pro Val Arg Ala Gly Gln Arg Val Thr Asp Asn
40                  45                  50                  55

GAT GTG GCT AAT ATT GTC CGC TCT TTA TTC GTA AGT GGT CGA TTC GAT       546
Asp Val Ala Asn Ile Val Arg Ser Leu Phe Val Ser Gly Arg Phe Asp
                60                  65                  70

GAT GTG AAA GCG CAT CAA GAA GGC GAT GTG CTT GTT GTT AGC GTT GTG       594
Asp Val Lys Ala His Gln Glu Gly Asp Val Leu Val Val Ser Val Val
            75                  80                  85

GCT AAA TCG ATC ATT TCA GAT GTT AAA ATC AAA GGT AAC TCT GTT ATT       642
Ala Lys Ser Ile Ile Ser Asp Val Lys Ile Lys Gly Asn Ser Val Ile
        90                  95                 100

CCC ACT GAA GCA CTT AAA CAA AAC TTA GAT GCT AAC GGG TTT AAA GTT       690
Pro Thr Glu Ala Leu Lys Gln Asn Leu Asp Ala Asn Gly Phe Lys Val
    105                 110                 115

GGC GAT GTT TTA ATT CGA GAA AAA TTA AAT GAA TTT GCC AAA AGT GTA       738
Gly Asp Val Leu Ile Arg Glu Lys Leu Asn Glu Phe Ala Lys Ser Val
120                 125                 130                 135

AAA GAG CAC TAT GCA AGT GTA GGT CGC TAT AAC GCA ACA GTT GAA CCT       786
Lys Glu His Tyr Ala Ser Val Gly Arg Tyr Asn Ala Thr Val Glu Pro
                140                 145                 150
```

```
ATT GTC AAT ACG CTA CCA AAT AAT CGC GCT GAA ATT TTA ATT CAA ATC      834
Ile Val Asn Thr Leu Pro Asn Asn Arg Ala Glu Ile Leu Ile Gln Ile
            155                 160                 165

AAT GAA GAT GAT AAA GCA AAA TTG GCA TCA TTA ACT TTC AAG GGG AAC      882
Asn Glu Asp Asp Lys Ala Lys Leu Ala Ser Leu Thr Phe Lys Gly Asn
            170                 175                 180

GAA TCT GTT AGT AGC AGT ACA TTA CAA GAA CAA ATG GAA TTA CAA CCT      930
Glu Ser Val Ser Ser Ser Thr Leu Gln Glu Gln Met Glu Leu Gln Pro
        185                 190                 195

GAT TCT TGG TGG AAA TTA TGG GGA AAT AAA TTT GAA GGT GCG CAA TTC      978
Asp Ser Trp Trp Lys Leu Trp Gly Asn Lys Phe Glu Gly Ala Gln Phe
200                 205                 210                 215

GAG AAA GAT TTG CAG TCA ATT CGT GAT TAT TAT TTA AAT AAT GGC TAT     1026
Glu Lys Asp Leu Gln Ser Ile Arg Asp Tyr Tyr Leu Asn Asn Gly Tyr
                220                 225                 230

GCC AAA GCA CAA ATT ACT AAA ACG GAT GTT CAG CTA AAT GAT GAA AAA     1074
Ala Lys Ala Gln Ile Thr Lys Thr Asp Val Gln Leu Asn Asp Glu Lys
            235                 240                 245

ACA AAA GTT AAT GTA ACC ATT GAT GTA AAT GAA GGT TTA CAG TAT GAC     1122
Thr Lys Val Asn Val Thr Ile Asp Val Asn Glu Gly Leu Gln Tyr Asp
        250                 255                 260

CTT CGT AGT GCA CGC ATT ATA GGT AAT CTG GGA GGT ATG TCT GCC GAG     1170
Leu Arg Ser Ala Arg Ile Ile Gly Asn Leu Gly Gly Met Ser Ala Glu
265                 270                 275

CTT GAA CCT TTA CTT TCA GCA TTA CAT TTA AAT GAT ACT TTC CGC CGT     1218
Leu Glu Pro Leu Leu Ser Ala Leu His Leu Asn Asp Thr Phe Arg Arg
280                 285                 290                 295

AGT GAT ATT GCA GAT GTA GAA AAT GCA ATT AAA GCA AAA CTT GGA GAA     1266
Ser Asp Ile Ala Asp Val Glu Asn Ala Ile Lys Ala Lys Leu Gly Glu
                300                 305                 310

CGC GGT TAC GGT AGC GCA ACG GTA AAT TCA GTA CCT GAT TTT GAT GAT     1314
Arg Gly Tyr Gly Ser Ala Thr Val Asn Ser Val Pro Asp Phe Asp Asp
            315                 320                 325

GCA AAT AAA ACA TTA GCG ATA ACC CTT GTT GTT GAT GCT GGA CGA CGT     1362
Ala Asn Lys Thr Leu Ala Ile Thr Leu Val Val Asp Ala Gly Arg Arg
        330                 335                 340

TTA ACT GTT CGC CAA CTT CGC TTT GAA GGA AAT ACC GTT TCT GCT GAT     1410
Leu Thr Val Arg Gln Leu Arg Phe Glu Gly Asn Thr Val Ser Ala Asp
345                 350                 355

AGC ACT TTA CGT CAG GAA ATG CGC CAA CAA GAA GGA ACT TGG TAT AAT     1458
Ser Thr Leu Arg Gln Glu Met Arg Gln Gln Glu Gly Thr Trp Tyr Asn
360                 365                 370                 375

TCA CAA TTA GTT GAG TTA GGA AAA ATT CGC TTA GAT CGT ACA GGT TTC     1506
Ser Gln Leu Val Glu Leu Gly Lys Ile Arg Leu Asp Arg Thr Gly Phe
                380                 385                 390

TTC GAA ACA GTC GAA AAC CGA ATT GAT CCT ATC AAT GGT AGT AAT GAT     1554
Phe Glu Thr Val Glu Asn Arg Ile Asp Pro Ile Asn Gly Ser Asn Asp
            395                 400                 405

GAA GTG GAT GTC GTA TAT AAA GTC AAA GAA CGT AAC ACG GGT AGT ATC     1602
Glu Val Asp Val Val Tyr Lys Val Lys Glu Arg Asn Thr Gly Ser Ile
        410                 415                 420

AAC TTT GGT ATT GGT TAC GGT ACA GAG AGT GGT ATT AGT TAT CAA GCA     1650
Asn Phe Gly Ile Gly Tyr Gly Thr Glu Ser Gly Ile Ser Tyr Gln Ala
425                 430                 435

AGT GTT AAA CAA GAT AAT TTC TTG GGA ACA GGG GCG GCA GTA AGT ATA     1698
Ser Val Lys Gln Asp Asn Phe Leu Gly Thr Gly Ala Ala Val Ser Ile
440                 445                 450                 455

GCT GGT ACG AAA AAT GAT TAT GGT ACG AGT GTC AAT TTG GGT TAT ACC     1746
Ala Gly Thr Lys Asn Asp Tyr Gly Thr Ser Val Asn Leu Gly Tyr Thr
                460                 465                 470
```

-continued

| | | |
|---|---|---|
| GAG CCC TAT TTT ACT AAA GAT GGT GTA AGT CTT GGT GGA AAT GTT TTC<br>Glu Pro Tyr Phe Thr Lys Asp Gly Val Ser Leu Gly Gly Asn Val Phe<br>475                      480               485 | 1794 |
| TTT GAA AAC TAC GAT AAC TCT AAA AGT GAT ACA TCC TCT AAC TAT AAG<br>Phe Glu Asn Tyr Asp Asn Ser Lys Ser Asp Thr Ser Ser Asn Tyr Lys<br>490                     495               500 | 1842 |
| CGT ACG ACT TAC GGA AGT AAT GTT ACT TTA GGT TTC CCT GTA AAT GAA<br>Arg Thr Thr Tyr Gly Ser Asn Val Thr Leu Gly Phe Pro Val Asn Glu<br>505                     510               515 | 1890 |
| AAT AAC TCC TAT TAT GTA GGA TTA GGT CAT ACC TAT AAT AAA ATT AGT<br>Asn Asn Ser Tyr Tyr Val Gly Leu Gly His Thr Tyr Asn Lys Ile Ser<br>520                 525              530              535 | 1938 |
| AAC TTT GCT CTA GAA TAT AAC CGT AAT TTA TAT ATT CAA TCA ATG AAA<br>Asn Phe Ala Leu Glu Tyr Asn Arg Asn Leu Tyr Ile Gln Ser Met Lys<br>540                     545               550 | 1986 |
| TTT AAA GGT AAT GGC ATT AAA ACA AAT GAC TTT GAT TTT TCT TTT GGT<br>Phe Lys Gly Asn Gly Ile Lys Thr Asn Asp Phe Asp Phe Ser Phe Gly<br>555                     560               565 | 2034 |
| TGG AAC TAT AAC AGC CTT AAT AGA GGC TAT TTC CCA ACT AAA GGG GTT<br>Trp Asn Tyr Asn Ser Leu Asn Arg Gly Tyr Phe Pro Thr Lys Gly Val<br>570                     575               580 | 2082 |
| AAA GCA AGT CTT GGT GGA CGA GTT ACT ATT CCA GGT TCT GAT AAC AAA<br>Lys Ala Ser Leu Gly Gly Arg Val Thr Ile Pro Gly Ser Asp Asn Lys<br>585                     590               595 | 2130 |
| TAC TAC AAA CTA AGT GCA GAT GTA CAG GGT TTC TAC CCA TTA GAC AGA<br>Tyr Tyr Lys Leu Ser Ala Asp Val Gln Gly Phe Tyr Pro Leu Asp Arg<br>600                     605               610              615 | 2178 |
| GAT CAC CTC TGG GTT GTA TCT GCA AAA GCA TCT GCA GGA TAT GCA AAT<br>Asp His Leu Trp Val Val Ser Ala Lys Ala Ser Ala Gly Tyr Ala Asn<br>620                 625               630 | 2226 |
| GGT TTT GGA AAC AAG CGT TTA CCG TTC TAT CAA ACT TAT ACA GCG GGT<br>Gly Phe Gly Asn Lys Arg Leu Pro Phe Tyr Gln Thr Tyr Thr Ala Gly<br>635                     640               645 | 2274 |
| GGC ATC GGT TCA TTA CGT GGT TTT GCT TAT GGT AGT ATT GGA CCT AAC<br>Gly Ile Gly Ser Leu Arg Gly Phe Ala Tyr Gly Ser Ile Gly Pro Asn<br>650                     655               660 | 2322 |
| GCA ATT TAT GCC GAA TAT GGT AAT GGT AGT GGT ACT GGT ACT TTT AAG<br>Ala Ile Tyr Ala Glu Tyr Gly Asn Gly Ser Gly Thr Gly Thr Phe Lys<br>665                     670               675 | 2370 |
| AAG ATA AGT TCT GAT GTG ATT GGT GGT AAT GCA ATC GCT ACA GCT AGC<br>Lys Ile Ser Ser Asp Val Ile Gly Gly Asn Ala Ile Ala Thr Ala Ser<br>680                     685               690              695 | 2418 |
| GCA GAG TTA ATT GTG CCA ACT CCA TTT GTG AGC GAT AAG AGC CAA AAT<br>Ala Glu Leu Ile Val Pro Thr Pro Phe Val Ser Asp Lys Ser Gln Asn<br>700                     705               710 | 2466 |
| ACG GTC CGA ACC TCC TTA TTT GTT GAT GCG GCA AGT GTT TGG AAT ACT<br>Thr Val Arg Thr Ser Leu Phe Val Asp Ala Ala Ser Val Trp Asn Thr<br>715                     720               725 | 2514 |
| AAA TGG AAA TCA GAT AAA AAT GGA TTA GAG AGC GAT GTA TTA AAA AGA<br>Lys Trp Lys Ser Asp Lys Asn Gly Leu Glu Ser Asp Val Leu Lys Arg<br>730                     735               740 | 2562 |
| TTG CCT GAT TAT GGC AAA TCA AGC CGT ATT CGC GCC TCT ACA GGT GTC<br>Leu Pro Asp Tyr Gly Lys Ser Ser Arg Ile Arg Ala Ser Thr Gly Val<br>745                     750               755 | 2610 |
| GGA TTC CAA TGG CAA TCT CCT ATT GGG CCA TTG GTA TTC TCT TAT GCC<br>Gly Phe Gln Trp Gln Ser Pro Ile Gly Pro Leu Val Phe Ser Tyr Ala<br>760                     765               770              775 | 2658 |
| AAA CCA ATT AAA AAA TAT GAA AAT GAT GAT GTC GAA CAG TTC CAA TTT<br>Lys Pro Ile Lys Lys Tyr Glu Asn Asp Asp Val Glu Gln Phe Gln Phe<br>780                     785               790 | 2706 |

```
AGT ATT GGA GGT TCT TTC TAATAAATTG AACTTTTTTC TTCATCAGAA         2754
Ser Ile Gly Gly Ser Phe
            795

CTCAAAAACA ACGTTCTCTG CCTAATTTAA TTGGGCAGAG AAAATATTAA ACCCATCATT  2814

TAATTAAGGA TATTTATCAA ATGAAAAACA TCGCAAAAGT AACCGCACTT GCTTTAGGTA  2874

TTGCACTTGC TTCAGGCTAT GCTTCCGCTG AAGAAAAAAT TGCTTTCATT AATGCGGGTT  2934

ATATTTCAAG GCAAGG                                                  2950
```

(2) INFORMATION FOR SEQ ID NO: 6:

(i) SEQUENCE CHARACTERISTICS:
        (A) LENGTH: 797 amino acids
        (B) TYPE: amino acid
        (D) TOPOLOGY: linear (ii) MOLECULE TYPE: protein (xi) SEQUENCE DESCRIPTION: SEQ ID NO: 6:

```
Met Lys Lys Leu Leu Ile Ala Ser Leu Leu Phe Gly Thr Thr Thr Thr
 1               5                  10                  15

Val Phe Ala Ala Pro Phe Val Ala Lys Asp Ile Arg Val Asp Gly Val
                20                  25                  30

Gln Gly Asp Leu Glu Gln Gln Ile Arg Ala Ser Leu Pro Val Arg Ala
            35                  40                  45

Gly Gln Arg Val Thr Asp Asn Asp Val Ala Asn Ile Val Arg Ser Leu
        50                  55                  60

Phe Val Ser Gly Arg Phe Asp Asp Val Lys Ala His Gln Glu Gly Asp
 65                  70                  75                  80

Val Leu Val Val Ser Val Val Ala Lys Ser Ile Ile Ser Asp Val Lys
                85                  90                  95

Ile Lys Gly Asn Ser Val Ile Pro Thr Glu Ala Leu Lys Gln Asn Leu
            100                 105                 110

Asp Ala Asn Gly Phe Lys Val Gly Asp Val Leu Ile Arg Glu Lys Leu
        115                 120                 125

Asn Glu Phe Ala Lys Ser Val Lys Glu His Tyr Ala Ser Val Gly Arg
    130                 135                 140

Tyr Asn Ala Thr Val Glu Pro Ile Val Asn Thr Leu Pro Asn Asn Arg
145                 150                 155                 160

Ala Glu Ile Leu Ile Gln Ile Asn Glu Asp Asp Lys Ala Lys Leu Ala
                165                 170                 175

Ser Leu Thr Phe Lys Gly Asn Glu Ser Val Ser Ser Thr Leu Gln
            180                 185                 190

Glu Gln Met Glu Leu Gln Pro Asp Ser Trp Trp Lys Leu Trp Gly Asn
        195                 200                 205

Lys Phe Glu Gly Ala Gln Phe Glu Lys Asp Leu Gln Ser Ile Arg Asp
    210                 215                 220

Tyr Tyr Leu Asn Asn Gly Tyr Ala Lys Ala Gln Ile Thr Lys Thr Asp
225                 230                 235                 240

Val Gln Leu Asn Asp Glu Lys Thr Lys Val Asn Val Thr Ile Asp Val
                245                 250                 255

Asn Glu Gly Leu Gln Tyr Asp Leu Arg Ser Ala Arg Ile Ile Gly Asn
            260                 265                 270

Leu Gly Gly Met Ser Ala Glu Leu Glu Pro Leu Leu Ser Ala Leu His
        275                 280                 285

Leu Asn Asp Thr Phe Arg Arg Ser Asp Ile Ala Asp Val Glu Asn Ala
```

```
            290                 295                 300
Ile Lys Ala Lys Leu Gly Glu Arg Gly Tyr Gly Ser Ala Thr Val Asn
305                 310                 315                 320

Ser Val Pro Asp Phe Asp Ala Asn Lys Thr Leu Ala Ile Thr Leu
                    325                 330                 335

Val Val Asp Ala Gly Arg Arg Leu Thr Val Arg Gln Leu Arg Phe Glu
                340                 345                 350

Gly Asn Thr Val Ser Ala Asp Ser Thr Leu Arg Gln Glu Met Arg Gln
                355                 360                 365

Gln Glu Gly Thr Trp Tyr Asn Ser Gln Leu Val Glu Leu Gly Lys Ile
370                 375                 380

Arg Leu Asp Arg Thr Gly Phe Phe Glu Thr Val Glu Asn Arg Ile Asp
385                 390                 395                 400

Pro Ile Asn Gly Ser Asn Asp Glu Val Asp Val Tyr Lys Val Lys
                405                 410                 415

Glu Arg Asn Thr Gly Ser Ile Asn Phe Gly Ile Gly Tyr Gly Thr Glu
                420                 425                 430

Ser Gly Ile Ser Tyr Gln Ala Ser Val Lys Gln Asp Asn Phe Leu Gly
                435                 440                 445

Thr Gly Ala Ala Val Ser Ile Ala Gly Thr Lys Asn Asp Tyr Gly Thr
                450                 455                 460

Ser Val Asn Leu Gly Tyr Thr Glu Pro Tyr Phe Thr Lys Asp Gly Val
465                 470                 475                 480

Ser Leu Gly Gly Asn Val Phe Phe Glu Asn Tyr Asp Asn Ser Lys Ser
                485                 490                 495

Asp Thr Ser Ser Asn Tyr Lys Arg Thr Thr Tyr Gly Ser Asn Val Thr
                500                 505                 510

Leu Gly Phe Pro Val Asn Glu Asn Asn Ser Tyr Tyr Val Gly Leu Gly
                515                 520                 525

His Thr Tyr Asn Lys Ile Ser Asn Phe Ala Leu Glu Tyr Asn Arg Asn
                530                 535                 540

Leu Tyr Ile Gln Ser Met Lys Phe Lys Gly Asn Gly Ile Lys Thr Asn
545                 550                 555                 560

Asp Phe Asp Phe Ser Phe Gly Trp Asn Tyr Asn Ser Leu Asn Arg Gly
                565                 570                 575

Tyr Phe Pro Thr Lys Gly Val Lys Ala Ser Leu Gly Gly Arg Val Thr
                580                 585                 590

Ile Pro Gly Ser Asp Asn Lys Tyr Lys Leu Ser Ala Asp Val Gln
                595                 600                 605

Gly Phe Tyr Pro Leu Asp Arg Asp His Leu Trp Val Val Ser Ala Lys
                610                 615                 620

Ala Ser Ala Gly Tyr Ala Asn Gly Phe Gly Asn Lys Arg Leu Pro Phe
625                 630                 635                 640

Tyr Gln Thr Tyr Thr Ala Gly Ile Gly Ser Leu Arg Gly Phe Ala
                645                 650                 655

Tyr Gly Ser Ile Gly Pro Asn Ala Ile Tyr Ala Glu Tyr Gly Asn Gly
                660                 665                 670

Ser Gly Thr Gly Thr Phe Lys Lys Ile Ser Ser Asp Val Ile Gly Gly
                675                 680                 685

Asn Ala Ile Ala Thr Ala Ser Ala Glu Leu Ile Val Pro Thr Pro Phe
                690                 695                 700

Val Ser Asp Lys Ser Gln Asn Thr Val Arg Thr Ser Leu Phe Val Asp
705                 710                 715                 720
```

```
Ala Ala Ser Val Trp Asn Thr Lys Trp Lys Ser Asp Lys Asn Gly Leu
            725                 730                 735

Glu Ser Asp Val Leu Lys Arg Leu Pro Asp Tyr Gly Lys Ser Ser Arg
            740                 745                 750

Ile Arg Ala Ser Thr Gly Val Gly Phe Gln Trp Gln Ser Pro Ile Gly
            755                 760                 765

Pro Leu Val Phe Ser Tyr Ala Lys Pro Ile Lys Lys Tyr Glu Asn Asp
            770                 775                 780

Asp Val Glu Gln Phe Gln Phe Ser Ile Gly Gly Ser Phe
785                 790                 795
```

(2) INFORMATION FOR SEQ ID NO: 7:

(i) SEQUENCE CHARACTERISTICS:
        (A) LENGTH: 2974 base pairs
        (B) TYPE: nucleic acid
        (C) STRANDEDNESS: single
        (D) TOPOLOGY: linear (ii) MOLECULE TYPE: DNA (genomic)

(ix) FEATURE:
        (A) NAME/KEY: CDS
        (B) LOCATION: 386..2761

(xi) SEQUENCE DESCRIPTION: SEQ ID NO: 7:

```
GGCATTGAAA AAACAGGACA GCTTTCCCTT TTAACCTTGA AAATATTAGG GAAATTACTT      60

ACTGGCGATT TGTCATTAAA TAATTTAAGT GGGCCAATTT CTATTGCAAA AGGTGCTGGC     120

GCATCAGCAA ATATTGGATT GGTGTATTTT TTAAGTTTTA TGGCATTGAT TAGTGTAAAT     180

TTAGGGATTA TGAATTTATT TCCATTACCA GTATTAGATG GCGGTCATTT AGTTTTTTTA     240

ACAATGGAAG CTGTTAAAGG AAAACCTGTT TCTGAGCGGG TGCAAAGCAT CTGTTATCGA     300

ATTGGCGCAG CACTGTTATT AAGCTTAACG GTGTTTGCAT TATTTAATGA TTTTTTACGT     360

CTATAATTTA TATAGGATAC AATCG ATG AAA AAA CTT CTA ATC GCA AGT TTA      412
                           Met Lys Lys Leu Leu Ile Ala Ser Leu
                            1               5

TTA TTC GGT ACG ACA ACG ACT GTG TTT GCC GCA CCT TTT GTG GCA AAA      460
Leu Phe Gly Thr Thr Thr Thr Val Phe Ala Ala Pro Phe Val Ala Lys
 10              15                  20                  25

GAT ATT CGT GTG GAT GGT GTT CAA GGT GAC TTA GAA CAA CAA ATC CGA      508
Asp Ile Arg Val Asp Gly Val Gln Gly Asp Leu Glu Gln Gln Ile Arg
             30                  35                  40

GCA AGT TTA CCT GTT CGT GCC GGT CAG CGT GTG ACT GAC AAT GAT GTG      556
Ala Ser Leu Pro Val Arg Ala Gly Gln Arg Val Thr Asp Asn Asp Val
         45                  50                  55

GCT AAT ATT GTC CGC TCT TTA TTC GTA AGT GGT CGA TTC GAT GAT GTG      604
Ala Asn Ile Val Arg Ser Leu Phe Val Ser Gly Arg Phe Asp Asp Val
     60                  65                  70

AAA GCG CAT CAA GAA GGC GAT GTG CTT GTT GTT AGC GTT GTG GCT AAA      652
Lys Ala His Gln Glu Gly Asp Val Leu Val Val Ser Val Val Ala Lys
 75                  80                  85

TCG ATC ATT TCA GAT GTT AAA ATC AAA GGT AAC TCT ATT ATT CCA CCT      700
Ser Ile Ile Ser Asp Val Lys Ile Lys Gly Asn Ser Ile Ile Pro Pro
 90                  95                 100                 105

GAA GCA CTA AAA CAA AAC TTA GAT GCT AAC GGG TTT AAA GTT GGC GAT      748
Glu Ala Leu Lys Gln Asn Leu Asp Ala Asn Gly Phe Lys Val Gly Asp
                110                 115                 120

ATT TTA ATT CGA GAA AAA TTA AAT GAA TTT GCC CAA AGT GTA AAA GAG      796
Ile Leu Ile Arg Glu Lys Leu Asn Glu Phe Ala Gln Ser Val Lys Glu
            125                 130                 135
```

```
CAC TAT GCA AGT GTA GGT CGC TAT AAC GCA ACC GTT GAA CCT ATT GTC          844
His Tyr Ala Ser Val Gly Arg Tyr Asn Ala Thr Val Glu Pro Ile Val
        140                 145                 150

AAT ACG CTA CCA AAT AAT CGC GCT GAA ATT TTA ATT CAA ATC AAT GAA          892
Asn Thr Leu Pro Asn Asn Arg Ala Glu Ile Leu Ile Gln Ile Asn Glu
155                 160                 165

GAT GAT AAA GCC AAA TTG GCA TCA TTA ACT TTC AAG GGG AAC GAA TCT          940
Asp Asp Lys Ala Lys Leu Ala Ser Leu Thr Phe Lys Gly Asn Glu Ser
170                 175                 180                 185

GTT AGT AGC AGT ACA TTA CAA GAA CAA ATG GAA TTA CAA CCT GAT TCT          988
Val Ser Ser Ser Thr Leu Gln Glu Gln Met Glu Leu Gln Pro Asp Ser
                190                 195                 200

TGG TGG AAA TTA TGG GGA AAT AAA TTT GAA GGT GCG CAA TTC GAG AAA         1036
Trp Trp Lys Leu Trp Gly Asn Lys Phe Glu Gly Ala Gln Phe Glu Lys
        205                 210                 215

GAT TTG CAG GCA ATT CGT GAT TAT TAT TTA AAT AAT GGC TAT GCC AAA         1084
Asp Leu Gln Ala Ile Arg Asp Tyr Tyr Leu Asn Asn Gly Tyr Ala Lys
        220                 225                 230

GCA CAA ATC ACT AAA GCG GAT GTT CAG CTA AAT GAT GAA AAA ACA AAA         1132
Ala Gln Ile Thr Lys Ala Asp Val Gln Leu Asn Asp Glu Lys Thr Lys
235                 240                 245

GTT AAT GTA ACC ATT GAT GTA AAT GAA GGT TTA CAG TAT GAC CTT CGT         1180
Val Asn Val Thr Ile Asp Val Asn Glu Gly Leu Gln Tyr Asp Leu Arg
250                 255                 260                 265

AGT GCA CGC ATT ATA GGT AAT CTG GGA GGT ATG TCT GCC GAG CTT GAA         1228
Ser Ala Arg Ile Ile Gly Asn Leu Gly Gly Met Ser Ala Glu Leu Glu
                270                 275                 280

CCT TTA CTT TCA GCA TTA CAT TTA AAT GAT ACT TTC CGC CGT AGT GAT         1276
Pro Leu Leu Ser Ala Leu His Leu Asn Asp Thr Phe Arg Arg Ser Asp
            285                 290                 295

ATT GCA GAT GTA GAA AAT GCA ATT AAA GCA AAA CTT GGG GAA CGA GGT         1324
Ile Ala Asp Val Glu Asn Ala Ile Lys Ala Lys Leu Gly Glu Arg Gly
        300                 305                 310

TAC GGT AAC ACA ACA GTA AAT TCT GTA CCT GAT TTT GAC GAT GCA AAT         1372
Tyr Gly Asn Thr Thr Val Asn Ser Val Pro Asp Phe Asp Asp Ala Asn
315                 320                 325

AAA ACA TTA GCG ATA ACC TTT GTT GTT GAT GCT GGA CGA CGT TTA ACT         1420
Lys Thr Leu Ala Ile Thr Phe Val Val Asp Ala Gly Arg Arg Leu Thr
330                 335                 340                 345

GTT CAC CAA CTT CGC TTT GAA GGA AAT ACC GTT TCT GCT GAT AGT ACT         1468
Val His Gln Leu Arg Phe Glu Gly Asn Thr Val Ser Ala Asp Ser Thr
                350                 355                 360

TTA CGT CAG GAA ATG CGC CAA CAA GAA GGA ACT TGG TAT AAT TCA CAA         1516
Leu Arg Gln Glu Met Arg Gln Gln Glu Gly Thr Trp Tyr Asn Ser Gln
            365                 370                 375

TTA GTT GAG TTA GGA AAA ATT CGC TTA GAT CGT ACA GGT TTC TTC GAA         1564
Leu Val Glu Leu Gly Lys Ile Arg Leu Asp Arg Thr Gly Phe Phe Glu
        380                 385                 390

ACA GTT GAA AAC CGA ATT GAT CCT ATC AAT GGT AGC AAT GAT GAA GTG         1612
Thr Val Glu Asn Arg Ile Asp Pro Ile Asn Gly Ser Asn Asp Glu Val
395                 400                 405

GAT GTC GTA TAT AAA GTC AAA GAA CGT AAC ACG GGT AGT ATC AAC TTT         1660
Asp Val Val Tyr Lys Val Lys Glu Arg Asn Thr Gly Ser Ile Asn Phe
410                 415                 420                 425

GGT ATT GGT TAC GGT ACA GAG AGT GGT ATT AGT TAT CAA GCA AGT GTC         1708
Gly Ile Gly Tyr Gly Thr Glu Ser Gly Ile Ser Tyr Gln Ala Ser Val
                430                 435                 440

AAA CAA GAT AAT TTC TTG GGA ACA GGG GCG GCA GTA AGT ATA GCT GGT         1756
Lys Gln Asp Asn Phe Leu Gly Thr Gly Ala Ala Val Ser Ile Ala Gly
            445                 450                 455
```

| | | |
|---|---|---|
| ACG AAA AAT GAT TAT GGT ACG AGT GTC AAT TTG GGT TAT ACC GAG CCC<br>Thr Lys Asn Asp Tyr Gly Thr Ser Val Asn Leu Gly Tyr Thr Glu Pro<br>460                            465                           470 | 1804 |
| TAT TTT ACT AAA GAT GGT GTA AGT CTT GGT GGA AAT GTT TTC TTT GAA<br>Tyr Phe Thr Lys Asp Gly Val Ser Leu Gly Gly Asn Val Phe Phe Glu<br>475                           480                         485 | 1852 |
| AAC TAC GAT AAC TCT AAA AGT GAT ACA TCC TCT AAC TAT AAG CGT ACG<br>Asn Tyr Asp Asn Ser Lys Ser Asp Thr Ser Ser Asn Tyr Lys Arg Thr<br>490                        495                     500                    505 | 1900 |
| ACT TAT GGA AGT AAT GTT ACT TTA GGT TTC CCT GTA AAT GAA AAT AAC<br>Thr Tyr Gly Ser Asn Val Thr Leu Gly Phe Pro Val Asn Glu Asn Asn<br>                     510                     515                    520 | 1948 |
| TCC TAT TAT GTA GGA TTA GGC CAT ACC TAT AAT AAA ATT AGT AAC TTT<br>Ser Tyr Tyr Val Gly Leu Gly His Thr Tyr Asn Lys Ile Ser Asn Phe<br>           525                     530                     535 | 1996 |
| GCT CTA GAA TAT AAC CGT AAT TTA TAT ATT CAA TCA ATG AAA TTT AAA<br>Ala Leu Glu Tyr Asn Arg Asn Leu Tyr Ile Gln Ser Met Lys Phe Lys<br>          540                     545                    550 | 2044 |
| GGT AAT GGC ATT AAA ACA AAT GAC TTT GAT TTT TCT TTT GGT TGG AAC<br>Gly Asn Gly Ile Lys Thr Asn Asp Phe Asp Phe Ser Phe Gly Trp Asn<br>555                           560                     565 | 2092 |
| TAT AAC AGC CTT AAT AGA GGC TAT TTC CCA ACT AAA GGG GTT AAA GCA<br>Tyr Asn Ser Leu Asn Arg Gly Tyr Phe Pro Thr Lys Gly Val Lys Ala<br>570                        575                    580                  585 | 2140 |
| AGT CTT GGT GGA CGA GTT ACA ATT CCA GGT TCT GAT AAC AAA TAC TAC<br>Ser Leu Gly Gly Arg Val Thr Ile Pro Gly Ser Asp Asn Lys Tyr Tyr<br>                     590                     595                    600 | 2188 |
| AAA CTA AGT GCA GAT GTA CAG GGT TTC TAC CCA TTA GAC AGA GAT CAC<br>Lys Leu Ser Ala Asp Val Gln Gly Phe Tyr Pro Leu Asp Arg Asp His<br>          605                     610                    615 | 2236 |
| CTC TGG GTT GTA TCT GCA AAA GCA TCT GCA GGA TAT GCA AAT GGT TTT<br>Leu Trp Val Val Ser Ala Lys Ala Ser Ala Gly Tyr Ala Asn Gly Phe<br>             620                     625                    630 | 2284 |
| GGA AAC AAG CGT TTA CCG TTC TAT CAA ACT TAT ACA GCG GGT GGC ATT<br>Gly Asn Lys Arg Leu Pro Phe Tyr Gln Thr Tyr Thr Ala Gly Gly Ile<br>635                           640                     645 | 2332 |
| GGT TCA TTA CGC GGT TTT GCT TAT GGT AGC ATT GGG CCT AAC GCA ATT<br>Gly Ser Leu Arg Gly Phe Ala Tyr Gly Ser Ile Gly Pro Asn Ala Ile<br>650                        655                    660                  665 | 2380 |
| TAT CAA GGT CAA AAT AAT AAA TTT AAT AAG ATA AGT TCT GAT GTG ATT<br>Tyr Gln Gly Gln Asn Asn Lys Phe Asn Lys Ile Ser Ser Asp Val Ile<br>                     670                     675                    680 | 2428 |
| GGT GGT AAT GCA ATC GCT ACA GCT AGC GCA GAG TTA ATT GTG CCA ACT<br>Gly Gly Asn Ala Ile Ala Thr Ala Ser Ala Glu Leu Ile Val Pro Thr<br>             685                     690                    695 | 2476 |
| CCA TTT GTG AGT GAT AAG AGT CAA AAT ACA GTC CGA ACC TCC CTA TTT<br>Pro Phe Val Ser Asp Lys Ser Gln Asn Thr Val Arg Thr Ser Leu Phe<br>          700                     705                    710 | 2524 |
| GTT GAT GCG GCA AGT GTT TGG AAT ACT AAA TGG AAA TCA GAT AAA AAT<br>Val Asp Ala Ala Ser Val Trp Asn Thr Lys Trp Lys Ser Asp Lys Asn<br>715                           720                     725 | 2572 |
| GGA TTA GAG AGC AAT GTC TTG AAA GAC TTA CCC GAT TAT GGC AAA TCA<br>Gly Leu Glu Ser Asn Val Leu Lys Asp Leu Pro Asp Tyr Gly Lys Ser<br>730                        735                    740                  745 | 2620 |
| AGC CGT ACT CGC GCC TCT ACA GGT GTC GGA TTC CAA TGG CAA TCT CCT<br>Ser Arg Thr Arg Ala Ser Thr Gly Val Gly Phe Gln Trp Gln Ser Pro<br>             750                     755                    760 | 2668 |
| AGT GGA CCA GTG GTA TTT TCT TAT GCT AAA CCA ATT AAA AAA TAT GAA<br>Ser Gly Pro Val Val Phe Ser Tyr Ala Lys Pro Ile Lys Lys Tyr Glu<br>             765                     770                    775 | 2716 |

```
AAT GAT GAT GTC GAA CAG TTC CAA TTT AGT ATT GGG GGT TCT TTC         2761
Asn Asp Asp Val Glu Gln Phe Gln Phe Ser Ile Gly Gly Ser Phe
            780                 785                 790

TAATAAATTG AACTTTTTTC GTCATCAGAA CTCAAAAACA ACGTTCTCTG CCTAATTTAA    2821

TTGGGCAGAG AAAATATTAA AACCATCATT TAATTAAGGA TATTTATCAA ATGAAAAACA    2881

TCGCCAAAGT AACCGCACTT GCTTTAGGTA TTGCACTTGC TTCAGGCTAT GCTGCAGCTG    2941

AAGAAAAAAT TGCTTTTATT AATGCAGGTT ATA                                2974
```

(2) INFORMATION FOR SEQ ID NO: 8:

(i) SEQUENCE CHARACTERISTICS:
        (A) LENGTH: 792 amino acids
        (B) TYPE: amino acid
        (D) TOPOLOGY: linear (ii) MOLECULE TYPE: protein (xi) SEQUENCE DESCRIPTION: SEQ ID NO: 8:

```
Met Lys Lys Leu Leu Ile Ala Ser Leu Leu Phe Gly Thr Thr Thr Thr
 1               5                   10                  15

Val Phe Ala Ala Pro Phe Val Ala Lys Asp Ile Arg Val Asp Gly Val
            20                  25                  30

Gln Gly Asp Leu Glu Gln Gln Ile Arg Ala Ser Leu Pro Val Arg Ala
        35                  40                  45

Gly Gln Arg Val Thr Asp Asn Asp Val Ala Asn Ile Val Arg Ser Leu
    50                  55                  60

Phe Val Ser Gly Arg Phe Asp Asp Val Lys Ala His Gln Glu Gly Asp
65                  70                  75                  80

Val Leu Val Val Ser Val Val Ala Lys Ser Ile Ser Asp Val Lys
                85                  90                  95

Ile Lys Gly Asn Ser Ile Ile Pro Pro Glu Ala Leu Lys Gln Asn Leu
                100                 105                 110

Asp Ala Asn Gly Phe Lys Val Gly Asp Ile Leu Ile Arg Glu Lys Leu
            115                 120                 125

Asn Glu Phe Ala Gln Ser Val Lys Glu His Tyr Ala Ser Val Gly Arg
        130                 135                 140

Tyr Asn Ala Thr Val Glu Pro Ile Val Asn Thr Leu Pro Asn Asn Arg
145                 150                 155                 160

Ala Glu Ile Leu Ile Gln Ile Asn Glu Asp Asp Lys Ala Lys Leu Ala
                165                 170                 175

Ser Leu Thr Phe Lys Gly Asn Glu Ser Val Ser Ser Thr Leu Gln
            180                 185                 190

Glu Gln Met Glu Leu Gln Pro Asp Ser Trp Trp Lys Leu Trp Gly Asn
        195                 200                 205

Lys Phe Glu Gly Ala Gln Phe Glu Lys Asp Leu Gln Ala Ile Arg Asp
210                 215                 220

Tyr Tyr Leu Asn Asn Gly Tyr Ala Lys Ala Gln Ile Thr Lys Ala Asp
225                 230                 235                 240

Val Gln Leu Asn Asp Glu Lys Thr Lys Val Asn Val Thr Ile Asp Val
                245                 250                 255

Asn Glu Gly Leu Gln Tyr Asp Leu Arg Ser Ala Arg Ile Ile Gly Asn
            260                 265                 270

Leu Gly Gly Met Ser Ala Glu Leu Glu Pro Leu Leu Ser Ala Leu His
        275                 280                 285

Leu Asn Asp Thr Phe Arg Arg Ser Asp Ile Ala Asp Val Glu Asn Ala
    290                 295                 300
```

-continued

```
Ile Lys Ala Lys Leu Gly Glu Arg Gly Tyr Gly Asn Thr Thr Val Asn
305                 310                 315                 320

Ser Val Pro Asp Phe Asp Ala Asn Lys Thr Leu Ala Ile Thr Phe
            325                 330                 335

Val Val Asp Ala Gly Arg Arg Leu Thr Val His Gln Leu Arg Phe Glu
                340                 345                 350

Gly Asn Thr Val Ser Ala Asp Ser Thr Leu Arg Gln Glu Met Arg Gln
            355                 360                 365

Gln Glu Gly Thr Trp Tyr Asn Ser Gln Leu Val Glu Leu Gly Lys Ile
370                 375                 380

Arg Leu Asp Arg Thr Gly Phe Phe Glu Thr Val Glu Asn Arg Ile Asp
385                 390                 395                 400

Pro Ile Asn Gly Ser Asn Asp Glu Val Asp Val Val Tyr Lys Val Lys
            405                 410                 415

Glu Arg Asn Thr Gly Ser Ile Asn Phe Gly Ile Gly Tyr Gly Thr Glu
            420                 425                 430

Ser Gly Ile Ser Tyr Gln Ala Ser Val Lys Gln Asp Asn Phe Leu Gly
            435                 440                 445

Thr Gly Ala Ala Val Ser Ile Ala Gly Thr Lys Asn Asp Tyr Gly Thr
    450                 455                 460

Ser Val Asn Leu Gly Tyr Thr Glu Pro Tyr Phe Thr Lys Asp Gly Val
465                 470                 475                 480

Ser Leu Gly Gly Asn Val Phe Phe Glu Asn Tyr Asp Asn Ser Lys Ser
                485                 490                 495

Asp Thr Ser Ser Asn Tyr Lys Arg Thr Thr Tyr Gly Ser Asn Val Thr
            500                 505                 510

Leu Gly Phe Pro Val Asn Glu Asn Asn Ser Tyr Tyr Val Gly Leu Gly
    515                 520                 525

His Thr Tyr Asn Lys Ile Ser Asn Phe Ala Leu Glu Tyr Asn Arg Asn
            530                 535                 540

Leu Tyr Ile Gln Ser Met Lys Phe Lys Gly Asn Gly Ile Lys Thr Asn
545                 550                 555                 560

Asp Phe Asp Phe Ser Phe Gly Trp Asn Tyr Asn Ser Leu Asn Arg Gly
                565                 570                 575

Tyr Phe Pro Thr Lys Gly Val Lys Ala Ser Leu Gly Gly Arg Val Thr
            580                 585                 590

Ile Pro Gly Ser Asp Asn Lys Tyr Tyr Lys Leu Ser Ala Asp Val Gln
            595                 600                 605

Gly Phe Tyr Pro Leu Asp Arg Asp His Leu Trp Val Val Ser Ala Lys
    610                 615                 620

Ala Ser Ala Gly Tyr Ala Asn Gly Phe Gly Asn Lys Arg Leu Pro Phe
625                 630                 635                 640

Tyr Gln Thr Tyr Thr Ala Gly Gly Ile Gly Ser Leu Arg Gly Phe Ala
            645                 650                 655

Tyr Gly Ser Ile Gly Pro Asn Ala Ile Tyr Gln Gly Gln Asn Asn Lys
            660                 665                 670

Phe Asn Lys Ile Ser Ser Asp Val Ile Gly Gly Asn Ala Ile Ala Thr
            675                 680                 685

Ala Ser Ala Glu Leu Ile Val Pro Thr Pro Phe Val Ser Asp Lys Ser
    690                 695                 700

Gln Asn Thr Val Arg Thr Ser Leu Phe Val Asp Ala Ala Ser Val Trp
705                 710                 715                 720

Asn Thr Lys Trp Lys Ser Asp Lys Asn Gly Leu Glu Ser Asn Val Leu
```

```
                       725                 730                 735
Lys Asp Leu Pro Asp Tyr Gly Lys Ser Ser Arg Thr Arg Ala Ser Thr
            740                 745                 750
Gly Val Gly Phe Gln Trp Gln Ser Pro Ser Gly Pro Val Val Phe Ser
            755                 760                 765
Tyr Ala Lys Pro Ile Lys Lys Tyr Glu Asn Asp Val Glu Gln Phe
            770                 775                 780
Gln Phe Ser Ile Gly Gly Ser Phe
785                 790
```

(2) INFORMATION FOR SEQ ID NO: 9:

(i) SEQUENCE CHARACTERISTICS:
        (A) LENGTH: 2989 base pairs
        (B) TYPE: nucleic acid
        (C) STRANDEDNESS: single
        (D) TOPOLOGY: linear (ii) MOLECULE TYPE: DNA (genomic)

(ix) FEATURE:
        (A) NAME/KEY: CDS
        (B) LOCATION: 390..2768

(xi) SEQUENCE DESCRIPTION: SEQ ID NO: 9:

```
AAAAGGCATT GAAAAAACAG GACAACTTTC CCTTTTAACC TTGAAAATAT TAGGGAAATT      60

ACTTACTGGC GATTTGTCAT TAAATAATTT AAGTGGGCCA ATTTCTATTG CAAAAGGTGC     120

TGGTGCATCA GCAAATATTG GATTGGTGTA TTTTTTAAGT TTTATGGCAT TGATTAGTGT     180

AAATTTAGGG ATTATGAATT TATTTCCATT ACCAGTATTA GATGGCGGTC ATTTAGTTTT     240

TTTAACAATG GAAGCTGTTA AAGGAAAACC TGTTTCTGAG CGGGTGCAAA GCATCTGTTA     300

TCGAATTGGC GCAGCACTGT TATTAAGCTT AACGGTGTTT GCATTATTTA ATGATTTTTT     360

ACGTCTATAA TTTATATAGG ATACAATCG ATG AAA AAA CTT CTA ATC GCA AGT      413
                                 Met Lys Lys Leu Leu Ile Ala Ser
                                  1               5

TTA TTA TTC GGT GCG ACA ACG ACT GTG TTT GCC GCA CCT TTT GTG CCA      461
Leu Leu Phe Gly Ala Thr Thr Thr Val Phe Ala Ala Pro Phe Val Pro
 10                  15                  20

AAA GAT ATT CGT GTG GAT GGT GTT CAA GGT GAC TTA GAA CAA CAA ATC      509
Lys Asp Ile Arg Val Asp Gly Val Gln Gly Asp Leu Glu Gln Gln Ile
 25                  30                  35                  40

CGA GCA AGT TTA CCT GTT CGT GCT GGT CAG CGT GTG ACT GAC AAT GAT      557
Arg Ala Ser Leu Pro Val Arg Ala Gly Gln Arg Val Thr Asp Asn Asp
                 45                  50                  55

GTG GCT AAT ATT GTC CGC TCT TTA TTC GTA AGT GGT CGA TTC GAT GAT      605
Val Ala Asn Ile Val Arg Ser Leu Phe Val Ser Gly Arg Phe Asp Asp
             60                  65                  70

GTG AAA GCG CAT CAA GAA GGC GAT GTG CTT GTT GTT AGC GTT GTG GCT      653
Val Lys Ala His Gln Glu Gly Asp Val Leu Val Val Ser Val Val Ala
         75                  80                  85

AAA TCG ATC ATT TCA GAT GTT AAA ATC AAA GGT AAC TCT GTT ATT CCC      701
Lys Ser Ile Ile Ser Asp Val Lys Ile Lys Gly Asn Ser Val Ile Pro
     90                  95                 100

ACT GAA GCA CTT AAA CAA AAC TTA GAT GCT AAC GGG TTT AAA GTT GGC      749
Thr Glu Ala Leu Lys Gln Asn Leu Asp Ala Asn Gly Phe Lys Val Gly
105                 110                 115                 120

GAT GTT TTA ATT CGA GAA AAA TTA AAT GAA TTT GCC AAA AGT GTA AAA      797
Asp Val Leu Ile Arg Glu Lys Leu Asn Glu Phe Ala Lys Ser Val Lys
                125                 130                 135

GAG CAC TAT GCA AGT GTA GGT CGC TAT AAC GCA ACC GTT GAA CCT ATT      845
```

```
                Glu His Tyr Ala Ser Val Gly Arg Tyr Asn Ala Thr Val Glu Pro Ile
                            140                 145                 150

GTC AAT ACG CTG CCA AAT AAT CGT GCT GAA ATT TTA ATT CAA ATC AAT          893
Val Asn Thr Leu Pro Asn Asn Arg Ala Glu Ile Leu Ile Gln Ile Asn
            155                 160                 165

GAA GAT GAT AAA GCA AAA TTG GCA TCA TTA ACT TTC AAG GGG AAC GAA          941
Glu Asp Asp Lys Ala Lys Leu Ala Ser Leu Thr Phe Lys Gly Asn Glu
170                 175                 180

TCT GTT AGT AGC AGT ACA TTA CAA GAA CAA ATG GAA TTA CAA CCT GAT          989
Ser Val Ser Ser Ser Thr Leu Gln Glu Gln Met Glu Leu Gln Pro Asp
185                 190                 195                 200

TCT TGG TGG AAA TTA TGG GGA AAT AAA TTT GAA GGT GCG CAA TTC GAG         1037
Ser Trp Trp Lys Leu Trp Gly Asn Lys Phe Glu Gly Ala Gln Phe Glu
            205                 210                 215

AAA GAT CTG CAG GCA ATT CGT GAT TAT TAT TTA AAT AAT GGC TAT GCC         1085
Lys Asp Leu Gln Ala Ile Arg Asp Tyr Tyr Leu Asn Asn Gly Tyr Ala
            220                 225                 230

AAA GCA CAA ATC ACT AAA ACG GAT GTT CAG CTA AAT GAT GAA AAA ACA         1133
Lys Ala Gln Ile Thr Lys Thr Asp Val Gln Leu Asn Asp Glu Lys Thr
            235                 240                 245

AAA GTT AAT GTA ACC ATT GAT GTA AAT GAA GGT TTA CAG TAT GAC CTT         1181
Lys Val Asn Val Thr Ile Asp Val Asn Glu Gly Leu Gln Tyr Asp Leu
250                 255                 260

CGT AGT GCA CGC ATT ATA GGT AAT CTG GGA GGT ATG TCT GCC GAG CTT         1229
Arg Ser Ala Arg Ile Ile Gly Asn Leu Gly Gly Met Ser Ala Glu Leu
265                 270                 275                 280

GAA CCT TTA CTT TCA GCA TTA CAT TTA AAT GAT ACT TTC CGC CGT AGT         1277
Glu Pro Leu Leu Ser Ala Leu His Leu Asn Asp Thr Phe Arg Arg Ser
                285                 290                 295

GAT ATT GCA GAT GTA GAA AAT GCA ATT AAA GCA AAA CTT GGG GAA CGA         1325
Asp Ile Ala Asp Val Glu Asn Ala Ile Lys Ala Lys Leu Gly Glu Arg
                300                 305                 310

GGT TAC GGT AAC ACA ACA GTA AAT TCT GTA CCT GAT TTT GAC GAT GCA         1373
Gly Tyr Gly Asn Thr Thr Val Asn Ser Val Pro Asp Phe Asp Asp Ala
            315                 320                 325

AAT AAA ACA TTA GCG ATA ACC TTT GTT GTT GAT GCT GGA CGA CGT TTA         1421
Asn Lys Thr Leu Ala Ile Thr Phe Val Val Asp Ala Gly Arg Arg Leu
            330                 335                 340

ACT GTT CGC CAA CTT CGC TTT GAA GGA AAT ACC GTT TCT GCT GAT AGT         1469
Thr Val Arg Gln Leu Arg Phe Glu Gly Asn Thr Val Ser Ala Asp Ser
345                 350                 355                 360

ACT TTA CGT CAG GAA ATG CGA CAA CAA GAA GGA ACT TGG TAT AAT TCA         1517
Thr Leu Arg Gln Glu Met Arg Gln Gln Glu Gly Thr Trp Tyr Asn Ser
                365                 370                 375

CAA TTA GTT GAG TTA GGA AAA ATT CGC TTA GAT CGT ACA GGT TTC TTC         1565
Gln Leu Val Glu Leu Gly Lys Ile Arg Leu Asp Arg Thr Gly Phe Phe
            380                 385                 390

GAA ACA GTT GAA AAC CGA ATT GAT CCT ATC AAT GGT AGC AAT GAT GAA         1613
Glu Thr Val Glu Asn Arg Ile Asp Pro Ile Asn Gly Ser Asn Asp Glu
            395                 400                 405

GTG GAT GTC GTA TAT AAA GTC AAA GAA CGT AAC ACG GGT AGT ATC AAC         1661
Val Asp Val Val Tyr Lys Val Lys Glu Arg Asn Thr Gly Ser Ile Asn
            410                 415                 420

TTT GGT ATT GGT TAC GGT ACA GAG AGT GGT ATC AGT TAT CAA ACA AGT         1709
Phe Gly Ile Gly Tyr Gly Thr Glu Ser Gly Ile Ser Tyr Gln Thr Ser
425                 430                 435                 440

ATT AAA CAA GAT AAT TTC TTG GGA ACA GGG GCG GCA GTA AGT ATA GCT         1757
Ile Lys Gln Asp Asn Phe Leu Gly Thr Gly Ala Ala Val Ser Ile Ala
                445                 450                 455

GGT ACG AAA AAT GAT TAT GGT ACG AGT GTC AAT TTG GGT TAT ACC GAA         1805
```

```
Gly Thr Lys Asn Asp Tyr Gly Thr Ser Val Asn Leu Gly Tyr Thr Glu
            460                 465                 470

CCC TAT TTT ACT AAA GAT GGT GTA AGT CTT GGT GGA AAT ATT TTC TTT      1853
Pro Tyr Phe Thr Lys Asp Gly Val Ser Leu Gly Gly Asn Ile Phe Phe
            475                 480                 485

GAA AAC TAC GAT AAC TCT AAA AGT GAT ACA TCC TCT AAC TAT AAG CGT      1901
Glu Asn Tyr Asp Asn Ser Lys Ser Asp Thr Ser Ser Asn Tyr Lys Arg
            490                 495                 500

ACG ACT TAT GGA AGT AAT GTT ACT TTA GGT TTC CCT GTA AAT GAA AAT      1949
Thr Thr Tyr Gly Ser Asn Val Thr Leu Gly Phe Pro Val Asn Glu Asn
505                 510                 515                 520

AAC TCC TAT TAT GTA GGA TTA GGC CAT ACC TAT AAT AAA ATT AGT AAC      1997
Asn Ser Tyr Tyr Val Gly Leu Gly His Thr Tyr Asn Lys Ile Ser Asn
            525                 530                 535

TTT GCT CTA GAA TAT AAC CGT AAT TTA TAT ATT CAA TCA ATG AAA TTT      2045
Phe Ala Leu Glu Tyr Asn Arg Asn Leu Tyr Ile Gln Ser Met Lys Phe
            540                 545                 550

AAA GGT AAT GGC ATT AAA ACA AAT GAC TTT GAT TTT TCT TTT GGT TGG      2093
Lys Gly Asn Gly Ile Lys Thr Asn Asp Phe Asp Phe Ser Phe Gly Trp
            555                 560                 565

AAC TAT AAC AGC CTT AAT AGA GGC TAT TTC CCA ACT AAA GGG GTT AAA      2141
Asn Tyr Asn Ser Leu Asn Arg Gly Tyr Phe Pro Thr Lys Gly Val Lys
            570                 575                 580

GCA AGT CTT GGT GGA CGA GTT ACT ATT CCA GGT TCT GAT AAC AAA TAC      2189
Ala Ser Leu Gly Gly Arg Val Thr Ile Pro Gly Ser Asp Asn Lys Tyr
585                 590                 595                 600

TAC AAA CTA AGT GCA GAT GTA CAG GGT TTC TAC CCA TTA GAC AGA GAT      2237
Tyr Lys Leu Ser Ala Asp Val Gln Gly Phe Tyr Pro Leu Asp Arg Asp
            605                 610                 615

CAC CGC TGG GTT GTA TCT GCA AAA GCA TCT GCA GGA TAT GCA AAT GGT      2285
His Arg Trp Val Val Ser Ala Lys Ala Ser Ala Gly Tyr Ala Asn Gly
            620                 625                 630

TTT GGA AAC AAG CGT TTA CCG TTC TAT CAA ACT TAT ACA GCG GGT GGC      2333
Phe Gly Asn Lys Arg Leu Pro Phe Tyr Gln Thr Tyr Thr Ala Gly Gly
            635                 640                 645

ATT GGT TCA TTA CGC GGT TTT GCT TAT GGT AGT ATT GGG CCT AAT GCA      2381
Ile Gly Ser Leu Arg Gly Phe Ala Tyr Gly Ser Ile Gly Pro Asn Ala
650                 655                 660

ATT TAT GCC GAA CAT GGT AAT GGT ACT TTT AAT AAG ATA AGT TCT GAT      2429
Ile Tyr Ala Glu His Gly Asn Gly Thr Phe Asn Lys Ile Ser Ser Asp
665                 670                 675                 680

GTG ATT GGT GGT AAT GCA ATC ACA ACT GCG AGT GCA GAA CTT ATT GTA      2477
Val Ile Gly Gly Asn Ala Ile Thr Thr Ala Ser Ala Glu Leu Ile Val
            685                 690                 695

CCA ACT CCA TTT GTG AGT GAT AAA AGC CAA AAT ACA GTC CGA ACC TCC      2525
Pro Thr Pro Phe Val Ser Asp Lys Ser Gln Asn Thr Val Arg Thr Ser
            700                 705                 710

CTA TTT GTT GAT GCG GCA AGT GTT TGG AAT ACT AAA TGG AAA TCA GAT      2573
Leu Phe Val Asp Ala Ala Ser Val Trp Asn Thr Lys Trp Lys Ser Asp
            715                 720                 725

AAA AAT GGA TTA GAG AGC AAG GTC TTG AAA GAC TTA CCT GAT TAT GGC      2621
Lys Asn Gly Leu Glu Ser Lys Val Leu Lys Asp Leu Pro Asp Tyr Gly
            730                 735                 740

AAA TCA AGC CGT ATT CGC GCC TCT ACA GGT GTC GGA TTC CAA TGG CAA      2669
Lys Ser Ser Arg Ile Arg Ala Ser Thr Gly Val Gly Phe Gln Trp Gln
745                 750                 755                 760

TCT CCT ATT GGA CCA TTG GTA TTT TCT TAT GCT AAA CCA ATT AAA AAA      2717
Ser Pro Ile Gly Pro Leu Val Phe Ser Tyr Ala Lys Pro Ile Lys Lys
            765                 770                 775

TAT GAA AAT GAT GAT GTC GAA CAG TTC CAA TTT AGT ATT GGG GGC TCT      2765
```

```
Tyr Glu Asn Asp Asp Val Glu Gln Phe Gln Phe Ser Ile Gly Gly Ser
                 780                 785                 790

TTC  TAATAAATTG  AACTTTTTTC  GTCATCAGAA  CTCAAAAACG  ACGTTCTCTG                2818
Phe

CCTAATTGAA  TTGGGCAGAG  AAAATATTAA  ACCCATCATT  TAATTAAGGA  TATTTATCAA          2878

ATGAAAAACA  TCGCAAAAGT  AACCGCACTT  GCTTTAGGTT  TTGCACTTGC  TTCAGGCTAT          2938

GCTTCCGCTG  AAGAAAAAAT  TGCTTTCATT  AATGCAGGTT  ATATTTTTCA A                   2989

(2) INFORMATION FOR SEQ ID NO: 10:

(i) SEQUENCE CHARACTERISTICS:
        (A) LENGTH: 793 amino acids
        (B) TYPE: amino acid
        (D) TOPOLOGY: linear (ii) MOLECULE TYPE: protein (xi) SEQUENCE DESCRIPTION: SEQ ID NO: 10:

Met Lys Lys Leu Leu Ile Ala Ser Leu Leu Phe Gly Ala Thr Thr Thr
  1               5                  10                  15

Val Phe Ala Ala Pro Phe Val Pro Lys Asp Ile Arg Val Asp Gly Val
                 20                  25                  30

Gln Gly Asp Leu Glu Gln Gln Ile Arg Ala Ser Leu Pro Val Arg Ala
             35                  40                  45

Gly Gln Arg Val Thr Asp Asn Asp Val Ala Asn Ile Val Arg Ser Leu
         50                  55                  60

Phe Val Ser Gly Arg Phe Asp Asp Val Lys Ala His Gln Glu Gly Asp
 65                  70                  75                  80

Val Leu Val Val Ser Val Ala Lys Ser Ile Ser Asp Val Lys
                 85                  90                  95

Ile Lys Gly Asn Ser Val Ile Pro Thr Glu Ala Leu Lys Gln Asn Leu
                100                 105                 110

Asp Ala Asn Gly Phe Lys Val Gly Asp Val Leu Ile Arg Glu Lys Leu
            115                 120                 125

Asn Glu Phe Ala Lys Ser Val Lys Glu His Tyr Ala Ser Val Gly Arg
        130                 135                 140

Tyr Asn Ala Thr Val Glu Pro Ile Val Asn Thr Leu Pro Asn Asn Arg
145                 150                 155                 160

Ala Glu Ile Leu Ile Gln Ile Asn Glu Asp Asp Lys Ala Lys Leu Ala
                165                 170                 175

Ser Leu Thr Phe Lys Gly Asn Glu Ser Val Ser Ser Thr Leu Gln
            180                 185                 190

Glu Gln Met Glu Leu Gln Pro Asp Ser Trp Trp Lys Leu Trp Gly Asn
        195                 200                 205

Lys Phe Glu Gly Ala Gln Phe Glu Lys Asp Leu Gln Ala Ile Arg Asp
210                 215                 220

Tyr Tyr Leu Asn Asn Gly Tyr Ala Lys Ala Gln Ile Thr Lys Thr Asp
225                 230                 235                 240

Val Gln Leu Asn Asp Glu Lys Thr Lys Val Asn Val Thr Ile Asp Val
                245                 250                 255

Asn Glu Gly Leu Gln Tyr Asp Leu Arg Ser Ala Arg Ile Ile Gly Asn
            260                 265                 270

Leu Gly Gly Met Ser Ala Glu Leu Glu Pro Leu Leu Ser Ala Leu His
        275                 280                 285

Leu Asn Asp Thr Phe Arg Arg Ser Asp Ile Ala Asp Val Glu Asn Ala
290                 295                 300
```

-continued

| | | | | | | | | | | | | | | | |
|---|---|---|---|---|---|---|---|---|---|---|---|---|---|---|---|
|Ile|Lys|Ala|Lys|Leu|Gly|Glu|Arg|Gly|Tyr|Gly|Asn|Thr|Thr|Val|Asn|
|305| | | |310| | | |315| | | |  | | |320|

Ser Val Pro Asp Phe Asp Ala Asn Lys Thr Leu Ala Ile Thr Phe
            325                 330                335

Val Val Asp Ala Gly Arg Arg Leu Thr Val Arg Gln Leu Arg Phe Glu
            340                 345                350

Gly Asn Thr Val Ser Ala Asp Ser Thr Leu Arg Gln Glu Met Arg Gln
            355                 360                365

Gln Glu Gly Thr Trp Tyr Asn Ser Gln Leu Val Glu Leu Gly Lys Ile
370                 375                 380

Arg Leu Asp Arg Thr Gly Phe Phe Glu Thr Val Glu Asn Arg Ile Asp
385                 390                 395                400

Pro Ile Asn Gly Ser Asn Asp Glu Val Asp Val Val Tyr Lys Val Lys
            405                 410                415

Glu Arg Asn Thr Gly Ser Ile Asn Phe Gly Ile Gly Tyr Gly Thr Glu
            420                 425                430

Ser Gly Ile Ser Tyr Gln Thr Ser Ile Lys Gln Asp Asn Phe Leu Gly
            435                 440                445

Thr Gly Ala Ala Val Ser Ile Ala Gly Thr Lys Asn Asp Tyr Gly Thr
450                 455                 460

Ser Val Asn Leu Gly Tyr Thr Glu Pro Tyr Phe Thr Lys Asp Gly Val
465                 470                 475                480

Ser Leu Gly Gly Asn Ile Phe Phe Glu Asn Tyr Asp Asn Ser Lys Ser
            485                 490                495

Asp Thr Ser Ser Asn Tyr Lys Arg Thr Thr Tyr Gly Ser Asn Val Thr
            500                 505                510

Leu Gly Phe Pro Val Asn Glu Asn Asn Ser Tyr Tyr Val Gly Leu Gly
            515                 520                525

His Thr Tyr Asn Lys Ile Ser Asn Phe Ala Leu Glu Tyr Asn Arg Asn
            530                 535                540

Leu Tyr Ile Gln Ser Met Lys Phe Lys Gly Asn Gly Ile Lys Thr Asn
545                 550                 555                560

Asp Phe Asp Phe Ser Phe Gly Trp Asn Tyr Asn Ser Leu Asn Arg Gly
            565                 570                575

Tyr Phe Pro Thr Lys Gly Val Lys Ala Ser Leu Gly Gly Arg Val Thr
            580                 585                590

Ile Pro Gly Ser Asp Asn Lys Tyr Tyr Lys Leu Ser Ala Asp Val Gln
            595                 600                605

Gly Phe Tyr Pro Leu Asp Arg Asp His Arg Trp Val Val Ser Ala Lys
610                 615                 620

Ala Ser Ala Gly Tyr Ala Asn Gly Phe Gly Asn Lys Arg Leu Pro Phe
625                 630                 635                640

Tyr Gln Thr Tyr Thr Ala Gly Gly Ile Gly Ser Leu Arg Gly Phe Ala
            645                 650                655

Tyr Gly Ser Ile Gly Pro Asn Ala Ile Tyr Ala Glu His Gly Asn Gly
            660                 665                670

Thr Phe Asn Lys Ile Ser Ser Asp Val Ile Gly Gly Asn Ala Ile Thr
            675                 680                685

Thr Ala Ser Ala Glu Leu Ile Val Pro Thr Pro Phe Val Ser Asp Lys
690                 695                 700

Ser Gln Asn Thr Val Arg Thr Ser Leu Phe Val Asp Ala Ala Ser Val
705                 710                 715                720

Trp Asn Thr Lys Trp Lys Ser Asp Lys Asn Gly Leu Glu Ser Lys Val

```
                       725                 730                 735
Leu Lys Asp Leu Pro Asp Tyr Gly Lys Ser Ser Arg Ile Arg Ala Ser
            740                 745                 750

Thr Gly Val Gly Phe Gln Trp Gln Ser Pro Ile Gly Pro Leu Val Phe
        755                 760                 765

Ser Tyr Ala Lys Pro Ile Lys Lys Tyr Glu Asn Asp Val Glu Gln
        770                 775             780

Phe Gln Phe Ser Ile Gly Gly Ser Phe
785                 790
```

(2) INFORMATION FOR SEQ ID NO: 11:

(i) SEQUENCE CHARACTERISTICS:
        (A) LENGTH: 6 amino acids
        (B) TYPE: amino acid
        (C) STRANDEDNESS: single
        (D) TOPOLOGY: linear (xi) SEQUENCE DESCRIPTION: SEQ ID NO: 11:

```
Ala Pro Phe Val Ala Lys
1               5
```

(2) INFORMATION FOR SEQ ID NO: 12:

(i) SEQUENCE CHARACTERISTICS:
        (A) LENGTH: 23 amino acids
        (B) TYPE: amino acid
        (C) STRANDEDNESS: single
        (D) TOPOLOGY: linear (xi) SEQUENCE DESCRIPTION: SEQ ID NO: 12:

```
Ser Leu Phe Val Ser Gly Arg Phe Asp Asp Val Lys Ala His Gln Glu
1               5                   10                  15

Gly Asp Val Leu Val Val Ser
            20
```

(2) INFORMATION FOR SEQ ID NO: 13:

(i) SEQUENCE CHARACTERISTICS:
        (A) LENGTH: 9 amino acids
        (B) TYPE: amino acid
        (C) STRANDEDNESS: single
        (D) TOPOLOGY: linear (xi) SEQUENCE DESCRIPTION: SEQ ID NO: 13:

```
Met Ser Pro Ile Leu Gly Tyr Trp Lys
1               5
```

(2) INFORMATION FOR SEQ ID NO: 14:

(i) SEQUENCE CHARACTERISTICS:
        (A) LENGTH: 30 amino acids
        (B) TYPE: amino acid
        (C) STRANDEDNESS: single
        (D) TOPOLOGY: linear (xi) SEQUENCE DESCRIPTION: SEQ ID NO: 14:

```
Ala Pro Phe Val Ala Lys Asp Ile Arg Val Asp Gly Val Gln Gly Asp
1               5                   10                  15

Leu Glu Gln Gln Ile Arg Ala Ser Leu Pro Val Arg Ala Gly
            20                  25                  30
```

(2) INFORMATION FOR SEQ ID NO: 15:

(i) SEQUENCE CHARACTERISTICS:

(A) LENGTH: 30 amino acids
(B) TYPE: amino acid
(C) STRANDEDNESS: single
(D) TOPOLOGY: linear (xi) SEQUENCE DESCRIPTION: SEQ ID NO: 15:

```
Pro Val Arg Ala Gly Gln Arg Val Thr Asp Asn Asp Val Ala Met Ile
1               5                   10                  15

Val Arg Ser Leu Phe Val Ser Gly Arg Phe Asp Asp Val Lys
            20                  25                  30
```

(2) INFORMATION FOR SEQ ID NO: 16:

(i) SEQUENCE CHARACTERISTICS:
(A) LENGTH: 32 amino acids
(B) TYPE: amino acid
(C) STRANDEDNESS: single
(D) TOPOLOGY: linear (xi) SEQUENCE DESCRIPTION: SEQ ID NO: 16:

```
Gly Arg Phe Asp Asp Val Lys Ala His Gln Glu Gly Asp Val Leu Val
1               5                   10                  15

Val Ser Val Val Ala Lys Ser Ile Ile Ser Asp Val Lys Ile Lys Gly
            20                  25                  30
```

(2) INFORMATION FOR SEQ ID NO: 17:

(i) SEQUENCE CHARACTERISTICS:
(A) LENGTH: 30 amino acids
(B) TYPE: amino acid
(C) STRANDEDNESS: single
(D) TOPOLOGY: linear (xi) SEQUENCE DESCRIPTION: SEQ ID NO: 17:

```
Ser Asp Val Lys Ile Lys Gly Asn Ser Val Ile Pro Thr Glu Ala Leu
1               5                   10                  15

Lys Gln Asn Leu Asp Ala Asn Gly Phe Lys Val Gly Asp Val
            20                  25                  30
```

(2) INFORMATION FOR SEQ ID NO: 18:

(i) SEQUENCE CHARACTERISTICS:
(A) LENGTH: 30 amino acids
(B) TYPE: amino acid
(C) STRANDEDNESS: single
(D) TOPOLOGY: linear (xi) SEQUENCE DESCRIPTION: SEQ ID NO: 18:

```
Ala Asn Gly Phe Lys Val Gly Asp Val Leu Ile Arg Glu Lys Leu Asn
1               5                   10                  15

Glu Phe Ala Lys Ser Val Lys Glu His Tyr Ala Ser Val Gly
            20                  25                  30
```

(2) INFORMATION FOR SEQ ID NO: 19:

(i) SEQUENCE CHARACTERISTICS:
(A) LENGTH: 30 amino acids
(B) TYPE: amino acid
(C) STRANDEDNESS: single
(D) TOPOLOGY: linear (xi) SEQUENCE DESCRIPTION: SEQ ID NO: 19:

```
Val Lys Glu His Tyr Ala Ser Val Gly Arg Tyr Asn Ala Thr Val Glu
1               5                   10                  15

Pro Ile Val Asn Thr Leu Pro Asn Asn Arg Ala Glu Ile Leu
            20                  25                  30
```

(2) INFORMATION FOR SEQ ID NO: 20:

(i) SEQUENCE CHARACTERISTICS:
        (A) LENGTH: 31 amino acids
        (B) TYPE: amino acid
        (C) STRANDEDNESS: single
        (D) TOPOLOGY: linear (xi) SEQUENCE DESCRIPTION: SEQ ID NO: 20:

```
Pro Asn Asn Arg Ala Glu Ile Leu Ile Gln Ile Asn Glu Asp Asp Lys
1               5                   10                  15

Ala Lys Leu Ala Ser Leu Thr Phe Lys Gly Asn Glu Ser Val Ser
                20                  25                  30
```

(2) INFORMATION FOR SEQ ID NO: 21:

(i) SEQUENCE CHARACTERISTICS:
        (A) LENGTH: 31 amino acids
        (B) TYPE: amino acid
        (C) STRANDEDNESS: single
        (D) TOPOLOGY: linear (xi) SEQUENCE DESCRIPTION: SEQ ID NO: 21:

```
Phe Lys Gly Asn Glu Ser Val Ser Ser Thr Leu Gln Glu Gln Met
1               5                   10                  15

Glu Leu Gln Pro Asp Ser Trp Trp Lys Lys Leu Trp Gly Asn Lys
                20                  25                  30
```

(2) INFORMATION FOR SEQ ID NO: 22:

(i) SEQUENCE CHARACTERISTICS:
        (A) LENGTH: 30 amino acids
        (B) TYPE: amino acid
        (C) STRANDEDNESS: single
        (D) TOPOLOGY: linear (xi) SEQUENCE DESCRIPTION: SEQ ID NO: 22:

```
Pro Asp Ser Trp Trp Lys Leu Trp Gly Asn Lys Phe Glu Gly Ala Gln
1               5                   10                  15

Phe Glu Lys Asp Leu Gln Ser Ile Arg Asp Tyr Tyr Leu Asn
                20                  25                  30
```

(2) INFORMATION FOR SEQ ID NO: 23:

(i) SEQUENCE CHARACTERISTICS:
        (A) LENGTH: 31 amino acids
        (B) TYPE: amino acid
        (C) STRANDEDNESS: single
        (D) TOPOLOGY: linear (xi) SEQUENCE DESCRIPTION: SEQ ID NO: 23:

```
Leu Gln Ser Ile Arg Asp Tyr Tyr Leu Asn Asn Gly Tyr Ala Lys Ala
1               5                   10                  15

Gln Ile Thr Lys Thr Asp Val Gln Leu Asn Asp Glu Lys Thr Lys
                20                  25                  30
```

(2) INFORMATION FOR SEQ ID NO: 24:

(i) SEQUENCE CHARACTERISTICS:
        (A) LENGTH: 30 amino acids
        (B) TYPE: amino acid
        (C) STRANDEDNESS: single
        (D) TOPOLOGY: linear (xi) SEQUENCE DESCRIPTION: SEQ ID NO: 24:

-continued

```
    Val Gln Leu Asn Asp Glu Lys Thr Lys Val Asn Val Thr Ile Asp Val
    1               5                   10                  15

Asn Glu Gly Leu Gln Tyr Asp Leu Arg Ser Ala Arg Ile Ile
                20                  25                  30
```

(2) INFORMATION FOR SEQ ID NO: 25:

(i) SEQUENCE CHARACTERISTICS:
        (A) LENGTH: 30 amino acids
        (B) TYPE: amino acid
        (C) STRANDEDNESS: single
        (D) TOPOLOGY: linear (xi) SEQUENCE DESCRIPTION: SEQ ID NO: 25:

```
    Tyr Asp Leu Arg Ser Ala Arg Ile Ile Gly Asn Leu Gly Gly Met Ser
    1               5                   10                  15

Ala Glu Leu Glu Pro Leu Leu Ser Ala Leu His Leu Asn Asp
                20                  25                  30
```

(2) INFORMATION FOR SEQ ID NO: 26:

(i) SEQUENCE CHARACTERISTICS:
        (A) LENGTH: 31 amino acids
        (B) TYPE: amino acid
        (C) STRANDEDNESS: single
        (D) TOPOLOGY: linear (xi) SEQUENCE DESCRIPTION: SEQ ID NO: 26:

```
    Pro Leu Leu Ser Ala Leu His Leu Asn Asp Thr Phe Arg Arg Ser Asp
    1               5                   10                  15

Ile Ala Asp Val Glu Asn Ala Ile Lys Ala Lys Leu Gly Glu Arg
                20                  25                  30
```

(2) INFORMATION FOR SEQ ID NO: 27:

(i) SEQUENCE CHARACTERISTICS:
        (A) LENGTH: 30 amino acids
        (B) TYPE: amino acid
        (C) STRANDEDNESS: single
        (D) TOPOLOGY: linear (xi) SEQUENCE DESCRIPTION: SEQ ID NO: 27:

```
    Ala Ile Lys Ala Lys Leu Gly Glu Arg Gly Tyr Gly Ser Ala Thr Val
    1               5                   10                  15

Asn Ser Val Pro Asp Phe Asp Asp Ala Asn Lys Thr Leu Ala
                20                  25                  30
```

(2) INFORMATION FOR SEQ ID NO: 28:

(i) SEQUENCE CHARACTERISTICS:
        (A) LENGTH: 30 amino acids
        (B) TYPE: amino acid
        (C) STRANDEDNESS: single
        (D) TOPOLOGY: linear (xi) SEQUENCE DESCRIPTION: SEQ ID NO: 28:

```
    Phe Asp Asp Ala Asn Lys Thr Leu Ala Ile Thr Leu Val Val Asp Ala
    1               5                   10                  15

Gly Arg Arg Leu Thr Val Arg Gln Leu Arg Phe Glu Gly Asn
                20                  25                  30
```

(2) INFORMATION FOR SEQ ID NO: 29:

(i) SEQUENCE CHARACTERISTICS:
        (A) LENGTH: 30 amino acids
        (B) TYPE: amino acid (C) STRANDEDNESS: single
        (D) TOPOLOGY: linear (xi) SEQUENCE DESCRIPTION: SEQ ID NO: 29:

Val Arg Gln Leu Arg Phe Glu Gly Asn Thr Val Ser Ala Asp Ser Thr
    1               5                   10                  15

Leu Arg Gln Glu Met Arg Gln Gln Glu Gly Thr Trp Tyr Asn
                20                  25                  30

(2) INFORMATION FOR SEQ ID NO: 30:

(i) SEQUENCE CHARACTERISTICS:
        (A) LENGTH: 30 amino acids
        (B) TYPE: amino acid
        (C) STRANDEDNESS: single
        (D) TOPOLOGY: linear (xi) SEQUENCE DESCRIPTION: SEQ ID NO: 30:

Arg Gln Gln Glu Gly Thr Trp Tyr Asn Ser Gln Leu Val Glu Leu Gly
    1               5                   10                  15

Lys Ile Arg Leu Asp Arg Thr Gly Phe Phe Glu Thr Val Glu
                20                  25                  30

(2) INFORMATION FOR SEQ ID NO: 31:

(i) SEQUENCE CHARACTERISTICS:
        (A) LENGTH: 27 amino acids
        (B) TYPE: amino acid
        (C) STRANDEDNESS: single
        (D) TOPOLOGY: linear (xi) SEQUENCE DESCRIPTION: SEQ ID NO: 31:

Gly Phe Phe Glu Thr Val Glu Asn Arg Ile Asp Pro Ile Asn Gly Ser
    1               5                   10                  15

Asn Asp Glu Val Asp Val Val Tyr Lys Val Lys
                20                  25

(2) INFORMATION FOR SEQ ID NO: 32:

(i) SEQUENCE CHARACTERISTICS:
        (A) LENGTH: 26 amino acids
        (B) TYPE: amino acid
        (C) STRANDEDNESS: single
        (D) TOPOLOGY: linear (xi) SEQUENCE DESCRIPTION: SEQ ID NO: 32:

Asp Val Val Tyr Lys Val Lys Glu Arg Asn Thr Gly Ser Ile Asn Phe
    1               5                   10                  15

Gly Ile Gly Tyr Gly Thr Glu Ser Gly Ile
                20                  25

(2) INFORMATION FOR SEQ ID NO: 33:

(i) SEQUENCE CHARACTERISTICS:
        (A) LENGTH: 26 amino acids
        (B) TYPE: amino acid
        (C) STRANDEDNESS: single
        (D) TOPOLOGY: linear (xi) SEQUENCE DESCRIPTION: SEQ ID NO: 33:

Gly Thr Glu Ser Gly Ile Ser Tyr Gln Ala Ser Val Lys Gln Asp Asn
    1               5                   10                  15

Phe Leu Gly Thr Gly Ala Ala Val Ser Ile
                20                  25

(2) INFORMATION FOR SEQ ID NO: 34:

(i) SEQUENCE CHARACTERISTICS:
        (A) LENGTH: 28 amino acids
        (B) TYPE: amino acid
        (C) STRANDEDNESS: single
        (D) TOPOLOGY: linear (xi) SEQUENCE DESCRIPTION: SEQ ID NO: 34:

```
Gly Ala Ala Val Ser Ile Ala Gly Thr Lys Asn Asp Tyr Gly Thr Ser
1               5                   10                  15

Val Asn Leu Gly Tyr Thr Glu Pro Tyr Phe Thr Lys
            20                  25
```

(2) INFORMATION FOR SEQ ID NO: 35:

(i) SEQUENCE CHARACTERISTICS:
        (A) LENGTH: 27 amino acids
        (B) TYPE: amino acid
        (C) STRANDEDNESS: single
        (D) TOPOLOGY: linear (xi) SEQUENCE DESCRIPTION: SEQ ID NO: 35:

```
Thr Glu Pro Tyr Phe Thr Lys Asp Gly Val Ser Leu Gly Gly Asn Val
1               5                   10                  15

Phe Phe Glu Asn Tyr Asp Asn Ser Lys Ser Asp
            20                  25
```

(2) INFORMATION FOR SEQ ID NO: 36:

(i) SEQUENCE CHARACTERISTICS:
        (A) LENGTH: 26 amino acids
        (B) TYPE: amino acid
        (C) STRANDEDNESS: single
        (D) TOPOLOGY: linear (xi) SEQUENCE DESCRIPTION: SEQ ID NO: 36:

```
Tyr Asp Asn Ser Lys Ser Asp Thr Ser Ser Asn Tyr Lys Arg Thr Thr
1               5                   10                  15

Tyr Gly Ser Asn Val Thr Leu Gly Phe Pro
            20                  25
```

(2) INFORMATION FOR SEQ ID NO: 37:

(i) SEQUENCE CHARACTERISTICS:
        (A) LENGTH: 27 amino acids
        (B) TYPE: amino acid
        (C) STRANDEDNESS: single
        (D) TOPOLOGY: linear (xi) SEQUENCE DESCRIPTION: SEQ ID NO: 37:

```
Val Thr Leu Gly Phe Pro Val Asn Glu Asn Ser Tyr Tyr Val Gly
1               5                   10                  15

Leu Gly His Thr Tyr Asn Lys Ile Ser Asn Phe
            20                  25
```

(2) INFORMATION FOR SEQ ID NO: 38:

(i) SEQUENCE CHARACTERISTICS:
        (A) LENGTH: 28 amino acids
        (B) TYPE: amino acid
        (C) STRANDEDNESS: single
        (D) TOPOLOGY: linear (xi) SEQUENCE DESCRIPTION: SEQ ID NO: 38:

```
Tyr Asn Lys Ile Ser Asn Phe Ala Leu Glu Tyr Asn Arg Asn Leu Tyr
1               5                   10                  15
```

Ile Gln Ser Met Lys Phe Lys Gly Asn Gly Ile Lys
                    20                  25

(2) INFORMATION FOR SEQ ID NO: 39:

(i) SEQUENCE CHARACTERISTICS:
        (A) LENGTH: 29 amino acids
        (B) TYPE: amino acid
        (C) STRANDEDNESS: single
        (D) TOPOLOGY: linear (xi) SEQUENCE DESCRIPTION: SEQ ID NO: 39:

Lys Gly Asn Gly Ile Lys Thr Asn Asp Phe Asp Phe Ser Phe Gly Trp
    1               5                   10                  15

Asn Tyr Asn Ser Leu Asn Arg Gly Tyr Phe Pro Thr Lys
                    20                  25

(2) INFORMATION FOR SEQ ID NO: 40:

(i) SEQUENCE CHARACTERISTICS:
        (A) LENGTH: 27 amino acids
        (B) TYPE: amino acid
        (C) STRANDEDNESS: single
        (D) TOPOLOGY: linear (xi) SEQUENCE DESCRIPTION: SEQ ID NO: 40:

Gly Tyr Phe Pro Thr Lys Gly Val Lys Ala Ser Leu Gly Gly Arg Val
    1               5                   10                  15

Thr Ile Pro Gly Ser Asp Asn Lys Tyr Tyr Lys
                    20                  25

(2) INFORMATION FOR SEQ ID NO: 41:

(i) SEQUENCE CHARACTERISTICS:
        (A) LENGTH: 29 amino acids
        (B) TYPE: amino acid
        (C) STRANDEDNESS: single
        (D) TOPOLOGY: linear (xi) SEQUENCE DESCRIPTION: SEQ ID NO: 41:

Ser Asp Asn Lys Tyr Tyr Lys Leu Ser Ala Asp Val Gln Gly Phe Tyr
    1               5                   10                  15

Pro Leu Asp Arg Asp His Leu Trp Val Val Ser Ala Lys
                    20                  25

(2) INFORMATION FOR SEQ ID NO: 42:

(i) SEQUENCE CHARACTERISTICS:
        (A) LENGTH: 28 amino acids
        (B) TYPE: amino acid
        (C) STRANDEDNESS: single
        (D) TOPOLOGY: linear (xi) SEQUENCE DESCRIPTION: SEQ ID NO: 42:

Leu Trp Val Val Ser Ala Lys Ala Ser Ala Gly Tyr Ala Asn Gly Phe
    1               5                   10                  15

Gly Asn Lys Arg Leu Pro Phe Tyr Gln Thr Tyr Thr
                    20                  25

(2) INFORMATION FOR SEQ ID NO: 43:

(i) SEQUENCE CHARACTERISTICS:
        (A) LENGTH: 26 amino acids
        (B) TYPE: amino acid
        (C) STRANDEDNESS: single
        (D) TOPOLOGY: linear (xi) SEQUENCE DESCRIPTION: SEQ ID NO: 43:

Phe Tyr Gln Thr Tyr Thr Ala Gly Gly Ile Gly Ser Leu Arg Gly Phe
1               5                   10                  15

Ala Tyr Gly Ser Ile Gly Pro Asn Ala Ile
            20                  25

(2) INFORMATION FOR SEQ ID NO: 44:

(i) SEQUENCE CHARACTERISTICS:
        (A) LENGTH: 27 amino acids
        (B) TYPE: amino acid
        (C) STRANDEDNESS: single
        (D) TOPOLOGY: linear (xi) SEQUENCE DESCRIPTION: SEQ ID NO: 44:

Gly Pro Asn Ala Ile Tyr Ala Glu Tyr Gly Asn Gly Ser Gly Thr Gly
1               5                   10                  15

Thr Phe Lys Lys Ile Ser Ser Asp Val Ile Gly
            20                  25

(2) INFORMATION FOR SEQ ID NO: 45:

(i) SEQUENCE CHARACTERISTICS:
        (A) LENGTH: 29 amino acids
        (B) TYPE: amino acid
        (C) STRANDEDNESS: single
        (D) TOPOLOGY: linear (xi) SEQUENCE DESCRIPTION: SEQ ID NO: 45:

Lys Ile Ser Ser Asp Val Ile Gly Gly Asn Ala Ile Ala Thr Ala Ser
1               5                   10                  15

Ala Glu Leu Ile Val Pro Thr Pro Phe Val Ser Asp Lys
            20                  25

(2) INFORMATION FOR SEQ ID NO: 46:

(i) SEQUENCE CHARACTERISTICS:
        (A) LENGTH: 27 amino acids
        (B) TYPE: amino acid
        (C) STRANDEDNESS: single
        (D) TOPOLOGY: linear (xi) SEQUENCE DESCRIPTION: SEQ ID NO: 46:

Phe Val Ser Asp Lys Ser Gln Asn Thr Val Arg Thr Ser Leu Phe Val
1               5                   10                  15

Asp Ala Ala Ser Val Trp Asn Thr Lys Trp Lys
            20                  25

(2) INFORMATION FOR SEQ ID NO: 47:

(i) SEQUENCE CHARACTERISTICS:
        (A) LENGTH: 26 amino acids
        (B) TYPE: amino acid
        (C) STRANDEDNESS: single
        (D) TOPOLOGY: linear (xi) SEQUENCE DESCRIPTION: SEQ ID NO: 47:

Val Trp Asn Thr Lys Trp Lys Ser Asp Lys Asn Gly Leu Glu Ser Asp
1               5                   10                  15

Val Leu Lys Arg Leu Pro Asp Tyr Gly Lys
            20                  25

(2) INFORMATION FOR SEQ ID NO: 48:

(i) SEQUENCE CHARACTERISTICS:
            (A) LENGTH: 27 amino acids
            (B) TYPE: amino acid
            (C) STRANDEDNESS: single
            (D) TOPOLOGY: linear (xi) SEQUENCE DESCRIPTION: SEQ ID NO: 48:

Leu Pro Asp Tyr Gly Lys Ser Ser Arg Ile Arg Ala Ser Thr Gly Val
       1               5                   10                  15

Gly Phe Gln Trp Gln Ser Pro Ile Gly Pro Leu
                   20                  25

(2) INFORMATION FOR SEQ ID NO: 49:

(i) SEQUENCE CHARACTERISTICS:
            (A) LENGTH: 30 amino acids
            (B) TYPE: amino acid
            (C) STRANDEDNESS: single
            (D) TOPOLOGY: linear (xi) SEQUENCE DESCRIPTION: SEQ ID NO: 49:

Gly Pro Leu Val Phe Ser Tyr Ala Lys Pro Ile Lys Lys Tyr Glu Asn
       1               5                   10                  15

Asp Asp Val Glu Gln Phe Gln Phe Ser Ile Gly Gly Ser Phe
                   20                  25                  30

(2) INFORMATION FOR SEQ ID NO: 50:

(i) SEQUENCE CHARACTERISTICS:
            (A) LENGTH: 89 base pairs
            (B) TYPE: nucleic acid
            (C) STRANDEDNESS: single
            (D) TOPOLOGY: linear (xi) SEQUENCE DESCRIPTION: SEQ ID NO: 50:

TATGGCACCT TTTGTGGCAA AAGATATTCG TGTGGATGGT GTTCAAGGTG ACTTAGAATC        60

AACAAACCGA GCAAGTTTAC CTGTTCGTG                                         89

(2) INFORMATION FOR SEQ ID NO: 51:

(i) SEQUENCE CHARACTERISTICS:
            (A) LENGTH: 92 base pairs
            (B) TYPE: nucleic acid
            (C) STRANDEDNESS: single
            (D) TOPOLOGY: linear (xi) SEQUENCE DESCRIPTION: SEQ ID NO: 51:

ACCGTGGAAA ACACCGTTTT CTATAAGCAC ACCTACCACA AGTTCCACTG AATCTTGGTT        60

GTTTAGGCTC GTTCAAATGG ACAAGCACGG CC                                     92

(2) INFORMATION FOR SEQ ID NO: 52:

(i) SEQUENCE CHARACTERISTICS:
            (A) LENGTH: 23 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO: 52:

GGGGAATTCC AAAAGATGTT CGT                                               23

(2) INFORMATION FOR SEQ ID NO: 53:

(i) SEQUENCE CHARACTERISTICS:

(A) LENGTH: 19 base pairs
        (B) TYPE: nucleic acid
        (C) STRANDEDNESS: single
        (D) TOPOLOGY: linear (xi) SEQUENCE DESCRIPTION: SEQ ID NO: 53:

CACGAATTCC CTGCAAATC                                                    19

(2) INFORMATION FOR SEQ ID NO: 54:

(i) SEQUENCE CHARACTERISTICS:
        (A) LENGTH: 7 amino acids
        (B) TYPE: amino acid
        (C) STRANDEDNESS: single
        (D) TOPOLOGY: linear (xi) SEQUENCE DESCRIPTION: SEQ ID NO: 54:

Met Ala Pro Phe Val Lys Asp
    1               5

(2) INFORMATION FOR SEQ ID NO: 55:

(i) SEQUENCE CHARACTERISTICS:
        (A) LENGTH: 2987 base pairs
        (B) TYPE: nucleic acid
        (C) STRANDEDNESS: single
        (D) TOPOLOGY: linear (xi) SEQUENCE DESCRIPTION: SEQ ID NO: 55:

AAAAGGCATT GAAAAACAG GACAGCTTTC CCTTTTAACC TTGAAAATAT TAGGGAAATT          60

ACTTACTGGC GATTTGTCAT TAAATAATTT AAGTGGGCCA ATTTCTATTG CAAAAGGTGC        120

TGGCGCATCA GCAAATATTG GATTGGTGTA TTTTTTAAGT TTTATGGCAT GATTAGTGTA        180

AATTTAGGGA TTATGAATTT ATTTCCATTA CCAGTATTAG ATGGCGGTCA TTTAGTTTTT        240

TTAACAATGG AAGCTGTTAA AGGAAAACCT GTTTCTGAGC GGGTGCAAAG CATCTGTTAT        300

CGAATTGGCG CAGCACTGTT ATTAAGCTTA ACGGTGTTTG CATTATTTAA TGATTTTTTA        360

CGTCTATAAT TTATATAGGA TACAATCGAT GAAAAAACTT CTAATCGCAA GTTTATTATT        420

CGGTACGACA ACGACTGTGT TGCCGCACCC TTTTGTGGCA AAAGATATTC GTGTGGATGG        480

TGTTCAAGGT GACTTAGAAC AACAAATCCG AGCAAGTTTA CCTGTTCGTG CCGGTCAGCG        540

TGTGACTGAC AATGATGTGG CTAATATTGT CCGCTCTTTA TTCGTAAGTG GTCGATTCGA        600

TGATGTGAAA GCGCATCAAG AAGGCGATGT GCTTGTTGTT AGCGTTGTGG CTAAATCGAT        660

CATTTCAGAT GTTAAAATCA AAGGTAACTC TGTTATTCCC ACTGAAGCAC TTAAACAAAA        720

CTTAGATGCT AACGGGTTTA AGTTGGCGA TGTTTTAATT CGAGAAAAAT TAAATGAATT        780

TGCCAAAAGT GTAAAAGAGC ACTATGCAAG TGTAGGTCGC TATAACGCAA CAGTTGAACC        840

TATTGTCAAT ACGCTACCAA ATAATCGCGC TGAAATTTTA ATTCAAATCA ATGAAGATGA        900

TAAAGCAAAA TTGGCATCAT TAACTTTCAA GGGGAACGAA TCTGTTAGTA GCAGTACATT        960

ACAAGAACAA ATGGAATTAC AACCTGATTC TTGGTGGAAA TTATGGGGAA ATAAATTTGA       1020

AGGTGCGCAA TTCGAGAAAG ATTTGCAGTC AATTCGTGAT TATTATTTAA ATAATGGCTA       1080

TGCCAAAGCA CAAATTACTA AAACGGATGT TCAGCTAAAT GATGAAAAAA CAAAAGTTAA       1140

TGTAACCATT GATGTAAATG AAGGTTTACA GTATGACCTT CGTAGTGCAC GCATTATAGG       1200

TAATCTGGGA GGTATGTCTG CCGAGCTTGA ACCTTTACTT TCAGCATTAC ATTTAAATGA       1260

TACTTTCCGC CGTAGTGATA TTGCAGATGT AGAAAATGCA ATTAAAGCAA ACTTGGAGA       1320

ACGCGGTTAC GGTAGCGCAA CGGTAAATTC AGTACCTGAT TTTGATGATG CAAATAAAAC       1380

```
ATTAGCGATA ACCCTTGTTG TTGATGCTGG ACGACGTTTA ACTGTTCGCC AACTTCGCTT    1440

TGAAGGAAAT ACCGTTTCTG CTGATAGCAC TTTACGTCAG GAAATGCGCC AACAAGAAGG    1500

AACTTGGTAT AATTCACAAT TAGTTGAGTT AGGAAAAATT CGCTTAGATC GTACAGGTTT    1560

CTTCGAAACA GTCGAAAACC GAATTGATCC TATCAATGGT AGTAATGATG AAGTGGATGT    1620

CGTATATAAA GTCAAAGAAC GTAACACGGG TAGTATCAAC TTTGGTATTG GTTACGGTAC    1680

AGAGAGTGGT ATTAGTTATC AAGCAAGTGT TAAACAAGAT AATTTCTTGG GAACAGGGGC    1740

GGCAGTAAGT ATAGCTGGTA CGAAAAATGA TTATGGTACG AGTGTCAATT TGGGTTATAC    1800

CGAGCCCTAT TTTACTAAAG ATGGTGTAAG TCTTGGTGGA AATGTTTTCT TTGAAAACTA    1860

CGATAACTCT AAAAGTGATA CATCCTCTAA CTATAAGCGT ACGACTTACG GAAGTAATGT    1920

TACTTTAGGT TTCCCTGTAA ATGAAAATAA CTCCTATTAT GTAGGATTAG GTCATACCTA    1980

TAATAAAATT AGTAACTTTG CTCTAGAATA TAACCGTAAT TTATATATTC AATCAATGAA    2040

ATTTAAAGGT AATGGCATTA AAACAAATGA CTTTGATTTT TCTTTTGGTT GGAACTATAA    2100

CAGCCTTAAT AGAGGCTATT TCCCAACTAA AGGGGTTAAA GCAAGTCTTG GTGGACGAGT    2160

TACTATTCCA GGTTCTGATA ACAAATACTA CAAACTAAGT GCAGATGTAC AGGGTTTCTA    2220

CCCATTAGAC AGAGATCACC TCTGGGTTGT ATCTGCAAAA GCATCTGCAG GATATGCAAA    2280

TGGTTTTGGA AACAAGCGTT TACCGTTCTA TCAAACTTAT ACAGCGGGTG GCATCGGTTC    2340

ATTACGTGGT TTTGCTTATG GTAGTATTGG ACCTAACGCA ATTTATGCCG AATATGGTAA    2400

TGGTAGTGGT ACTGGTACTT TTAAGAAGAT AAGTTCTGAT GTGATTGGTG GTAATGCAAT    2460

CGCTACAGCT AGCGCAGAGT TAATTGTGCC AACTCCATTT GTGAGCGATA AGAGCCAAAA    2520

TACGGTCCGA ACCTCCTTAT TTGTTGATGC GGCAAGTGTT TGGAATACTA AATGGAAATC    2580

AGATAAAAAT GGATTAGAGA GCGATGTATT AAAAAGATTG CCTGATTATG GCAAATCAAG    2640

CCGTATTCGC GCCTCTACAG GTGTCGGATT CCAATGGCAA TCTCCTATTG GGCCATTGGT    2700

ATTCTCTTAT GCCAAACCAA TTAAAAAATA TGAAAATGAT GATGTCGAAC AGTTCCAATT    2760

TAGTATTGGA GGTTCTTTCT AATAAATTGA ACTTTTTTCT TCATCAGAAC TCAAAAACAA    2820

CGTTCTCTGC CTAATTTAAT TGGGCAGAGA AAATATTAAA CCCATCATTT AATTAAGGAT    2880

ATTTATCAAA TGAAAAACAT CGCAAAAGTA ACCGCACTTG CTTTAGGTAT TGCACTTGCT    2940

TCAGGCTATG CTTCCGCTGA AGAAAAAATT GCTTTCATTA ATGCAGT                 2987
```